(12) United States Patent
Niewöhner et al.

(10) Patent No.: US 7,696,206 B2
(45) Date of Patent: *Apr. 13, 2010

(54) 2-PHENYL SUBSTITUTED IMIDAZOTRIAZINONES AS PHOSPHODIESTERASE INHIBITORS

(75) Inventors: Ulrich Niewöhner, Wermelskirchen (DE); Maria Niewöhner, legal representative, Wermelskirchen (DE); Mazen Es-Sayed, Langenfeld (DE); Helmut Haning, Wuppertal (DE); Thomas Schenke, Bergisch Gladbach (DE); Karl-Heinz Schlemmer, Wuppertal (DE); Jorg Keldenich, Wuppertal (DE); Erwin Bischoff, Wuppertal (DE); Elisabeth Perzborn, Wuppertal (DE); Klaus Dembowsky, Boston, MA (US); Peter Serno, Bergisch Gladbach (DE); Marc Nowakowski, Wuppertal (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/569,720

(22) Filed: Sep. 29, 2009

(65) Prior Publication Data

US 2010/0016323 A1 Jan. 21, 2010

Related U.S. Application Data

(63) Continuation of application No. 12/004,933, filed on Dec. 21, 2007, which is a continuation of application No. 11/409,417, filed on Apr. 21, 2006, now Pat. No. 7,314,871, which is a continuation of application No. 10/923,544, filed on Aug. 20, 2004, now Pat. No. 7,122,540, which is a continuation of application No. 10/365,740, filed on Feb. 12, 2003, now Pat. No. 6,890,922, which is a continuation of application No. 09/943,530, filed on Aug. 30, 2001, now Pat. No. 6,566,360, which is a continuation of application No. 09/554,162, filed as application No. PCT/EP98/06910 on Oct. 31, 1998, now Pat. No. 6,362,178.

(30) Foreign Application Priority Data

| Nov. 12, 1997 | (DE) | ............................ 197 50 085 |
| Mar. 23, 1998 | (DE) | ............................ 198 12 462 |
| Sep. 4, 1998 | (DE) | ............................ 198 40 289 |

(51) Int. Cl.
*C07D 403/12* (2006.01)
*A61K 31/53* (2006.01)
*A61P 15/10* (2006.01)

(52) U.S. Cl. ........................ 514/243; 544/184
(58) Field of Classification Search ............... 514/243; 544/184

See application file for complete search history.

(56) References Cited

U.S. PATENT DOCUMENTS

| 2,705,715 A | 4/1955 | Baker et al. |
| 3,036,070 A | 5/1962 | Druey et al. |
| 3,169,129 A | 2/1965 | Rodgers et al. |
| 3,331,840 A | 7/1967 | Fry et al. |
| RE26,565 E | 4/1969 | Rodgers et al. |
| 3,840,537 A | 10/1974 | Garside et al. |
| 4,039,544 A | 8/1977 | Broughton et al. |
| 4,052,390 A | 10/1977 | Broughton et al. |

(Continued)

FOREIGN PATENT DOCUMENTS

BE           865125        9/1978

(Continued)

OTHER PUBLICATIONS

H. S. Ahn et al.: "Calcium-Calmodulin-Stimulated and Cyclic-GMP-Specific Phosphodiesterases," Advances in Second Messenger and Phosphoprotein Research, 25: pp. 271-284 (1992).

(Continued)

*Primary Examiner*—Bruck Kifle
(74) *Attorney, Agent, or Firm*—Edwards Angell Palmer & Dodge LLP; Ralph A. Loren; Nicholas J. DiCeglie, Jr.

(57) ABSTRACT

The application claims a compound of the formula

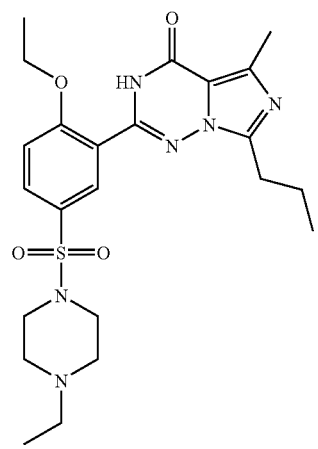

or a salt, a hydrate, or a hydrate of a salt thereof.

The compounds inhibit cGMP-metabolizing phosphodiesterases and are suitable for use as active compounds in pharmaceuticals, for the treatment of erectile dysfunction.

6 Claims, No Drawings

U.S. PATENT DOCUMENTS

| | | | |
|---|---|---|---|
| 4,060,615 | A | 11/1977 | Matier et al. |
| 4,159,330 | A | 6/1979 | Doria et al. |
| 4,167,568 | A | 9/1979 | Knowles et al. |
| 4,278,673 | A | 7/1981 | Hartley et al. |
| 4,379,788 | A | 4/1983 | Heider et al. |
| 4,431,440 | A | 2/1984 | Bhalla et al. |
| 4,666,908 | A | 5/1987 | Hamilton |
| 4,885,301 | A | 12/1989 | Coates |
| 4,923,874 | A | 5/1990 | McMahon et al. |
| 5,047,404 | A | 9/1991 | Coates et al. |
| 5,073,559 | A | 12/1991 | Coates |
| 5,075,310 | A | 12/1991 | Coates et al. |
| 5,147,875 | A | 9/1992 | Coates et al. |
| 5,250,534 | A | 10/1993 | Bell et al. |
| 5,254,571 | A | 10/1993 | Coates et al. |
| 5,272,147 | A | 12/1993 | Bell et al. |
| 5,294,612 | A | 3/1994 | Bacon et al. |
| 5,316,906 | A | 5/1994 | Haugland et al. |
| 5,346,901 | A | 9/1994 | Bell et al. |
| 5,426,107 | A | 6/1995 | Bell et al. |
| 5,482,941 | A | 1/1996 | Terrett |
| 5,591,742 | A | 1/1997 | Bell et al. |
| 5,719,283 | A | 2/1998 | Bell et al. |
| 5,734,053 | A | 3/1998 | Terrett |
| 6,100,270 | A | 8/2000 | Campbell |
| 6,362,178 | B1 | 3/2002 | Neiwohner et al. |
| 6,566,360 | B1 | 5/2003 | Neiwohner et al. |
| 6,890,922 | B2 | 5/2005 | Neiwohner et al. |
| 7,122,540 | B2 | 10/2006 | Neiwohner et al. |
| 7,314,871 | B2 | 1/2008 | Neiwohner et al. |

FOREIGN PATENT DOCUMENTS

| | | |
|---|---|---|
| DE | 2255172 | 5/1973 |
| DE | 2811780 | 9/1978 |
| DE | 2364076 | 7/1994 |
| EP | 0009384 | 4/1980 |
| EP | 0162715 | 11/1985 |
| EP | 0201188 | 12/1986 |
| EP | 0293063 | 11/1988 |
| EP | 0347146 | 12/1989 |
| EP | 0349239 | 1/1990 |
| EP | 0351058 | 1/1990 |
| EP | 0371731 | 6/1990 |
| EP | 0352960 | 9/1990 |
| EP | 0442204 | 8/1991 |
| EP | 0463756 | 1/1992 |
| EP | 0526004 | 2/1993 |
| EP | 0636626 | 2/1995 |
| EP | 0669324 | 8/1995 |
| EP | 0702555 | 3/1996 |
| EP | 0812845 | 12/1997 |
| GB | 1338235 | 1/1973 |
| GB | 1 584 461 | 2/1981 |
| WO | WO9306104 | 4/1993 |
| WO | WO9307149 | 4/1993 |
| WO | WO9312095 | 6/1993 |
| WO | WO9400453 | 1/1994 |
| WO | WO9405661 | 3/1994 |
| WO | WO 94/28902 | 12/1994 |
| WO | WO9429277 | 12/1994 |
| WO | WO 96/16657 | 6/1996 |
| WO | WO9703675 | 2/1997 |

OTHER PUBLICATIONS

W. J. Aronson et al.: "The Role of Nitric Oxide and Cyclic GMP in Mediating Pelvic Nerve Stimulation Induced Erection in Dogs," J. Urology, 147: 454A (1992).

K. M. Azadzoi et al.: "Diabetes Mellitus Impairs Neurogenic and Endothelium-Dependent Relaxation of Rabbit Corpus Cavernosum Smooth Muscle," J. Urol. 148: 1587-1591 (Nov. 1992).

K. M. Azadzoi et al.: "Endothelium-Derived Nitric Oxie and Cyclooxygenase Products Modulate Corpus Cavernosum Smooth Muscle Tone," J. Urol. 147: 220-225 (Jan. 1992).

K. M. Azadzoi et al.: "Hypercholesterolemia Impairs Endothelium-Dependent Relaxation of Rabbit Corpus Cavernosum Smooth Muscle," J. Urol., 146: 238-240 (Jul. 1991).

J. A. Beavo: "Cyclic Nucleotide Phosphodiesterases: Functional Implications of Multiple Isoforms," Physiological Reviews, 75(4): 725-748 (Oct. 1995).

J. A. Beavo et al.: "Multiple Cyclic Nucleotide Phosphodiesterase," Mol. Pharmacol., 46: 399-405 (1994).

J. A. Beavo et al.: "Primary Sequence of Cyclic Nucleotide Phosphodiestearse Isozymes and the Design of Selective Inhibitors," TIPS, 11: 150-155 (Apr. 1990).

A. Bowman et al.: "Cyclic GMP Mediates Neurogenic Relaxation in the Bovine Retractor Penis Muscle," Br. J. Pharmac., 81: 665-674 (1984).

A. Burger: "Relation of Chemical Structure and Biological Activity," Med. Chem., 2$^{nd}$ Ed., Interscience Publishers, inc., New York, pp. 36-45, (1960).

M. A. Bush, : "The Role of the L-Arginine-Nitric Oxide-Cyclic GMP Pathway in Relaxation of Corpus Cavernosum Smooth Muscle," PhD Thesis, University of California, Los Angeles (1993).

P. A. Bush et al.: "Biosynthesis of Nitric Oxide and Citrulline from L-Arginine by Constitutive Nitric Oxide Synthase Present in Rabbit Corpus Cavernosum," Biochem & BioBiophys. Res. Comm., 186(1): 308-314 (Jul. 1992).

P. A. Bush et al.: "Comparison of Nonadrenergic, Noncholingergic- and Nitric Oxide-Mediated Relaxation of Corpus Cavernosum," Int. J. Impotence Res., 4: 85-93 (1992).

P. A. Bush et al.: "Nitric Oxide is a potent Relaxant of Human and Rabbit Corpus Cavernosum," J. Urology, 147: 1650-1655 (Jun. 1992).

B. Dumaitre et al.: "Synthesis and Cyclic GMP Phosphodiesterase Inhibitory Activity of a Series of 6-Phenylpyrazolo[3,4-d]pyrimidones," J. Med. Chem., 39: 1635-1644 (1996).

Goodman and Gilman's, *The Pharmacological Basis of Therapeutics*, Ed. Gilman, et al., McGraw Hill, 8$^{th}$ Ed., (1990), pp. 33-43.

H. W. Hamilton et al.: "Synthesis and Structure-Activity Relationship of Pyrazolo[4,3-d]pyrimidin-7-ones as Adenosine Receptor Antagonists," J. Med. Chem., 30: 91-96 (1987).

F. Holmquist et al.: "Actions of 3-Morpholinosydnonimin (SIN-1) on Rabbit Isolated Penile Erectile Tissue," J. Urology, 150:1310-1315 (Oct. 1993).

F. Holmquist et al.: "Effects of the Nitric Oxide Synthase Inhibitor N$^c$—Nitro-L-Arginine on the Erectile Response to Cavernosum Nerve Stimulation in the Rabbit," Acta Physiol. Scand., 143: 299-304 (1991).

L. J. Ignarro at al.: "Neurotransmitter Identity Doubt," Nature, 347: 131 (Sep. 1990).

L. J. Ignarro at al.: "Nitric Oxide and Cyclic GMP Formation upon Electrical Field Stimulation Cause Relaxation of Corpus Cavernosum Smooth Muscle," Biochem & Biophys. Res. Comm., 170(2): 843-850 (Jul. 1990).

N. Kim et al.: "Oxygen Tension Regulates the Nitric Oxide Pathway Physiological Role in Penile Erection," J. Clin. Invest., 91: 437-442 (Feb. 1993).

N. Kim et al.: "A Nitric Oxide-like Factor Mediates Nonadrenergic-Noncholinergic Neurogenic Relaxation of Penile Corpus Cavernosum Smooth Muscle," J. Clin. Inv., 88: 112-118 (Jul. 1991).

S. G. Korenman et al.: "Treatment of Vasculogenic Sexual Dysfunction with Pentoxifylline," JAGS, 41(d): 363-366 (Apr. 1993).

S. J. Lee et al.: "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med. Chem., 38: 3547-3557 (1995).

R. T. Morrison and R. N. Boyd: *Organic Chemistry*, Allyn and Bacon, Inc., 3$_{rd}$ Ed., (1972), pp. 858-859.

K. J. Murray: "Phosphodiesterase VA Inhibitors," 6(3): 150-156 (Apr. 1993).

C. D. Nicholson et al.: "Differential Modulation of Tissue Function and Therapeutic Potential of Selective inhibitors of Cyclic Nucleotide Phosphodiesterase Isoenzymes," TIPS, 12: 19-27 (Jan. 1991).

J. Rajfer et al.: "Nitric Oxide as a Mediator of Relaxation of the Corpus Cavernosum in Response to Nonadrenergic, Noncholinergic Neurotransmission," The New England Journal of Medicine, 326(2): 90-94 (Jan. 1992).

I. Saenz de Tejada et al.: "Cholinergic Neurotransmission in Human Corpus Cavernosum. I. Responses of Isolated Tissue," Am. J. Physiol., 254: H459-H467, (1988).

I. Saenz de Tejada et al.: "Impaired Neurogenic and Endothelium-Mediated Relaxation of Penile Smooth Muscle from Diabetic Men with Impotence," N. Engl. Med., 320: 1025-1030 (Apr. 1989).

P. J. Silver et al.: "Cyclic GMP Potentiation by WIN 58237, a Novel Cyclic Nucleotide Phosphodiesterase Inhibitor," Journal of Pharmacology and Experimental Therapeutics, 271(3): 1143-1149 (1994).

C. G. Stief et al.: "Cyclic Nucleotide Phosphodiesterase (PDE) Isoenzymes in Human Cavernous Smooth Muscle: Characterization and Functional Effects of PDE-Inhibitors in Vitro and In Vivo," Int. J. Impot. Res. 7(1): 03 (Sep. 1995).

E. J. Sybertz et al.; "cGMP Phosphodiesterase Inhibition: A New Mechanism for the Discovery of Therapeutics Agents," Current Pharma. Design. 1(4): 373-390 (1995).

A. Taher et al.: "Cyclic Nucleotide Phosphodiesterase in human Cavernous Smooth Muscle," World J. Urol., 15: 32-35 (1997).

A. Taher et al.: "Phosphodiesterase Activity in Human Cavernous Tissue and the Effect of Various Selective Inhibitors," J. Urology, 149(4): 285 (Apr. 1993).

A. Taher et al.: "Cyclic Nucleotide Phosphodiesterase Activity in Human Cavernous Smooth Nuscle and the Effect of Various Selective Inhibitors," Int. J. Impotence Res., 4(2): 11 (1992).

Y. Takase et al.: "The Quinazole Derivatives as Novel Potent and Selective Inhibitors of Cyclic GMP-Phosphodiesterase," 206th American Chemical Society National Meeting, Chicago, Il. (1993).

W. J. Thompson: "Cyclic Nucleotide Phosphodiesterases: Pharmacology, Biochemistry and Functions," Pharmac. Ther., 5: 13-33 (1991).

T. J. Torphy et al.: "Characterization and Selective Inhibition of Cyclic Nucleotide Phosphodiesterase Isozymes in Canine Tracheal Smooth Muscle," Molecular Pharmacology, 37: 206-214 (1989).

A. J. Trapani et al.: "Hemodynamic Basis for the Depressor Activity of Zaprinast, a Selective Cyclic GMP Phosphodiesterase Inhibitor," J. Pharmacol. & Exp. Ther., 258: 269-274 (1991).

F. Trigo-Rocha et al.: "The Effect of Intracavernous Injection of Potassium Channel Openers in Monkeys and Dogs," Int. J. Impotence Res., 7: 41-48 (1995).

F. Trigo-Rocha et al.: "The Role of Cyclic Adenosine Monophosphate, Cyclic Guanosine Monophosphate, Endothelium and Nonadrenergic, Noncholinergic Neurotransmission in Canine Penile Erection," J. urology, 149: 872-887 (Apr. 1993).

F. Trigo-Rocha et al.: "Nitric Oxide and cGMP: Mediators of Pelvic Nerve-Stimulated Erection in Dogs," J. Am. Phys., 264(2): H419-H422 (Feb. 1993).

F. Trigo-Rocha et al.: "Intracellular Mechanism of Penile Erection in Monkeys," Neurology and Urodynamics, 13: 71-80 (1994).

M. Kozizumi et al.: "4(3H)-Quinazolines," Chugai Pharmaceutical Co., Ltd., Japan, Kokai, JP 52051378, Chem. Abstr. 87: 20171g (1977).

W. Draber and T. Fujita eds, *Rational Approaches to Structure, Activity, and Ecotoxicology of Agrochemicals*, CRC Press, Boca Ration, p. 4 (1992).

K. Korolkovas, *Essentials of Medicinal Chemistry*, 2nd Edition, John Wiley & Sons, New York, pp. 78-82 (1988).

A. Gibson: "Phosphodiesterase 5 Inhibitors and Nitregic Transmission—From Zaprinast to Sildenafil," Eur. J. Pharmacol., 411: 1-10 (2001).

Katz et al.: J. Am. Coll. Cardiol., 36(3): 845-851 (2000).

I. Charles et al.: "Bicyclic Heterocycles with Nitrogen at the Ring Junction. Part 2. Application of the Dakin-West Reaction to the Synthesis of Imidazo-[5,1-f]-1,2,4-triazin-4(3H)-ones," J. Chem. Soc., Perkin Transactions 1, No. 5, pp. 1139-1146 (May 1980).

Coste et al. "Characterization of a Novel Potent and Specific Inhibitor of Type V Phosphodiesterase,", Biochemical Pharmacology, vol. 50, No. 10, pp. 1577-1585 (1995).

Terret et al., "Sildenafil (VIAGRA.TM), A Potent and Selective Inhibitor of Type 5 CGMP Phosphodiesterase With Utility for the Treatment of Male Erectile Dysfunction," Bioorganic & Medicinal Chemistry Letters, vol. 6, No. 15, pp. 1819-1824 (1996).

Teva Pharmaceuticals USA, Paragraph IV Certification/Notice Letter dated May 19, 2009.

Teva Pharmaceuticals USA, Paragraph IV Certification/Notice Letter dated Jul. 10, 2009.

Teva Pharmaceuticals USA, Paragraph IV Certification/Notice Letter dated Sep. 4, 2009.

Specification and Pending Claims of Co-Pending U.S. Appl. No. 12/004,933.

2-PHENYL SUBSTITUTED IMIDAZOTRIAZINONES AS PHOSPHODIESTERASE INHIBITORS

The present invention relates to 2-phenyl-substituted imidazotriazinones, to processes for their preparation and to their use as pharmaceuticals, in particular as inhibitors of cGMP-metabolizing phosphodiesterases.

The published specification DE 28 11 780 describes imidazotriazines as bronchodilators having spasmolytic activity and inhibitory activity against phosphodiesterases which metabolize cyclic adenosin monophosphate (cAMP-PDEs, nomenclature according to Beavo: PDE-III and PDE-IV). An inhibitory action against phosphodiesterases which metabolize cyclic guanosin monophosphate (cGMP-PDEs, nomenclature according to Beavo and Reifsnyder (Trends in Pharmacol. Sci. 11, 150-155, 1990) PDE-I, PDE-II and PDE-V) has not been described. Compounds having a sulphonamide group in the aryl radical in the 2-position are not claimed. Furthermore, FR 22 13 058, CH 59 46 71, DE 22 55 172, DE 23 64 076 and EP 000 9384 describe imidazotriazinones which do not have a substituted aryl radical in the 2-position and are likewise said to be bronchodilators having cAMP-PDE inhibitory action.

WO 94/28902 describes pyrazolopyrimidinones which are suitable for treating impotence.

The compounds according to the invention are potent inhibitors either of one or of more of the phosphodiesterases which metabolize cyclic guanosin 3',5'-monophosphate (cGMP-PDEs). According to the nomenclature of Beavo and Reifsnyder (Trends in Pharmacol. Sci. 11, 150-155, 1990) these are the phosphodiesterase isoenzymes PDE-I, PDE-II and PDE-V.

An increase of the cGMP concentration can lead to beneficial antiaggregatory, antithrombotic, antiprolific, antivasospastic, vasodilative, natriuretic and diuretic effects. It can influence the short- or long-term modulation of vascular and cardiac inotropy, of the pulse and of cardiac conduction (J. C. Stoclet, T. Keravis, N. Komas and C. Kugnier, Exp. Opin. Invest. Drugs (1995), 4 (11), 1081-1100).

The present invention, accordingly, provides 2-phenyl-substituted imidazotriazinones of the general formula (I)

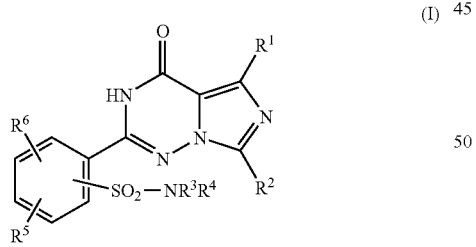

(I)

in which
R$^1$ represents hydrogen or straight-chain or branched alkyl having up to 4 carbon atoms,
R$^2$ represents straight-chain alkyl having up to 4 carbon atoms,
R$^3$ and R$^4$ are identical or different and each represents hydrogen or represents straight-chain or branched alkenyl or alkoxy having in each case up to 8 carbon atoms, or
represents a straight-chain or branched alkyl chain having up to 10 carbon atoms which is optionally interrupted by an oxygen atom and which is optionally mono- or polysubstituted by identical or different substituents selected from the group consisting of trifluoromethyl, trifluoromethoxy, hydroxyl, halogen, carboxyl, benzyloxycarbonyl, straight-chain or branched alkoxycarbonyl having up to 6 carbon atoms and/or by radicals of the formulae —SO$_3$H, -(A)$_a$-NR$^7$R$^8$, —O—CO—NR$^7$'R$^8$', —S(O)$_b$—R$^9$, —P(O)(OR$^{10}$)(OR$^{11}$),

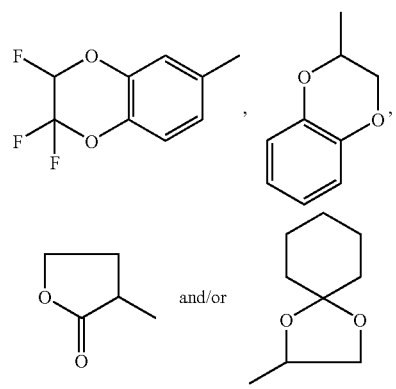

in which
a and b are identical or different and each represents a number 0 or 1,
A represents a radical CO or SO$_2$,
R$^7$, R$^7$', R$^8$ and R$^8$' are identical or different and each represents hydrogen, or
represents cycloalkyl having 3 to 8 carbon atoms, aryl having 6 to 10 carbon atoms, a 5- to 6-membered unsaturated, partially unsaturated or saturated, optionally benzo-fused heterocycle having up to 3 heteroatoms from the group consisting of S, N and O, where the abovementioned ring systems are optionally mono- or polysubstituted by identical or different substituents selected from the group consisting of hydroxyl, nitro, trifluoromethyl, trifluoromethoxy, carboxyl, halogen, straight-chain or branched alkoxy or alkoxycarbonyl having in each case up to 6 carbon atoms or by a group of the formula —(SO$_2$)$_c$—NR$^{12}$R$^{13}$,
in which
c represents a number 0 or 1,
R$^{12}$ and R$^{13}$ are identical or different and each represents hydrogen or straight-chain or branched alkyl having up to 5 carbon atoms,
or
R$^7$, R$^7$', R$^8$ and R$^8$' each represent straight-chain or branched alkoxy having up to 6 carbon atoms, or
represents straight-chain or branched alkyl having up to 8 carbon atoms which is optionally mono- or polysubstituted by identical or different substituents selected from the group consisting of hydroxyl, halogen, aryl having 6 to 10 carbon atoms, straight-chain or branched alkoxy or alkoxycarbonyl having in each case up to 6 carbon atoms or by a group of the formula —(CO)$_d$—NR$^{14}$R$^{15}$,
in which
R$^{14}$ and R$^{15}$ are identical or different and each represents hydrogen or straight-chain or branched alkyl having up to 4 carbon atoms, and d represents a number 0 or 1, or R$^7$ and R$^8$ and/or R$^{7'}$ and R$^{8'}$ together with the nitrogen atom form a 5- to 7-membered saturated heterocycle which may optionally contain a further heteroatom from the group consisting of S and O or a radical of the formula —NR$^{16}$, in which R$^{16}$ represents hydrogen, aryl having 6 to 10 carbon atoms, benzyl, a 5- to 7-membered aromatic or saturated heterocycle having up to 3 heteroatoms from the group consisting of S, N and O which is optionally substituted by methyl, or represents straight-chain or branched alkyl having up to 6 carbon atoms which is optionally substituted by hydroxyl, R$^9$ represents aryl having 6 to 10 carbon atoms, or represents straight-chain or branched alkyl having up to 4 carbon atoms, R$^{10}$ and R$^{11}$ are identical or different and each represents hydrogen or straight-chain or branched alkyl having up to 4 carbon atoms, and/or the alkyl chain listed above under R$^3$/R$^4$ is optionally substituted by cycloalkyl having 3 to 8 carbon atoms, aryl having 6 to 10 carbon atoms or by a 5- to 7-membered partially unsaturated, saturated or unsaturated, optionally benzo-fused heterocycle which may contain up to 4 heteroatoms from the group consisting of S, N and O or a radical of the formula —NR$^{17}$, in which R$^{17}$ represents hydrogen, hydroxyl, formyl, trifluoromethyl, straight-chain or branched acyl or alkoxy having in each case up to 4 carbon atoms, or represents straight-chain or branched alkyl having up to 6 carbon atoms which is optionally mono- or polysubstituted by identical or different substituents selected from the group consisting of hydroxyl and straight-chain or branched alkoxy having up to 6 carbon atoms, and where aryl and the heterocycle are optionally mono- or polysubstituted by identical or different substituents selected from the group consisting of nitro, halogen, —SO$_3$H, straight-chain or branched alkyl or alkoxy having in each case up to 6 carbon atoms, hydroxyl, trifluoromethyl, trifluoromethoxy and/or by a radical of the formula —SO$_2$—NR$^{18}$R$^{19}$, in which R$^{18}$ and R$^{19}$ are identical or different and each represents hydrogen or straight-chain or branched alkyl having up to 6 carbon atoms, and/or R$^3$ or R$^4$ represents a group of the formula —NR$^{20}$R$^{21}$, in which R$^{20}$ and R$^{21}$ have the meanings of R$^{18}$ and R$^{19}$ given above and are identical to or different from them, and/or R$^3$ or R$^4$ represents adamantyl, or represents radicals of the formulae

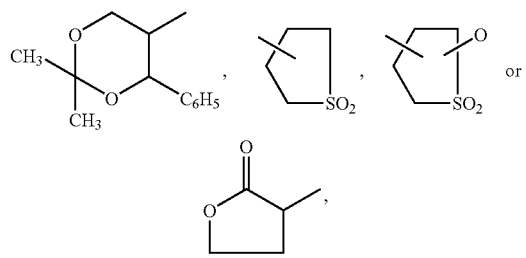

or represents cycloalkyl having 3 to 8 carbon atoms, aryl having 6 to 10 carbon atoms or represents a 5- to 7-membered partially unsaturated, saturated or unsaturated, optionally benzo-fused heterocycle which may contain up to 4 heteroatoms from the group consisting of S, N and O, or a radical of the formula —NR$^{22}$, in which R$^{22}$ has the meaning of R$^{16}$ given above and is identical to or different from it, or represents carboxyl, formyl or straight-chain or branched acyl having up to 5 carbon atoms, and where cycloalkyl, aryl and/or the heterocycle are optionally mono- or polysubstituted by identical or different substituents selected from the group consisting of halogen, triazolyl, trifluoromethyl, trifluoromethoxy, carboxyl, straight-chain or branched acyl or alkoxycarbonyl having in each case up to 6 carbon atoms, nitro and/or by groups of the formulae —SO$_3$H, —OR$^{23}$, (SO$_2$)$_e$NR$^{24}$R$^{25}$, —P(O)(OR$^{26}$)(OR$^{27}$), in which e represents a number 0 or 1, R$^{23}$ represents a radical of the formula

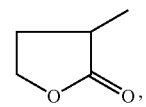

represents cycloalkyl having 3 to 7 carbon atoms, or represents hydrogen or straight-chain or branched alkyl having up to 4 carbon atoms which is optionally substituted by cycloalkyl having 3 to 7 carbon atoms, benzyloxy, tetrahydropyranyl, tetrahydrofuranyl, straight-chain or branched alkoxy or alkoxycarbonyl having in each case up to 6 carbon atoms, carboxyl, benzyloxycarbonyl or phenyl which for its part may be mono- or polysubstituted by identical or different substituents selected from the group consisting of straight-chain or branched alkoxy having up to 4 carbon atoms, hydroxyl and halogen, and/or alkyl which is optionally substituted by radicals of the formulae —CO—NR$^{28}$R$^{29}$ or —CO—R$^{30}$, in which R$^{28}$ and R$^{29}$ are identical or different and each represents hydrogen or straight-chain or branched alkyl having up to 8 carbon atoms, or R$^{28}$ and R$^{29}$ together with the nitrogen atom form a 5- to 7-membered saturated heterocycle which may optionally contain a further heteroatom from the group consisting of S and O, and R$^{30}$ represents phenyl or adamantyl, $R^{24}$ and $R^{25}$ have the meanings of $R^{18}$ and $R^{19}$ given above and are identical to or different from them, $R^{26}$ and $R^{27}$ have the meanings of $R^{10}$ and $R^{11}$ given above and are identical to or different from them and/or cycloalkyl, aryl and/or the heterocycle are optionally substituted by straight-chain or branched alkyl having up to 6 carbon atoms which is optionally substituted by hydroxyl, carboxyl, by a 5- to 7-membered heterocycle having up to 3 heteroatoms from the group consisting of S, N and O, or by groups of the formula —$SO_2$—$R^{31}$, $P(O)(OR^{32})(OR^{33})$ or —$NR^{34}R^{35}$, in which $R^{31}$ represents hydrogen or has the meaning of $R^9$ given above and is identical to or different from it, $R^{32}$ and $R^{33}$ have the meanings of $R^{10}$ and $R^{11}$ given above and are identical to or different from them, $R^{34}$ and $R^{35}$ are identical or different and each represents hydrogen or straight-chain or branched alkyl having up to 6 carbon atoms which is optionally substituted by hydroxyl or by straight-chain or branched alkoxy having up to 4 carbon atoms, or $R^{34}$ and $R^{35}$ together with the nitrogen atom form a 5- to 6-membered saturated heterocycle which may contain a further heteroatom from the group consisting of S and O, or a radical of the formula —$NR^{36}$, in which $R^{36}$ represents hydrogen, hydroxyl, straight-chain or branched alkoxycarbonyl having up to 7 carbon atoms or straight-chain or branched alkyl having up to 5 carbon atoms which is optionally substituted by hydroxyl, or $R^3$ and $R^4$ together with the nitrogen atom form a 5- to 7-membered unsaturated or saturated or partially unsaturated, optionally benzo-fused heterocycle which may optionally contain up to 3 heteroatoms from the group consisting of S, N and O, or a radical of the formula —$NR^7$, in which $R^{37}$ represents hydrogen, hydroxyl, formyl, trifluoromethyl, straight-chain or branched acyl, alkoxy or alkoxycarbonyl having in each case up to 4 carbon atoms, or represents straight-chain or branched alkyl having up to 6 carbon atoms which is optionally mono- or polysubstituted by identical or different substituents selected from the group consisting of hydroxyl, trifluoromethyl, carboxyl, straight-chain or branched alkoxy or alkoxycarbonyl having in each case up to 6 carbon atoms, or by groups of the formula -$(D)_f$-$NR^{38}R^{39}$, —CO—$(CH_2)_g$—O—CO—$R^{40}$, —CO—$(CH_2)_h$—$OR^{41}$ or —$P(O)(OR^{42})(OR^{43})$, in which g and h are identical or different and each represents a number 1, 2, 3 or 4, and f represents a number 0 or 1, D represents a group of the formula —CO or —$SO_2$, $R^{38}$ and $R^{39}$ are identical or different and each has the meaning of $R^7$ and $R^8$ given above, $R^{40}$ represents straight-chain or branched alkyl having up to 6 carbon atoms, $R^{41}$ represents straight-chain or branched alkyl having up to 6 carbon atoms, $R^{42}$ and $R^{43}$ are identical or different and each represents hydrogen or straight-chain or branched alkyl having up to 4 carbon atoms, or $R^{37}$ represents a radical of the formula —$(CO)_i$-E, in which i represents a number 0 or 1, E represents cycloalkyl having 3 to 7 carbon atoms or benzyl, represents aryl having 6 to 10 carbon atoms or a 5- to 6-membered aromatic heterocycle having up to 4 heteroatoms from the group consisting of S, N and O, where the abovementioned ring systems are optionally mono- or polysubstituted by identical or different constituents selected from the group consisting of nitro, halogen, —$SO_3H$, straight-chain or branched alkoxy having up to 6 carbon atoms, hydroxyl, trifluoromethyl, trifluoromethoxy, or by a radical of the formula —$SO_2$—$NR^{44}R^{45}$, in which $R^{44}$ and $R^{45}$ have the meanings of $R^{18}$ and $R^{19}$ given above and are identical to or different from them, or E represents radicals of the formulae

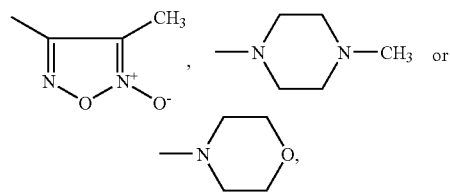

and the heterocycle listed under $R^3$ and $R^4$, which is formed together with the nitrogen atom, is optionally mono- or polysubstituted, if appropriate also geminally, by identical or different substituents selected from the group consisting of hydroxyl, formyl, carboxyl, straight-chain or branched acyl or alkoxycarbonyl having in each case up to 6 carbon atoms, nitro and groups of the formulae —$P(O)(OR^{46})(OR^{47})$,

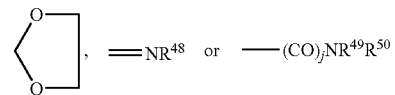

in which $R^{46}$ and $R^{47}$ have the meanings of $R^{10}$ and $R^{11}$ given above and are identical to or different from them, $R^{48}$ represents hydroxyl or straight-chain or branched alkoxy having up to 4 carbon atoms, j represents a number 0 or 1, and $R^{49}$ and $R^{50}$ are identical or different and have the meanings of $R^{14}$ and $R^{15}$ given above, and/or the heterocycle listed under $R^3$ and $R^4$, which is formed together with the nitrogen atom, is optionally substituted by straight-chain or branched alkyl having up to 6 carbon atoms which is optionally mono- or polysubstituted by identical or different substituents selected from the group consisting of hydroxyl, halogen, carboxyl, cycloalkyl or cycloalkyloxy having in each case 3 to 8 carbon atoms, straight-chain or branched alkoxy or alkoxycarbonyl having in each case up to 6 carbon atoms, or by a radical of the formula —SO$_3$H, —NR$^{51}$R$^{52}$ or P(O)OR$^{53}$OR$^{54}$, in which R$^{51}$ and R$^{52}$ are identical or different and each represents hydrogen, phenyl, carboxyl, benzyl or straight-chain or branched alkyl or alkoxy having in each case up to 6 carbon atoms, R$^{53}$ and R$^{54}$ are identical or different and have the meanings of R$^{10}$ and R$^{11}$ given above, and/or the alkyl is optionally substituted by aryl having 6 to 10 carbon atoms which for its part may be mono- or polysubstituted by identical or different substituents selected from the group consisting of halogen, hydroxyl, straight-chain or branched alkoxy having up to 6 carbon atoms, or by a group of the formula —NR$^{51'}$R$^{52'}$, in which R$^{51'}$ and R$^{52'}$ have the meanings of R$^{51}$ and R$^{52}$ given above and are identical to or different from them, and/or the heterocycle listed under R$^3$ and R$^4$, which is formed together with the nitrogen atom, is optionally substituted by aryl having 6 to 10 carbon atoms or by a 5- to 7-membered saturated, partially unsaturated or unsaturated heterocycle having up to 3 heteroatoms from the group consisting of S, N and O, optionally also attached via a nitrogen function, where the ring systems for their part may be substituted by hydroxyl or by straight-chain or branched alkyl or alkoxy having in each case up to 6 carbon atoms, or R$^3$ and R$^4$ together with the nitrogen atom form radicals of the formulae

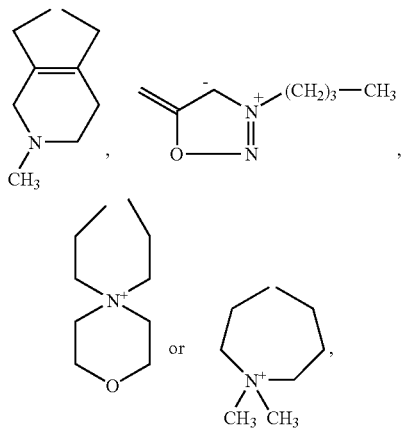

R$^5$ and R$^6$ are identical or different and each represents hydrogen, straight-chain or branched alkyl having up to 6 carbon atoms, hydroxyl or represents straight-chain or branched alkoxy having up to 6 carbon atoms, and their salts, hydrates, N-oxides and isomeric forms.

The compounds according to the invention may exist in stereoisomeric forms which are related either as image and mirror image (enantiomers), or which are not related as image and mirror image (diastereomers). The invention relates both to the enantiomers or diastereomers and to their respective mixtures. The racemic forms can, just like the diastereomers, be separated in a known manner into the stereoisomerically pure constituents.

The substances according to the invention may also be present as salts. In the context of the invention, preference is given to physiologically acceptable salts.

Physiologically acceptable salts can be salts of the compounds according to the invention with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

Physiologically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine.

In the context of the invention, an optionally benzo-fused heterocycle generally represents a saturated, partially unsaturated or unsaturated 5- to 7-membered heterocycle which may contain up to 4 heteroatoms from the group consisting of S, N and O. Examples which may be mentioned are: azepine, diazepine, indolyl, isoquinolyl, quinolyl, benzo[b]thiophene, benzo[b]furanyl, pyridyl, thienyl, tetrahydrofuranyl, tetrahydropyranyl, furyl, pyrrolyl, thiazolyl, triazolyl, tetrazolyl, isoxazolyl, imidazolyl, morpholinyl, thiomorpholinyl, pyrrolidinyl, piperazinyl, N-methylpiperazinyl or piperidinyl. Preference is given to quinolyl, furyl, pyridyl, thienyl, piperidinyl, pyrrolidinyl, piperazinyl, azepine, diazepine, thiazolyl, triazolyl, tetrazolyl, tetrahydrofuranyl, tetrahydropyranyl, morpholinyl and thiomorpholinyl.

In the context of the invention, a straight-chain or branched acyl radical having 1 to 6 carbon atoms represents, for example acetyl, ethylcarbonyl, propylcarbonyl, isopropylcarbonyl, butylcarbonyl, isobutylcarbonyl, pentylcarbonyl and hexylcarbonyl. Preference is given to a straight-chain or branched acyl radical having 1 to 4 carbon atoms. Particular preference is given to acetyl and ethylcarbonyl.

In the context of the invention, a straight-chain or branched alkoxy radical having 1 to 6 or 1 to 4 carbon atoms represents methoxy, ethoxy, n-propoxy, isopropoxy, tert-butoxy, n-pentoxy and n-hexoxy. Preference is given to a straight-chain or branched alkoxy radical having 1 to 6, 1 to 4 or 1 to 3 carbon atoms. Particular preference is given to a straight-chain or branched alkoxy radical having 1 to 3 carbon atoms.

In the context of the invention, a straight-chain or branched alkoxycarbonyl radical having 1 to 6 carbon atoms represents, for example, methoxycarbonyl, ethoxycarbonyl, n-propoxycarbonyl, isopropoxycarbonyl and tert-butoxycarbonyl. Preference is given to a straight-chain or branched alkoxycarbonyl radical having 1 to 4 carbon atoms. Particular preference is given to a straight-chain or branched alkoxycarbonyl radical having 1 to 3 carbon atoms.

In the context of the invention, a straight-chain or branched alkyl radical having 1 to 4, 1 to 6, 1 to 8 and 1-10 carbon atoms represents, for example, methyl, ethyl, n-propyl, isopropyl, tert-butyl, n-pentyl, n-hexyl, n-heptyl, n-octyl, n-nonyl and n-decyl. Preference is given to straight-chain or branched alkyl radicals having 1 to 3, 1 to 4 or 1 to 8 carbon atoms. Particular preference is given to straight-chain or branched alkyl radicals having 1 to 4 or 1 to 3 carbon atoms.

In the context of the invention, straight-chain alkyl having up to 4 carbon atoms represents, for example, methyl, ethyl, n-propyl and n-butyl.

($C_6$-$C_{10}$)-Aryl generally represents an aromatic radical having 6 to 10 carbon atoms. Preferred aryl radicals are phenyl and naphthyl.

In the context of the invention, cycloalkyl having 3 to 8 or 3 to 7 carbon atoms represents, for example, cyclopropyl, cyclopentyl, cyclobutyl, cyclohexyl, cycloheptyl or cyclooctyl. Preference is given to: cyclopropyl, cyclopentyl and cyclohexyl.

In the context of the invention, cycloalkyloxy having 3 to 8 carbon atoms represents cyclopropyloxy, cyclopentyloxy, cyclobutyloxy, cyclohexyloxy, cycloheptyloxy or cyclooctyloxy. Preference is given to: cyclopropyloxy, cyclopentyloxy and cyclohexyloxy.

In the context of the invention, halogen generally represents fluorine, chlorine, bromine and iodine. Preference is given to fluorine, chlorine and bromine. Particular preference is given to fluorine and chlorine.

In the context of the invention and depending on the abovementioned substituents, a 5- to 6-membered or 7-membered saturated heterocycle, which may contain a further heteroatom from the group consisting of S, N and O represents, for example, morpholinyl, piperidinyl, piperazinyl, tetrahydropyranyl or tetrahydrofuranyl. Preference is given to morpholinyl, tetrahydropyranyl, piperidinyl and piperazinyl.

In the context of the invention, a 5- to 6-membered aromatic heterocycle having up to 3 or 4 heteroatoms from the group consisting of S, O and N represents, for example, pyridyl, pyrimidyl, pyridazinyl, thienyl, furyl, pyrrolyl, thiazolyl, oxazolyl or imidazolyl. Preference is given to pyridyl, pyrimidyl, pyridazinyl, furyl and thiazolyl.

In the context of the invention, a 5- to 6-membered unsaturated, partially unsaturated and saturated heterocycle which may contain up to 3 or 4 heteroatoms from the group consisting of S, O and N represents, for example, pyridyl, pyrimidyl, pyridazinyl, thienyl, furyl, pyrrolyl, thiazolyl, oxazolyl, imidazolyl, piperidinyl, piperazinyl or morpholinyl. Preference is given to pyridyl, pyrimidyl, piperazinyl, pyridazinyl, morpholinyl, furyl and thiazolyl.

The compounds according to the invention, in particular the salts, may also be present as hydrates. In the context of the invention, hydrates are those compounds which contain water in the crystal. Such compounds may contain one or more, typically 1 to 5, equivalents of water. Hydrates can be prepared, for example, by crystallizing the compound in question from water or from a water-containing solvent.

Preference is given to compounds of the general formula (I) according to the invention in which $R^1$ represents straight-chain or branched alkyl having up to 3 carbon atoms, $R^2$ represents straight-chain alkyl having up to 3 carbon atoms, $R^3$ and $R^4$ are identical or different and each represents hydrogen or represents straight-chain or branched alkenyl or alkoxy having in each case up to 6 carbon atoms, or represents a straight-chain or branched alkyl chain having up to 8 carbon atoms which is optionally interrupted by an oxygen atom and which is optionally mono- to trisubstituted by identical or different substituents selected from the group consisting of hydroxyl, fluorine, chlorine, carboxyl, benzyloxycarbonyl, straight-chain or branched alkoxycarbonyl having up to 5 carbon atoms, and/or by radicals of the formulae —$SO_3H$, -(A)$_a$-$NR^7R^8$, —O—CO—$NR^{7'}R^{8'}$, —S(O)$_b$—$R^9$, —P(O)(OR$^{10}$)(OR$^{11}$),

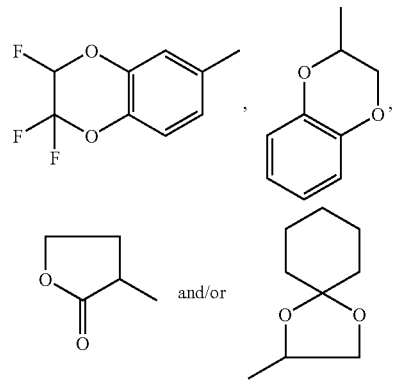

in which a and b are identical or different and each represents a number 0 or 1, A represents a radical CO or $SO_2$, $R^7$, $R^{7'}$, $R^8$ and $R^{8'}$ are identical or different and each represents hydrogen, or cyclopropyl, cyclopentyl, cyclohexyl, cycloheptyl, phenyl, piperidinyl and pyridyl, where the abovementioned ring systems are optionally mono- to trisubstituted by identical or different substituents selected from the group consisting of hydroxyl, nitro, trifluoromethyl, trifluoromethoxy, carboxyl, fluorine, chlorine, straight-chain or branched alkoxy or alkoxycarbonyl having in each case up to 4 carbon atoms, or by a group of the formula —$(SO_2)_c$—$NR^{12}R^{13}$, in which c represents a number 0 or 1, $R^{12}$ and $R^{13}$ are identical or different and each represents hydrogen or straight-chain or branched alkyl having up to 4 carbon atoms, or $R^7$, $R^{7'}$, $R^8$ and $R^{8'}$ each represent straight-chain or branched alkoxy having up to 3 carbon atoms, or represents straight-chain or branched alkyl having up to 7 carbon atoms which is optionally mono- or polysubstituted by identical or different substituents selected from the group consisting of hydroxyl, fluorine, chlorine, phenyl, straight-chain or branched alkoxy or alkoxycarbonyl having in each case up to 4 carbon atoms, or by a group of the formula —$(CO)_d$—$NR^{14}R^{15}$, in which $R^{14}$ and $R^{15}$ are identical or different and each represents hydrogen or straight-chain or branched alkyl having up to 3 carbon atoms, and d represents a number 0 or 1, or $R^7$ and $R^8$ and/or $R^{7'}$ and $R^{8'}$ together with the nitrogen atom form a pyrrolidinyl, morpholinyl, piperidinyl or triazolyl ring or radicals of the formulae

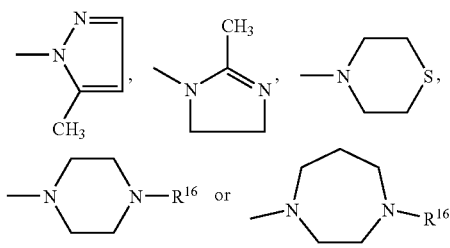 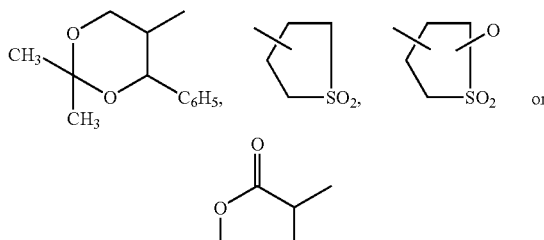

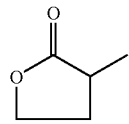

in which
R$^{16}$ represents hydrogen, phenyl, benzyl, morpholinyl, pyrrolidinyl, piperidinyl, piperazinyl or N-methylpiperazinyl, or represents straight-chain or branched alkyl having up to 5 carbon atoms which is optionally substituted by hydroxyl,
R$^9$ represents straight-chain or branched alkyl having up to 3 carbon atoms,
R$^{10}$ and R$^{11}$ are identical or different and each represents hydrogen or straight-chain or branched alkyl having up to 3 carbon atoms,
and/or the alkyl chain listed under R$^3$/R$^4$ is optionally substituted by cyclopropyl, cyclopentyl, cyclohexyl, cycloheptyl, phenyl, pyridyl, quinolyl, pyrrolidinyl, pyrimidyl, morpholinyl, furyl, piperidinyl, tetrahydrofuranyl or by radicals of the formulae

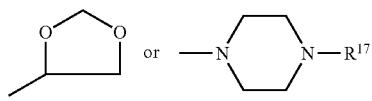

in which
R$^{17}$ represents hydrogen, hydroxyl, formyl, trifluoromethyl, straight-chain or branched acyl or alkoxy having in each case up to 3 carbon atoms,
or represents straight-chain or branched alkyl having up to 4 carbon atoms which is optionally mono- to trisubstituted by identical or different substituents selected from the group consisting of hydroxyl and straight-chain or branched alkoxy having up to 4 carbon atoms,
and where phenyl and the heterocycles are optionally mono- to trisubstituted by identical or different substituents selected from the group consisting of nitro, fluorine, chlorine, —SO$_3$H, straight-chain or branched alkyl or alkoxy having in each case up to 4 carbon atoms, hydroxyl, and/or by a radical of the formula —SO$_2$—NR$^{18}$R$^{19}$,
in which
R$^{18}$ and R$^{19}$ are identical or different and each represents hydrogen or straight-chain or branched alkyl having up to 4 carbon atoms,
and/or
R$^3$ or R$^4$ represents a group of the formula —NR$^{20}$R$^{21}$,
in which
R$^{20}$ and R$^{21}$ have the meanings of R$^{18}$ and R$^{19}$ given above and are identical to or different from them,
and/or
R$^3$ or R$^4$ represents adamantyl, or represents radicals of the formulae or represents cyclopentyl, cyclohexyl, cycloheptyl, phenyl, morpholinyl, oxazolyl, thiazolyl, quinolyl, isoxazolyl, pyridyl, tetrahydrofuranyl, tetrahydropyranyl or represents radicals of the formulae

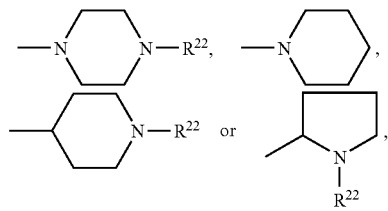

in which
R$^{22}$ has the meaning of R$^{16}$ given above and is identical to or different from it, or
represents carboxyl, formyl or straight-chain or branched acyl having up to 3 carbon atoms,
and where cycloalkyl, phenyl and/or the heterocycles are optionally mono- to trisubstituted by identical or different substituents selected from the group consisting of fluorine, chlorine, triazolyl, trifluoromethyl, trifluoromethoxy, carboxyl, straight-chain or branched acyl or alkoxycarbonyl having in each case up to 5 carbon atoms, nitro and/or by groups of the formulae —SO$_3$H, OR$^{23}$, (SO$_2$)$_e$NR$^{24}$R$^{25}$, —P(O)(OR$^{26}$)(OR$^{27}$),
in which
e represents a number 0 or 1,
R$^{23}$ represents a radical of the formula

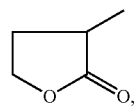

represents cyclopropyl, cyclopentyl, cyclobutyl, cyclohexyl or cycloheptyl,
represents hydrogen or straight-chain or branched alkyl having up to 4 carbon atoms which may optionally be substituted by cyclopropyl, cyclopentyl, cyclohexyl, benzyloxy, tetrahydropyranyl, tetrahydrofuranyl, straight-chain or branched alkoxy or alkoxycarbonyl having in each case up to 4 carbon atoms, benzyloxycarbonyl or phenyl which for its part may be mono- or polysubstituted by identical or different substituents selected from the group consisting of straight-chain or branched alkoxy having up to 3 carbon atoms, hydroxyl, fluorine and chlorine,
and/or where alkyl is optionally substituted by radicals of the formulae —CO—NR$^{28}$R$^{29}$ or —CO—R$^{30}$, in which $R^{28}$ and $R^{29}$ are identical or different and each represents hydrogen or straight-chain or branched alkyl having up to 5 carbon atoms, or $R^{28}$ and $R^{29}$ together with the nitrogen atom form a morpholinyl, pyrrolidinyl or piperidinyl ring, and $R^{30}$ represents phenyl or adamantyl, $R^{24}$ and $R^{25}$ have the meanings of $R^{18}$ and $R^{19}$ given above and are identical to or different from them, $R^{26}$ and $R^{27}$ have the meanings of $R^{10}$ and $R^{11}$ given above and are identical to or different from them and/or cycloalkyl, phenyl and/or the heterocycles are optionally substituted by straight-chain or branched alkyl having up to 4 carbon atoms which is optionally substituted by hydroxyl, carboxyl, pyridyl, pyrimidyl, pyrrolidinyl, piperidinyl, tetrahydrofuranyl, triazolyl or by groups of the formula —SO$_2$—R$^{31}$, —P(O)(OR$^{32}$)(OR$^{33}$) or —NR$^{34}$R$^{35}$, in which $R^{31}$ has the meaning of $R^9$ given above and is identical to or different from it, $R^{32}$ and $R^{33}$ have the meanings of $R^{10}$ and $R^{11}$ given above and are identical to or different from them, $R^{34}$ and $R^{35}$ are identical or different and each represents hydrogen or straight-chain or branched alkyl having up to 5 carbon atoms which is optionally substituted by hydroxyl or straight-chain or branched alkoxy having up to 3 carbon atoms, or $R^{34}$ and $R^{35}$ together with the nitrogen atom form a morpholinyl, triazolyl or thiomorpholinyl ring or a radical of the formula

in which $R^{36}$ represents hydrogen, hydroxyl, straight-chain or branched alkoxycarbonyl having up to 5 carbon atoms or straight-chain or branched alkyl having up to 4 carbon atoms which is optionally substituted by hydroxyl, or $R^3$ and $R^4$ together with the nitrogen atom form a morpholinyl, thiomorpholinyl, pyrrolidinyl, piperidinyl ring, or a radical of the formula

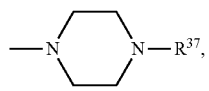

in which $R^{37}$ represents hydrogen, hydroxyl, formyl, trifluoromethyl, straight-chain or branched acyl, alkoxy or alkoxycarbonyl having in each case up to 4 carbon atoms, or represents straight-chain or branched alkyl having up to 5 carbon atoms which is optionally mono- to trisubstituted by identical or different substituents selected from the group consisting of hydroxyl, trifluoromethyl, carboxyl, straight-chain or branched alkoxy or alkoxycarbonyl having in each case up to 4 carbon atoms, or by groups of the formula -(D)$_f$-NR$^{38}$R$^{39}$, —CO—(CH$_2$)$_g$—O—CO—R$^{40}$, —CO—(CH$_2$)$_h$—OR$^{41}$ or —P(O)(OR$^{42}$)(OR$^{43}$), in which g and h are identical or different and each represents a number 1, 2 or 3, and f represents a number 0 or 1, D represents a group of the formula —CO or —SO$_2$, $R^{38}$ and $R^{39}$ are identical or different and have the meanings of $R^7$ and $R^8$ given above, $R^{40}$ represents straight-chain or branched alkyl having up to 4 carbon atoms, $R^{41}$ represents straight-chain or branched alkyl having up to 4 carbon atoms, $R^{42}$ and $R^{43}$ are identical or different and each represents hydrogen or straight-chain or branched alkyl having up to 3 carbon atoms, or $R^{37}$ represents a radical of the formula —(CO)$_i$-E, in which i represents a number 0 or 1, E represents cyclopentyl, cyclohexyl, cycloheptyl, benzyl, phenyl, pyridyl, pyrimidyl or furyl, where the abovementioned ring systems are optionally mono- or disubstituted by identical or different substituents selected from the group consisting of nitro, fluorine, chlorine, —SO$_3$H, straight-chain or branched alkoxy having up to 4 carbon atoms, hydroxyl, trifluoromethyl, trifluoromethoxy or by a radical of the formula —SO$_2$—NR$^{44}$R$^{45}$, in which $R^{44}$ and $R^{45}$ have the meanings of $R^{18}$ and $R^{19}$ given above and are identical to or different from them, or E represents radicals of the formulae

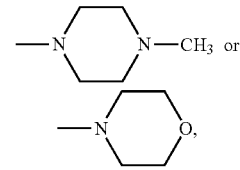

and the heterocycles listed under $R^3$ and $R^4$, which are formed together with the nitrogen atom, are optionally mono- to trisubstituted, optionally also geminally, by identical or different substituents selected from the group consisting of hydroxyl, formyl, carboxyl, straight-chain or branched acyl or alkoxycarbonyl having in each case up to 5 carbon atoms, nitro and groups of the formulae —P(O)(OR$^{46}$)(OR$^{47}$),

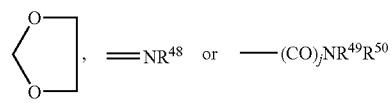

in which $R^{46}$ and $R^{47}$ have the meanings of $R^{10}$ and $R^{11}$ given above and are identical to or different from them, $R^{48}$ represents hydroxyl or straight-chain or branched alkoxy having up to 3 carbon atoms, j represents a number 0 or 1, and R$^{49}$ and R$^{50}$ are identical or different and have the meanings of R$^{14}$ and R$^{15}$ given above, and/or the heterocycles listed under R$^3$ and R$^4$, which are formed together with the nitrogen atom, are optionally substituted by straight-chain or branched alkyl having up to 5 carbon atoms which is optionally mono- or polysubstituted by identical or different substituents selected from the group consisting of hydroxyl, fluorine, chlorine, carboxyl, cyclopropyl, cyclopentyl, cyclohexyl, cycloheptyl, straight-chain or branched alkoxy or alkoxycarbonyl having in each case up to 4 carbon atoms, or by a radical of the formula —SO$_3$H, —NR$^{51}$R$^{52}$ or —P(O)OR$^{53}$OR$^{54}$, in which R$^{51}$ and R$^{52}$ are identical or different and each represents hydrogen, phenyl, carboxyl, benzyl or straight-chain or branched alkyl or alkoxy having in each case up to 4 carbon atoms, R$^{53}$ and R$^{54}$ are identical or different and have the meanings of R$^{10}$ and R$^{11}$ given above, and/or the alkyl is optionally substituted by phenyl which for its part may be mono- to trisubstituted by identical or different substituents selected from the group consisting of fluorine, chlorine, hydroxyl, straight-chain or branched alkoxy having up to 4 carbon atoms, or by a group of the formula —NR$^{51'}$R$^{52'}$, in which R$^{51'}$ and R$^{52'}$ have the meanings of R$^{51}$ and R$^{52}$ given above and are identical to or different from them, and/or the heterocycles listed under R$^3$ and R$^4$, which are formed together with the nitrogen atom, are optionally substituted by phenyl, pyridyl, piperidinyl, pyrrolidinyl or tetrazolyl, optionally also attached via a nitrogen function, where the ring systems for their part may be substituted by hydroxyl or by straight-chain or branched alkyl or alkoxy having in each case up to 5 carbon atoms, or R$^3$ and R$^4$ together with the nitrogen atom form radicals of the formulae

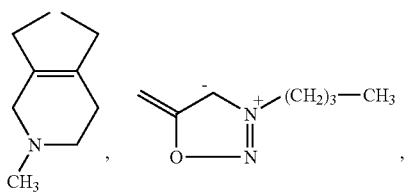

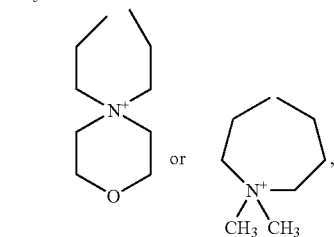

R$^5$ and R$^6$ are identical or different and each represents hydrogen, hydroxyl or represents straight-chain or branched alkoxy having up to 4 carbon atoms, and their salts, N-oxides, hydrates and isomeric forms.

Particular preference is given to compounds of the general formula (I) according to the invention in which R$^1$ represents straight-chain or branched alkyl having up to 3 carbon atoms, R$^2$ represents straight-chain alkyl having up to 3 carbon atoms, R$^3$ and R$^4$ are identical or different and each represents hydrogen or represents straight-chain or branched alkenyl or alkoxy having in each case up to 4 carbon atoms, or represents a straight-chain or branched alkyl chain having up to 6 carbon atoms which is optionally interrupted by an oxygen atom and which is optionally mono- to trisubstituted by identical or different substituents selected from the group consisting of hydroxyl, fluorine, chlorine, carboxyl, straight-chain or branched alkoxycarbonyl having up to 4 carbon atoms, and/or by radicals of the formulae —SO$_3$H, -(A)$_a$-NR$^7$R$^8$, —O—CO—NR$^7$R$^8$, —S(O)$_b$—R$^9$, —P(O)(OR$^{10}$)(OR$^{11}$),

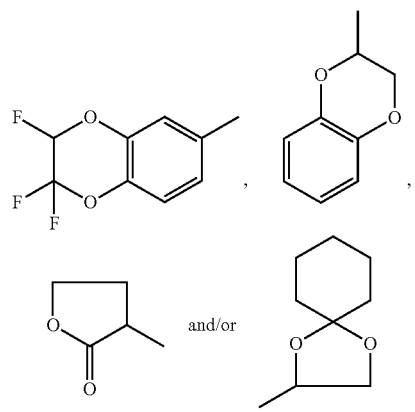

in which a and b are identical or different and each represents a number 0 or 1, A represents a radical CO or SO$_2$, R$^7$, R$^{7'}$, R$^8$ and R$^{8'}$ are identical or different and each represents hydrogen, or represents cyclopentyl, cyclohexyl, cycloheptyl, phenyl, piperidinyl and pyridyl, where the abovementioned ring systems are optionally mono- or disubstituted by identical or different substituents selected from the group consisting of hydroxyl, nitro, carboxyl, fluorine, chlorine, straight-chain or branched alkoxy or alkoxycarbonyl having in each case up to 3 carbon atoms, or by a group of the formula —(SO$_2$)$_c$—NR$^{12}$R$^{13}$, in which c represents a number 0 or 1, R$^{12}$ and R$^{13}$ are identical or different and each represents hydrogen or straight-chain or branched alkyl having up to 3 carbon atoms, or R$^7$, R$^{7'}$, R$^8$ and R$^{8'}$ each represent methoxy, or represent straight-chain or branched alkyl having up to 6 carbon atoms which is optionally mono- or disubstituted by identical or different substituents selected from the group consisting of hydroxyl, fluorine, chlorine, phenyl, straight-chain or branched alkoxy or alkoxycarbonyl having in each case up to 3 carbon atoms, or by a group of the formula —(CO)$_d$—NR$^{14}$R$^{15}$, in which
$R^{14}$ and $R^{15}$ are identical or different and each represents hydrogen, methyl or ethyl,
and
d represents a number 0 or 1,
or
$R^7$ and $R^8$ and/or $R^{7'}$ and $R^{8'}$ together with the nitrogen atom form a morpholinyl, piperidinyl or triazolyl ring or radicals of the formulae

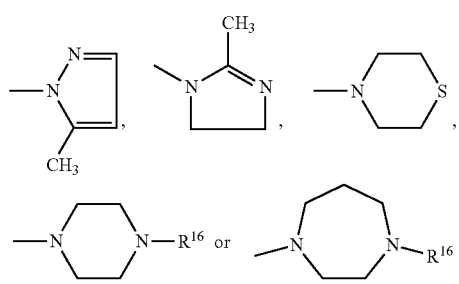

in which
$R^{16}$ represents hydrogen, phenyl, benzyl, morpholinyl, pyrrolidinyl, piperidinyl, piperazinyl or N-methylpiperazinyl, or represents straight-chain or branched alkyl having up to 3 carbon atoms which is optionally substituted by hydroxyl,
$R^9$ represents methyl,
$R^{10}$ and $R^{11}$ are identical or different and each represents hydrogen, methyl or ethyl,
and/or the alkyl chain listed under $R^3/R^4$ is optionally substituted by cyclopropyl, cyclopentyl, cyclohexyl, cycloheptyl, morpholinyl, furyl, tetrahydrofuranyl, or by radicals of the formulae

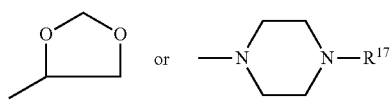

in which
$R^{17}$ represents hydrogen, hydroxyl, formyl, acetyl or alkoxy having up to 3 carbon atoms,
or represents straight-chain or branched alkyl having up to 3 carbon atoms which is optionally mono- or disubstituted by identical or different substituents selected from the group consisting of hydroxyl and straight-chain or branched alkoxy having up to 3 carbon atoms,
and where phenyl and the heterocycles are optionally mono- to trisubstituted by identical or different substituents selected from the group consisting of fluorine, chlorine, —SO$_3$H, straight-chain or branched alkyl or alkoxy having in each case up to 3 carbon atoms, hydroxyl, and/or by a radical of the formula —SO$_2$NR$^{18}$R$^{19}$,
in which
$R^{18}$ and $R^{19}$ are identical or different and each represents hydrogen or straight-chain or branched alkyl having up to 3 carbon atoms,
and/or
$R^3$ or $R^4$ represents a group of the formula —NR$^2$OR$^{21}$, in which
$R^{20}$ and $R^{21}$ have the meanings of $R^{18}$ and $R^{19}$ given above and are identical to or different from them,
and/or
$R^3$ or $R^4$ represents adamantyl, or represents radicals of the formulae

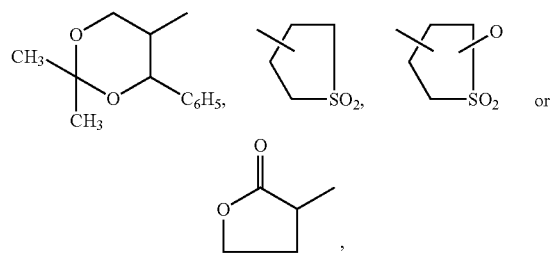

or represents cyclopentyl, cyclohexyl, cycloheptyl, phenyl, morpholinyl, oxazolyl, thiazolyl, quinolyl, isoxazolyl, pyridyl, tetrahydrofuranyl, tetrahydropyranyl, or represents radicals of the formulae

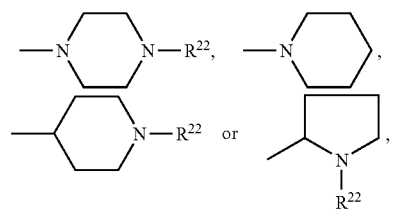

in which
$R^{22}$ has the meaning of $R^{16}$ given above and is identical to or different from it, or represents formyl or acetyl,
and where cycloalkyl, phenyl and/or the heterocycles are optionally mono- or disubstituted by identical or different substituents selected from the group consisting of fluorine, chlorine, triazolyl, carboxyl, straight-chain or branched acyl or alkoxycarbonyl having in each case up to 4 carbon atoms, nitro, and/or by groups of the formulae —SO$_3$H, —OR$^{23}$, (SO$_2$)$_e$NR$^{24}$R$^{25}$, —P(O)(OR$^{26}$)(OR$^{27}$),
in which
e represents a number 0 or 1,
$R^{23}$ represents a radical of the formula

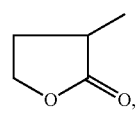

represents cyclopropyl, cyclopentyl, cyclobutyl or cyclohexyl, represents hydrogen or straight-chain or branched alkyl having up to 3 carbon atoms which is optionally substituted by cyclopropyl, cyclohexyl, benzyloxy, tetrahydropyranyl, straight-chain or branched alkoxy or alkoxycarbonyl having in each case up to 3 carbon atoms, benzyloxycarbonyl or phenyl which for its part may be mono- or disubstituted by identical or different substituents selected from the group consisting of methoxy, hydroxyl, fluorine or chlorine, and/or where alkyl is optionally substituted by radicals of the formulae —CO—NR$^{28}$R$^{29}$ or —CO—R$^{30}$,
in which
R$^{28}$ and R$^{29}$ are identical or different and each represents hydrogen or straight-chain or branched alkyl having up to 4 carbon atoms, or
R$^{28}$ and R$^{29}$ together with the nitrogen atom form a morpholinyl, pyrrolidinyl or piperidinyl ring,
and
R$^{30}$ represents phenyl or adamantyl,
R$^{24}$ and R$^{25}$ have the meanings of R$^{18}$ and R$^{19}$ given above and are identical to or different from them,
R$^{26}$ and R$^{27}$ have the meanings of R$^{10}$ and R$^{11}$ given above and are identical to or different from them
and/or cycloalkyl, phenyl and/or the heterocycles are optionally substituted by straight-chain or branched alkyl having up to 3 carbon atoms which is optionally substituted by hydroxyl, carboxyl, pyridyl, pyrimidyl, pyrrolidinyl, piperidinyl, tetrahydrofuranyl, triazolyl or by groups of the formula —SO$_2$—R$^{31}$, P(O)(OR$^{32}$)(OR$^{33}$) or —NR$^{34}$R$^{35}$,
in which
R$^{31}$ represents methyl,
R$^{32}$ and R$^{33}$ have the meanings of R$^{10}$ and R$^{11}$ given above and are identical to or different from them,
R$^{34}$ and R$^{35}$ are identical or different and each represents hydrogen or straight-chain or branched alkyl having up to 3 carbon atoms which is optionally substituted by hydroxyl or methoxy, or
R$^{34}$ and R$^{35}$ together with the nitrogen atom form a morpholinyl, triazolyl or thiomorpholinyl ring, or a radical of the formula

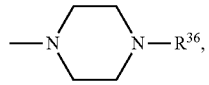

in which
R$^{36}$ represents hydrogen, hydroxyl, straight-chain or branched alkoxycarbonyl having up to 3 carbon atoms or straight-chain or branched alkyl having up to 3 carbon atoms which is optionally substituted by hydroxyl,
or
R$^3$ and R$^4$ together with the nitrogen atom form a morpholinyl, thiomorpholinyl, pyrrolidinyl, piperidinyl ring, or a radical of the formula

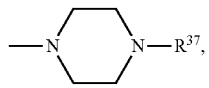

in which
R$^{37}$ represents hydrogen, hydroxyl, formyl, straight-chain or branched acyl, alkoxy or alkoxycarbonyl having in each case up to 3 carbon atoms,
or represents straight-chain or branched alkyl having up to 4 carbon atoms which is optionally mono- or disubstituted by identical or different substituents selected from the group consisting of hydroxyl, straight-chain or branched alkoxy or alkoxycarbonyl having in each case up to 3 carbon atoms, or by groups of the formula -(D)$_f$-NR$^{38}$R$^{39}$, —CO—(CH$_2$)$_g$—O—CO—R$^{40}$, —CO—(CH$_2$)$_h$—OR$^{41}$ or —P(O)(OR$^{42}$)(OR$^{43}$),
in which
g and h are identical or different and each represents a number 1 or 2,
and
f represents a number 0 or 1,
D represents a group of the formula —CO or —SO$_2$,
R$^{38}$ and R$^{39}$ are identical or different and have the meanings of R$^7$ and R$^8$ given above,
R$^{40}$ represents straight-chain or branched alkyl having up to 3 carbon atoms,
R$^{41}$ represents straight-chain or branched alkyl having up to 3 carbon atoms,
R$^{42}$ and R$^{43}$ are identical or different and each represents hydrogen, methyl or ethyl,
or
R$^{37}$ represents a radical of the formula —(CO)$_i$-E,
in which
i represents a number 0 or 1,
E represents cyclopentyl, benzyl, phenyl, pyridyl, pyrimidyl or furyl, where the abovementioned ring systems are optionally mono- or disubstituted by identical or different substituents selected from the group consisting of nitro, fluorine, chlorine, —SO$_3$H, straight-chain or branched alkoxy having up to 3 carbon atoms, hydroxyl, or by a radical of the formula —SO$_2$—NR$^{44}$R$^{45}$,
in which
R$^{44}$ and R$^{45}$ have the meanings of R$^{18}$ and R$^{19}$ given above and are identical to or different from them,
or
E represents radicals of the formulae

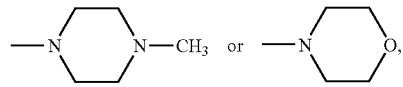

and the heterocycles listed under R$^3$ and R$^4$, which are formed together with the nitrogen atom, are optionally mono- to trisubstituted, optionally also geminally, by identical or different substituents selected from the group consisting of hydroxyl, formyl, carboxyl, straight-chain or branched acyl or alkoxycarbonyl having in each case up to 3 carbon atoms, or groups of the formulae —P(O)(OR$^{46}$)(OR$^{47}$),

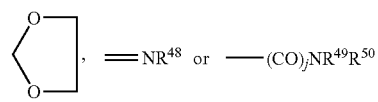

in which
R$^{46}$ and R$^{47}$ have the meanings of R$^{10}$ and R$^{11}$ given above and are identical to or different from them,
R$^{48}$ represents hydroxyl or methoxy,
j represents a number 0 or 1,
and
R$^{49}$ and R$^{50}$ are identical or different and have the meanings of R$^{14}$ and R$^{15}$ given above,
and/or the heterocycles listed under R$^3$ and R$^4$, which are formed together with the nitrogen atom, are optionally substituted by straight-chain or branched alkyl having up to 4 carbon atoms which is optionally mono- to trisubstituted by identical or different substituents selected from the group consisting of hydroxyl, fluorine, chlorine, carboxyl, cyclopropyl, cycloheptyl, straight-chain or branched alkoxy or alkoxycarbonyl having in each case up to 3 carbon atoms, or by a radical of the formula —$SO_3H$, —$NR^{51}R^{52}$ or $P(O)OR^{53}OR^{54}$, in which $R^{51}$ and $R^{52}$ are identical or different and each represents hydrogen, phenyl, carboxyl, benzyl or straight-chain or branched alkyl or alkoxy having in each case up to 3 carbon atoms, $R^{53}$ and $R^{54}$ are identical or different and have the meanings of $R^{10}$ and $R^{11}$ given above, and/or the alkyl is optionally substituted by phenyl which for its part may be mono- to disubstituted by identical or different substituents selected from the group consisting of fluorine, chlorine, hydroxyl, methoxy, or by a group of the formula —$NR^{51'}R^{52'}$, in which $R^{51'}$ and $R^{52'}$ have the meanings of $R^{51}$ and $R^{52}$ given above and are identical to or different from them, and/or the heterocycles listed under $R^3$ and $R^4$, which are formed together with the nitrogen atom, are optionally substituted by phenyl, pyridyl, piperidinyl, pyrrolidinyl or tetrazolyl, if appropriate also attached via a nitrogen function, where the ring systems for their part may be substituted by hydroxyl or by straight-chain or branched alkyl or alkoxy having in each case up to 3 carbon atoms, or $R^3$ and $R^4$ together with the nitrogen atom form radicals of the formulae

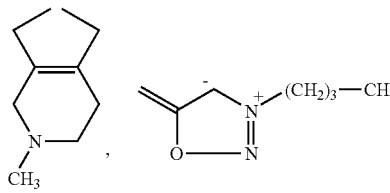

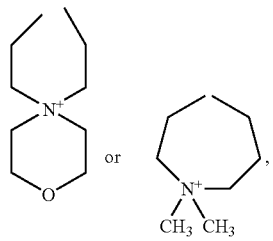

$R^5$ and $R^6$ are identical or different and each represents hydrogen, hydroxyl or represents straight-chain or branched alkoxy having up to 3 carbon atoms, and their salts, N-oxides, hydrates and isomeric forms.

Very particular preference is given to compounds of the general formula (I), in which $R^1$ represents methyl or ethyl, $R^2$ represents ethyl or propyl, $R^3$ and $R^4$ are identical or different and each represents a straight-chain or branched alkyl chain having up to 5 carbon atoms which is optionally substituted up to two times by identical or different substituents selected from the group consisting of hydroxyl and methoxy, or $R^3$ and $R^4$ together with the nitrogen atom form a piperidinyl, morpholinyl, thiomorpholinyl ring, or a radical of the formula

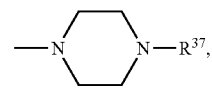

in which $R^{37}$ represents hydrogen, formyl, straight-chain or branched acyl or alkoxycarbonyl having in each case up to 3 carbon atoms, or represents straight-chain or branched alkyl having up to 3 carbon atoms which is optionally mono- or disubstituted by identical or different substituents selected from the group consisting of hydroxyl, carboxyl, straight-chain or branched alkoxy or alkoxycarbonyl having in each case up to 3 carbon atoms, or by groups of the formulae -(D)$_f$-$NR^{38}R^{39}$ or —$P(O)(OR^{42})(OR^{43})$, in which f represents a number 0 or 1, D represents a group of the formula —CO, $R^{38}$ and $R^{39}$ are identical or different and each represents hydrogen or methyl, $R^{42}$ and $R^{43}$ are identical or different and each represents hydrogen, methyl or ethyl, or $R^{37}$ represents cyclopentyl, and the heterocycles listed under $R^3$ and $R^4$, which are formed together with the nitrogen atom, are optionally mono- or disubstituted, optionally also geminally, by identical or different substituents selected from the group consisting of hydroxyl, formyl, carboxyl, straight-chain or branched acyl or alkoxycarbonyl having in each case up to 3 carbon atoms, or groups of the formulae —$P(O)(OR^{46})(OR^{47})$ or —$(CO)_jNR^{49}R^{50}$, in which $R^{46}$ and $R^{47}$ are identical or different and each represents hydrogen, methyl or ethyl, j represents a number 0 or 1, and $R^{49}$ and $R^{50}$ are identical or different and each represents hydrogen or methyl and/or the heterocycles listed under $R^3$ and $R^4$, which are formed together with the nitrogen atom, are optionally substituted by straight-chain or branched alkyl having up to 3 carbon atoms which is optionally mono- or disubstituted by identical or different substituents selected from the group consisting of hydroxyl, carboxyl, or by a radical of the formula $P(O)OR^{53}OR^{54}$, in which $R^{53}$ and $R^{54}$ are identical or different and each represents hydrogen, methyl or ethyl, and/or the heterocycles listed under $R^3$ and $R^4$, which are formed together with the nitrogen atom, are optionally substituted by pyrrolidinyl or piperidinyl attached via nitrogen, $R^5$ represents hydrogen, and $R^6$ represents ethoxy or propoxy, and their salts, hydrates, N-oxides and isomeric forms.

Likewise, very particular preference is given to those compounds of the general formula (I) according to the invention in which $R^5$ represents hydrogen and the radicals $R^6$ and —$SO_2NR^3R^4$ are in a position para to one another at the phenyl ring.
Particularly preferred compounds are listed in Table A.
TABLE A
Structure
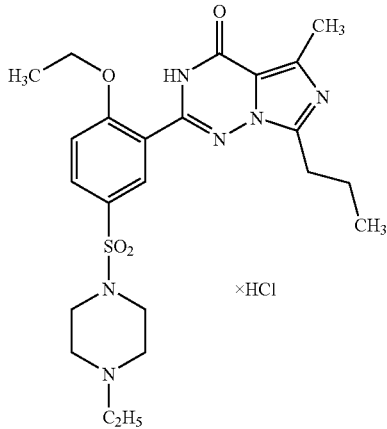
×HCl
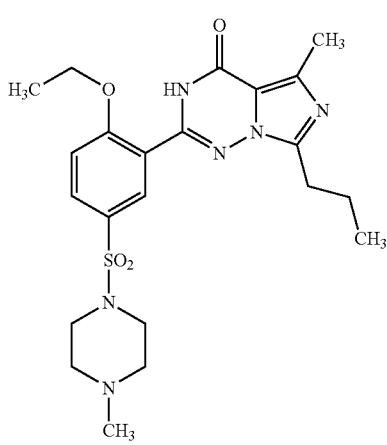
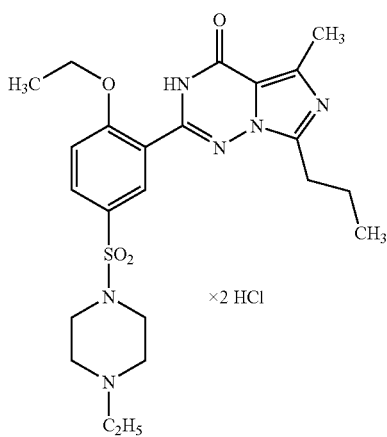
×2 HCl
TABLE A-continued
Structure
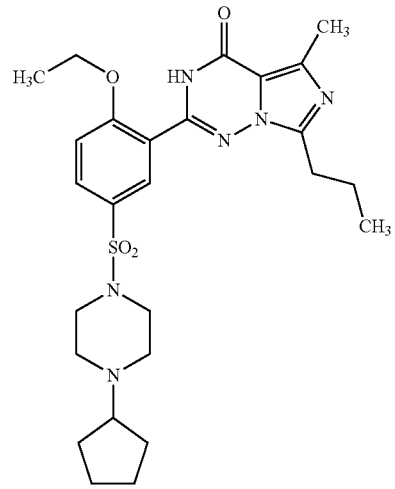
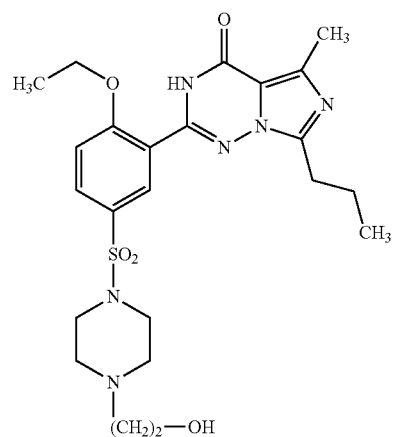
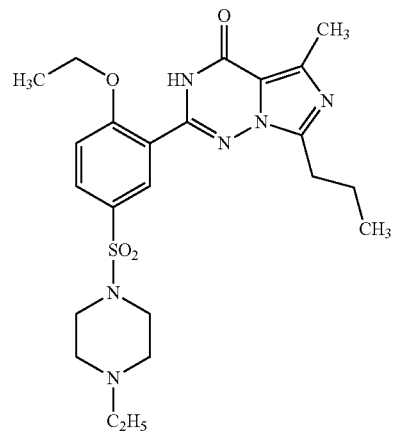

TABLE A-continued
Structure
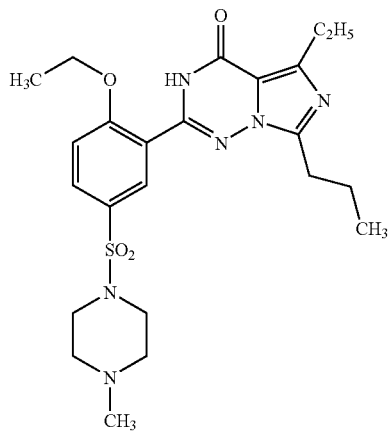
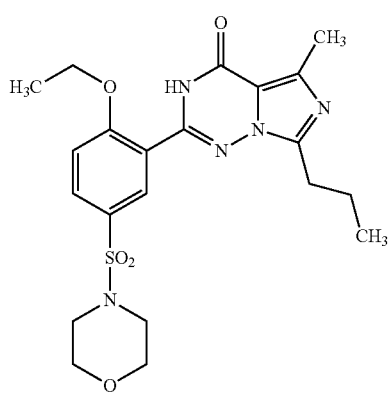
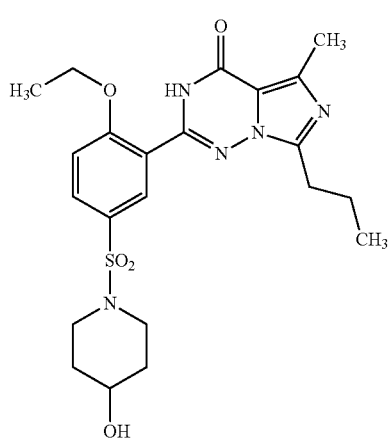
TABLE A-continued
Structure
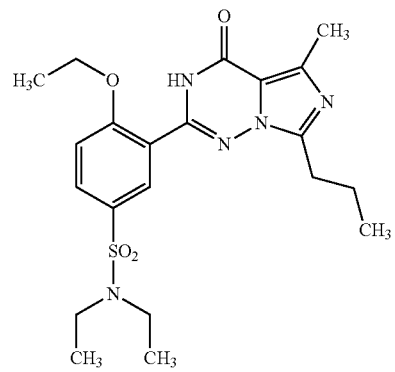
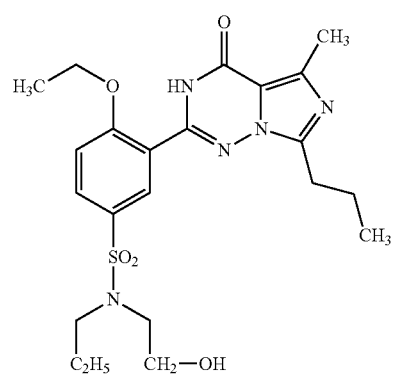
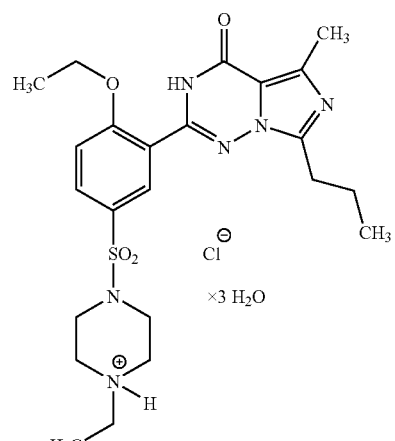
The invention furthermore provides a process for preparing the compounds of the general formula (I) according to the invention, characterized in that
initially compounds of the general formula (II)
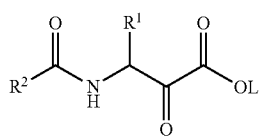
(II)
in which
$R^1$ and $R^2$ are each as defined above and L represents straight-chain or branched alkyl having up to 4 carbon atoms, are converted with compounds of the general formula (III)

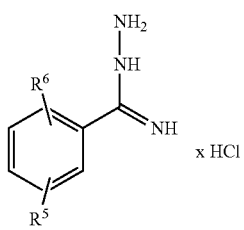
(III)

in which

R[5] and R[6] are each as defined above, in a two-step reaction in the systems ethanol and phosphorus oxytrichloride/dichloroethane into the compounds of the general formula (IV)

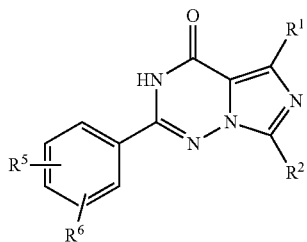
(IV)

in which

R[1], R[2], R[5] and R[6] are each as defined above, which are reacted in a further step with chlorosulphonic acid to give the compounds of the general formula (V)

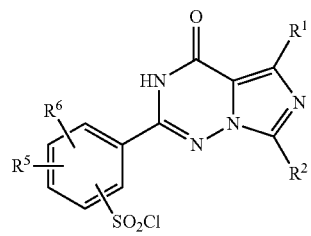
(V)

in which

R[1], R[2], R[5] and R[6] are each as defined above, which are finally reacted with amines of the general formula (VI)

HN[3]R[4]  (VI)

in which

R[3] and R[4] are each as defined above, in inert solvents.

The process according to the invention can be illustrated using the following scheme as an example:

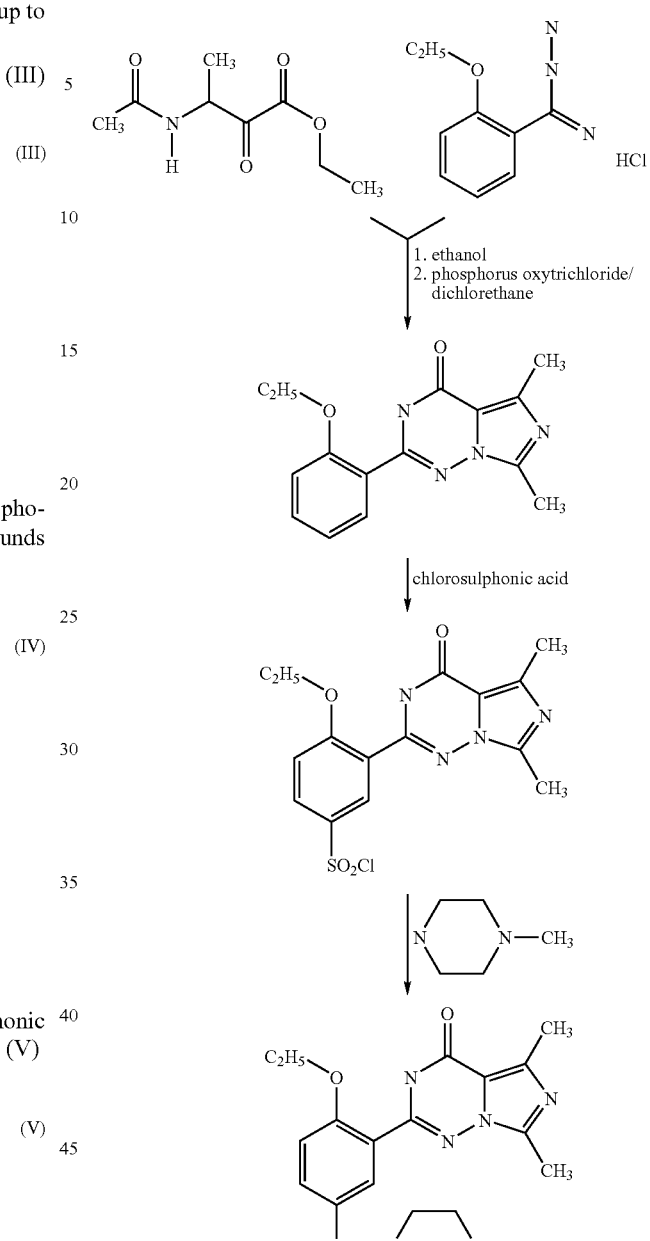

Solvents which are suitable for the individual steps are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethane, trichloroethylene or chlorobenzene, or ethyl acetate, dimethylformamide, hexamethylphosphoric triamide, acetonitrile, acetone, dimethoxyethane or pyridine. It is also possible to use mixtures of the abovementioned solvents. Particular preference is given to ethanol for the first step and dichloroethane for the second step.

The reaction temperature can generally be varied within a relatively wide range. In general, the reaction is carried out in a range of from −20° C. to 200° C., preferably of from 0° C. to 70° C.

The process steps according to the invention are generally carried out under atmospheric pressure. However, it is also possible to operate under superatmospheric pressure or under reduced pressure (for example, in a range of from 0.5 to 5 bar).

The reaction to give the compounds of the general formula (V) is carried out in a temperature range of from 0° C. to room temperature, and at atmospheric pressure.

The reaction with the amines of the general formula (VI) is carried out in one of the abovementioned chlorinated halogens, preferably in dichloromethane.

The reaction temperature can generally be varied within a relatively wide range. In general, the reaction is carried out at temperatures in a range of from −20° C. to 200° C., preferably of from 0° C. to room temperature.

The reaction is generally carried out at atmospheric pressure. However, it is also possible to operate under superatmospheric pressure or under reduced pressure (for example in a range of from 0.5 to 5 bar).

Some of the compounds of the general formula (II) are known, or they are novel, and they can then be prepared by converting compounds of the general formula (VII)

$$R^2-CO-T \qquad (VII)$$

in which $R^2$ is as defined above and

T represents halogen, preferably chlorine, initially by reaction with compounds of the general formula (VIII)

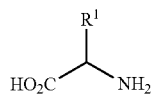
(VIII)

in which $R^1$ is as defined above in inert solvents, if appropriate in the presence of a base and trimethylsilyl chloride, into the compounds of the general formula (IX)

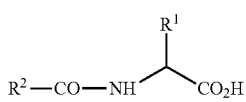
(IX)

in which $R^1$ and $R^2$ are each as defined above, and finally reacting with the compound of the formula (X)

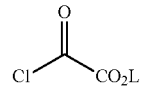
(X)

in which L is as defined above, in inert solvents, if appropriate in the presence of a base.

Suitable solvents for the individual steps of the process are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, dimethylformamide, hexamethylphosphoric triamide, acetonitrile, acetone, dimethoxyethane or pyridine. It is also possible to use mixtures of the abovementioned solvents. Particular preference is given to dichloromethane for the first step and to a mixture of tetrahydrofuran and pyridine for the second step.

Suitable bases are generally alkali metal hydrides or alkali metal alkoxides, such as, for example, sodium hydride or potassium tert-butoxide, or cyclic amines, such as, for example, piperidine, pyridine, dimethylaminopyridine or $C_1$-$C_4$ alkylamines, such as, for example, triethylamine. Preference is given to triethylamine, pyridine and/or dimethylaminopyridine.

The base is generally employed in an amount of from 1 mol to 4 mol, preferably from 1.2 mol to 3 mol, in each case based on 1 mol of the compound of the formula (X).

The reaction temperature can generally be varied within a relatively wide range. In general, the reaction is carried out in a range of from −20° C. to 200° C., preferably of from 0° C. to 100° C.

The compounds of the general formulae (VII), (VIII), (IX) and (X) are known per se, or they can be prepared by customary methods.

The compounds of the general formula (III) can be prepared by reacting compounds of the general formula (XI)

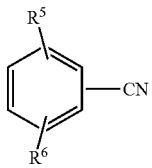
(XI)

in which $R^5$ and $R^6$ are each as defined above with ammonium chloride in toluene and in the presence of trimethylaluminium in hexane in a temperature range of from −20° C. to room temperature, preferably at 0° C. and atmospheric pressure, and reacting the resulting amidine, if appropriate in situ, with hydrazine hydrate.

The compounds of the general formula (XI) are known per se, or they can be prepared by customary methods.

Some of the compounds of the general formula (IV) are known, or they are novel, in which case they can be prepared by known methods [cf. David R. Marshall, Chemistry and Industry, 2 May 1983, 331-335].

Compounds of the general formula (V) are novel per se, however, they can be prepared from the compounds of the general formula (IV) in accordance with the publication Organikum, VEB Deutscher Verlag der Wissenschaften, Berlin 1974, pages 338-339.

The compounds of the general formula (I) according to the invention have an unforeseeable useful pharmacological activity spectrum.

They inhibit either one or more of the cGMP-metabolizing phosphodiesterases (PDE I, PDE II and PDE V). This results in an increase of cGMP. The differentiated expression of the phosphodiesterases in different cells, tissues and organs, as well as the differentiated subcellular localization of these enzymes, in combination with the selective inhibitors according to the invention make it possible to selectively address the various cGMP-regulated processes.

Moreover, the compounds according to the invention enhance the activity of substances such as, for example EDRF (endothelium derived relaxing factor), ANP (atrial natriuretic peptide), of nitrovasodilators and all other substances which increase the cGMP concentration in a manner different from that of phosphodiesterase inhibitors.

They can therefore be employed in pharmaceuticals for treating cardiovascular disorders, such as, for example, for treating hypertension, neuronal hypertonia, stable and unstable angina, peripheral and cardial vascularpathies, arrhythmiae, for treating thromboembolic disorders and ischaemias such as myocardial infarction, stroke, transistory and ischaemic attacks, angina pectoris, obstruction of peripheral circulation, prevention of restenoses after thrombolysis therapy, percutaneous transluminal angioplasty (PTA), percutaneous transluminal coronary angioplasties (PTCA) and bypass. Furthermore, they may also be of significance for cerebrovascular disorders. Owing to their relaxing action on smooth muscles, they are suitable for treating disorders of the urogenital system such as hypertrophy of the prostate, incontinence and in particular for treating erectile dysfunction and female sexual dysfunction.

Activity of the Phosphodiesterases (PDEs)

The cGMP-stimulated PDE II, the cGMP-inhibited PDE III and the cAMP-specific PDE IV were isolated either from porcine or bovine heart myocardium. The $Ca^{2+}$-calmodulin-stimulated PDE I was isolated from porcine aorta, porcine brain or, preferably, from bovine aorta. The cGMP-specific PDE V was obtained from porcine small intestine, porcine aorta, human platelets and, preferably, from bovine aorta. Purification was carried out by anion exchange chromatography over MonoQ® Pharmacia, essentially following the method of M. Hoey and Miles D. Houslay, Biochemical Pharmacology, Vol. 40, 193-202 (1990) and C. Lugman et al., Biochemical Pharmacology, Vol. 35, 1743-1751 (1986).

The enzyme activity is determined using a test mixture of 100 ml in 20 mM tris/HCl-buffer pH 7.5 containing 5 mM $MgCl_2$, 0.1 mg/ml of bovine serum albumin and either 800 Bq[$^3$H]cAMP or [$^3$H]cGMP. The final concentration of the nucleotides in question is $10^{-6}$ mol/l. The reaction is initiated by addition of the enzyme and the amount of enzyme is such that during the incubation time of 30 min, approximately 50% of the substrate are converted. To test the cGMP-stimulated PDE II, [$^3$H]cAMP is used as substrate and $10^{-6}$ mol/l of non-labelled cGMP are added to the mixture. To test the $Ca^{2+}$-calmodulin-dependent PDE I, 1 mM of $CaCl_2$ and 0.1 mM of calmodulin are added to the reaction mixture. The reaction is quenched by addition of 100 ml of acetonitrile containing 1 mM cAMP and 1 mM AMP. 100 ml of the reaction mixture are separated by HPLC, and the cleavage products are determined quantitatively on-line using a continuous scintillation counter. The substance concentration measured is the concentration at which the reaction rate is reduced by 50%. Additionally, the "phosphodiesterase [$^3$H] cAMP-SPA enzyme assay" and the "phosphodiesterase [$^3$H] cGMP-SPA enzyme assay" from Amersham Life Science were used for testing. The test was carried out according to the test protocol of the manufacturer. To determine the activity of PDE II, the [$^3$H]cAMP SPA assay was used, and $10^{-6}$ M cGMP were added to the reaction mixture to activate the enzyme. To measure PDE I, $10^{-7}$ M calmodulin and 1 mM $CaCl_2$ were added to the reaction mixture. PDE V was measured using the [$^3$H]cGMP SPA assay.

Inhibition of the Phosphodiesterases In Vitro

| Ex. No. | PDE I $IC_{50}$ [nM] | PDE II $IC_{50}$ [nM] | PDE V $IC_{50}$ [nM] |
|---|---|---|---|
| 16 | 300 | >1000 | 2 |
| 19 | 200 | >1000 | 2 |
| 20 | 200 | >1000 | 2 |
| 26 | 100 | >1000 | 1 |
| 27 | 200 | >1000 | 3 |
| 32 | 100 | >1000 | 4 |
| 260 | 300 | >1000 | 10 |
| 275 | 50 | >1000 | 3 |
| 338 | 200 | >1000 | 5 |

In principle, inhibition of one or more phosphodiesterases of this type results in an increase of the cGMP concentration. Thus, the compounds are of interest for all therapies in which an increase of the cGMP concentration is considered to be beneficial.

The cardiovascular effects were investigated using SH-rats and dogs. The substances were administered intravenously or orally.

The erection-stimulating action was investigated using rabbits which were awake [Naganuma H, Egashira T, Fuji J, Clinical and Experimental Pharmacology and Physiology 20, 177-183 (1993)]. The substances were administered intravenously, orally or parenterally.

The novel active compounds and their physiologically acceptable salts (for example hydrochlorides, maleates or lactates) can be converted in a known manner into the customary formulations, such as tablets, coated tablets, pills, granules, aerosols, syrups, emulsions, suspensions and solutions, using inert non-toxic, pharmaceutically suitable excipients or solvents. In this case the therapeutically active compound should in each case be present in a concentration from approximately 0.5 to 90% by weight of the total mixture, i.e. in amounts which are sufficient in order to achieve the dosage range indicated.

The formulations are prepared, for example, by extending the active compounds using solvents and/or excipients, if appropriate using emulsifiers and/or dispersants, it optionally being possible, for example, to use organic solvents as auxiliary solvents if the diluent used is water.

Administration is carried out in a customary manner, preferably orally, transdermally or parenterally, for example perlingually, buccally, intravenously, nasally, rectally or inhalatively.

For human use, in the case of oral administration, it is good practice to administer doses of from 0.001 to 50 mg/kg, preferably of 0.01 mg/kg-20 mg/kg. In the case of parenteral administration, such as, for example, via mucous membranes nasally, buccally or inhalatively, it is good practice to use doses of 0.001 mg/kg-0.5 mg/kg.

In spite of this, if appropriate it may be necessary to depart from the amounts mentioned, namely depending on the body weight or the type of administration route, on the individual response towards the medicament, the manner of its formulation and the time or interval at which administration takes place. Thus, in some cases it may be adequate to manage with less than the abovementioned minimum amounts, while in other cases the upper limit mentioned has to be exceeded. In the case of the administration of relatively large amounts, it may be advisable to divide these into several individual doses over the course of the day.

The compounds according to the invention are also suitable for use in veterinary medicine. For use in veterinary medicine, the compounds or their non-toxic salts can be administered in a suitable formulation in accordance with general veterinary practice. Depending on the kind of animal to be treated, the veterinary surgeon can determine the nature of use and the dosage.

Starting Materials

EXAMPLE 1A

2-Butyrylaminopropionic acid

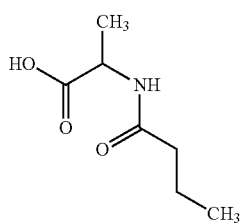

22.27 g (250 mmol) of D,L-alanine and 55.66 g (550 mmol) of triethylamine are dissolved in 250 ml of dichloromethane, and the solution is cooled to 0° C. 59.75 g (550 mmol) of trimethylsilyl chloride are added dropwise, and the solution is stirred for 1 hour at room temperature and for 1 hour at 40° C. After cooling to −10° C., 26.64 g (250 mmol) of butyryl chloride are added dropwise, and the resulting mixture is stirred for 2 hours at −10° C. and for one hour at room temperature.

With ice-cooling, 125 ml of water are added dropwise and the reaction mixture is stirred at room temperature for 15 minutes. The aqueous phase is evaporated to dryness, the residue is titrated with acetone and the mother liquor is filtered off with suction. The solvent is removed and the residue is chromatographed. The resulting product is dissolved in 3N aqueous sodium hydroxide solution and the resulting solution is evaporated to dryness. The residue is taken up in conc. HCl and once more evaporated to dryness. The residue is stirred with acetone, precipitated solid is filtered off with suction and the solvent is removed under reduced pressure. This gives 28.2 g (71%) of a viscous oil which crystallizes after some time.

200 MHz $^1$H-NMR (DMSO-d6): 0.84, t, 3H, 1.22, d, 3H, 1.50, hex, 2H, 2.07, t, 2H, 4.20, quin., 1H, 8.09, d, 1H.

EXAMPLE 2A

2-Butyrylamino butyric acid

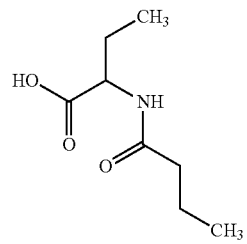

25.78 g of 2-aminobutyric acid (250 mmol) and 55.66 g (550 mmol) of triethylamine are dissolved in 250 ml of dichloromethane, and the solution is cooled to 0° C. 59.75 g (550 mmol) of trimethylsilyl chloride are added dropwise, and the solution is stirred for 1 hour at room temperature and for 1 hour at 40° C. After cooling to −10° C., 26.64 g (250 mmol) of butyryl chloride are added dropwise, and the resulting mixture is stirred for 2 hours at −10° C. and for one hour at room temperature.

With ice-cooling, 125 ml of water are added dropwise, and the reaction mixture is stirred at room temperature for 15 minutes. The organic phase is admixed with aqueous sodium hydroxide solution and the organic solvent is removed under reduced pressure. After acidification, the precipitated solid is stirred once with water and twice with petroleum ether and dried at 45° C. under reduced pressure. This gives 29.1 g (67%) of a colourless solid.

200 MHz $^1$H-NMR (DMSO-d6): 0.88, 2t, 6H, 1.51, quart., 2H, 1.65, m, 2H, 2.09, t, 2H, 4.10, m, 1H, 8.01, d, 1H, 12.25, s, m 1H.

EXAMPLE 3A

2-Ethoxybenzonitrile

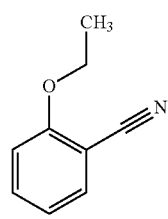

25 g (210 mmol) of 2-hydroxybenzonitrile are refluxed with 87 g of potassium carbonate and 34.3 g (314.8 mmol) of ethyl bromide in 500 ml of acetone overnight. The solid is filtered off, the solvent is removed under reduced pressure and the residue is distilled under reduced pressure. This gives 30.0 g (97%) of a colourless liquid.

200 MHz $^1$H-NMR (DMSO-d6): 1.48, t, 3H, 4.15, quart., 2H, 6.99, dt, 2H, 7.51, dt, 2H.

EXAMPLE 4A

2-Ethoxybenzamidine hydrochloride

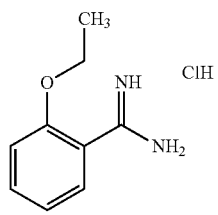

21.4 g (400 mmol) of ammonium chloride are suspended in 375 ml of toluene, and the suspension is cooled to 0° C. 200 ml of a 2M solution of trimethylaluminium in hexane are added dropwise, and the mixture is stirred at room temperature until the evolution of gas has ceased. After addition of 29.44 g (200 mmol) of 2-ethoxybenzonitrile, the reaction mixture is stirred at 80° C. (bath) overnight.

With ice-cooling, the cooled reaction mixture is added to a suspension of 100 g of silica gel and 950 ml of chloroform, and the mixture is stirred at room temperature for 30 minutes. The mixture is filtered off with suction, and the filter residue is washed with the same amount of methanol. The mother liquor is concentrated, the resulting residue is stirred with a mixture of dichloromethane and methanol (9:1), the solid is filtered off with suction and the mother liquor is concentrated. This gives 30.4 g (76%) of a colourless solid.

200 MHz $^1$H-NMR (DMSO-d6): 1.36, t, 3H, 4.12, quart., 2H, 7.10, t, 1H, 7.21, d, 1H, 7.52, m, 2H, 9.30, s, broad, 4H.

EXAMPLE 5A

2-Propoxybenzonitrile

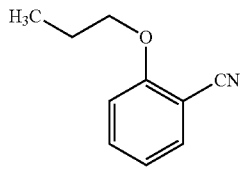

75 g (630 ml) of 2-hydroxybenzonitrile are refluxed with 174 g (1.26 mol) of potassium carbonate and 232.2 g (1.89 mol) of ethyl bromide in 1 l of acetone overnight. The solid is filtered off, the solvent is removed under reduced pressure and the residue is distilled under reduced pressure.

b.p.: 89° C. (0.7 mbar)

Yield: 95.1 g (93.7%)

EXAMPLE 6A

2-Propoxybenzamidine hydrochloride

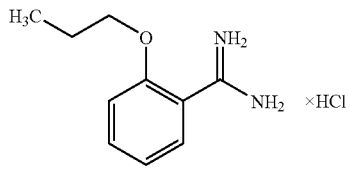

21.41 g (400 mmol) of ammonium chloride are suspended in 400 ml of toluene and cooled to 0-5° C. 200 ml of a 2M solution of triethylaluminium in hexane are added dropwise, and the mixture is stirred at room temperature until the evolution of gas has ceased. After addition of 32.2 g (200 mmol) of 2-propoxybenzonitrile, the reaction mixture is stirred at 80° C. (bath) overnight. With ice-cooling, the cooled reaction mixture is added to a suspension of 300 g of silica gel and 2.85 l of ice-cooled chloroform, and the mixture is stirred for 30 minutes. The mixture is filtered off with suction and the filter residue is washed with the same amount of methanol. The solvent is distilled off under reduced pressure, the residue is stirred with 500 ml of a mixture of dichloromethane and methanol (9:1), the solid is filtered off and the mother liquor is concentrated. The residue is stirred with petroleum ether and filtered off with suction. This gives 22.3 g (52%) of product.

$^1$H-NMR (200 MHz, CD$_3$OD): 1.05 (3H); 1.85 (sex, 2H); 4.1 (A, 2H); 7.0-7.2 (m, 2H); 7.5-7.65 (m, 2H).

EXAMPLE 7A

2-Ethoxy-4-methoxybenzonitrile

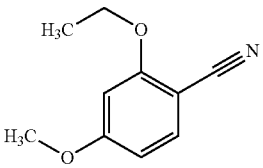

30.0 g (201 mmol) of 2-hydroxy-4-methoxybenzonitrile are refluxed with 83.4 g of potassium carbonate (603 mmol) and 32.88 g (301 mmol) of bromoethane in 550 ml of acetone for 18 hours. After filtration, the solvent is removed under reduced pressure and the residue is purified by silica gel chromatography (cyclohexane:ethyl acetate=10:1): 35.9 g of an oil $R_f$=0.37 (cyclohexane:ethyl acetate=3:1)

200 MHz $^1$H-NMR (CDCl$_3$): 1.48, t, 3H, 3.85, s, 3H, 4.12, quart., 2H, 6.46, m, 2H, 7.48, d, 1H.

EXAMPLE 8A

2-Ethoxy-4-methoxybenzamidine hydrochloride

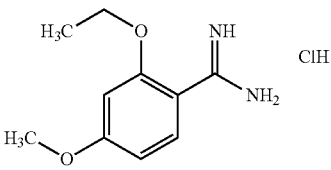

6.98 g (130 mmol) of ammonium chloride are suspended in 150 ml of toluene, and the suspension is cooled to 0° C. 70 ml of a 2M solution of trimethylaluminium in hexane are added dropwise, and the mixture is stirred at room temperature until the evolution of gas has ceased. After addition of 11.56 g (65 mmol) of 2-ethoxy-4-methoxybenzonitrile, the reaction mixture is stirred at 80° C. (bath) overnight.

With ice-cooling, the cooled reaction mixture is added to a suspension of 100 g of silica gel and 950 ml of dichloromethane, and the mixture is stirred at room temperature for 30 minutes. The mixture is filtered off with suction and the filter residue is washed with the same amount of methanol. The mother liquor is concentrated, the resulting residue is stirred with a mixture of dichloromethane and methanol (9:1), the solid is filtered off with suction and the mother liquor is concentrated. The residue is stirred with petroleum ether and filtered off with suction. This gives 7.95 g (50%) of a solid.

200 MHz $^1$H-NMR (DMSO-d6): 1.36, t, 3H, 3.84, s, 3H, 4.15, quart., 2H, 6.71, m, 2H, 7.53, d, 1H, 8.91, s, broad, 3H.

EXAMPLE 9A 2-(2-Ethoxyphenyl)-5,7-dimethyl-3H-imidazo[5,1-f][1,2,4]triazin-4-one

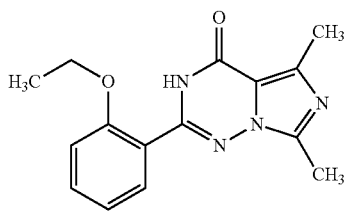

24.4 g (0.186 mol) of N-acetyl-D,L-alanine are initially charged in 200 ml of absolute tetrahydrofuran, and 45 ml of absolute pyridine and 0.5 g of 4-dimethylaminopyridine are added. The mixture is heated to reflux, and 51.85 g (0.372 mol) of ethyl oxalyl chloride are added dropwise. The mixture is heated under reflux for a further 90 minutes, cooled, poured into ice-water and extracted three times with ethyl acetate. The organic phase is dried over sodium sulphate, concentrated and taken up in 62.5 ml of methanol. 9 g of sodium bicarbonate are added and the mixture is stirred under reflux for 2.5 hours and filtered.

With ice-cooling, 9.54 g (190.65 mmol) of hydrazine hydrate are added dropwise to a solution of 38.26 g (190.65 mmol) of 2-ethoxy-4-methoxybenzamidine hydrochloride in 250 ml of methanol, and the resulting suspension is stirred at room temperature for another 30 minutes. The methanolic solution described above is added to this reaction mixture, and the mixture is stirred at a bath temperature of 70° C. for 4 hours. After filtration, the mixture is concentrated, the residue is partitioned between dichloromethane and water, the organic phase is dried over sodium sulphate and the solvent is removed under reduced pressure.

The residue is taken up in 250 ml of 1,2-dichloroethane, 32.1 ml (348 mmol) of phosphorus oxychloride are added dropwise and the mixture is heated under reflux for two hours. The mixture is cooled, concentrated, taken up in a little methylene chloride and admixed with diethyl ether, and the solid is filtered off with suction. After the silica gel chromatography (methylene chloride/methanol 95:5), the solution is concentrated and the crystalline residue is stirred with diethyl ether.

Yield: 8.1 g (14.9% of theory)

200 MHz $^1$H-NMR (CDCl$_3$): 1.58, t, 3H, 2.62, s, 3H, 2.68, s, 3H, 4.25, q, 2H, 7.04, d, 1H; 7.12, t, 1H; 7.5, dt, 1H; 8.19, dd, 1H; 10.02, s, 1H.

EXAMPLE 10A 2-(2-Ethoxy-phenyl)-5-methyl-7-propyl-3H-imidazo[5,1-f][1,2,4]triazin-4-one

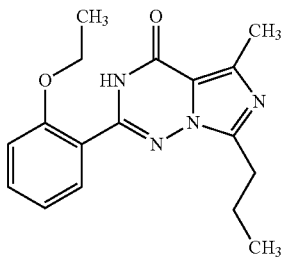

7.16 g (45 mmol) of 2-butyrylamino-propionic acid and 10.67 g of pyridine are dissolved in 45 ml of THF and, after addition of a spatula tip of DMAP, heated to reflux. 12.29 g (90 mmol) of ethyl oxalyl chloride are slowly added dropwise, and the reaction mixture is refluxed for 3 hours. The mixture is poured into ice-water and extracted three times with ethyl acetate and the organic phase is dried over sodium sulphate and concentrated using a rotary evaporator. The residue is taken up in 15 ml of ethanol and refluxed with 2.15 g of sodium bicarbonate for 2.5 hours. The cooled solution is filtered.

With ice-cooling, 2.25 g (45 mmol) of hydrazine hydrate are added dropwise to a solution of 9.03 g (45 mmol) of 2-ethoxybenzamidine hydrochloride in 45 ml of ethanol, and the resulting suspension is stirred at room temperature for another 10 minutes. The ethanolic solution described above is added to this reaction mixture, and the mixture is stirred at a bath temperature of 70° C. for 4 hours. After filtration, the mixture is concentrated, the residue is partitioned between dichloromethane and water, the organic phase is dried over sodium sulphate and the solvent is removed under reduced pressure.

This residue is dissolved in 60 ml of 1,2-dichloroethane and, after addition of 7.5 ml of phosphorus oxychloride, refluxed for 2 hours. The mixture is diluted with dichloromethane and neutralized by addition of sodium bicarbonate solution and solid sodium bicarbonate. The organic phase is dried and the solvent is removed under reduced pressure. Chromatography using ethyl acetate and crystallization afford 4.00 g (28%) of a colourless solid, R$_f$=0.42 (dichloromethane/methanol=95:5)

200 MHz ¹H-NMR (CDCl₃): 1.02, t, 3H, 1.56, t, 3H, 1.89, hex, 2H, 2.67, s, 3H, 3.00, t, 2H, 4.26, quart., 2H, 7.05, m, 2H, 7.50, dt, 1H, 8.17, dd, 1H, 10.00, s, 1H.

EXAMPLE 11A 2-(2-Propoxy-phenyl)-5-methyl-7-propyl-3H-imidazo[5,1-f][1,2,4]triazin-4-one

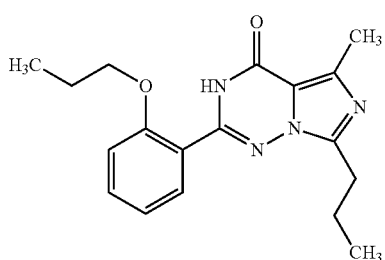

7.16 g (45 mmol) of 2-butyrylaminopropionic acid and 10.67 g of pyridine are dissolved in 45 ml of tetrahydrofuran and, after addition of a spatula tip of dimethylaminopyridine, heated to reflux. 12.29 g (90 mmol) of ethyl oxalyl chloride are slowly added dropwise, and the reaction mixture is refluxed for 3 hours. The mixture is poured into ice-water and extracted three times with ethyl acetate, and the organic phase is dried over sodium sulphate and concentrated using a rotary evaporator. The residue is taken up in 15 ml of ethanol and refluxed with 2.15 g of sodium bicarbonate for 2.5 hours. The cooled solution is filtered.

With ice-cooling, 2.25 g (45 mmol) of hydrazine hydrate are added dropwise to a solution of 9.66 g (45 mmol) of 2-propoxybenzamidine hydrochloride in 45 ml of ethanol, and the resulting suspension is stirred at room temperature for another 10 minutes. The ethanolic solution described above is added to this reaction mixture, and the mixture is stirred at a bath temperature of 70° C. for 4 hours. After filtration, the mixture is concentrated, the residue is partitioned between dichloromethane and water, the organic phase is dried over sodium sulphate and the solvent is reduced under reduced pressure.

This residue is dissolved in 60 ml of 1,2-dichloroethane and, after addition of 7.5 ml of phosphorus oxychloride, refluxed for 2 hours. The mixture is diluted with dichloromethane and neutralized by addition of sodium bicarbonate solution and solid sodium bicarbonate. The organic phase is dried and the solvent is removed under reduced pressure. Crystallization from ethyl acetate gives 2.85 g (19.1%) of a yellow solid, chromatographic purification of the mother liquor gives a further 1.25 g (8.4%) of the product. $R_f$=0.45 (dichloromethane/methanol=95:5)

200 MHz ¹H-NMR (CDCl₃): 1.03, t, 3H, 1.15, t, 3H, 1.92, m, 4H, 2.67, s, 3H, 3.01, t, 2H, 4.17, t, 2H, 7.09, m, 2H, 7.50, dt, 1H, 8.17, dd, 1H, 10.02, s, 1H.

EXAMPLE 12A 2-(2-Ethoxy-4-methoxyphenyl)-5-methyl-7-propyl-3H-imidazo[5,1-j][1,2,4]triazin-4-one

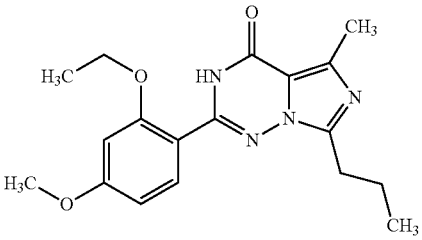

5.50 g (34.8 mmol) of 2-butyrylaminopropionic acid and 8.19 g of pyridine are dissolved in 35 ml of tetrahydrofuran and, after addition of a spatula tip of dimethylaminopyridine, heated to reflux. 9.43 g (69 mmol) of ethyl oxalyl chloride are slowly added dropwise, and the reaction mixture is refluxed for 3 hours. The mixture is poured into ice-water and extracted three times with ethyl acetate, and the organic phase is dried over sodium sulphate and concentrated using a rotary evaporator. The residue is taken up in 11 ml of methanol and refluxed with 1.65 g of sodium bicarbonate for 2.5 hours. The cooled solution is filtered.

With ice-cooling, 1.73 g (34.5 mmol) of hydrazine hydrate are added dropwise to a solution of 7.95 g (34.5 mmol) of 2-ethoxy-4-methoxybenzamidine hydrochloride in 35 ml of ethanol, and the resulting suspension is stirred at room temperature for another 30 minutes. The methanolic solution described above is added to this reaction mixture, and the mixture is stirred at a bath temperature of 70° C. for 4 hours. After filtration, the mixture is concentrated, the residue is partitioned between dichloromethane and water, the organic phase is dried over sodium sulphate and the solvent is removed under reduced pressure.

This residue is dissolved in 46 ml of 1,2-dichloroethane and, after addition of 5.74 ml of phosphorus oxychloride, refluxed for 2 hours. The mixture is diluted with dichloromethane and neutralized by addition of sodium bicarbonate solution and solid sodium bicarbonate. The organic phase is dried and the solvent is removed under reduced pressure. Chromatography (dichloromethane:methanol=50:1) gives 0.31 g (2.5%) of a solid.

$R_f$=0.46 (dichloromethane:methanol=20:1)

200 MHz ¹H-NMR (CDCl₃): 1.03, t, 3H, 1.58, t, 3H, 1.88, m, 2H, 2.62, s, 3H, 2.98, t, 2H, 3.89, s, 3H, 4.25, quart., 2H, 6.54, d, 1H, 6.67, dd, 1H, 8.14, d, 1H; 9.54, s, 1H.

EXAMPLE 13A 2-(2-Ethoxyphenyl)-5-ethyl-7-propyl-3H-imidazo[5,1-f][1,2,4]triazin-4-one

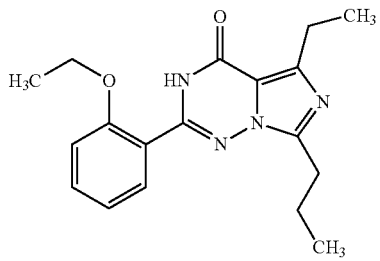

29.06 g (167.8 mmol) of 2-butyrylaminobutyric acid and 39.76 g of pyridine are dissolved in 170 ml of tetrahydrofuran and, after addition of a spatula tip of dimethylaminopyridine, heated to reflux. 45.81 g (335.5 mmol) of ethyl oxalyl chloride are slowly added dropwise, and the reaction mixture is refluxed for 3 hours. The mixture is poured into ice-water and extracted three times with ethyl acetate, and the organic phase is dried over sodium sulphate and concentrated using a rotary evaporator. The residue is taken up in 15 ml of methanol, and half of the solution is refluxed with 7.96 g of sodium bicarbonate for 2.5 hours. The cooled solution is filtered.

With ice-cooling, 4.20 g (83.9 mmol) of hydrazine hydrate are added dropwise to a solution of 16.83 g (83.9 mmol) of 2-ethoxybenzamidine hydrochloride in 85 ml of ethanol, and the resulting suspension is stirred at room temperature for another 10 minutes. The methanolic solution described above is added to this reaction mixture, and the mixture is stirred at a bath temperature of 70° C. for 4 hours. After filtration, the mixture is concentrated, the residue is partitioned between dichloromethane and water, the organic phase is dried over sodium sulphate and the solvent is removed under reduced pressure.

This residue is dissolved in 112 ml of 1,2-dichloroethane and, after addition of 1.4 ml of phosphorus oxychloride, refluxed for 2 hours. The mixture is diluted with dichloromethane and neutralized by addition of sodium bicarbonate solution and solid sodium bicarbonate. The organic phase is dried and the solvent is removed under reduced pressure. Chromatography (dichloromethane:methanol=50:1) gives 3.69 g (12.4%) of a colourless solid, $R_f$=0.46 (dichloromethane:methanol=20:1)

200 MHz $^1$H-NMR (CDCl$_3$): 1.32, t, 3H, 1.57, t, 3H, 1.94, m, 8H, 3.03, quart., 2H, 3.64, quin., 1H; 4.27, quart., 2H, 7.06, d, 1H; 7.12, t, 1H, 7.50, dt, 1H, 8.16, dd, 1H; 9.91, s, 1H.

EXAMPLE 14A

4-Ethoxy-3-(5,7-dimethyl-4-oxo-3,4-dihydroimidazo[5,1-f][1,2,4]triazin-2-yl)-benzenesulphonyl chloride

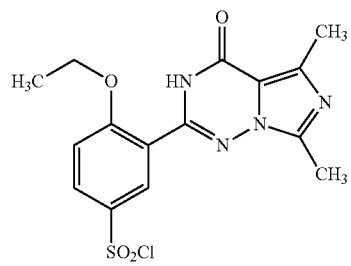

7.25 g (25.5 mmol) of 2-(2-ethoxyphenyl)-5,7-dimethyl-3H-imidazo[5,1-f][1,2,4]-triazin-4-one are initially charged, and 26.74 g (0.23 mol) of chlorosulphonic acid are added with ice-cooling. The mixture is stirred at room temperature overnight and poured into ice-water, and the crystals are filtered off with suction and dried in a vacuum desiccator.

Yield: 9.5 g (97% of theory)

200 MHz $^1$H-NMR (d$^6$-DMSO): 1.32, t, 3H, 2.63, s, 3H, 2.73, s, 3H, 4.13, q, 2H, 7.15, d, 1H, 7.77, m, 2H, 12.5, s, 1H;

EXAMPLE 15A

4-Ethoxy-3-(5-methyl-4-oxo-7-propyl-3,4-dihydro-imidazo[5,1-f][1,2,4]triazin-2-yl)-benzenesulphonyl chloride

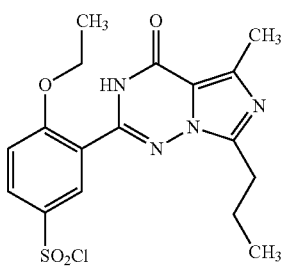

At 0° C., 2.00 g (6.4 mmol) of 2-(2-ethoxy-phenyl)-5-methyl-7-propyl-3H-imidazo[5,1-f][1,2,4]triazin-4-one are slowly added to 3.83 ml of chlorosulphonic acid. At room temperature, the reaction mixture is stirred overnight, and then poured into ice-water and extracted with dichloromethane. This gives 2.40 g (91%) of a colourless foam.

200 MHz $^1$H-NMR (CDCl$_3$): 1.03, t, 3H, 1.61, t, 2H, 1.92, hex, 2H, 2.67, s, 3H, 3.10, t, 2H, 4.42, quart., 2H, 7.27, t, 1H; 8.20, dd, 1H, 8.67, d, 1H, 10.18, s, 1H.

EXAMPLE 16A

4-Propoxy-3-(5-methyl-4-oxo-7-propyl-3,4-dihydro-imidazo[5,1-f][1,2,4]triazin-2-yl)-benzenesulphonyl chloride

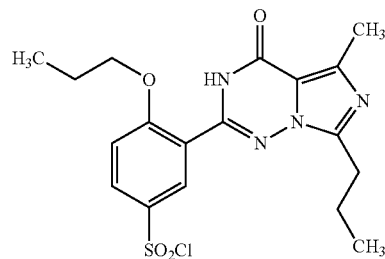

At 0° C., 2.80 g (8.6 mmol) of 2-(2-propoxy-phenyl)-5-methyl-7-propyl-3H-imidazo[5,1-f][1,2,4]triazin-4-one are added slowly to 5.13 ml of chlorosulphonic acid. The reaction mixture is stirred at room temperature overnight and then poured into ice-water and extracted with dichloromethane. This gives 3.50 g (96%) of a colourless foam.

$R_f$=0.49 (dichloromethane/methanol=95:5)

200 MHz $^1$H-NMR (CDCl$_3$): 1.03, 2t, 6H, 1.95, m, 4H, 2.81, s, 3H, 3.22, t, 2H, 4.11, t, 2H, 7.09, m, 1H, 8.06, dd, 1H, 8.21 m, 1H, 12.0, s, 1H.

EXAMPLE 17A

4-Ethoxy-2-methoxy-5-(5-methyl-4-oxo-7-propyl-3,4-dihydroimidazo[5,1-f][1,2,4]triazin-2-yl)-benzene-sulphonyl cloride

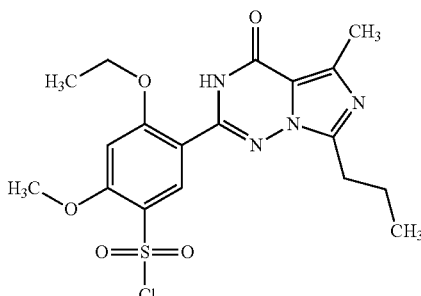

At 0° C., 0.31 g (0.9 mmol) of 2-(2-ethoxy-4-methoxyphenyl)-5-methyl-7-propyl-3H-imidazo[5,1-f]-[1,2,4]triazin-4-one are added slowly to 0.54 ml of chlorosulphonic acid. The reaction mixture is stirred at room temperature overnight and then poured into ice-water and extracted with dichloromethane. This gives 0.355 g (89%) of a colourless foam.

$R_f$=0.50 (dichloromethane/methanol=20:1)

200 MHz $^1$H-NMR (CDCl$_3$): 1.05, t, 3H, 1.66, t, 3H, 1.95, m, 2H, 2.61, s, 3H, 3.11, t, 2H, 4.15, s, 3H, 4.40, quart., 2H, 6.65, s, 1H, 8.72, s, 1H, 9.75, s, 1H.

EXAMPLE 18A

4-Ethoxy-3-(5-ethyl-4-oxo-7-propyl-3,4-dihydroimidazo[5,1-f][1,2,4]triazin-2-yl)-benzene-sulphonyl chloride

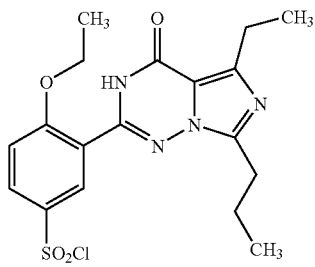

At 0° C., 1.70 g (5.21 mmol) of 2-(2-ethoxy-phenyl)-5-ethyl-7-propyl-3H-imidazo[5,1-f][1,2,4]triazin-4-one are added slowly to 3.12 ml of chlorosulphonic acid. The reaction mixture is stirred at room temperature overnight and then poured into ice-water and extracted with dichloromethane. This gives 2.10 g (94%) of a colourless foam.

400 MHz $^1$H-NMR (CDCl$_3$): 1.03, t, 3H, 1.35, t, 3H, 1.62, t, 3H, 1.92, sex., 2H, 3.07, quart., 2H, 3.12, t, 2H, 4.42, quart., 2H, 7.38, d, 1H, 8.19, dd, 1H, 8.70, d, 1H, 10.08, s, broad, 1H.

EXAMPLE 19A

Diethyl (4-piperidinylmethyl)-phosphonate

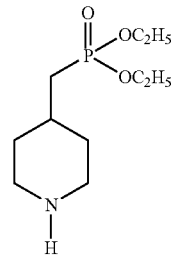

2.11 g (528 mmol) of 60% strength sodium hydride are initially charged in 50 ml of absolute tetrahydrofuran, and 15.7 g (52.8 mmol) of diethyl methanediphosphonate are added dropwise. The mixture is stirred at room temperature for another 30 minutes, and 10.1 g (52.8 mmol) of 1-benzyl-4-piperidone are then added. The mixture is stirred for one hour at room temperature and for one hour under reflux, concentrated, admixed with water and extracted three times with dichloromethane, and the organic phases are dried over sodium sulphate and concentrated. The residue is hydrogenated in 50 ml of ethanol over 1.7 g of 10% palladium-carbon at room temperature and 3 bar. The catalyst is filtered off with suction and the filtrate is concentrated.

Yield: 12.5 g (100% of theory)

400 MHz, $^1$H-NMR (CDCl$_3$): 1.13, m, 2H, 1.32, t, 6H, 1.69, dd, 2H, 1.74-1.95, m, 4H, 2.62, dt, 2H, 3.05, m, 2H, 4.1, m, 4H.

EXAMPLE 20A

5-Methyl-4-furoxanecarbaldehyde

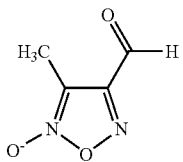

40 g (571 mmol) of crotonaldehyde are dissolved in 80 ml of acetic acid and, at 0° C., admixed dropwise with a solution of 137 g (1.99 mol) of sodium nitrite in 300 ml of water. The mixture is stirred at room temperature for 2 hours, diluted with 800 ml of water and extracted 3 times with dichloromethane. The organic phase is dried, and chromatography (cyclohexane/ethyl acetate) gives 13.8 g (18.9%) of 5-methyl-4-furoxanecarbaldehyde.

200 MHz $^1$H-NMR (CDCl$_3$): 2.39, s, 3H, 10.10, s, 1H.

EXAMPLE 21A

5-Methyl-4-furoxanecarbonyl chloride

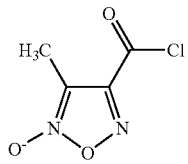

13.5 g (105 mmol) of 5-methyl-4-furoxanecarbaldehyde are dissolved in 200 ml of acetone and, at 0° C., admixed dropwise with a solution of 16.86 g (168 mmol) of chromium trioxide in 120 ml of a 2.2M sulphuric acid. The mixture is stirred at 10-15° C. for 2 hours and then at room temperature overnight. With cooling, 100 ml of isopropanol are added dropwise and, after 30 minutes, the solvent is removed under reduced pressure. The aqueous phase is extracted 3 times with ether, the organic phase is dried over magnesium sulphate and the solvent is removed under reduced pressure. The residue is dissolved in 1M sodium hydroxide solution and the solution is extracted 3 times with ether. The aqueous phase is acidified and extracted 3 times with ether. The organic phase is dried and the solvent is removed under reduced pressure. The residue is stirred with petroleum ether and filtered off with suction.

6.92 g of the residue are refluxed with 10 ml of thionyl chloride in 20 ml of dichloromethane for 6 hours. The mixture is diluted with toluene, filtered and concentrated using a rotary evaporator. The residue is once more taken up in dichloromethane, admixed with 10 ml of thionyl chloride and refluxed for 48 hours. The solvent is removed under reduced pressure and the residue is distilled under reduced pressure. This gives 2.00 g (25%) of colourless crystals.

200 MHz $^1$H-NMR (CDCl$_3$): 2.41, s.

EXAMPLE 22A 1-(5-Methyl-4-furoxanecarbonyl)-4-tert-butyl-oxycarbonyl-piperazine

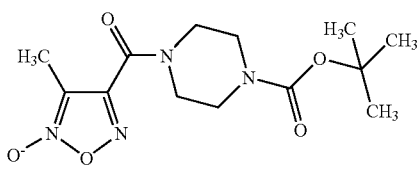

2.75 g (14.7 mmol) of Boc-piperazine and 1.49 g of triethylamine are dissolved in 20 ml of dichloromethane and, at 0° C., admixed a little at a time with 2.00 g (12.3 mmol) of 5-methyl-4-furoxanecarbonyl chloride. The mixture is stirred for 30 minutes at 0° C. and for 2 hours at room temperature, diluted with dichloromethane and washed with water. The solvent is removed under reduced pressure and the residue is purified by chromatography (cyclohexane/ethyl acetate). This gives 3.33 g (87%) of 1-(5-methyl-4-furoxanecarbonyl)-4-tert-butyl-oxycarbonyl-piperazine.

200 MHz $^1$H-NMR (CDCl$_3$): 1.50, s, 9H, 2.30, s, 3H, 3.55, m, 4H, 3.78, m, 2H, 3.87, m, 2H.

EXAMPLE 23A 1-(5-Methyl-4-furoxanecarbonyl)-piperazine trifluoroacetate

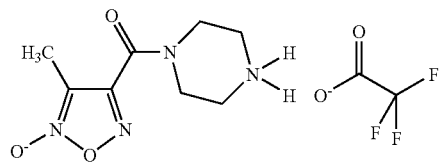

3.12 g (10 mmol) of 1-(5-methyl-4-furoxanecarbonyl)-4-tert-butyl-oxycarbonyl-piperazine are dissolved in 20 ml of dichloromethane and, at 0° C., admixed with 2 ml of trifluoroacetic acid. The mixture is allowed to warm to room temperature and stirred for 72 hours. After addition of 10 ml of ether, the precipitate is filtered off with suction and dried. This gives 2.47 g (83%) of 1-(5-methyl-4-furoxanecarbonyl)-piperazine trifluoroacetate.

200 MHz $^1$H-NMR (DMSO-d$_6$): 2.18, s, 3H, 3.18, m, 2H, 3.25, m, 2H, 3.83, m, 2H, 3.90, m, 2H, 8.89, s, broad, 2H.

PREPARATION EXAMPLES

Example 1

2-[2-Ethoxy-5-(4-methyl-piperazine-1-sulphonyl)-phenyl]-5,7-dimethyl-3H-imidazo[5,1-f]-[1,2,4]triazin-4-one

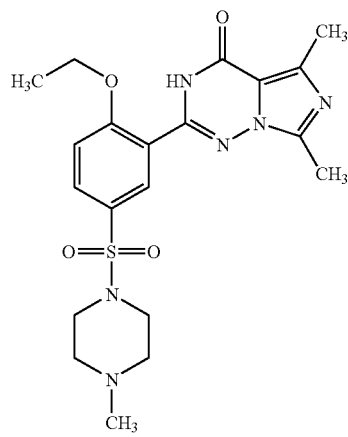

0.1 g (0.26 mmol) of 4-ethoxy-3-(5,7-dimethyl-4-oxo-3,4-dihydroimidazo-[5,1-f][1,2,4]triazin-2-yl)-benzenesulphonyl chloride are dissolved in 10 ml of dichloromethane and cooled to 0° C. After addition of a spatula tip of DMAP, 80 mg (0.784 mmol) of N-methylpiperazine are added and the reaction mixture is stirred at room temperature overnight. The mixture is diluted with dichloromethane, the organic phase is washed with ammonium chloride solution and dried over sodium sulphate and the solvent is removed under reduced pressure. The residue is chromatographed over silica gel (dichloromethane/methanol 9:1).

Yield: 40 mg (34.5% of theory)
Mass spectrum: 447 (M+H); 284; 256; 224.

Example 2

2-[2-Ethoxy-5-(4-hydroxyethylpiperazine-1-sulphonyl)-phenyl]-5,7-dimethyl-3H-imidazo[5,1-f]-[1,2,4]triazin-4-one

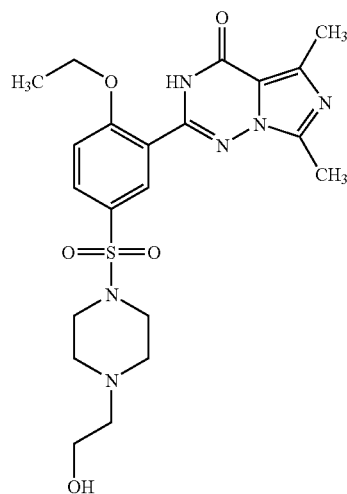

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 100 mg (0.784 mmol) of 4-hydroxypiperazine, 45 mg (36.1% of theory) of 2-[2-ethoxy-5-(4-hydroxy-ethylpiperazine-1-sulphonyl)-phenyl]-5,7-dimethyl-3H-imidazo[5,1-f]-[1,2,4]triazin-4-one are obtained.
Mass spectrum: 477 (M+H); 284; 256; 239.

Example 3

2-[2-Ethoxy-5-(4-hydroxypiperidine-1-sulphonyl)-phenyl]-5,7-dimethyl-3H-imidazo[5,1-f]-[1,2,4]triazin-4-one

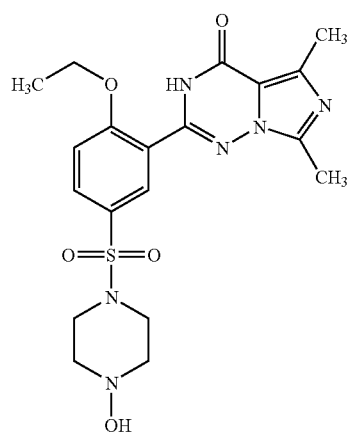

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 80 mg (0.784 mmol) of 4-hydroxypiperidine, 35 mg (29.8% of theory) of 2-[2-ethoxy-5-(4-hydroxy-piperidine-1-sulphonyl)-phenyl]-5,7-dimethyl-3H-imidazo[5,1-f]-[1,2,4]triazin-4-one are obtained.
200 MHz $^1$H-NMR (CDCl$_3$): 1.61, t, 3H, 1.69, m, 2H, 1.94, m, 2H, 2.67, s, 3H, 2.70, s, 3H, 3.02, m, 2H, 3.30, m, 2H, 3.84, m, 1H, 4.37, q, 2H, 7.18, d, 1H, 7.90, dd, 1H, 8.52, d, 1H, 9.73, s, 1H.

Example 4

2-[2-Ethoxy-5-(4-hydroxymethylpiperidine-1-sulphonyl)-phenyl]-5,7-dimethyl-3H-imidazo[5,1-f][1,2,4]triazin-4-one

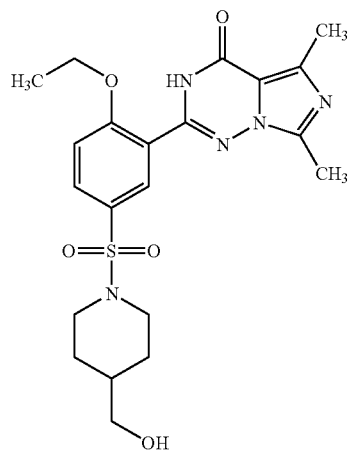

By the same method, starting with 100 mg (0.261 mmol) of 4-ethoxy-3-(5,7-dimethyl-4-oxo-3,4-dihydroimidazo[5,1-][1,2,4]triazin-2-yl)-benzenesulphonyl chloride and 90 mg (0.784 mmol) of 4-hydroxymethylpiperidine, 22 mg (18% of theory) of 2-[2-ethoxy-5-(4-hydroxy-methylpiperidine-1-sulphonyl)-phenyl]-5,7-dimethyl-3H-imidazo[5,1-f][1,2,4]triazin-4-one are obtained.
200 MHz $^1$H-NMR (CDCl$_3$): 1.38, dt, 2H, 1.62, t, 3H, 1.82, dd, 2H, 2.35, dt, 2H, 2.78, s, 3H, 2.84, s, 3H, 3.5, d, 2H, 3.87, d, 2H, 4.39, q, 2H, 7.21, d, 1H, 7.95, dd, 1H, 8.51, d, 1H, 10.03, bs, 1H.

Example 5

2-[2-Ethoxy-5-(3-hydroxypyrrolidine-1-sulphonyl)-phenyl]-5,7-dimethyl-3H-imidazo[5,1-f]-[1,2,4]triazin-4-one

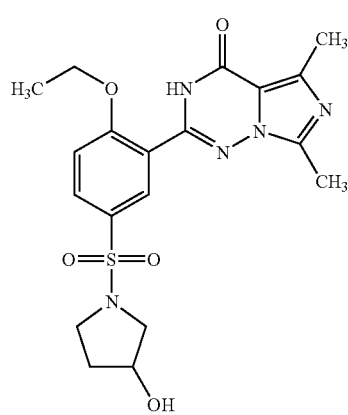

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 70 mg (0.784 mmol) of 3-hydroxypyrrolidine, 13 mg (11.1% of theory) of 2-[2-ethoxy-5-(3-hydroxy-pyrrolidine-1-sulphonyl)-phenyl]-5,7-dimethyl-3H-imidazo-[5,1-f][1,2,4]triazin-4-one are obtained.

Mass spectrum: 434 (M+H)

Example 6

4-Ethoxy-N-ethyl-N-(2-hydroxyethyl)-3-(5,7-dimethyl-4-oxo-3,4-dihydro-imidazo[5,1-f]-[1,2,4]triazin-2-yl)benzenesulphonamide

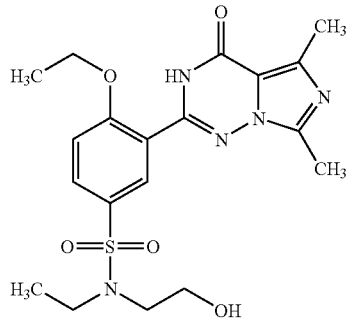

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 70 mg (0.784 mmol) of 2-(ethylamino)-ethanol, 23 mg (20.1% of theory) of 4-ethoxy-N-ethyl-N-(2-hydroxyethyl)-3-(5,7-dimethyl-4-oxo-3,4-dihydroimidazo-[5,1-f][1,2,4]triazin-2-yl)-benzene-sulphonamide are obtained.

200 MHz $^1$H-NMR (CDCl$_3$): 1.2, t, 3H, 1.6, t, 3H, 2.17, bs, 1H, 2.69, s, 3H, 2.75, s, 3H, 3.33, m, 4H, 3.8, t, 2H, 4.36, q, 2H, 7.18, d, 1H, 7.99, dd, 1H, 8.6, d, 1H, 9.84, bs, 1H.

Example 7

N,N-Diethyl-4-ethoxy-3-(5,7-dimethyl-4-oxo-3,4-dihydroimidazo[5,1-f][1,2,4]triazin-2-yl)-benzene-sulphonamide

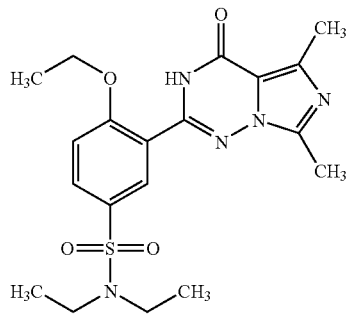

By the same method, starting with 100 mg (0.261 mmol) of 4-ethoxy-3-(5,7-dimethyl-4-oxo-3,4-dihydroimidazo[5,1-f][1,2,4]triazin-2-yl)-benzene-sulphonyl chloride and 60 mg (0.784 mmol) of diethylamine, 21 mg (18.6% of theory) of N,N-diethyl-4-ethoxy-3-(5,7-dimethyl-4-oxo-3,4-dihydro-imidazo[5,1-f][1,2,4]triazin-2-yl)-benzenesulphonamide are obtained.

200 MHz $^1$H-NMR (CDCl$_3$): 1.18, t, 6H, 1.61, t, 3H, 2.68, s, 3H, 2.72, s, 3H, 3.29, q, 4H, 4.35, q, 2H, 7.15, d, 1H, 7.95, dd, 1H, 8.58, d, 1H, 9.8, bs, 1H.

Example 8

2-[2-Ethoxy-5-(4-(2-pyrimidinyl)-piperazine-1-sulphonyl)-phenyl]-5,7-dimethyl-3H-imidazo-[5,1-f][1,2,4]triazin-4-one

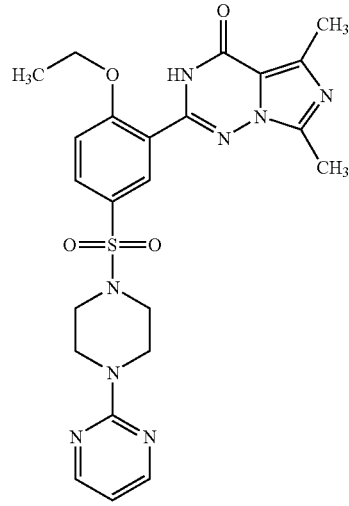

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 130 mg (0.784 mmol) of 1-(2-pyrimidinyl)-piperazine, 38 mg (28.2% of theory) of 2-[2-ethoxy-5-(4-(2-pyrimidinyl)-piperazine-1-sulphonyl)-phenyl]-5,7-dimethyl-3H-imidazo-[5,1-f][1,2,4]triazin-4-one are obtained.

200 MHz $^1$H-NMR (CDCl$_3$): 1.6, t, 3H, 2.68, s, 3H, 2.72, s, 3H, 3.12, t, 4H, 3.96, t, 4H, 4.34, q, 2H, 6.5, t, 1H, 7.18, d, 1H, 7.9, dd, 1H, 8.28, d, 2H, 8.51, d, 1H; 9.7, bs, 1H.

Example 9

2-[2-Ethoxy-5-(morpholine-4-sulphonyl)-phenyl]-5,7-dimethyl-3H-imidazo[5,1-f][1,2,4]triazin-4-one

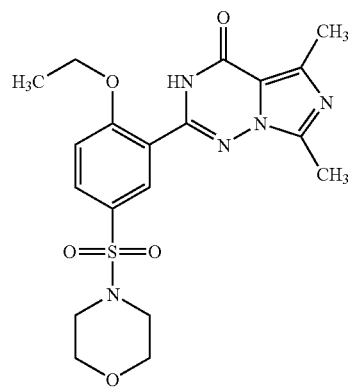

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 70 mg (0.784 mmol) of morpholine, 28 mg (24.2% of theory) of 2-[2-ethoxy-5-(morpholine-4-sulphonyl)-phenyl]-5,7-dimethyl-3H-imidazo[5,1-f][1,2,4]triazin-4-one are obtained.

200 MHz $^1$H-NMR (CDCl$_3$): 1.53, t, 3H, 2.69, s, 3H, 2.72, s, 3H, 3.06, t, 4H, 3.77, t, 4H, 4.39, q, 2H, 7.2, d, 1H, 7.91, dd, 1H, 8.51, d, 1H, 9.78, bs, 1H.

Example 10

2-[2-Ethoxy-5-(1,4-dioxa-6-azaspiro[4.4]nonane-6-sulphonyl)-phenyl]-5,7-dimethyl-3H-imidazo[5,1-f][1,2,4]triazin-4-one

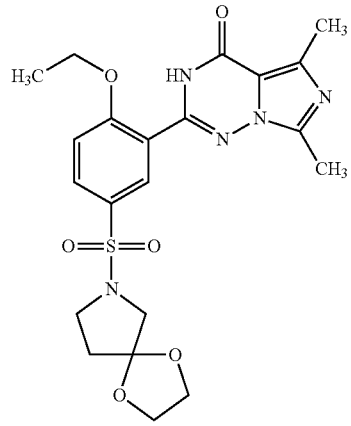

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 100 mg (0.784 mmol) of 1,4-dioxa-6-azaspiro[4.4]nonane, 45 mg (35.3% of theory) of 2-[2-ethoxy-5-(1,4-dioxa-6-azaspiro[4.4]nonane-6-sulphonyl)-phenyl]-5,7-dimethyl-3H-imidazo[5,1-f][1,2,4]-triazin-4-one.

200 MHz $^1$H-NMR (CDCl$_3$): 1.58, t, 3H, 2.02, t, 2H, 2.61, s, 3H, 2.65, s, 3H, 3.32, s, 2H, 3.41, t, 2H, 3.88, m, 4H, 4.34, q, 2H, 7.17, d, 1H, 7.92, dd, 1H, 8.51, d, 1H, 9.92, bs, 1H.

Example 11

N,N-Bis-(2-methoxyethyl)-4-ethoxy-3-(5,7-dimethyl-4-oxo-3,4-dihydro-imidazo[5,1-]-[1,2,4]triazin-2-yl)-benzenesulphonamide

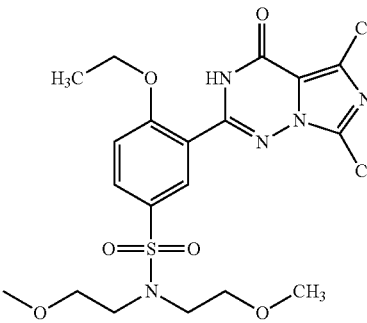

By the same method, starting with 100 mg (0.261 mmol) of 4-ethoxy-3-(5,7-dimethyl-4-oxo-3,4-dihydroimidazo[5,1-f][1,2,4]triazin-2-yl)-benzene-sulphonyl chloride and 100 mg (0.784 mmol) of bis-(2-methoxyethyl)-amine, 37 mg (27.5% of theory) of N,N-bis-(2-methoxy-ethyl)-4-ethoxy-3-(5,7-dimethyl-4-oxo-3,4-dihydroimidazo[5,1-f][1,2,4]triazin-2-yl)-benzenesulphonamide are obtained.

200 MHz $^1$H-NMR (CDCl$_3$): 1.58, t, 3H, 2.61, s, 3H, 2.64, s, 3H, 3.3, s, 6H, 3.46, t, 4H, 3.56, t, 4H, 4.32, q, 2H, 7.12, d, 1H, 7.95, dd, 1H, 8.51, d, 1H, 9.9, bs, 1H

Example 12

N-(3-Isoxazolyl)-4-ethoxy-3-(5,7-dimethyl-4-oxo-3,4-dihydro-imidazo[5,1-f][1,2,4]triazin-2-yl)-benzenesulphonamide

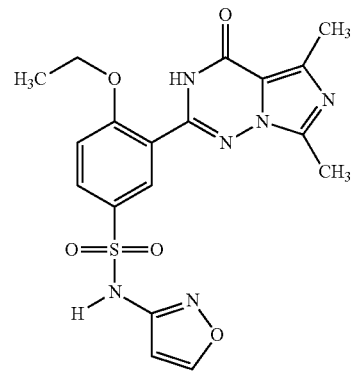

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 70 mg (0.784 mmol) of 3-aminoisoxazol, 20 mg (17.2% of theory) N-(3-isoxazolyl)-4-ethoxy-3-(5,7-dimethyl-4-oxo-3,4-dihydroimidazo[5,1-f][1,2,4]triazin-2-yl)-benzenesulphonamide are obtained.

200 MHz $^1$H-NMR (CDCl$_3$): 1.6, t, 3H, 2.73, s, 3H, 2.81, s, 3H, 4.35, q, 2H, 6.6, d, 1H, 7.14, d, 1H, 8.05, dd, 1H, 8.27, d, 1H, 8.63, d, 1H, 9.61, bs, 1H.

Example 13

2-[2-Ethoxy-5-(2-t-butoxycarbonylaminomethylmorpholine-4-sulphonyl)-phenyl]-5,7-dimethyl-3H-imidazo[5,1-f][1,2,4]triazin-4-one

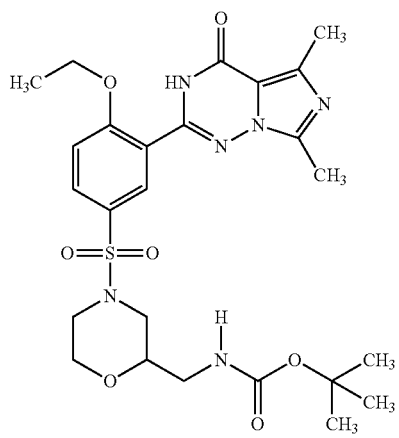

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 170 mg (0.784 mmol) of 2-t-butoxycarbonyl-aminomethylmorpholine, 64 mg (42.2% of theory) of 2-[2-ethoxy-5-(2-t-butoxycarbonylaminomethylmorpholine-4-sulphonyl)-phenyl]-5,7-dimethyl-3H-imidazo[5,1-f][1,2,4]triazin-4-one are obtained.

Mass spectrum: 563 (M+H)

Example 14

2-[2-Ethoxy-5-(4-phenylpiperazine-1-sulphonyl)-phenyl]-5,7-dimethyl-3H-imidazo[5,1-f]-[1,2,4]triazin--one

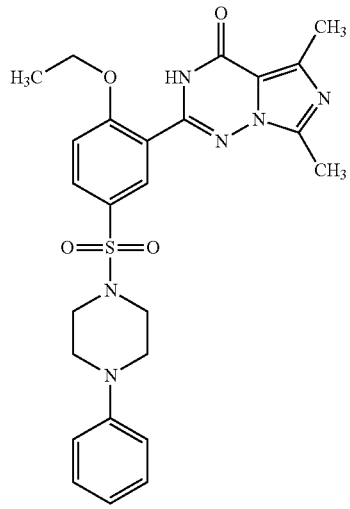

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 130 mg (0.784 mmol) of 1-phenylpiperazine, 38 mg (28.3% of theory) of 2-[2-ethoxy-5-(4-phenylpiperazine-1-sulphonyl)-phenyl]-5,7-dimethyl-3H-imidazo[5,1-f][1,2,4]triazin-4-one are obtained.

200 MHz $^1$H-NMR (CDCl$_3$): 1.62, t, 3H, 2.72, s, 3H, 2.77, s, 3H, 3.25, m, 8H, 4.38, q, 2H, 6.92, m, 2H, 7.02, d, 1H, 7.18-7.37, m, 3H, 7.94, dd, 1H, 8.55, m, 1H, 9.79, bs, 1H.

Example 15

2-[2-Ethoxy-5-(3-hydroxy-3-methoxymethylpyrrolidine-1-sulphonyl)-phenyl]-5,7-dimethyl-3H-imidazo[5,1-f][1,2,4]triazin-4-one

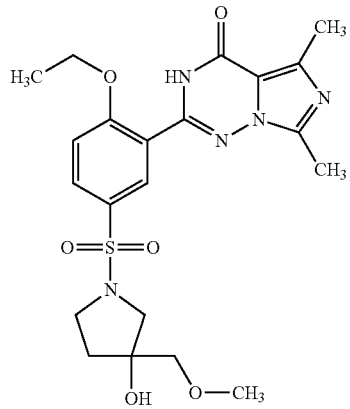

By the same method, starting with 100 mg (0.261 mmol) of 4-ethoxy-3-(5,7-dimethyl-4-oxo-3,4-dihydroimidazo[5,1-f][1,2,4]triazin-2-yl)-benzenesulphonyl chloride and 100 mg (0.784 mmol) of 3-hydroxy-3-methoxymethylpyrrolidine, 30 mg (23.5% of theory) of 2-[2-ethoxy-5-(3-hydroxy-3-methoxymethylpyrrolidine-1-sulphonyl)-phenyl]-5,7-dimethyl-3H-imidazo[5,1-f][1,2,4]triazin-4-one are obtained.

Mass spectrum: 478 (M+H)

Example 16

2-[2-Ethoxy-5-(4-methyl-piperazine-1-sulphonyl)-phenyl]-5-methyl-7-propyl-3H-imidazo[5,1-f][1,2,4]triazin-4-one

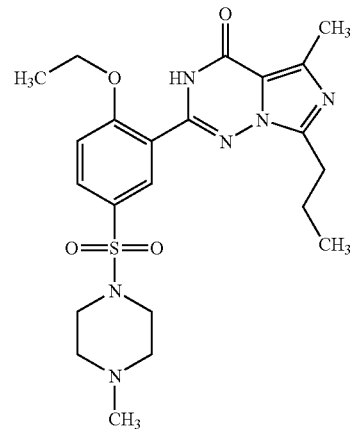

1.23 g (3 mmol) of 4-ethoxy-3-(5-methyl-4-oxo-7-propyl-3,4-dihydro-imidazo[5,1-f][1,2,4]triazin-2-yl)-benzenesulphonyl chloride are dissolved in 40 ml of dichloromethane and cooled to 0° C. After addition of a spatula tip of DMAP, 0.90 g (9.00 mmol) of N-methylpiperazine are added, and the reaction mixture is stirred at room temperature overnight. The mixture is diluted with dichloromethane, the organic phase is washed twice with water and dried over sodium sulphate and the solvent is removed under reduced pressure. Crystallization from ether gives 1.25 g (88%) of a colourless solid.

200 MHz $^1$H-NMR (CDCl$_3$): 1.01, t, 3H, 1.59, t, 3H, 1.88, hex, 2H, 2.29, s, 3H, 2.51, m, 4H, 2.63, s, 3H, 3.00, t, 2H, 3.08, m, 4H, 4.33, quart., 2H, 7.17, d, 1H, 7.88, dd, 1H, 8.44, d, 1H, 9.75, s, 1H.

Example 17

2-[2-Ethoxy-5-(4-methyl-piperazine-1-sulphonyl)-phenyl]-5-methyl-7-propyl-3H-imidazo[5,1-f][1,2,4]triazin-4-one lactate

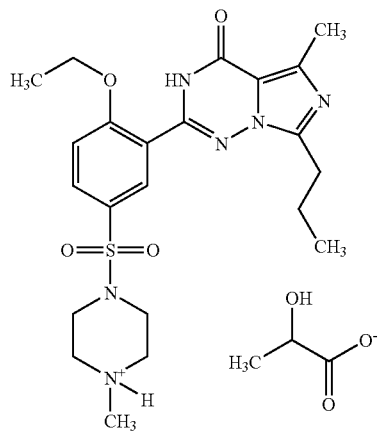

100 mg (0.211 mmol) of 2-[2-ethoxy-5-(4-methyl-piperazine-1-sulphonyl)-phenyl]-5-methyl-7-propyl-3H-imidazo[5,1-f][1,2,4]triazin-4-one are suspended in 5 ml of ether and admixed with 20 mg of an 85% strength solution of lactic acid in water. The mixture is stirred at room temperature for 10 minutes and evaporated to dryness. The residue is titrated with ether and filtered off with suction. This gives 110 mg (92%) of 2-[2-ethoxy-5-(4-methyl-piperazine-1-sulphonyl)-phenyl]-5-methyl-7-propyl-3H-imidazo[5,1-f][1,2,4]triazin-4-one lactate.

200 MHz $^1$H-NMR (DMSO-$d_6$): 0.92, t, 3H, 1.22, d, 3H, 1.31, t, 3H, 1.74, m, 1H, 2.15, s, 3H, 2.38, m, 4H, 2.81, t, 2H, 2.91, m, 4H, 4.05, quart., 1H, 4.21, quart., 2H, 7.40, d, 1H; 7.85, m, 2H, 11.71, s, broad, 1H.

Example 18

2-[2-Ethoxy-5-(4-methyl-piperazine-1-sulphonyl)-phenyl]-5-methyl-7-propyl-3H-imidazo[5,1-f][1,2,4]triazin-4-one hydrochloride

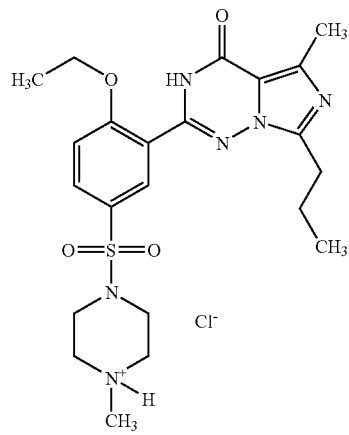

100 mg (0.211 mmol) of 2-[2-ethoxy-5-(4-methyl-piperazine-1-sulphonyl)-phenyl]-5-methyl-7-propyl-3H-imidazo[5,1-f][1,2,4]triazin-4-one are suspended in 5 ml of diethyl ether, admixed with 0.23 ml of a 1M solution of HCl in ether and stirred at room temperature for 15 minutes. The solvent is removed under reduced pressure. This gives 107 mg (97%) of 2-[2-ethoxy-5-(4-methyl-piperazine-1-sulphonyl)-phenyl]-5-methyl-7-propyl-3H-imidazo[5,1-f][1,2,4]triazin-4-one hydrochloride.

200 MHz $^1$H-NMR (DMSO-$d_6$): 0.93, t, 3H, 1.35, t, 3H, 1.75, sex., 2H, 2.72, s, 3H, 2.86, m, 4H, 3.15, m, 2H, 3.45, m, 2H, 3.81, m, 2H, 4.25, quart., 2H, 7.45, d, 1H, 7.95, m, 2H, 11.39, s, 1H, 11.90, s, 1H.

Example 19

2-[2-Ethoxy-5-(4-ethyl-piperazine-1-sulphonyl)-phenyl]-5-methyl-7-propyl-3H-imidazo[5,1-f][1,2,4]triazin-4-one

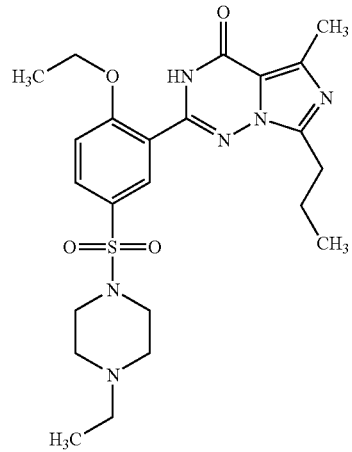

470 mg (1.14 mmol) of 4-ethoxy-3-(5-methyl-4-oxo-7-propyl-3,4-dihydro-imidazo[5,1-f][1,2,4]triazin-2-yl)-benzenesulphonyl chloride are dissolved in 20 ml of dichloromethane and cooled to 0° C. 390 mg (3.42 mmol) of N-ethylpiperazine are added, and the reaction mixture is stirred at room temperature overnight. The mixture is diluted with dichloromethane, the organic phase is washed twice with water and dried over sodium sulphate and the solvent is removed under reduced pressure. Crystallization from ether gives 370 mg (66%) of a colourless solid.

400 MHz $^1$H-NMR (CDCl$_3$): 1.01, t, 3H, 1.59, t, 3H, 1.88, hex, 2H, 2.42, quart., 2H, 2.56, m, 4H, 2.63, s, 3H, 3.00, t, 2H, 3.10, m, 4H; 4.33, quart., 2H, 7.17, d, 1H, 7.88, dd, 1H, 8.44, d, 1H, 9.75, s, 1H.

Example 20

2-[2-Ethoxy-5-(4-ethyl-piperazine-1-sulphonyl)-phenyl]-5-methyl-7-propyl-3H-imidazo[5,1-f][1,2,4]triazin-4-one hydrochloride

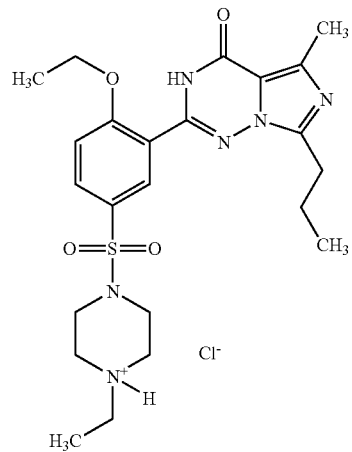

0.35 g (0.712 mmol) of 2-[2-ethoxy-5-(4-ethyl-piperazine-1-sulphonyl)-phenyl]-5-methyl-7-propyl-3H-imidazo[5,1-f][1,2,4]triazin-4-one are suspended in 8 ml of ether and dichloromethane is added until a homogeneous solution is formed. 0.8 ml of a 1M solution of HCl in ether is added, and the mixture is stirred at room temperature for 20 minutes and filtered off with suction. This gives 372 mg (99%) of 2-[2-ethoxy-5-(4-ethyl-piperazine-1-sulphonyl)-phenyl]-5-methyl-7-propyl-3H-imidazo[5,1-f][1,2,4]triazin-4-one hydrochloride.

200 MHz $^1$H-NMR (DMSO-$d_6$): 0.96, t, 3H, 1.22, t, 3H, 1.36, t, 3H, 1.82, sex., 2H, 2.61, s, 3H, 2.88, m, 2H, 3.08, m, 6H, 3.50, m, 2H, 3.70, m, 2H, 4.25, quart., 2H, 7.48, d, 1H, 7.95, m, 2H, 11.42, s, 1H, 12.45, s, 1H.

Example 21

2-[2-Ethoxy-5-(4-methyl-1-amino-piperazine-1-sulphonyl)-phenyl]-5-methyl-7-propyl-3H-imidazo[5,1-f][1,2,4]triazin-4-one

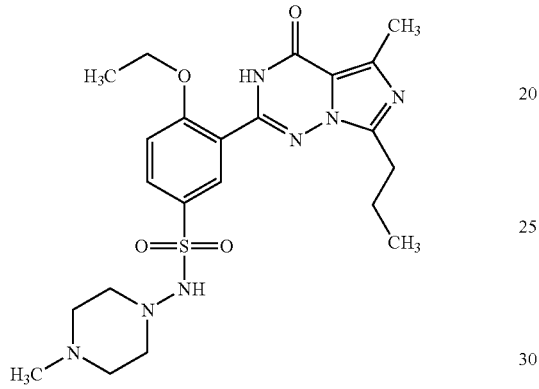

By the same method, starting with 0.04 g (0.097 mmol) of 4-ethoxy-3-(5-methyl-4-oxo-7-propyl-3,4-dihydro-imidazo[5,1-f][1,2,4]triazin-2-yl)-benzenesulphonyl chloride and 0.03 g (0.29 mmol) of 1-amino-4-methylpiperazine, 40 mg (83%) of 2-[2-ethoxy-5-(4-methyl-1-amino-piperazine-1-sulphonyl)-phenyl]-5-methyl-7-propyl-3H-imidazo[5,1-f][1,2,4]triazin-4-one are obtained.

$R_f$=0.09 (dichloromethane/methanol=19:1)

200 MHz $^1$H-NMR (CDCl$_3$): 1.02, t, 3H, 1.59, t, 3H, 1.90, sex., 2H, 2.22, s, 3H, 2.40, m, 4H, 2.62, s, 3H, 2.71, m, 4H, 3.00, m, 2H, 4.32, quart., 2H, 7.14, d, 1H, 8.05, dd, 1H, 8.60, d, 1H.

Example 22

2-[2-Ethoxy-5-(4-hydroxyethyl-1-amino-piperazine-1-sulphonyl)-phenyl]-5-methyl-7-propyl-3H-imidazo[5,1-f][1,2,4]triazin-4-one

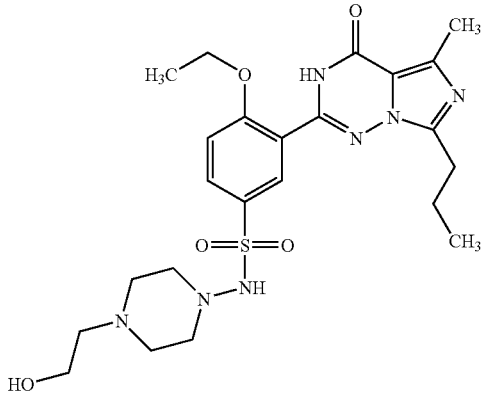

By the same method, starting with 0.04 g (0.097 mmol) of 4-ethoxy-3-(5-methyl-4-oxo-7-propyl-3,4-dihydro-imidazo[5,1-f][1,2,4]triazin-2-yl)-benzenesulphonyl chloride and 0.04 g (0.29 mmol) of 1-amino-4-hydroxyethylpiperazine, 46 mg (91%) of 2-[2-ethoxy-5-(4-hydroxyethyl-1-amino-piperazine-1-sulphonyl)-phenyl]-5-methyl-7-propyl-3H-imidazo[5,1-f][1,2,4]triazin-4-one are obtained.

$R_f$=0.08 (dichloromethane/methanol=19:1)

200 MHz $^1$H-NMR (CDCl$_3$): 1.02, t, 3H, 1.59, t, 3H, 1.90, sex., 2H, 2.49, m, 6H, 2.62, s, 3H, 2.71, m, 4H, 3.00, t, 2H, 3.55, t, 2H, 4.31, quart., 2H, 7.14, d, 1H, 8.05, dd, 1H, 8.60, d, 1H.

Example 23

2-[2-Ethoxy-5-(N,N-bishydroxyethyl-1-sulphonyl)-phenyl]-5-methyl-7-propyl-3H-imidazo[5,1-f][1,2,4]triazin-4-one

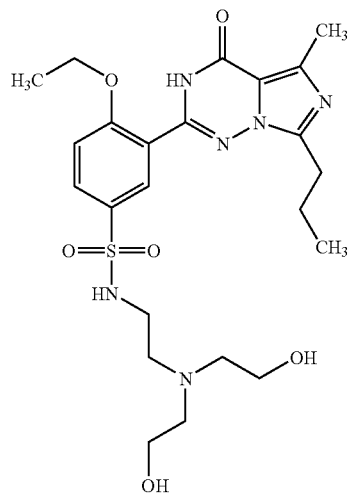

By the same method, starting with 0.04 g (0.097 mmol) of 4-ethoxy-3-(5-methyl-4-oxo-7-propyl-3,4-dihydro-imidazo[5,1-f][1,2,4]triazin-2-yl)-benzenesulphonyl chloride and 0.04 g (0.29 mmol) of 1-amino-4-hydroxyethylpiperazine, 46 mg (91%) of 2-[2-ethoxy-5-(N,N-bishydroxyethyl-1-sulphonyl)-phenyl]-5-methyl-7-propyl-3H-imidazo[5,1-f][1,2,4]triazin-4-one are obtained.

$R_f$=0.08 (dichloromethane/methanol=19:1)

200 MHz $^1$H-NMR (CDCl$_3$): 1.02, t, 3H, 1.53, t, 3H, 1.70, m, 2H, 1.86, sex., 2H, 2.9, m, 9H, 2.95, t, 2H, 3.09, t, 2H, 3.65, t, 4H, 4.28, quart., 2H, 7.14, d, 1H, 7.95, dd, 1H, 8.35, d, 1H.

Example 24

2-[2-Ethoxy-5-(4-dimethoxyphosphorylmethyl-piperazine-1-sulphonyl)-phenyl]-5-methyl-7-propyl-3H-imidazo[5,1-f][1,2,4]triazin-4-one

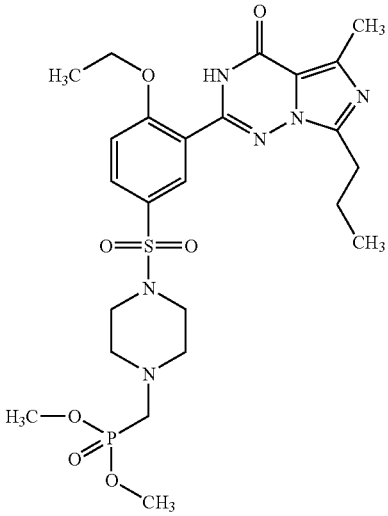

By the same method, starting with 0.4 g (0.97 mmol) of 4-ethoxy-3-(5-methyl-4-oxo-7-propyl-3,4-dihydro-imidazo[5,1-f][1,2,4]triazin-2-yl)-benzenesulphonyl chloride, 390 mg of triethylamine and 0.86 g (2.99 mmol) of 4-dimethoxyphosphorylmethyl-piperazine trifluoroacetate, 321 mg (53%) of 2-[2-ethoxy-5-(4-dimethoxyphosphoryl-methyl-piperazine-1-sulphonyl)-phenyl]-5-methyl-7-propyl-3H-imidazo[5,1-f][1,2,4]triazin-4-one are obtained.

$R_f$=0.4 (dichloromethane/methanol=20:1)

200 MHz $^1$H-NMR (CDCl$_3$): 1.02, t, 3H, 1.60, t, 3H, 1.88, sex., 2H, 2.62, s, 3H, 2.75, m, 4H, 3.02, t, 2H, 3.11, m, 4H, 3.70, s, 3H, 3.75, s, 3H, 4.35, quart., 2H, 5.30, s, 2H, 7.18, d, 1H, 7.88, dd, 1H, 8.45, d, 1H, 9.71, s, 1H.

Example 25

2-[2-Ethoxy-5-(4-diethoxyphosphorylmethyl-piperidine-1-sulphonyl)-phenyl]-5-methyl-7-propyl-3H-imidazo[5,1-f][1,2,4]triazin-4-one

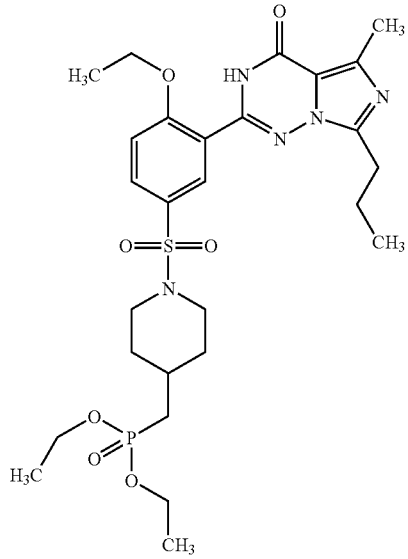

By the same method, starting with 0.4 g (0.97 mmol) of 4-ethoxy-3-(5-methyl-4-oxo-7-propyl-3,4-dihydro-imidazo[5,1-f][1,2,4]triazin-2-yl)-benzenesulphonyl chloride and 0.86 g (3.7 mmol) of 4-diethoxyphosphorylmethyl-piperidine, 366 mg (49%) of 2-[2-ethoxy-5-(4-diethoxyphosphorylmethyl-piperidine-1-sulphonyl)-phenyl]-5-methyl-7-propyl-3H-imidazo[5,1-f][1,2,4]triazin-4-one are obtained.

$R_f$=0.4 (dichloromethane/methanol=20:1)

200 MHz $^1$H-NMR (DMSO-d$_6$): 0.92, t, 3H, 1.20, t, 6H, 1.35, t, 3H, 1.75, m, 7H, 2.25, m, 2H, 2.82, t, 2H, 3.61, d, 2H, 3.95, quin., 4H, 4.21, quart., 2H, 7.38, d, 1H, 7.87, m, 2H, 11.70, s, 1H.

Example 26

2-[2-Ethoxy-5-(4-hydroxy-piperidine-1-sulphonyl)-phenyl]-5-methyl-7-propyl-3H-imidazo[5,1-f][1,2,4]triazin-4-one

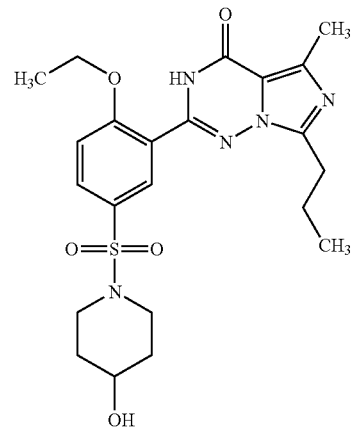

By the same method, starting with 531 mg (1.29 mmol) of 4-ethoxy-3-(5-methyl-4-oxo-7-propyl-3,4-dihydro-imidazo[5,1-f][1,2,4]triazin-2-yl)-benzenesulphonyl chloride and 393 mg (3.88 mmol) of 4-hydroxypiperidine, 400 mg (64%) of 2-[2-ethoxy-5-(4-hydroxy-piperidine-1-sulphonyl)-phenyl]-5-methyl-7-propyl-3H-imidazo[5,1-f][1,2,4]triazin-4-one are obtained.

200 MHz $^1$H-NMR (DMSO-d6): 0.941, t, 3H, 1.32, t, 3H, 1.45, m, 2H, 1.71, m, 4H, 2.48, s, 3H, 2.82, m, 4H, 3.11, m, 2H, 3.55, m, 1H; 4.20, quart., 2H, 4.72, d, 1H, 7.39, d, 1H, 7.87, m, 2H, 11.70, s, 1H.

Example 27

2-{2-Ethoxy-5-[4-(2-hydroxy-ethyl)-piperazine-1-sulphonyl]-phenyl}-5-methyl-7-propyl-3H-imidazo[5,1-f][1,2,4]triazin-4-one

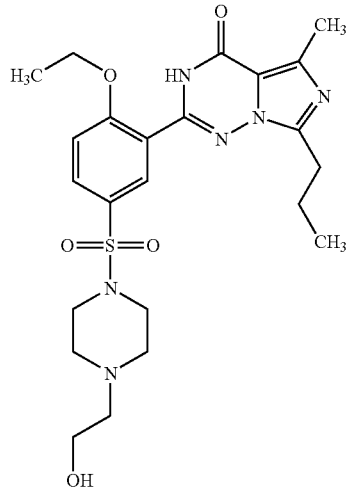

By the same method, starting with 411 mg (1 mmol) of 4-ethoxy-3-(5-methyl-4-oxo-7-propyl-3,4-dihydro-imidazo[5,1-f][1,2,4]triazin-2-yl)-benzenesulphonyl chloride and 391 mg (3 mmol) of 4-hydroxyethylpiperazine, 380 mg (75%) of 2-{2-ethoxy-5-[4-(2-hydroxy-ethyl)-piperazine-1-sulphonyl]-phenyl}-5-methyl-7-propyl-3H-imidazo[5,1-f][1,2,4]triazin-4-one are obtained.

$R_f$=0.198 (dichloromethane/methanol=95:5)

200 MHz $^1$H-NMR (CDCl$_3$): 1.02, t, 3H, 1.61, t, 3H, 1.87, hex., 3H, 2.60, m, 7H, 3.00, t, 2H, 3.10, m, 4H, 3.60, t, 2H, 4.36, quart., 2H, 7.18, d, 1H, 7.89, dd, 1H, 8.47, d, 1H, 9.71, s, 1H.

Example 28

2-{2-Ethoxy-5-[4-(2-hydroxy-ethyl)-piperazine-1-sulphonyl]-phenyl}-5-methyl-7-propyl-3H-imidazo[5,1-f][1,2,4]triazin-4-one hydrochloride

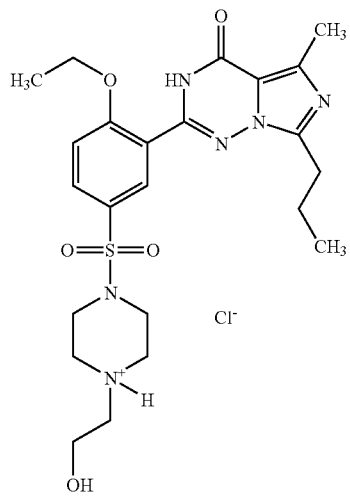

200 mg (0.39 mmol) of 2-{2-ethoxy-5-[4-(2-hydroxy-ethyl)-piperazine-1-sulphonyl]-phenyl}-5-methyl-7-propyl-3H-imidazo[5,1-f][1,2,4]triazin-4-one are suspended in ether, admixed with 2 ml of a 1M solution of HCl in ether and stirred at room temperature for 20 minutes. The solvent is removed, giving 209 mg (100%) of 2-{2-ethoxy-5-[4-(2-hydroxy-ethyl)-piperazine-1-sulphonyl]-phenyl}-5-methyl-7-propyl-3H-imidazo[5,1-f][1,2,4]triazin-4-one hydrochloride.

200 MHz $^1$H-NMR (DMSO-d6): 0.96, t, 3H, 1.35, t, 3H, 1.70, sex., 2H, 2.59, s, 3H, 2.85, t, 2H, 2.99, t, 2H, 3.18, m, 4H, 3.59, d, 2H, 3.75, m, 4H, 4.25, quart., 2H, 7.49, d, 1H, 7.95, m, 2H, 10.62, s, 1H, 12.31, s, 1H.

Example 29

2-{2-Ethoxy-5-[4-(3-hydroxy-propyl)-piperazine-1-sulphonyl]-phenyl}-5-methyl-7-propyl-3H-imidazo[5,1-f][1,2,4]triazin-4-one

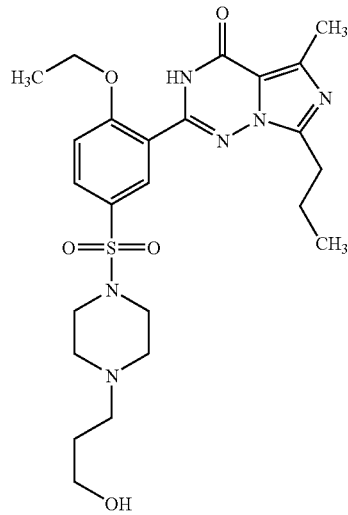

By the same method, starting with 150 mg (0.37 mmol) of 4-ethoxy-3-(5-methyl-4-oxo-7-propyl-3,4-dihydro-imidazo[5,1-f][1,2,4]triazin-2-yl)-benzenesulphonyl chloride and 158 mg (1.09 mmol) of 4-(3-hydroxypropyl)-piperazine, 167 mg (83%) of 2-{2-ethoxy-5-[4-(3-hydroxy-propyl)-piperazine-1-sulphonyl]-phenyl}-5-methyl-7-propyl-3H-imidazo[5,1-f][1,2,4]triazin-4-one are obtained.

$R_f$=0.52 (dichloromethane/methanol=10:1)

200 MHz $^1$H-NMR (CDCl$_3$): 1.02, t, 3H, 1.61, t, 3H, 1.70, m, 5; 2.62 m, 8H, 3.00, t, 2H, 3.10, m, 4H, 3.72, t, 2H, 4.36, quart., 2H, 7.18, d, 1H, 7.89, dd, 1H, 8.47, d, 1H, 9.71, s, 1H.

Example 30

N-Allyl-4-ethoxy-N-(2-hydroxy-ethyl)-3-(5-methyl-4-oxo-7-propyl-3,4-dihydro-imidazo[5,1-f][1,2,4]triazin-2-yl)benzenesulphonamide

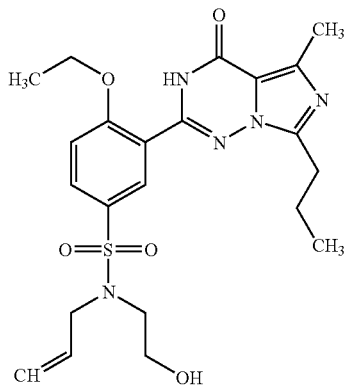

By the same method, starting with 420 mg (1.02 mmol) (1 mmol) of 4-ethoxy-3-(5-methyl-4-oxo-7-propyl-3,4-dihydro-imidazo[5,1-f][1,2,4]triazin-2-yl)-benzenesulphonyl chloride and 300 mg (3 mmol) of allylhydroxyethylamine, 400 mg (82%) of N-allyl-4-ethoxy-N-(2-hydroxy-ethyl)-3-(5-methyl-4-oxo-7-propyl-3,4-dihydro-imidazo[5,1-f][1,2,4]triazin-2-yl)benzenesulphonamide are obtained.

$R_f$=0.345 (dichloromethane/methanol=95:5)

200 MHz $^1$H-NMR (CDCl$_3$): 1.02, t, 3H, 1.61, t, 3H, 1.90, m, 2H, 2.22, s, broad, 1H, 2.62, s, 3H, 2.99, t, 2H, 3.31, t, 2H, 3.78, t, 2H, 3.92, d, 2H, 4.37, quart., 2H, 5.23, m, 2H, 5.71, m, 1H, 7.15, d, 1H, 7.98, dd, 1H, 8.56, d, 1H, 9.66, s, 1H.

Example 31

N-Ethyl-4-ethoxy-N-(2-hydroxy-ethyl)-3-(5-methyl-4-oxo-7-propyl-3,4-dihydro-imidazo[5,1-f][1,2,4]triazin-2-yl)benzenesulphonamide

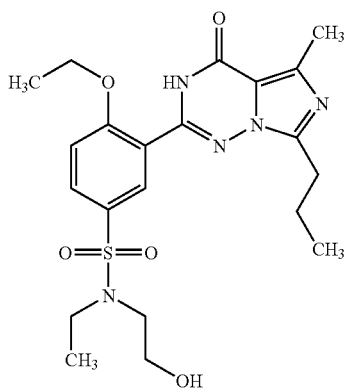

By the same method, starting with 411 mg (1.0 mmol) of 4-ethoxy-3-(5-methyl-4-oxo-7-propyl-3,4-dihydro-imidazo[5,1-f][1,2,4]triazin-2-yl)-benzenesulphonyl chloride and 267 mg (3 mmol) of ethylhydroxyethylamine, 325 mg (70%) of N-ethyl-4-ethoxy-N-(2-hydroxy-ethyl)-3-(5-methyl-4-oxo-7-propyl-3,4-dihydro-imidazo[5,1-f][1,2,4]triazin-2-yl)benzenesulphonamide are obtained.

$R_f$=0.29 (dichloromethane/methanol=95:5)

200 MHz $^1$H-NMR (CDCl$_3$): 1.02, t, 3H, 1.20, t, 3H, 1.61, t, 3H, 1.88, sex., 2H, 2.30, s, broad, 1H, 2.62, s, 3H, 2.99, t, 2H, 3.32, m, 4H, 3.78, t, 2H, 3.80, m, 2H, 4.37, quart., 2H, 7.15, d, 1H, 7.98, dd, 1H, 8.56, d, 1H, 9.70, s, 1H.

Example 32

N,N-Diethyl-4-ethoxy-3-(5-methyl-4-oxo-7-propyl-3,4-dihydro-imidazo[5,1-f][1,2,4]triazin-2-yl)benzenesulphonamide

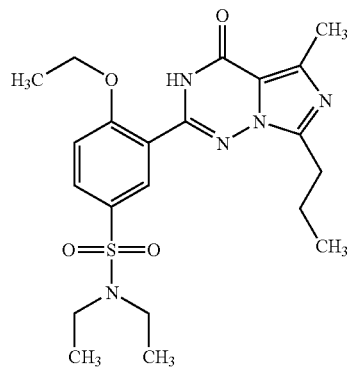

By the same method, starting with 400 mg (0.97 mmol) of 4-ethoxy-3-(5-methyl-4-oxo-7-propyl-3,4-dihydro-imidazo[5,1-f][1,2,4]triazin-2-yl)-benzenesulphonyl chloride and 210 mg (2.92 mmol) of diethylamine, 398 mg (89%) of N,N-diethyl-4-ethoxy-3-(5-methyl-4-oxo-7-propyl-3,4-dihydro-imidazo[5,1-f][1,2,4]triazin-2-yl)benzenesulphonamide are obtained.

$R_f$=0.49 (dichloromethane/methanol=20:1)

200 MHz $^1$H-NMR (CDCl$_3$): 1.02, t, 3H, 1.20, t, 6H, 1.49, t, 1.61, t, 3H, 1.88, sex., 2H, 2.30, s, broad, 1H, 2.62, s, 3H, 2.99, t, 2H, 3.32, m, 4H, 3.78, t, 2H, 3.80, m, 2H, 4.37, quart., 2H, 7.15, d, 1H, 7.98, dd, 1H, 8.56, d, 1H, 9.70, s, 1H.

Example 33

N-(2-Methoxyethyl)-3-(5-methyl-4-oxo-7-propyl-3,4-dihydro-imidazo[5,1-f][1,2,4]triazin-2-yl)-4-ethoxy-benzenesulphonamide

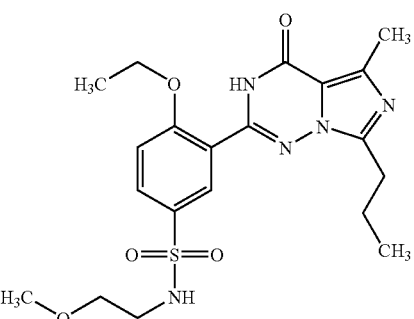

By the same method, starting with 1.23 g (3 mmol) of 4-ethoxy-3-(5-methyl-4-oxo-7-propyl-3,4-dihydro-imidazo[5,1-f][1,2,4]triazin-2-yl)-benzenesulphonyl chloride and 680 mg (9 mmol) of 2-methoxyethylamine, 900 mg (67%) of N-(2-methoxyethyl)-3-(5-methyl-4-oxo-7-propyl-3,4-dihydro-imidazo[5,1-f][1,2,4]triazin-2-yl)-4-ethoxy-benzenesulphonamide are obtained.

$R_f$=0.25 (dichloromethane/methanol=95:5)

400 MHz $^1$H-NMR (CDCl$_3$): 1.01, t, 3H, 1.58, t, 3H, 1.88, sex., 2H, 2.62, s, 3H, 3.01, t, 2H, 3.18, quart., 2H, 3.30, s, 3H, 3.45, t, 2H, 4.32, quart., 2H, 5.12, t, 1H, 7.13, d, 1H, 7.97, dd, 1H, 8.53, d, 1H, 9.82, s, 1H.

Example 34

N-(2-N,N-Dimethylethyl)-3-(5-methyl-4-oxo-7-propyl-3,4-dihydro-imidazo[5,1-f][1,2,4]triazin-2-yl)-4-ethoxy-benzenesulphonamide

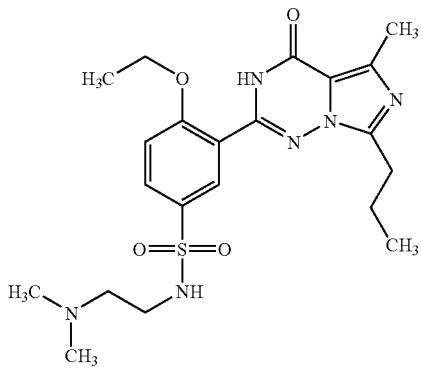

By the same method, starting with 210 mg (0.49 mmol) of 4-ethoxy-3-(5-methyl-4-oxo-7-propyl-3,4-dihydro-imidazo[5,1-f][1,2,4]triazin-2-yl)-benzenesulphonyl chloride and 130 mg (9 mmol) of 2-N,N-dimethylethylamine, 150 mg (59%) of N-(2-N,N-dimethylethyl)-3-(5-methyl-4-oxo-7-propyl-3,4-dihydro-imidazo[5,1-f][1,2,4]triazin-2-yl)-4-ethoxy-benzenesulphonamide are obtained.

200 MHz $^1$H-NMR (CDCl$_3$): 1.01, t, 3H, 1.62, m, 4H, 1.88, sex., 2H, 2.11, s, 6H, 2.39, t, 2H, 2.63, s, 3H, 3.01, m, 3H, 4.38, quart., 2H, 7.13, d, 1H, 7.97, dd, 1H, 8.53, d, 1H; 9.82, s, 1H.

Example 35

N-[3-(1-Morpholino)propyl]-3-(5-methyl-4-oxo-7-propyl-3,4-dihydro-imidazo[5,1-f][1,2,4]triazin-2-yl)-4-ethoxy-benzenesulphonamide

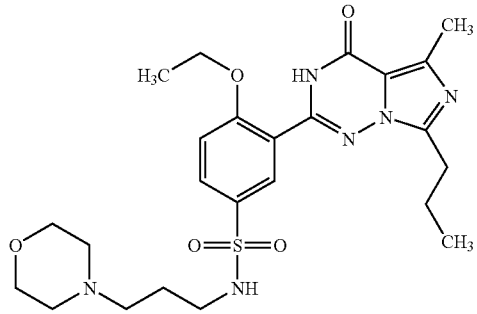

By the same method, starting with 1.23 g (3 mmol) of 4-ethoxy-3-(5-methyl-4-oxo-7-propyl-3,4-dihydro-imidazo[5,1-f][1,2,4]triazin-2-yl)-benzenesulphonyl chloride and 1.3 g (9 mmol) of 3-(1-morpholino)-propylamine, 1.38 g (88%) of N-[3-(1-morpholino)propyl]-3-(5-methyl-4-oxo-7-propyl-3,4-dihydro-imidazo[5,1-f][1,2,4]triazin-2-yl)-4-ethoxy-benzenesulphonamide are obtained.

$R_f$=0.23 (dichloromethane/methanol=95:5)

200 MHz $^1$H-NMR (CDCl$_3$): 1.01, t, 3H, 1.58, t, 3H, 1.72, m, 2H, 1.88, sex., 2H, 2.46, m, 6H, 2.62, s, 3H, 3.01, t, 2H, 3.15, t, 2H, 3.71, t, 4H, 4.32, quart., 2H, 7.13, d, 1H, 7.97, dd, 1H, 8.53, d, 1H, 9.79, s, 1H.

Example 36

N-{3-[1-(4-Methyl)piperazino]-propyl}-3-(5-methyl-4-oxo-7-propyl-3,4-dihydro-imidazo[5,1-f][1,2,4]triazin-2-yl)-4-ethoxy-benzenesulphonamide

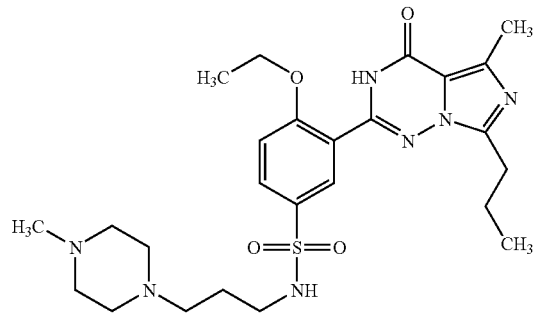

By the same method, starting with 0.04 g (0.097 mmol) of 4-ethoxy-3-(5-methyl-4-oxo-7-propyl-3,4-dihydro-imidazo[5,1-f][1,2,4]triazin-2-yl)-benzenesulphonyl chloride and 0.05 g (0.29 mmol) of 3-[1-(4-methyl-)piperazino]-propylamine, 0.04 g (77%) of N-{3-[1-(4-methyl)piperazino]-propyl}-3-(5-methyl-4-oxo-7-propyl-3,4-dihydro-imidazo[5,1-f][1,2,4]triazin-2-yl)-4-ethoxy-benzenesulphonamide is obtained.

$R_f$=0.11 (dichloromethane/methanol=95:5)

200 MHz $^1$H-NMR (CDCl$_3$): 1.01, t, 3H, 1.55, t, 3H, 1.68, m, 2H, 1.88, sex., 2H, 2.27, s, 3H, 2.45, m, 8H, 2.62, s, 3H, 2.98, m, 3H, 3.10, t, 2H, 3.46, s, 1H, 4.30, quart., 2H, 7.13, d, 1H, 7.97, dd, 1H, 8.53, d, 1H.

Example 37

2-{2-Ethoxy-5-[4-(2-methoxy-ethyl)-piperazine-1-sulphonyl]-phenyl}-5-methyl-7-propyl-3H-imidazo[5,1-f][1,2,4]triazin-4-one

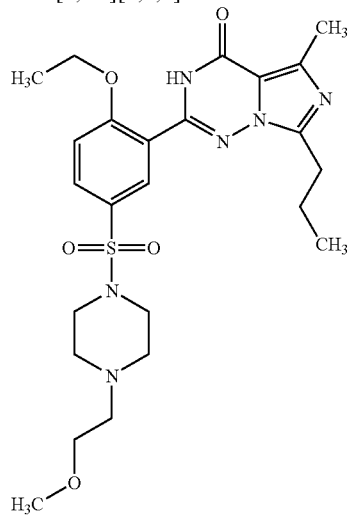

By the same method, starting with 40 mg (0.097 mmol) of 4-ethoxy-3-(5-methyl-4-oxo-7-propyl-3,4-dihydro-imidazo[5,1-f][1,2,4]triazin-2-yl)-benzenesulphonyl chloride and 40 mg (0.29 mmol) of 4-methoxyethylpiperazine, 50 mg (99%) of 2-{2-ethoxy-5-[4-(2-methoxy-ethyl)-piperazine-1-sulphonyl]-phenyl}-5-methyl-7-propyl-3H-imidazo[5,1-f][1,2,4]triazin-4-one are obtained.

$R_f$=0.27 (dichloromethane/methanol=95:5)

200 MHz $^1$H-NMR (CDCl$_3$): 1.02, t, 3H, 1.61, t, 3H, 1.87, hex., 3H, 2.60, m, 9H, 2.97, t, 2H, 3.10, m, 4H, 3.60, s, 3H, 3.46, t, 2H, 4.36, quart., 2H, 7.18, d, 1H, 7.89, dd, 1H, 8.47, d, 1H, 9.71, s, 1H.

Example 38

2-{2-Ethoxy-5-[4-(2-N,N-dimethyl-ethyl)-piperazine-1-sulphonyl]-phenyl}-5-methyl-7-propyl-3H-imidazo[5,1-f][1,2,4]triazin-4-one

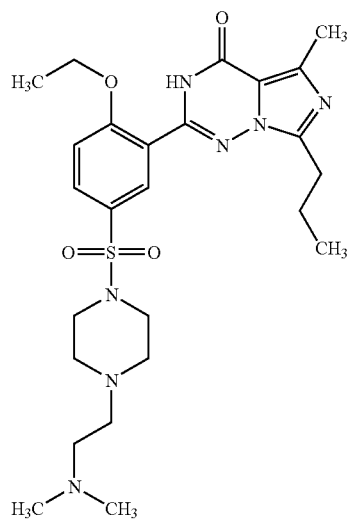

By the same method, starting with 40 mg (0.097 mmol) of 4-ethoxy-3-(5-methyl-4-oxo-7-propyl-3,4-dihydro-imidazo[5,1-f][1,2,4]triazin-2-yl)-benzenesulphonyl chloride and 50 mg (0.29 mmol) of 4-(2-N,N-dimethyl)-ethylpiperazine, 50 mg (99%) of 2-{2-ethoxy-5-[4-(2-N,N-dimethyl-ethyl)-piperazine-1-sulphonyl]-phenyl}-5-methyl-7-propyl-3H-imidazo[5,1-f][1,2,4]triazin-4-one are obtained.

$R_f$=0.11 (dichloromethane/methanol=95:5)

200 MHz $^1$H-NMR (CDCl$_3$): 1.02, t, 3H, 1.61, t, 3H, 1.87, hex., 3H, 2.20, s, 6H, 2.42, m, 4H, 2.58, m, 4H, 2.63, s, 3H, 2.99, m, 3H, 3.10, m, 4H, 4.36, quart., 2H, 7.18, d, 1H, 7.89, dd, 1H, 8.47, d, 1H, 9.71, s, 1H.

Example 39

2-{2-Ethoxy-5-[4-(3-N,N-dimethyl-propyl)-piperazin-1-sulphonyl]-phenyl}-5-methyl-7-propyl-3H-imidazo[5,1-f][1,2,4]triazin-4-one

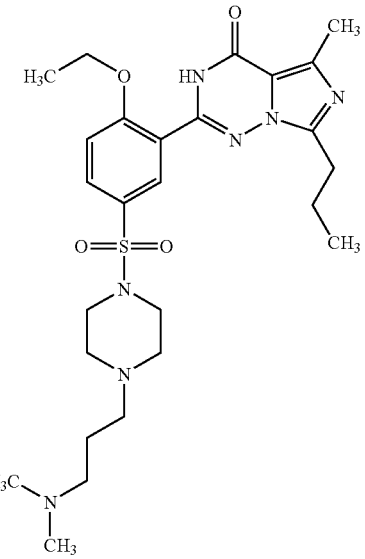

By the same method, starting with 100 mg (0.243 mmol) of 4-ethoxy-3-(5-methyl-4-oxo-7-propyl-3,4-dihydro-imidazo[5,1-f][1,2,4]triazin-2-yl)-benzenesulphonyl chloride and 130 mg (0.73 mmol) of 4-(3-N,N-dimethyl)-propylpiperazine, 72 mg (54%) of 2-{2-ethoxy-5-[4-(3-N,N-dimethyl-propyl)-piperazine-1-sulphonyl]-phenyl}-5-methyl-7-propyl-3H-imidazo[5,1-f][1,2,4]triazin-4-one are obtained.

$R_f$=0.08 (dichloromethane/methanol=95:5)

200 MHz $^1$H-NMR (CDCl$_3$): 1.02, t, 3H, 1.61, t, 3H, 1.87, sex., 3H, 2.20, s, 6H, 2.25, m, 2H, 2.38, t, 2H, 2.52, m, 4H, 2.63, s, 3H, 2.99, m, 6H, 4.33, quart., 2H, 7.18, d, 1H, 7.89, dd, 1H, 8.47, d, 1H, 9.71, s, 1H.

Example 40

2-[2-Ethoxy-5-(4-dioxolano-piperidine-1-sulphonyl)-phenyl]-5-methyl-7-propyl-3H-imidazo[5,1-f][1,2,4]triazin-4-one

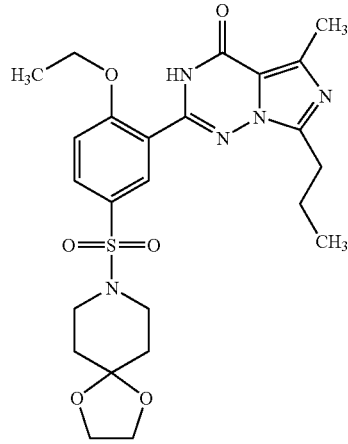

By the same method, starting with 100 mg (0.243 mmol) of 4-ethoxy-3-(5-methyl-4-oxo-7-propyl-3,4-dihydro-imidazo[5,1-f][1,2,4]triazin-2-yl)-benzenesulphonyl chloride and 100 mg (0.73 mmol) of 4-dioxolanopiperidine, 111 mg (88%) of 2-[2-ethoxy-5-(4-dioxolano-piperidine-1-sulphonyl)-phenyl]-5-methyl-7-propyl-3H-imidazo[5,1-f][1,2,4]triazin-4-one are obtained.

200 MHz ¹H-NMR (CDCl₃): 1.02, t, 3H, 1.61, t, 3H, 1.80, m, 6H, 2.63, s, 3H, 2.99, t, 2H, 3.20, m, 4H, 3.90, s, 4H, 4.33, quart., 2H, 7.18, d, 1H, 7.89, dd, 1H, 8.47, d, 1H, 9.71, s, 1H.

Example 41

2-[2-Ethoxy-5-(4-(5-methyl-4-furoxanecarbonyl)-piperazine-1-sulphonyl)-phenyl]-5-methyl-7-propyl-3H-imidazo[5,1-f][1,2,4]triazin-4-one

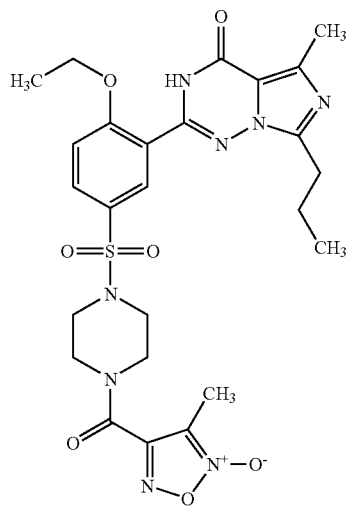

410 mg (1.0 mmol) of 4-ethoxy-3-(5-methyl-4-oxo-7-propyl-3,4-dihydro-imidazo[5,1-f][1,2,4]triazin-2-yl)-benzenesulphonyl chloride are dissolved in 10 ml of dichloromethane and cooled to 0° C. 590 mg (2.00 mmol) of 1-(5-methyl-4-furoxanecarbonyl)-piperazine trifluoroacetate and 400 mg of triethylamine are added, and the reaction mixture is stirred at room temperature overnight. The mixture is diluted with dichloromethane, the organic phase is washed with ammonium chloride solution, 1M hydrochloric acid and water and dried over sodium sulphate and the solvent is removed under reduced pressure. Crystallization from ether gives 448 mg (74%) of a colourless solid.

200 MHz ¹H-NMR (CDCl₃): 1.01, t, 3H, 1.59, t, 3H, 1.88, hex, 2H, 2.25, s, 3H, 2.63, s, 3H, 3.00, t, 2H, 3.20, m, 4H, 3.90, m, 2H, 4.02, m, 2H, 4.33, quart., 2H, 7.19, d, 1H, 7.89, dd, 1H, 8.48, d, 1H, 9.57, s, 1H.

Example 42

2-{2-Ethoxy-5-[4-acetyl-piperazine-1-sulphonyl]-phenyl}-5-methyl-7-propyl-3H-imidazo[5,1-f][1,2,4]triazin-4-one

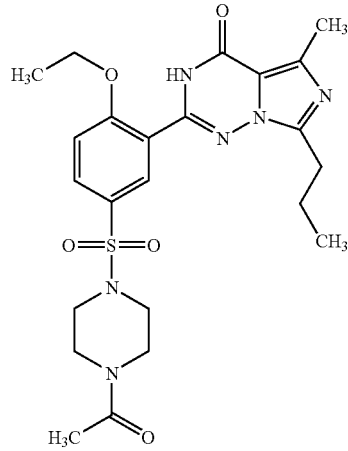

By the same method, starting with 40 mg (0.097 mmol) of 4-ethoxy-3-(5-methyl-4-oxo-7-propyl-3,4-dihydro-imidazo[5,1-f][1,2,4]triazin-2-yl)-benzenesulphonyl chloride and 40 mg (0.29 mmol) of N-acetylpiperazine, 9 mg (18%) of 2-{2-ethoxy-5-[4-acetyl-piperazine-1-sulphonyl]-phenyl}-5-methyl-7-propyl-3H-imidazo[5,1-f][1,2,4]triazin-4-one are obtained.

R_f=0.34 (dichloromethane/methanol=95:5)

200 MHz ¹H-NMR (CDCl₃): 1.02, t, 3H, 1.61, t, 3H, 1.87, sex., 3H, 2.05, s, 3H, 2.63, s, 3H, 3.00, m, 6H, 3.59, m, 2H, 3.72, m, 2H, 4.33, quart., 2H, 7.18, d, 1H, 7.89, dd, 1H, 8.47, d, 1H, 9.71, s, 1H.

Example 43

2-{2-Ethoxy-5-[4-formyl-piperazine-1-sulphonyl]-phenyl}-5-methyl-7-propyl-3H-imidazo[5,1-f][1,2,4]triazin-4-one

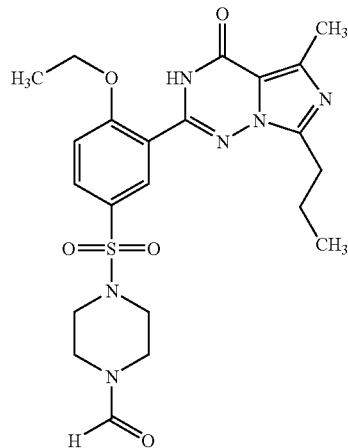

By the same method, starting with 40 mg (0.097 mmol) of 4-ethoxy-3-(5-methyl-4-oxo-7-propyl-3,4-dihydro-imidazo[5,1-f][1,2,4]triazin-2-yl)-benzenesulphonyl chloride and 30 mg (0.29 mmol) of N-formylpiperazine, 35 mg (73%) of 2-{2-ethoxy-5-[4-formyl-piperazine-1-sulphonyl]-phenyl}-5-methyl-7-propyl-3H-imidazo[5,1-f][1,2,4]triazin-4-one are obtained.

$R_f$=0.29 (dichloromethane/methanol=95:5)

200 MHz $^1$H-NMR (CDCl$_3$): 1.02, t, 3H, 1.61, t, 3H, 1.87, sex., 3H, 2.05, s, 3H, 2.63, s, 3H, 3.00, m, 6H, 3.50, m, 2H, 3.69, m, 2H, 4.33, quart., 2H, 7.18, d, 1H, 7.89, dd, 1H, 8.00, s, 1H, 8.47, d, 1H, 9.71, s, 1H.

Example 44

2-[2-Ethoxy-5-(3-butylsydnoneimine)-1-sulphonyl)-phenyl]-5-methyl-7-propyl-3H-imidazo[5,1-f][1,2,4]triazin-4-one

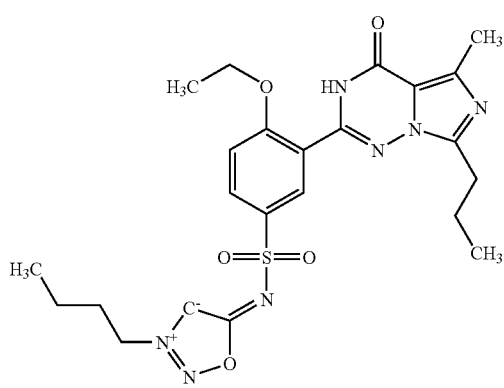

110 mg (0.6 mmol) of 3-butylsydnoneimine hydrochloride are dissolved in 2.5 ml of pyridine and cooled to 0° C. 210 mg (0.5 mmol) of 4-ethoxy-3-(5-methyl-4-oxo-7-propyl-3,4-dihydro-imidazo[5,1-f][1,2,4]triazin-2-yl)-benzenesulphonyl chloride are added, and the reaction mixture is stirred for 2 hours at 0° C. and overnight at room temperature. The mixture is diluted with dichloromethane, the organic phase is washed with water and dried over sodium sulphate and the solvent is removed under reduced pressure. Chromatography (dichloromethane/methanol) gives 16 mg (6%) of 2-[2-ethoxy-5-(3-butylsydnoneimine)-1-sulphonyl)-phenyl]-5-methyl-7-propyl-3H-imidazo[5,1-f][1,2,4]triazin-4-one.

$R_f$=0.41 (dichloromethane/methanol=95:5)

200 MHz $^1$H-NMR (CDCl$_3$): 1.01, 2t, 6H, 1.47, sex., 2H, 1.55, t, 3H, 1.88, m, 2H, 2.04, quin., 2H, 2.62, s, 3H, 2.98, t, 2H, 4.29, quart., 2H, 4.41, t, 2H, 7.08, d, 1H, 7.56, s, 1H, 7.98, dd, 1H, 8.58, d, 1H; 9.79, s, broad, 1H.

Example 45

5-Methyl-2-[5-(4-methyl-piperazine-1-sulphonyl)-2-propoxy-phenyl]-7-propyl-3H-imidazo[5,1-f][1,2,4]triazin-4-one

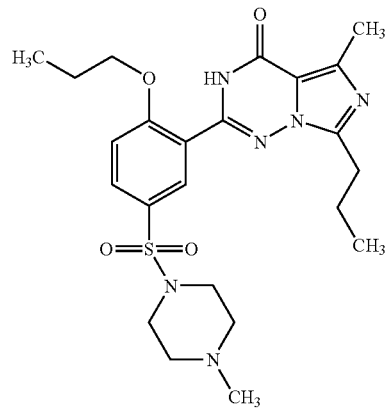

0.85 g (2 mmol) of 4-propoxy-3-(5-methyl-4-oxo-7-propyl-3,4-dihydro-imidazo[5,1-f][1,2,4]-triazin-2-yl)-benzenesulphonyl chloride are dissolved in 20 ml of dichloromethane and cooled to 0° C. After addition of a spatula tip of DMAP, 0.60 g (6.00 mmol) of N-methylpiperazine is added and the reaction mixture is stirred at room temperature overnight. The mixture is diluted with dichloromethane, the organic phase is washed with ammonium chloride solution and dried over sodium sulphate and the solvent is removed under reduced pressure. Crystallization from ether gives 0.80 g (77%) of a colourless solid.

$R_f$=0.233 (dichloromethane/methanol=95:5)

200 MHz $^1$H-NMR (CDCl$_3$): 1.00, t, 3H, 1.15, t, 3H, 1.87, hex, 2H, 1.99, hex., 2H, 2.30, s, 3H, 2.52, m, 4H, 2.62, s, 3H, 2.99, t, 2H, 3.10, m, 4H, 4.21, t, 2H, 7.17, d, 1H, 7.87, dd, 1 h, 8.48, d, 1H, 9.70, s, 1H.

Example 46

5-Methyl-2-[5-(4-methyl-piperazine-1-sulphonyl)-2-propoxy-phenyl]-7-propyl-3H-imidazo[5,1-f][1,2,4]triazin-4-one hydrochloride

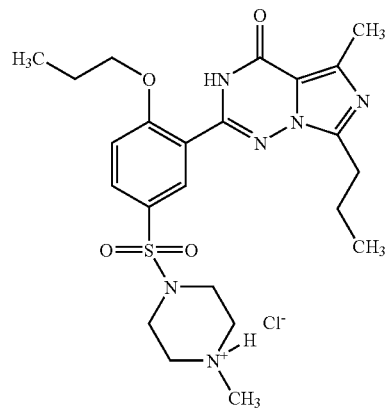

22 mg (0.045 mmol) of 5-methyl-2-[5-(4-methyl-piperazine-1-sulphonyl)-2-propoxy-phenyl]-7-propyl-3H-imidazo[5,1-f][1,2,4]triazin-4-one are dissolved in 2 ml of ether and 1 ml of dichloromethane and admixed with 0.1 ml of a 1M solution of HCl in ether. After 20 minutes, the precipitate is filtered off with suction and dried.

200 MHz $^1$H-NMR (CDCl$_3$): 0.95, t, 3H, 1.75, m, 2H, 2.56, s, 3H, 2.75, m, 4H, 2.97, t, 2H, 3.15, m, 2H, 3.44, m, 2H, 3.81, m, 2H, 4.15, t, 2H, 7.47, d, 1H, 7.95, m, 2H, 11.12, s, 1H, 12.22, s, 1H.

Example 47

2-[5-(4-Hydroxypiperidine-1-sulphonyl)-2-propoxy-phenyl]-5-methyl-7-propyl-3H-imidazo[5,1-f][1,2,4]triazin-4-one

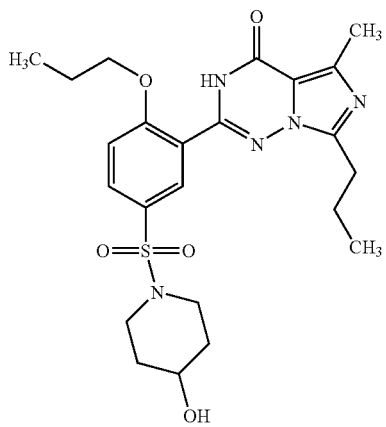

By the same method, starting with 850 mg (2 mmol) of 4-propoxy-3-(5-methyl-4-oxo-7-propyl-3,4-dihydro-imidazo[5,1-f][1,2,4]triazin-2-yl)-benzenesulphonyl chloride and 610 mg (6 mmol) of 4-hydroxypiperidine, 736 mg (75%) of 2-[5-(4-hydroxypiperidine-1-sulphonyl)-2-propoxy-phenyl]-5-methyl-7-propyl-3H-imidazo[5,1-f][1,2,4]triazin-4-one are obtained.

R$_f$=0.07 (dichloromethane/methanol=95:5)

200 MHz $^1$H-NMR (CDCl$_3$): 1.01, t, 3H, 1.16, t, 3H, 1.80, m, 9H, 2.65, s, 3H, 3.00, m, 4H, 3.32, m, 2H, 3.85 μm, 1H, 4.22, t., 2H, 7.17, d, 1H; 7.89, dd, 1H, 8.50, d, 1H, 11.70, s, 1H.

Example 48

2-[5-(4-Hydroxymethylpiperidine-1-sulphonyl)-2-propoxy-phenyl]-5-methyl-7-propyl-3H-imidazo[5,1-f][1,2,4]triazin-4-one

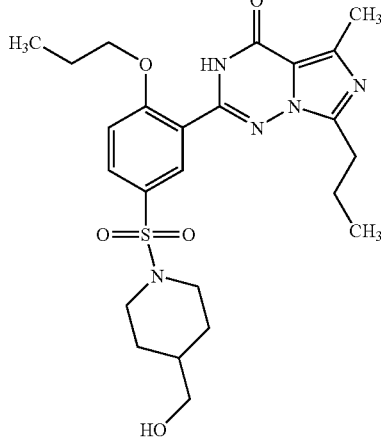

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 35 mg (0.3 mmol) of 4-hydroxymethylpiperidine, 41 mg (82%) of 2-[5-(4-hydroxymethylpiperidine-1-sulphonyl)-2-propoxy-phenyl]-5-methyl-7-propyl-3H-imidazo[5,1-f][1,2,4]triazin-4-one are obtained.

R$_f$=0.52 (dichloromethane/methanol=9:1)

200 MHz $^1$H-NMR (CDCl$_3$): 1.001, t, 3H, 1.16, t, 3H, 1.60, m, 4H, 1.82, m, 5H, 2.31, t, 2H, 2.62, s, 3H, 2.98, t, 2H; 3.48, d, 2H, 3.85, d, 2H, 4.21, t, 2H; 7.17, d, 1H, 7.88, dd, 1H, 8.45, d, 1H; 9.71, s, 1H.

Example 49

2-{5-[4-(2-hydroxyethyl)-piperazine-1-sulphonyl]-2-propoxy-phenyl}-5-methyl-7-propyl-3H-imidazo[5,1-f][1,2,4]triazin-4-one

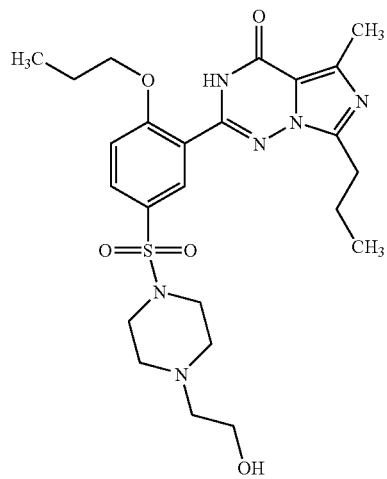

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 39 mg (0.3 mmol) of 4-hydroxymethylpiperazine, 50 mg (96%) of 2-{5-[4-(2-hydroxyethyl)-piperazine-1-sulphonyl]-2-propoxy-phenyl}-5-methyl-7-propyl-3H-imidazo[5,1-f][1,2,4]triazin-4-one are obtained.

R$_f$=0.43 (dichloromethane/methanol=9:1)

200 MHz $^1$H-NMR (CDCl$_3$): 1.01, t, 3H, 1.15, t, 3H, 1.88, m, 2H, 2.00, m, 2H, 2.62, m, 9H, 3.00, t, 2H, 3.07, m, 4H, 3.58, t, 2H, 4.23, t, 2H, 7.19, d, 1H, 7.88, dd, 1H, 8.43, d, 1H, 9.85, s, 1H.

Example 50

N-(1,1-Dioxotetrahydro-1)-1λ⁶-thiophene-3-yl)-3-(5-methyl-4-oxo-7-propyl-3,4-dihydro-imidazo-[5,1-f][1,2,4]triazin-2-yl)-4-propoxy-benzenesulphonamide

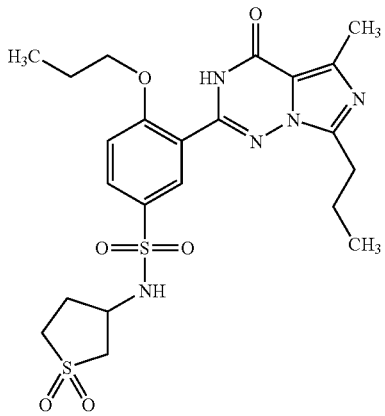

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 41 mg (0.3 mmol) of 2-aminosulpholane, 8 mg (14%) of N-(1,1-dioxotetrahydro-1λ⁶-thiophene-3-yl)-3-(5-methyl-4-oxo-7-propyl-3,4-dihydro-imidazo-[5,1-f][1,2,4]triazin-2-yl)-4-propoxy-benzenesulphonamide are obtained.

$R_f$=0.49 (dichloromethane/methanol=9:1)

200 MHz ¹H-NMR (CDCl₃): 1.01, t, 3H, 1.15, t, 3H, 1.85, m, 2H, 1.99, m, 2H, 2.30, m, 1H, 2.50, m, 1H, 2.62, s, 3H, 2.95, m, 4H, 3.21, m, 1H, 4.20, m, 3H, 5.98, s, 1H, 7.18, d, 1H, 7.98, dd, 1H, 8.51, d, 1H, 9.71, s, 1H.

Example 51

N-(2-Dimethylaminoethyl)-N-methyl-3-(5-methyl-4-oxo-7-propyl-3,4-dihydro-imidazo[5,1-f][1,2,4]triazin-2-yl)-4-propoxy-benzenesulphonamide

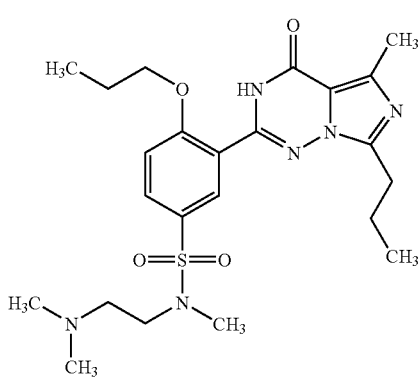

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 31 mg (0.3 mmol) of 1,1,4-trimethyldiaminoethane, 39 mg (79%) of N-(2-dimethylaminoethyl)-N-methyl-3-(5-methyl-4-oxo-7-propyl-3,4-dihydro-imidazo[5,1-f][1,2,4]triazin-2-yl)-4-propoxy-benzenesulphonamide are obtained.

$R_f$=0.28 (dichloromethane/methanol=9:1)

200 MHz ¹H-NMR (CDCl₃): 1.01, t, 3H, 1.15, t, 3H, 1.88, m, 2H, 2.01, m, 2H, 2.25, s, 6H, 2.50, t, 2H, 2.62, s, 3H, 2.82, s, 3H, 3.01, t, 2H, 3.18, t, 2H, 4.21, t, 2H, 7.16, d, 1H, 7.91, dd, 1H, 8.50, d, 1H, 9.70, s, 1H.

Example 52

3-(5-Methyl-4-oxo-7-propyl-3,4-dihydro-imidazo[5,1-f][1,2,4]triazin-2-yl)-N-(3-morpholin-4-yl-propyl)-4-propoxy-benzenesulphonamide

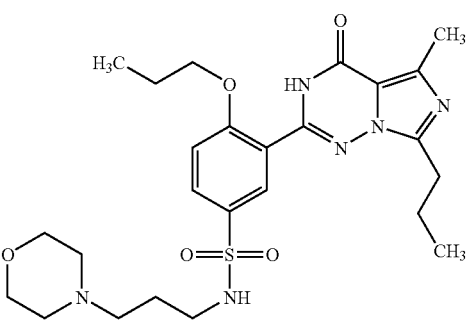

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 43 mg (0.3 mmol) of 1-(3-aminopropyl)-morpholine, 52 mg (97%) of 3-(5-methyl-4-oxo-7-propyl-3,4-dihydro-imidazo[5,1-f][1,2,4]triazin-2-yl)-N-(3-morpholin-4-yl-propyl)-4-propoxy-benzenesulphonamide are obtained.

$R_f$=0.33 (dichloromethane/methanol=9:1)

200 MHz ¹H-NMR (CDCl₃): 1.01, t, 3H, 1.15, t, 3H, 1.71, m, 2H, 1.93, m, 4H, 2.43, m, 6H, 2.62, s, 3H, 2.98, t, 2H, 3.12, t, 2H, 3.70, m, 4H, 4.21, t, 2H, 7.15, d, 1H, 7.96, dd, 1H, 8.55, d, 1H, 9.85, s, 1H.

Example 53

N,N-Bis-(2-hydroxyethyl)-3-(S-methyl-4-oxo-7-propyl-3,4-dihydro-imidazo[5,1-f][1,2,4]triazin-2-yl)-4-propoxy-benzenesulphonamide

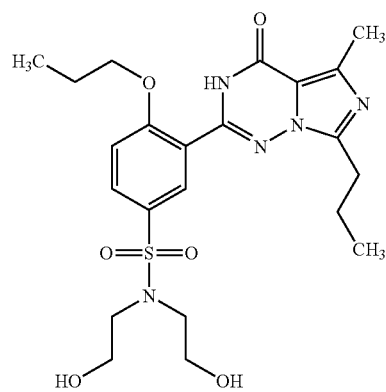

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 32 mg (0.3 mmol) of bishydroxyethylamine, 34 mg (69%) of N,N-bis-(2-hydroxyethyl)-3-(5-methyl-4-oxo-7-propyl-3,4-dihydro-imidazo[5,1-f][1,2,4]triazin-2-yl)-4-propoxy-benzenesulphonamide are obtained.

$R_f$=0.36 (dichloromethane/methanol=9:1)

200 MHz $^1$H-NMR (CDCl$_3$): 1.01, t, 3H, 1.15, t, 3H, 1.85, m, 2H, 1.97, m, 2H, 2.60, s, 3H, 2.98, t, 2H, 3.33, t, 4H, 3.87, t, 4H, 4.20, t, 2H, 7.15, d, 1H, 7.92, dd, 1H, 8.49, d, 1H; 9.85, s, 1H.

Example 54

N-(3-Hydroxybenzyl)-3-(5-methyl-4-oxo-7-propyl-3,4-dihydro-imidazo[5,1-f][1,2,4]triazin-2-yl)-4-propoxy-benzenesulphonamide

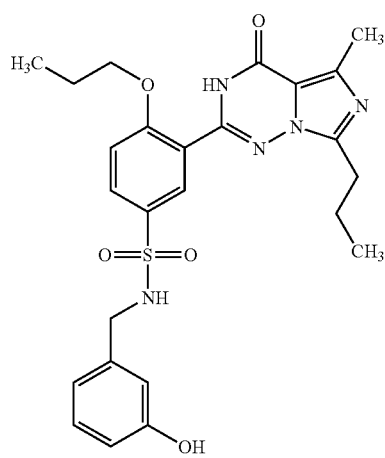

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 37 mg (0.3 mmol) of 3-hydroxybenzylamine, 4 mg (8%) of N-(3-hydroxybenzyl)-3-(5-methyl-4-oxo-7-propyl-3,4-dihydro-imidazo[5,1-f][1,2,4]triazin-2-yl)-4-propoxy-benzenesulphonamide are obtained.

$R_f$=0.43 (dichloromethane/methanol=9:1)

200 MHz $^1$H-NMR (CDCl$_3$): 1.01, t, 3H, 1.13, t, 3H, 1.83, m, 2H, 1.96, m, 2H, 2.59, s, 3H, 2.96, t, 2H, 4.16, m, 4H, 5.05, t, 1H, 6.52, s, 1H, 6.70, m, 2H, 7.06, m, 2H, 7.93, dd, 1H, 8.41, d, 1H, 9.77, s, 1H.

Example 55

N-Ethyl-N-(2-hydroxyethyl)-3-(5-methyl-4-oxo-7-propyl-3,4-dihydro-imidazo[5,1-f][1,2,4]triazin-2-yl)-4-propoxy-benzenesulphonamide

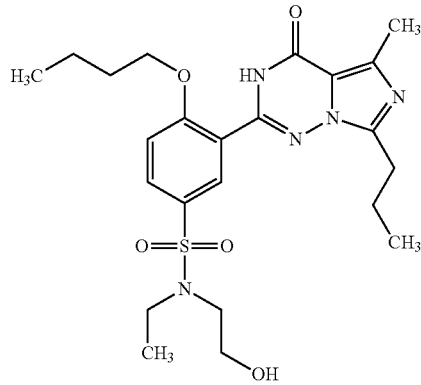

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 27 mg (0.3 mmol) of ethylhydroxyethylamine, 18 mg (38%) of N-ethyl-N-(2-hydroxyethyl)-3-(5-methyl-4-oxo-7-propyl-3,4-dihydro-imidazo[5,1-f][1,2,4]triazin-2-yl)-4-propoxy-benzenesulphonamide are obtained.

$R_f$=0.48 (dichloromethane/methanol=9:1)

200 MHz $^1$H-NMR (CDCl$_3$): 1.01, t, 3H, 1.15, 2t, 6H, 1.75, s, 2H, 1.85, m, 2H, 1.98, m, 2H, 2.40, s, 1H, 2.62, s, 3H, 2.99, t, 2H, 3.32, m, 4H, 3.90, quart., 2H, 4.21, quart., 2H, 7.15, d, 1H; 7.95, dd, 1H; 8.55, d, 1H, 9.73, s, 1H.

Example 56

N-(3-Ethoxypropyl)-3-(5-methyl-4-oxo-7-propyl-3,4-dihydro-imidazo[5,1-f][1,2,4]triazin-2-yl)-4-propoxy-benzenesulphonamide

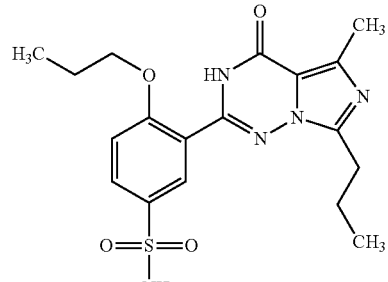

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 31 mg (0.3 mmol) of 3-ethoxypropylamine, 47 mg (96%) of N-(3-ethoxypropyl)-3-(5-methyl-4-oxo-7-propyl-3,4-dihydro-imidazo[5,1-f][1,2,4]triazin-2-yl)-4-propoxy-benzenesulphonamide are obtained.

$R_f$=0.60 (dichloromethane/methanol=9:1)

200 MHz $^1$H-NMR (CDCl$_3$): 1.01, t, 3H, 1.15, m, 6H, 1.89, m, 7H, 2.62, s, 3H, 3.00, t, 2H, 3.12, quart., 2H, 3.46, m, 4H, 4.20, t, 2H, 5.52, m, 1H, 7.15, d, 1H, 7.98, dd, 1H, 8.55, d, 1H, 9.85, s, 1H.

Example 57

2-[5 (4-Hydroxypiperidine-1-sulphonyl)-2-propoxyphenyl]-5-methyl-7-propyl-3H-imidazo[5,1-f][1,2,4]triazin-4-one

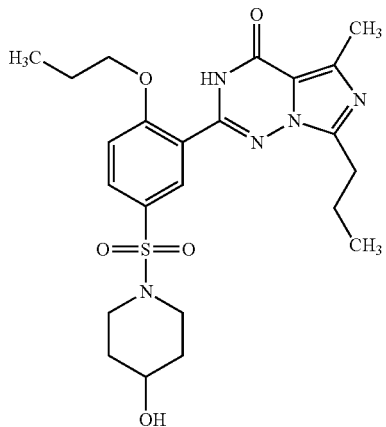

By the same method, starting with 212 mg (0.5 mmol) of 4-propoxy-3-(5-methyl-4-oxo-7-propyl-3,4-dihydro-imidazo[5,1-f][1,2,4]triazin-2-yl)-benzenesulphonyl chloride and 152 mg (1.5 mmol) of 4-hydroxypiperidine, 125 mg (50%) of 2-[5(4-hydroxypiperidine-1-sulphonyl)-2-propoxy-phenyl]-5-methyl-7-propyl-3H-imidazo[5,1-j][1,2,4]triazin-4-one are obtained.

$R_f$=0.07 (dichloromethane/methanol=19:1)

200 MHz $^1$H-NMR (CDCl$_3$): 1.05, t, 3H, 1.18, t, 3H, 1.98, m, 8H, 2.71, s, 3H, 3.10, m, 2H, 3.28, m, 4H, 3.88, m, 1H, 4.28, t, 2H, 7.21, d, 1H, 7.97, dd, 1H, 8.45, d, 1H. 10.45, s, 1H.

Example 58

3-(5-Methyl-4-oxo-7-propyl-3,4-dihydro-imidazo[5,1-f][1,2,4]triazin-2-yl)-4-propoxy-N-pyridin-4-yl-benzenesulphonamide

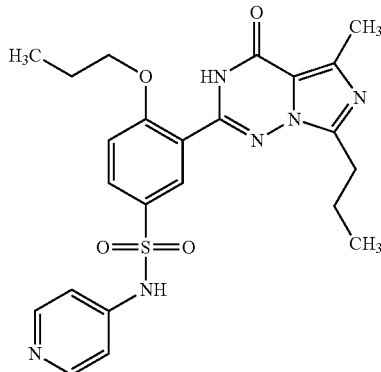

By the same method, starting with 85 mg (0.2 mmol) of 4-propoxy-3-(5-methyl-4-oxo-7-propyl-3,4-dihydro-imidazo[5,1-f][1,2,4]triazin-2-yl)-benzenesulphonyl chloride and 56 mg (0.6 mmol) of 4-aminopyridine, 24 mg (25%) of 3-(5-methyl-4-oxo-7-propyl-3,4-dihydro-imidazo[5,1-f][1,2,4]triazin-2-yl)-4-propoxy-N-pyridin-4-yl-benzenesulphonamide are obtained after 18 hours at reflux in 1 ml of THF.

$R_f$=0.13 (dichloromethane/methanol=9:1)

200 MHz $^1$H-NMR (CDCl$_3$+CD$_3$OD): 1.01, t, 3H, 1.09, t, 3H, 1.90, m, 4H, 2.60, s, 3H, 2.99, t, 2H, 4.16, t, 2H, 7.05, d, 2H, 7.15, d, 1H, 7.88, d, 2H, 8.05, dd, 1H, 8.41, d, 1H.

Example 59

N,N-Diethyl-3-(5-methyl-4-oxo-7-propyl-3,4-dihydro-imidazo[5,1-f][1,2,4]triazin-2-yl)-4-propoxy-benzenesulphonamide

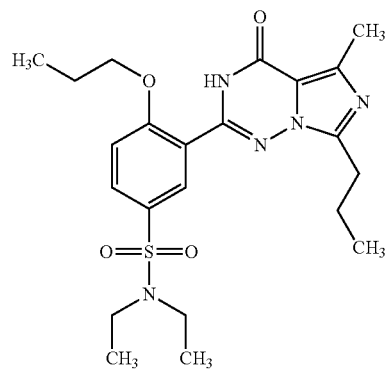

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 22 mg (0.6 mmol) of diethylamine, 42 mg (92%) of N,N-diethyl-3-(5-methyl-4-oxo-7-propyl-3,4-dihydro-imidazo[5,1-f][1,2,4]triazin-2-yl)-4-propoxy-benzenesulphonamide are obtained.

$R_f$=0.64 (dichloromethane/methanol=9:1)

200 MHz $^1$H-NMR (CDCl$_3$): 1.01, t, 3H, 1.18, 2t, 9H, 1.92, 2 hex., 4H, 2.62, s, 3H, 3.00, t, 2H, 3.29, quart., 4H, 4.21, t, 2H, 7.13, d, 1H, 7.93, dd, 1H, 8.51, d, 1H, 9.85, s, 1H.

Example 60

1-[3-(5-Methyl-4-oxo-7-propyl-3,4-dihydro-imidazo[5,1-f][1,2,4]triazin-2-yl)-4-propoxy-benzenesulphonyl]-piperidine-4-carboxylic acid

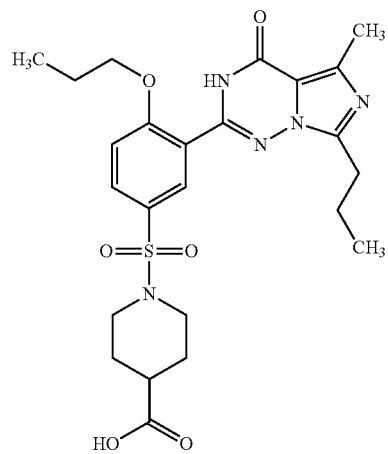

By the same method, starting from 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 14 mg (0.6 mmol) of piperidinecarboxylic acid in 1 ml of a mixture of THF and water (1:1) with 26.5 mg of sodium carbonate, 21 mg (41%) of 1-[3-(5-methyl-4-oxo-7-propyl-3,4-dihydro-imidazo[5,1-f][1,2,4]triazin-2-yl)-4-propoxy-benzenesulphonyl]-piperidine-4-carboxylic acid are obtained.

R$_f$=0.28 (dichloromethane/methanol=9:1)

200 MHz $^1$H-NMR (CDCl$_3$): 0.90, t, 3H, 1.04, t, 3H, 1.80, m, 4H, 2.21, m, 2H, 2.51, s, 3H, 2.85, m, 2H, 3.56, m, 6H, 4.10, t, 2H, 7.12, d, 1H, 7.71, dd, 1H, 8.10, d, 1H, 10.72, s, broad, 1H.

Example 61

5-Methyl-2-[5-(morpholine-4-sulphonyl)-2-propoxy-phenyl]-7-propyl-3H-imidazo[5,1-j][1,2,4]triazin-4-one

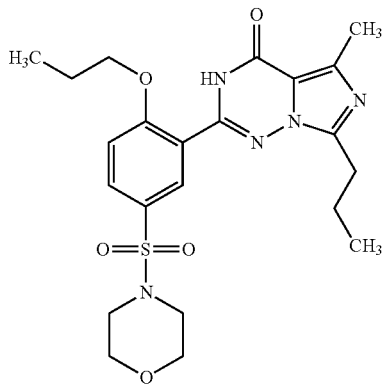

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 26 mg (0.3 mmol) of morpholine, 34 mg (71%) of 5-methyl-2-[5-(morpholine-4-sulphonyl)-2-propoxy-phenyl]-7-propyl-3H-imidazo[5,1f][1,2,4]triazin-4-one are obtained.

R$_f$=0.64 (dichloromethane/methanol=9:1)

200 MHz $^1$H-NMR (CDCl$_3$): 1.01, t, 3H, 1.16, t, 3H, 1.89, hex., 2H, 2.00, hex., 2H, 2.63, s, 3H, 3.02, m, 4H, 4.25, t, 2H, 7.19, d, 1H, 7.89, dd, 1H, 8.48, d, 1H, 9.78, s, 1H.

Example 62

N-(2-Hydroxyethyl)-N-methyl-3-(5-methyl-4-oxo-7-propyl-3,4-dihydro-imidazo[5,1-f][1,2,4]triazin-2-yl)-4-propoxy-benzenesulphonamide

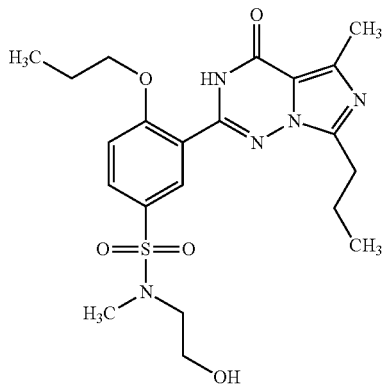

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 23 mg (0.63 mmol) of methylhydroxyethylamine, 25 mg (54%) of N-(2-hydroxyethyl)-N-methyl-3-(5-methyl-4-oxo-7-propyl-3,4-dihydro-imidazo[5,1-f][1,2,4]triazin-2-yl)-4-propoxy-benzenesulphonamide are obtained.

R$_f$=0.53 (dichloromethane/methanol=9:1)

200 MHz $^1$H-NMR (CDCl$_3$): 1.01, t, 3H, 1.15, t, 3H, 1.82, m, 2H, 1.99, hex., 2H, 2.40, s, broad, 1H, 2.62, s, 3H, 2.89, s, 3H, 2.99, t, 2H, 3.21, t, 2H, 3.80, s, broad, 2H, 4.21, t, 2H, 7.16, d, 1H, 7.92, dd, 1H, 8.50, d, 1H, 9.79, s, 1H.

Example 63

N-(2-Hydroxyethyl)-3-(5-methyl-4-oxo-7-propyl-3,4-dihydro-imidazo[5,1-f][1,2,4]triazin-2-yl)-4-propoxy-N-propyl-benzenesulphonamide

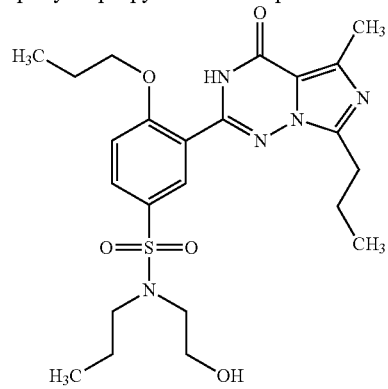

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 31 mg (0.6 mmol) of propylhydroxyethylamine, 20 mg (40%) of N-(2-hydroxyethyl)-3-(5-methyl-4-oxo-7-propyl-3,4-dihydro-imidazo[5,1-f][1,2,4]-triazin-2-yl)-4-propoxy-N-propyl-benzenesulphonamide are obtained.

R$_f$=0.52 (dichloromethane/methanol=9:1)

200 MHz $^1$H-NMR (CDCl$_3$): 0.90, t, 3H, 1.01, t, 3H, 1.15, t, 3H, 1.52, m, 2H, 1.88, m, 2H, 2.00, m, 2H, 2.40, s, 1H, 2.63, s, 3H, 3.01, t, 2H, 3.22, m, 4H, 3.80, quart., 2H, 4.21, t, 2H, 7.15, d, 2H, 7.95, dd, 1H, 8.55, d, 1H, 9.75, s, 1H.

Example 64

N-[2-(3,4-Dimethoxy-phenyl)ethyl]-N-methyl-3-(5-methyl-4-oxo-7-propyl-3,4-dihydro-imidazo[5,1-f][1,2,4]triazin-2-yl)-4-propoxy-benzenesulphonamide

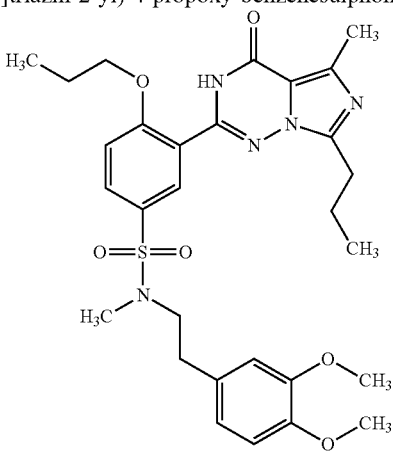

By the same method, starting with 42 mg (0.1 mmol) of 4-propoxy-3-(5-methyl-4-oxo-7-propyl-3,4-dihydroimidazo[5,1-f][1,2,4]triazin-2-yl)-benzenesulphonyl chloride and 59 mg (0.3 mmol) of N-methyl-3,4-dimethoxyphenylethylamine, 45 mg (78%) of N-[2-(3,4-dimethoxyphenyl)-ethyl]-N-methyl-3-(5-methyl-4-oxo-7-propyl-3,4-dihydro-imidazo[5,1-f][1,2,4]triazin-2-yl)-4-propoxy-benzenesulphonamide are obtained.

$R_f$=0.35 (dichloromethane/methanol=19:1)

200 MHz $^1$H-NMR (CDCl$_3$): 0.90, t, 3H, 1.07, t, 3H, 1.78, m, 2H, 1.92, m, 2H, 2.55, s, 3H, 2.73, s, 3H, 2.78, m, 2H, 2.89, t, 2H, 3.23, t, 2H, 3.80, s, 6H, 4.15, t, 2H, 6.65, m, 3H, 7.05, d, 1H, 7.75, dd, 1H, 8.41, d, 1H, 9.67, s, 1H.

Example 65

N-Allyl-N-(2-hydroxyethyl)-3-(5-methyl-4-oxo-7-propyl-3,4-dihydro-imidazo[5,1-f][1,2,4]triazin-2-yl)-4-propoxy-benzenesulphonamide

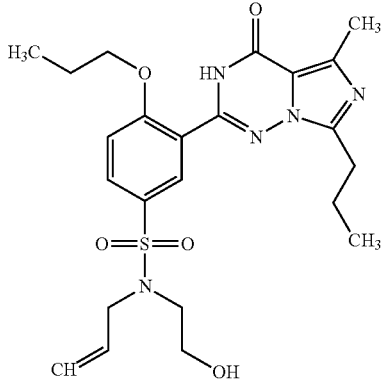

By the same method, starting with 42 mg (0.1 mmol) of 4-propoxy-3-(5-methyl-4-oxo-7-propyl-3,4-dihydroimidazo[5,1-f][1,2,4]triazin-2-yl)-benzenesulphonyl chloride and 31 mg (0.3 mmol) of allylhydroxyethylamine, 34 mg (70%) of N-allyl-N-(2-hydroxyethyl)-3-(5-methyl-4-oxo-7-propyl-3,4-dihydroimidazo[5,1-f][1,2,4]triazin-2-yl)-4-propoxy-benzenesulphonamide are obtained.

$R_f$=0.52 (dichloromethane/methanol=9:1)

200 MHz $^1$H-NMR (CDCl$_3$): 1.01, t, 3H, 1.15, t, 3H, 1.85, m, 2H, 1.99, m, 2H, 2.38, s, broad, 1H, 2.63, s, 3H, 3.00, t, 2H, 3.32, t, 2H, 3.86, t, 2H, 3.90, d, 2H, 4.25, t, 2H, 5.21, m, 2H, 5.71, m, 1H, 7.15, d, 1 h, 7.95, dd, 1H, 8.55, d, 1H, 9.77, s, 1H.

Example 66

N-Allyl-N-cyclopentyl-3-(5-methyl-4-oxo-7-propyl-3,4-dihydro-imidazo[5,1-f][1,2,4]triazin-2-yl)-4-propoxy-benzenesulphonamide

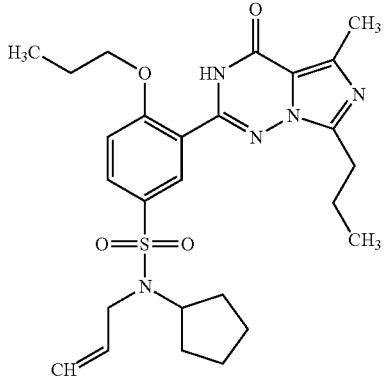

By the same method, starting with 42 mg (0.1 mmol) of 4-propoxy-3-(5-methyl-4-oxo-7-propyl-3,4-dihydroimidazo[5,1-f][1,2,4]triazin-2-yl)-benzenesulphonyl chloride and 38 mg (0.3 mmol) of allylcyclopentylamine, 33 mg (64%) of N-allyl-N-cyclopentyl-3-(5-methyl-4-oxo-7-propyl-3,4-dihydro-imidazo[5,1-f][1,2,4]triazin-2-yl)-4-propoxy-benzenesulphonamide are obtained.

$R_f$=0.43 (dichloromethane/methanol=19:1)

200 MHz $^1$H-NMR (CDCl$_3$): 1.01, t, 3H, 1.15, t, 3H, 1.53, m, 9H, 2.00, m, 4H, 2.63, s, 3H, 3.00, t, 2H, 3.80, m, 2H, 4.21, t, 2H, 5.20, m, 2H, 5.88, m, 1H, 7.12, d, 1H, 7.95, dd, 1H, 8.55, d, 1H, 9.75, s, 1H.

Example 67

N-Allyl-N-ethyl-3-(5-methyl-4-oxo-7-propyl-3,4-dihydroimidazo[5,1-f][1,2,4]-triazin-2-yl)-4-propoxybenzenesulphonamide

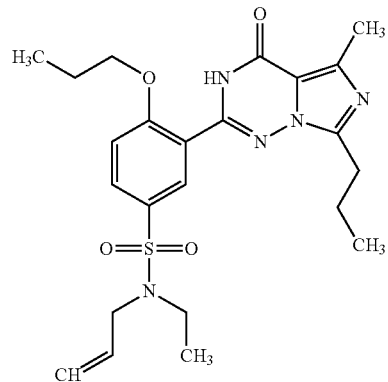

By the same method, starting with 42 mg (0.1 mmol) of 4-propoxy-3-(5-methyl-4-oxo-7-propyl-3,4-dihydro-imidazo[5,1-f][1,2,4]triazin-2-yl)-benzenesulphonyl chloride and 26 mg (0.3 mmol) of allylethylamine, 30 mg (64%) of N-allyl-N-ethyl-3-(5-methyl-4-oxo-7-propyl-3,4-dihydroimidazo[5,1-f][1,2,4]triazin-2-yl)-4-propoxy-benzenesulphonamide are obtained.

$R_f$=0.44 (dichloromethane/methanol=19:1)

200 MHz $^1$H-NMR (CDCl$_3$): 1.01, t, 3H, 1.15, t, 6H, 1.89, m, 2H, 2.01, m, 2H, 2.63, s, 3H, 3.00, t, 2H, 3.27, quart., 2H, 3.87, d, 2H, 4.23, t, 2H, 5.20, m, 2H, 5.72, m, 1H, 7.15, d, 1H, 7.95, dd, 1H, 8.55, d, 1H, 9.80, s, 1H.

Example 68

2-[2-Ethoxy-4-methoxy-5-(4-methylpiperazine-1-sulphonyl)-phenyl]-5-methyl-7-propyl-3H-imidazo[5,1-f][1,2,4]triazin-4-one

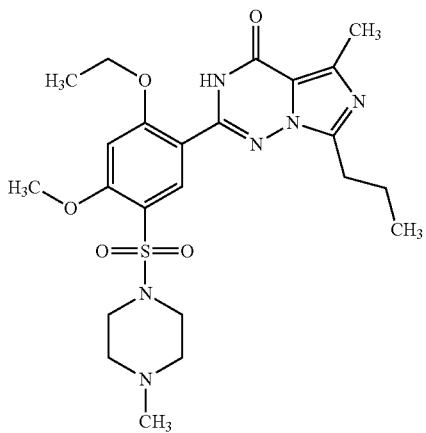

20 mg (0.045 mmol) of 4-ethoxy-2-methoxy-5-(5-methyl-4-oxo-7-propyl-3,4-dihydroimidazo-[5,1-f][1,2,4]triazin-2-yl)-benzenesulphonyl chloride are dissolved in 0.5 ml of dichloromethane and admixed with a spatula tip of dimethylaminopyridine and 14 mg (0.136 mmol) of N-methylpiperazine, and the reaction mixture is stirred at room temperature overnight. Purification over silica gel gives 12.8 mg (55%) of 2-[2-ethoxy-4-methoxy-5-(4-methylpiperazine-1-sulphonyl)phenyl]-5-methyl-7-propyl-3H-imidazo[5,1-f][1,2,4]triazin-4-one.

$R_f$=0.22 (dichloromethane/methanol=20:1).

200 MHz $^1$H-NMR (CDCl$_3$): 0.94, t, 3H, 1.55, t, 3H, 1.80, m, 2H, 2.24, s, 3H, 2.42, t, 4H, 2.55, s, 3H, 2.92, t, 2H, 3.19, t, 4H, 3.91, s, 3H, 4.25, quart., 2H, 6.48, s, 1H, 8.57, s, 1H, 9.54, s, 1H.

Example 69

2-{2-Ethoxy-5-[4-(2-hydroxyethyl)-piperazine-1-sulphonyl]-4-methoxy-phenyl}-5-methyl-7-propyl-3H-imidazo[5,1-f][1,2,4]triazin-4-one

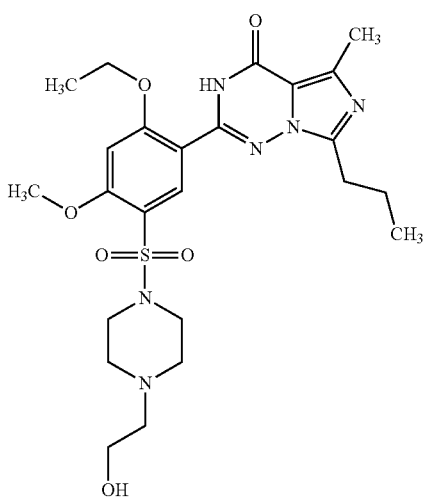

By the same method, starting with 20 mg (0.045 mmol) of 4-ethoxy-2-methoxy-5-(5-methyl-4-oxo-7-propyl-3,4-dihydroimidazo[5,1-f][1,2,4]triazin-2-yl)-benzenesulphonyl chloride and 18 mg (0.14 mmol) of 4-hydroxyethylpiperazine, 11 mg (46%) of 2-{2-ethoxy-5-[4-(2-hydroxyethyl)-piperazine-1-sulphonyl]-4-methoxyphenyl}-5-methyl-7-propyl-3H-imidazo[5,1-f][1,2,4]triazin-4-one are obtained.

$R_f$=0.34 (dichloromethane/methanol=15:1)

200 MHz $^1$H-NMR (CDCl$_3$): 0.94, t, 3H, 1.55, t, 3H, 1.80, m, 3H, 2.52, m, 9H, 2.92, t, 2H, 3.20, t, 4H, 3.44, t, 2H, 3.92, s, 3H, 4.25, quart., 2H, 6.49, s, 1H, 8.56, s, 1H, 9.55, s, 1H.

Example 70

4-Ethoxy-N-ethyl-N-(2-hydroxyethyl)-2-methoxy-5-(5-methyl-4-oxo-7-propyl-3,4-dihydro-imidazo[5,1-f][1,2,4]triazin-2-yl)-benzenesulphonamide

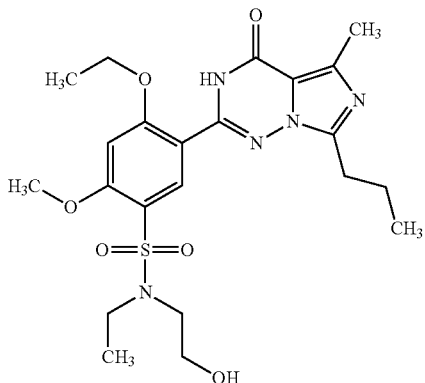

By the same method, starting from 20 mg (0.045 mmol) of 4-ethoxy-2-methoxy-5-(5-methyl-4-oxo-7-propyl-3,4-dihydro-imidazo[5,1-f][1,2,4]triazin-2-yl)-benzenesulphonyl chloride and 12 mg (0.14 mmol) of ethylhydroxyethylamine, 8 mg (34%) of 4-ethoxy-N-ethyl-N-(2-hydroxyethyl)-2-methoxy-5-(5-methyl-4-oxo-7-propyl-3,4-dihydro-imidazo[5,1-f][1,2,4]triazin-2-yl)-benzenesulphonamide are obtained.

$R_f$=0.45 (dichloromethane/methanol=15:1)

200 MHz $^1$H-NMR (CDCl$_3$): 1.02, t, 3H, 1.18, t, 3H, 1.61, t, 2H, 1.88, m, 2H, 2.39, s, broad, 1H, 2.65, s, 3H, 3.00, t, 2H, 3.38, quart., 2H, 3.45, t, 2H, 3.78, m, 2H, 4.01, s, 3H, 4.20, quart., 2H, 6.58, s, 1H, 8.67, s, 1H, 9.61, s, 1H.

Example 71

4-Ethoxy-N-(4-ethoxyphenyl)-2-methoxy-5-(5-methyl-4-oxo-7-propyl-3,4-dihydro-imidazo[5,1-f][1,2,4]triazin-2-yl)-benzenesulphonamide

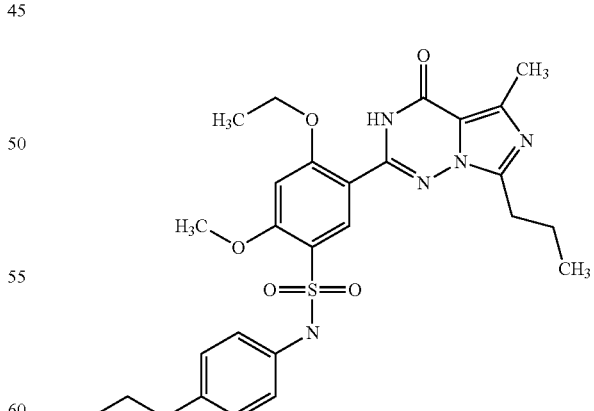

By the same method, starting with 20 mg (0.045 mmol) of 4-ethoxy-2-methoxy-5-(5-methyl-4-oxo-7-propyl-3,4-dihydro-imidazo[5,1-f][1,2,4]triazin-2-yl)-benzene-sulphonyl chloride and 19 mg (0.14 mmol) of 4-ethoxyaniline, 7 mg (34%) of 4-ethoxy-N-(4-ethoxyphenyl)-2-methoxy-5-(5- methyl-4-oxo-7-propyl-3,4-dihydro-imidazo[5,1-f][1,2,4]triazin-2-yl)-benzenesulphonamide are obtained.

R$_f$=0.36 (dichloromethane/methanol=20:1)

200 MHz $^1$H-NMR (CDCl$_3$): 1.02, t, 3H, 1.33, t, 3H, 1.59, t, 3H, 1.86, hex., 2H, 2.62, s, 3H, 3.02, t, 2H, 3.92, quart., 2H, 4.11, s, 3H, 4.31, quart., 2H, 6.58, s, 1H, 6.72, d, 2H, 6.88, s, broad, 1H, 6.99, d, 2H, 8.50, s, 1H, 9.59, s, 1H.

Example 72

4-Ethoxy-N-ethyl-N-(2-hydroxy-ethyl)-3-(5-ethyl-4-oxo-7-propyl-3,4-dihydro-imidazo[5,1-f][1,2,4]triazin-2-yl)benzenesulphnamide

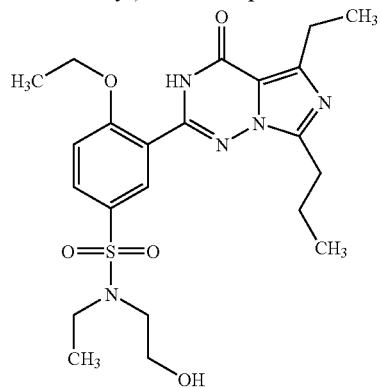

0.64 g (1.5 mmol) of 4-ethoxy-3-(5-ethyl-4-oxo-7-propyl-3,4-dihydro-imidazo[5,1-f][1,2,4]triazin-2-yl)-benzenesulphonyl chloride are dissolved in 20 ml of dichloromethane and cooled to 0° C. After addition of a spatula tip of dimethylaminopyridine, 0.40 g (4.50 mmol) of 2-(ethylamino)-ethanol are added, and the reaction mixture is stirred at room temperature overnight. The mixture is diluted with dichloromethane, the organic phase is washed with water and dried over sodium sulphate and the solvent is removed under reduced pressure. Chromatography (dichloromethane/methanol=95:5) gives 0.454 g (63%) of a colourless solid.

200 MHz $^1$H-NMR (CDCl$_3$): 1.02, t, 3H, 1.20, t, 3H, 1.35, t, 3H, 1.61, t, 3H, 1.88, sex., 2H, 2.25, s, broad, 1H; 3.01, m, 4H, 3.32, m, 4H, 3.70, m, 2H, 3.80, m, 2H, 4.37, quart., 2H, 7.15, d, 1H; 7.98, dd, 1H; 8.56, d, 1H, 9.70, s, 1H.

Example 73

N-(2-Methoxyethyl)-3-(5-ethyl-4-oxo-7-propyl-3,4-dihydro-imidazo[5,1-f][1,2,4]triazin-2-yl)-4-ethoxy-benzenesulphonamide

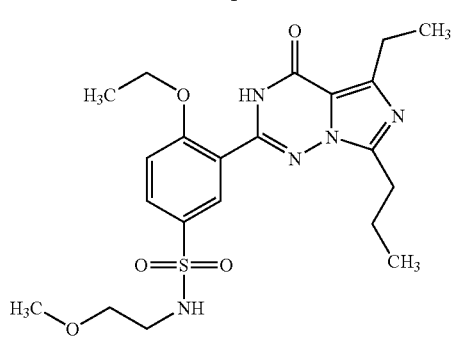

By the same method, starting with 40 mg (0.094 mmol) of 4-ethoxy-3-(5-ethyl-4-oxo-7-propyl-3,4-dihydroimidazo[5,1-f][1,2,4]triazin-2-yl)-benzenesulphonyl chloride and 21 mg (0.282 mmol) of 2-methoxyethylamine, 15 mg (34%) of N-(2-methoxyethyl)-3-(5-ethyl-4-oxo-7-propyl-3,4-dihydroimidazo[5,1-f][1,2,4]triazin-2-yl)-4-ethoxybenzenesulphonamide are obtained.

R$_f$=0.2 (ethyl acetate/cyclohexane=2:1)

200 MHz $^1$H-NMR (CDCl$_3$): 0.97, t, 3H, 1.25, t, 3H, 1.53, t, 3H, 1.82, sex., 2H, 2.97, m, 4H, 3.11, m, 2H, 3.22, s, 3H, 3.39, t, 2H, 4.37, quart., 2H, 5.00, t, 1H, 7.17, d, 1H, 7.97, dd, 1H, 8.53, d, 1H, 9.82, s, 1H.

Example 74

N,N-Bis-(2-methoxyethyl)-3-(5-ethyl-4-oxo-7-propyl-3,4-dihydro-imidazo[5,1-f][1,2,4]triazin-2-yl)-4-ethoxybenzenesulphonamide

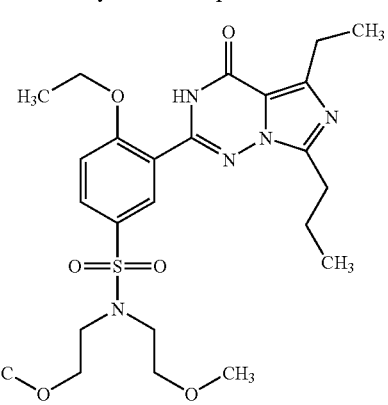

By the same method, starting with 40 mg (0.094 mmol) of 4-ethoxy-3-(5-ethyl-4-oxo-7-propyl-3,4-dihydro-imidazo[5,1-f][1,2,4]triazin-2-yl)-benzenesulphonyl chloride and 38 mg (0.28 mmol) of bismethoxyethylamine, 17 mg (34%) of N,N-bis-(2-methoxyethyl)-3-(5-ethyl-4-oxo-7-propyl-3,4-dihydroimidazo[5,1-f][1,2,4]triazin-2-yl)-4-ethoxybenzenesulphonamide are obtained.

R$_f$=0.34 (ethyl acetate/cyclohexane=2:1)

200 MHz $^1$H-NMR (CDCl$_3$): 0.97, t, 3H, 1.27, t, 3H, 1.53, t, 3H, 1.80, sex., 2H, 2.95, m, 4H, 3.22, s, 6H, 3.39, m, 4H, 3.49, m, 4H, 4.27, quart., 2H, 7.17, d, 1H, 7.97, dd, 1H, 8.53, d, 1H; 9.82, s, 1H.

Example 75

2-[5-(4-Hydroxypiperidine-1-sulphonyl)-2-ethoxyphenyl]-5-ethyl-7-propyl-3H-imidazo[5,1-f]-[1,2,4]triazin-4-one

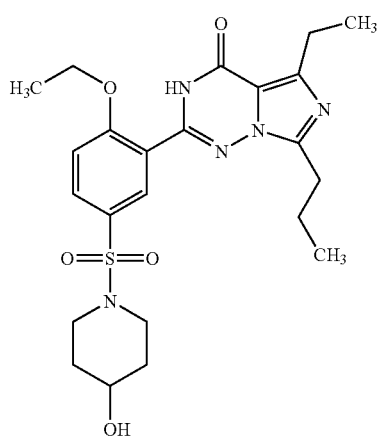

By the same method, starting with 640 mg (1.5 mmol) of 4-ethoxy-3-(5-ethyl-4-oxo-7-propyl-3,4-dihydroimidazo[5,1-f][1,2,4]triazin-2-yl)-benzenesulphonyl chloride and 460 mg (4.5 mmol) of 4-hydroxypiperidine, 485 mg (66%) of 2-[5-(4-hydroxy-piperidine-1-sulphonyl)-2-ethoxyphenyl]-5-ethyl-7-propyl-3H-imidazo[5,1-j][1,2,4]triazin-4-one are obtained.

$R_f$=0.37 (dichloromethane/methanol=19:1)

200 MHz $^1$H-NMR (CDCl$_3$): 1.02, t, 3H, 1.32, t, 3H, 1.60, t, 3H, 1.80, m, 7H, 2.97, m, 6H, 3.30, m, 2H, 3.82, m, 1H, 4.34, quart., 2H, 7.17, d, 1H, 7.90, dd, 1H, 8.45, d, 1H. 9.75, s, 1H.

Example 76

2-[5-(4-Hydroxymethylpiperidine-1-sulphonyl)-2-ethoxy-phenyl]-5-ethyl-7-propyl-3H-imidazo[5,1-f][1,2,4]triazin-4-one

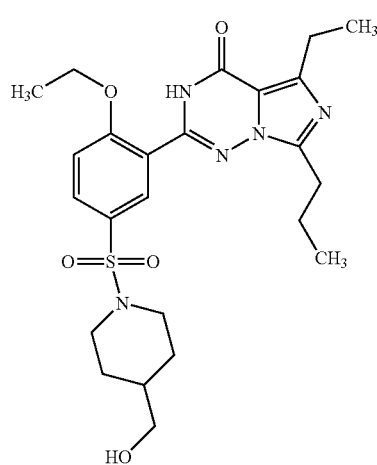

By the same method, starting with 40 mg (0.094 mmol) of 4-ethoxy-3-(5-ethyl-4-oxo-7-propyl-3,4-dihydroimidazo[5,1-f][1,2,4]triazin-2-yl)-benzenesulphonyl chloride and 33 mg (0.28 mmol) of 4-hydroxymethylpiperidine, 23 mg (48%) of 2-[5-(4-hydroxymethylpiperidine-1-sulphonyl)-2-ethoxyphenyl]-5-ethyl-7-propyl-3H-imidazo[5,1-f][1,2,4]triazin-4-one are obtained.

$R_f$=0.38 (dichloromethane/methanol=10:1)

200 MHz $^1$H-NMR (CDCl$_3$): 1.01, t, 3H, 1.33, t, 3H, 1.60, t, 3H, 1.80, m, 8H, 2.41, m, 2H, 3.00, m, 4H, 3.56, m, 4H, 4.35, quart, 2H; 7.17, d, 1H, 7.88, dd, 1H, 8.45, d, 1H, 9.71, s, 1H.

Example 77

2-{2-Ethoxy-5-[4-(2-hydroxyethyl)-piperazine-1-sulphonyl]-phenyl}-5-ethyl-7-propyl-3H-imidazo[5,1-f][1,2,4]triazin-4-one

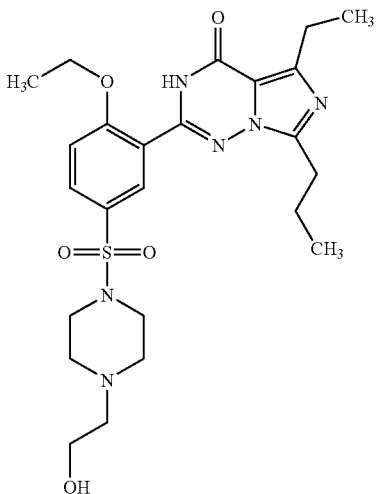

By the same method, starting with 40 mg (0.094 mmol) of 4-ethoxy-3-(5-ethyl-4-oxo-7-propyl-3,4-dihydroimidazo[5,1-f][1,2,4]triazin-2-yl)-benzenesulphonyl chloride and 37 mg (0.28 mmol) of 4-hydroxyethylpiperazine, 35 mg (71%) of 2-{2-ethoxy-5-[4-(2-hydroxyethyl)-piperazine-1-sulphonyl]-phenyl}-5-ethyl-7-propyl-3H-imidazo[5,1-f][1,2,4]triazin-4-one are obtained.

$R_f$=0.65 (dichloromethane/methanol=10:1)

Example 78

2-[2-Ethoxy-5-(4-methylpiperazine-1-sulphonyl)-phenyl]-5-ethyl-7-propyl-3H-imidazo[5,1-f]-[1,2,4]triazin-4-one

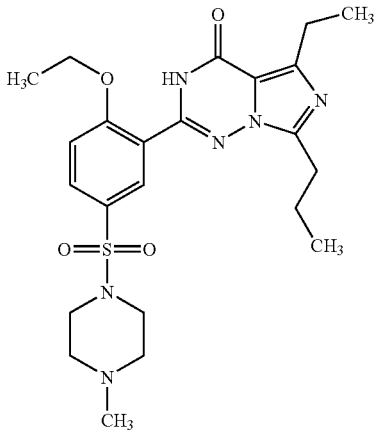

By the same method, starting with 640 mg (1.50 mmol) of 4-ethoxy-3-(5-ethyl-4-oxo-7-propyl-3,4-dihydro-imidazo[5,1-f][1,2,4]triazin-2-yl)-benzenesulphonyl chloride and 450 mg (4.5 mmol) of 4-hydroxyethylpiperazine, 495 mg (66%)

of 2-[2-ethoxy-5-(4-methylpiperazine-1-sulphonyl)-phenyl]-5-ethyl-7-propyl-3H-imidazo[5,1-f][1,2,4]triazin-4-one are obtained.

$R_f$=0.30 (dichloromethane/methanol=19:1)

200 MHz $^1$H-NMR (CDCl$_3$): 1.01, t, 3H, 1.35, t, 3H, 1.61, t, 3H, 1.89, sex., 2H, 2.31, s, 3H, 2.53, m, 4H, 3.05, m, 8H, 4.35, quart., 2H, 7.17, d, 1H, 7.89, dd, 1H, 8.48, d, 1H, 9.65, s, 1H.

Example 79

2-[2-Ethoxy-5-(4-methylpiperazine-1-sulphonyl)-phenyl]-5-ethyl-7-propyl-3H-imidazo[5,1-f][1,2,4]triazin-4-one hydrochloride

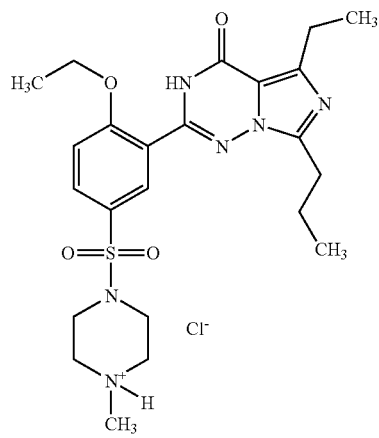

300 mg (0.61 mmol) of 2-[2-ethoxy-5-(4-methyl-piperazine-1-sulphonyl)-phenyl]-5-ethyl-7-propyl-3H-imidazo[5,1-f][1,2,4]triazin-4-one are dissolved in a mixture of ether and dichloromethane and admixed with 2 ml of a 1M solution of HCl in ether. After 20 minutes, the precipitated solid is filtered off with suction and dried.

200 MHz $^1$H-NMR (DMSO-d$_6$): 0.95, t, 3H, 1.32, 2t, 6H, 1.80, sex., 2H, 2.76, m, 4H, 3.01, m, 4H, 3.15, m, 2H, 3.44, m, 2H, 3.81, m, 2H, 4.25, quart., 2H, 7.49, d, 1H, 7.95, m, 2H, 11.25, s, 1H, 12.30, s, 1H.

Example 80

3-(5-Ethyl-4-oxo-7-propyl-3,4-dihydroimidazo[5,1-f][1,2,4]triazin-2-yl)-N-(3-morpholin-4-yl-propyl)-4-ethoxybenzenesulphonamide

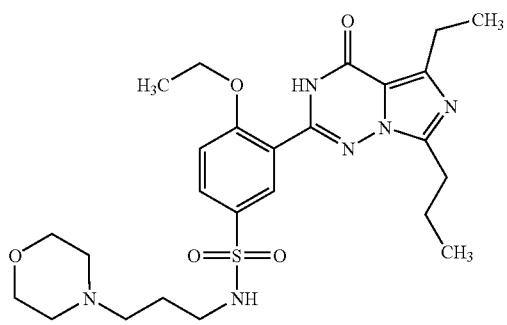

By the same method, starting with 640 mg (1.5 mmol) of 4-ethoxy-3-(5-ethyl-4-oxo-7-propyl-3,4-dihydroimidazo[5,1-f][1,2,4]triazin-2-yl)-benzenesulphonyl chloride and 650 mg (4.5 mmol) of 1-(3-aminopropyl)-morpholine, 476 mg (59%) of 3-(5-ethyl-4-oxo-7-propyl-3,4-dihydroimidazo[5,1-f][1,2,4]triazin-2-yl)-N-(3-morpholin-4-yl-propyl)-4-ethoxy-benzenesulphonamide are obtained.

$R_f$=0.18 (dichloromethane/methanol=19:1)

200 MHz $^1$H-NMR (CDCl$_3$): 1.01, t, 3H, 1.32, t, 3H, 1.60, t, 3H, 1.70, m, 3H, 1.89, sex., 2H, 2.43, m, 7H, 3.01, m, 4H, 3.15, t, 2H, 3.70, m, 4H, 4.35, quart., 2H, 7.15, d, 1H, 7.95, dd, 1H, 8.55, d, 1H; 9.82, s, 1H.

Example 81

N-(2-Hydroxyethyl)-3-(5-ethyl-4-oxo-7-propyl-3,4-dihydro-imidazo[5,1-f][1,2,4]triazin-2-yl)-4-ethoxy-N-propyl-benzenesulphonamide

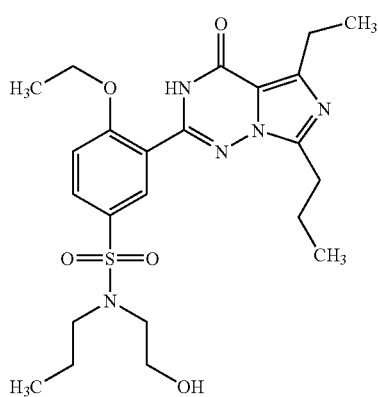

By the same method, starting with 640 mg (1.5 mmol) of 4-ethoxy-3-(5-ethyl-4-oxo-7-propyl-3,4-dihydroimidazo[5,1-f][1,2,4]triazin-2-yl)-benzenesulphonyl chloride and 464 mg (4.5 mmol) of propylhydroxyethylamine, 600 mg (81%) of N-(2-hydroxyethyl)-3-(5-ethyl-4-oxo-7-propyl-3,4-dihydro-imidazo[5,1-f][1,2,4]triazin-2-yl)-4-ethoxy-N-propyl-benzenesulphonamide are obtained.

$R_f$=0.73 (dichloromethane/methanol=10:1)

200 MHz $^1$H-NMR (CDCl$_3$): 0.91, t, 3H, 1.01, t, 3H, 1.32, t, 3H, 1.62, m, 5H, 1.88, m, 2H, 2.32, s, 1H, 3.01, m, 4H, 3.22, m, 4H, 3.80, m, 2H, 4.35, t, 2H, 7.15, d, 2H, 7.95, dd, 1H, 8.55, d, 1H, 9.75, s, 1H.

The sulphonamides listed in Tables 1, 2, 3, 4 and 6 below were prepared by means of automated parallelsynthesis from 4-ethoxy-3-(5-methyl-4-oxo-7-propyl-3,4-dihydro-imidazo[5,1-f][1,2,4]triazin-2-yl)-benzenesulphonyl chloride and the appropriate amine using one of the three standard procedures below.

The sulphonamides listed in Table 5 were prepared by the same methods by means of automated parallelsynthesis from 4-ethoxy-3-(5-ethyl-4-oxo-7-propyl-3,4-dihydro-imidazo[5,1-δ][1,2,4]triazin-2-yl)-benzenesulphonyl chloride and the appropriate amine.

The purity of the final products was determined by means of HPLC, and they were characterized by LC-MS. The content of the desired compound according to HPLC-MS is given in percent in the tables in the column "HPLC". Standard procedure A was used with amines having acidic functionalities, standard procedure B was used with amines having neutral functionalities, standard procedure C was used with amines having additional basic functionalities.

In the structural formulae of Tables 1, 2, 3, 4, 5 and 6 below, hydrogen atoms are in some cases not shown. Nitrogen atoms having a free valency are therefore to be understood as —NH— radical.

Standard Procedure A: Reaction of Amines Having Acidic Functionalities 0.05 mmol of amine, 0.042 mmol of sulphonyl chloride and 0.10 mmol of $Na_2CO_3$ are initially charged, and 0.5 ml of a mixture of $THF/H_2O$ is pipetted in by hand. After 24 h at RT, the mixture is admixed with 0.5 ml of 1M $H_2SO_4$ solution and filtered through a two-phase cartridge (500 mg of Extrelut (upper phase) and 500 mg of $SiO_2$, mobile phase ethyl acetate). The product is obtained after concentrating the filtrate under reduced pressure.

Standard Procedure B: Reaction of Amines Having Neutral Functionalities 0.125 mmol of amine are initially charged and 0.03 mmol of sulphonyl chloride as a solution in 1,2-dichloroethane is pipetted in by the synthesizer. After 24 h, the mixture is admixed with 0.5 ml of 1M $H_2SO_4$ and filtered through a two-phase cartridge (500 mg of Extrelut (upper phase) and 500 mg of $SiO_2$, mobile phase: ethyl acetate). The filtrate is concentrated under reduced pressure.

Standard Procedure C: Reaction of Amines Having Basic Functionalities 0.05 mmol of amine are initially charged and 0.038 mmol of sulphonyl chloride as a solution in 1,2-dichloroethane and 0.05 mmol of triethylamine as a solution in 1,2-dichloroethane is pipetted in by the synthesizer. After 24 h, the solution is initially admixed with 3 ml of saturated $NaHCO_3$ solution and the reaction mixture is filtered through a two-phase cartridge. The product is obtained after concentrating the filtrate under reduced pressure.

All reactions are monitored by thin-layer chromatography. If the reaction is not complete after 24 h at RT, the mixture is heated to 60° C. for a further 12 h and the experiment is subsequently terminated.

TABLE 1

| Ex. No. | Structure | MW [g/mol] | HPLC | MZ + H |
|---|---|---|---|---|
| 82 | 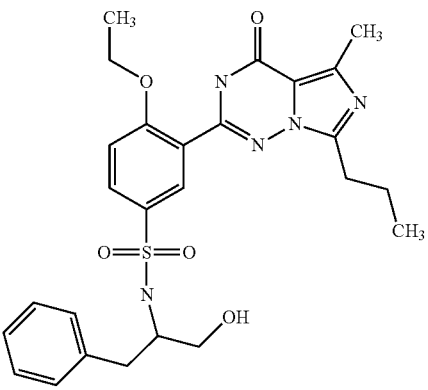 | 525.6315 | 83 | 526 |
| 83 | 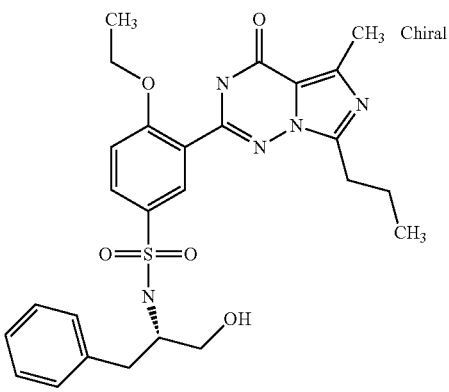 | 525.6315 | 71 | 526 |

TABLE 1-continued
| Ex. No. | Structure | MW [g/mol] | HPLC | MZ + H |
|---|---|---|---|---|
| 84 | 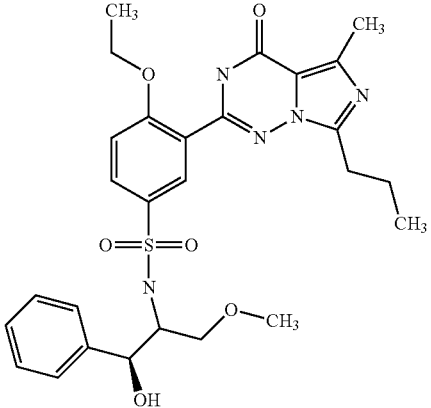 | 555.658 | 91 | 556 |
| 85 | 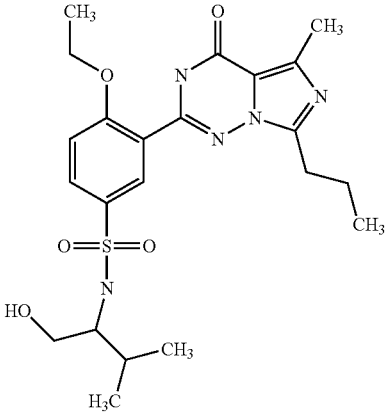 | 477.5869 | 76 | 478 |
| 86 | 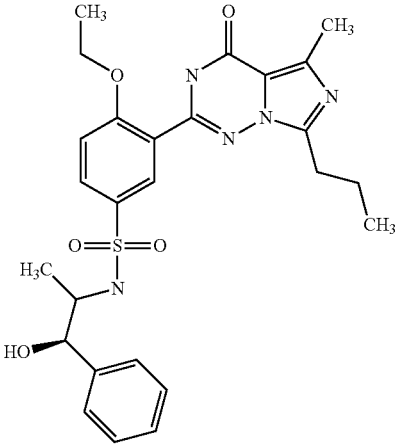 | 525.6315 | 81 | 526 |

TABLE 1-continued

| Ex. No. | Structure | MW [g/mol] | HPLC | MZ + H |
|---|---|---|---|---|
| 87 | 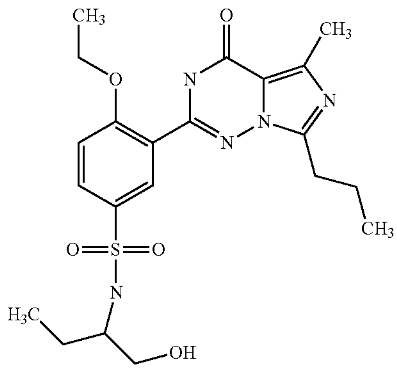 | 463.5598 | 65 | 464 |
| 88 | 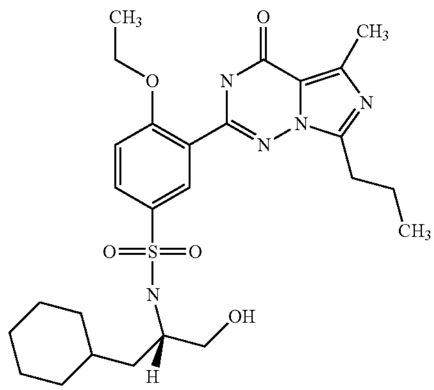 | 531.6793 | 83 | 532 |
| 89 | 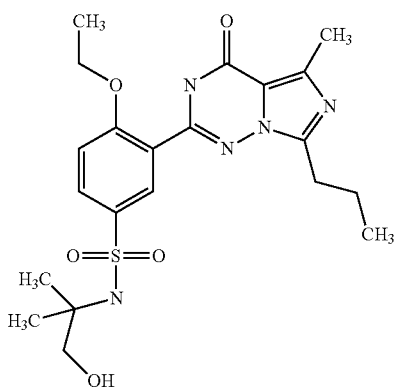 | 463.5598 | 40 | 464 |
| 90 | 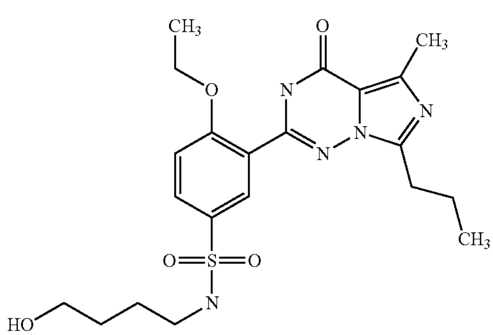 | 463.5598 | 44 | 464 |

TABLE 1-continued

| Ex. No. | Structure | MW [g/mol] | HPLC | MZ + H |
|---|---|---|---|---|
| 91 | 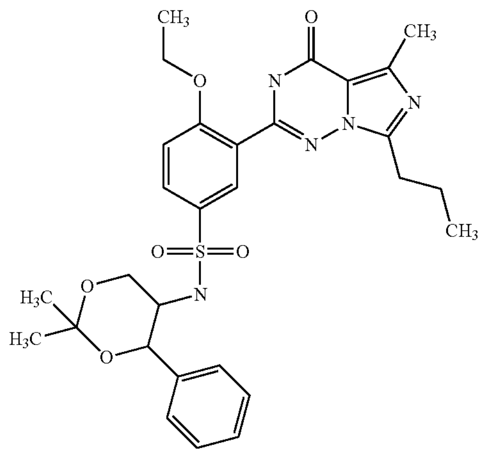 | 581.6962 | 76 | 582 |
| 92 | 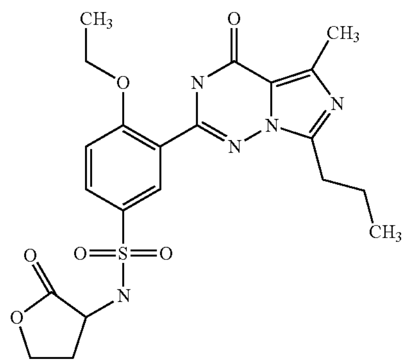 | 475.5273 | 61 | 476 |
| 93 | 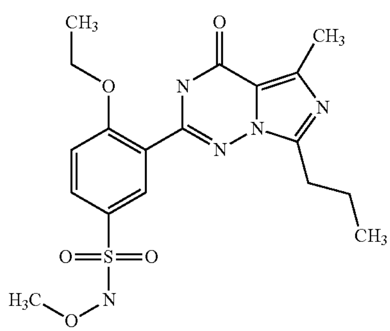 | 421.4785 | 80 | 422 |
| 94 | 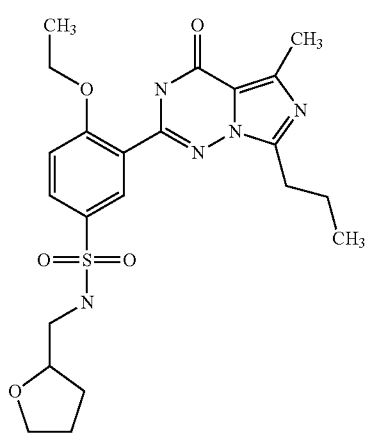 | 475.5709 | 81 | 476 |

TABLE 1-continued

| Ex. No. | Structure | MW [g/mol] | HPLC | MZ + H |
|---|---|---|---|---|
| 95 | 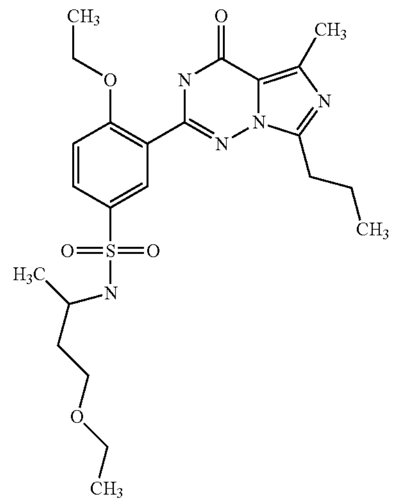 | 491.614 | 97 | 492 |
| 96 | 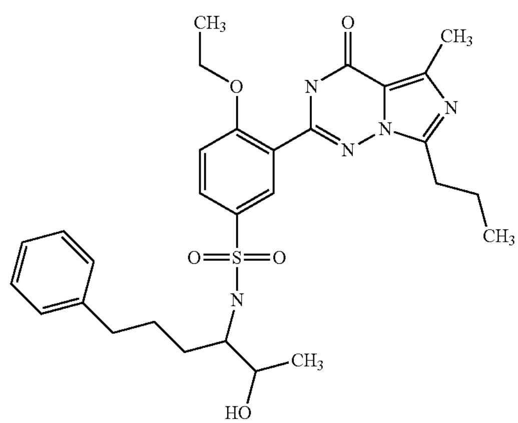 | 567.7127 | 80 | 568 |
| 97 | 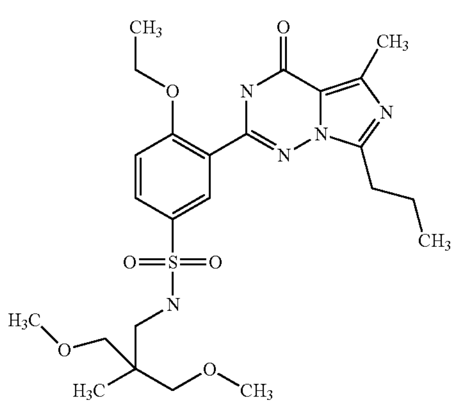 | 521.6405 | 94 | 522 |

TABLE 1-continued

| Ex. No. | Structure | MW [g/mol] | HPLC | MZ + H |
|---|---|---|---|---|
| 98 | 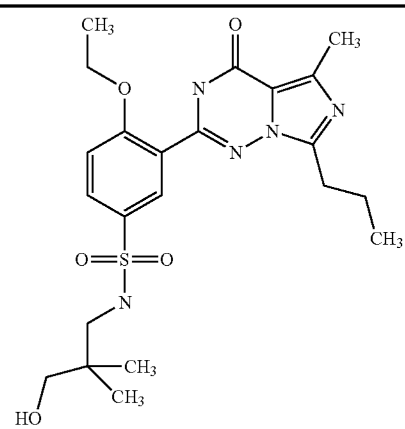 | 477.5869 | 70 | 478 |
| 99 | 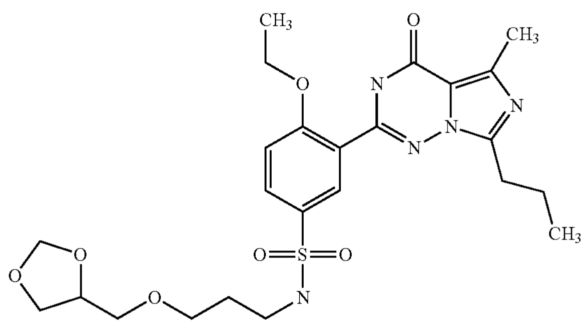 | 535.6239 | 88 | 536 |
| 100 | 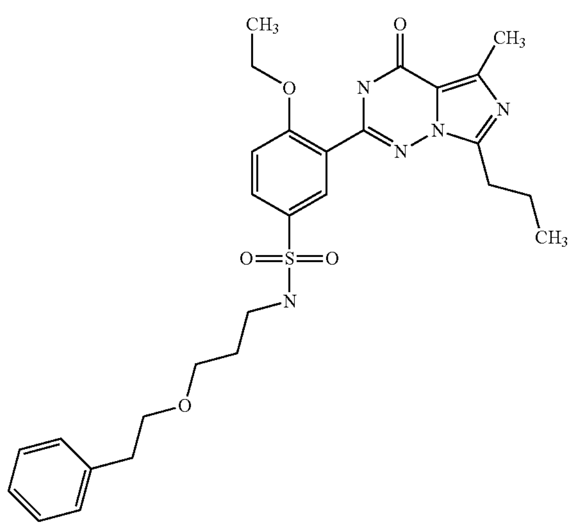 | 553.6857 | 88 | 554 |
| 101 | 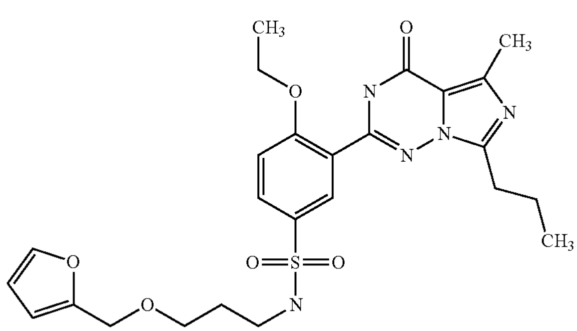 | 529.6197 | 85 | 530 |

TABLE 1-continued
| Ex. No. | Structure | MW [g/mol] | HPLC | MZ + H |
|---|---|---|---|---|
| 102 | 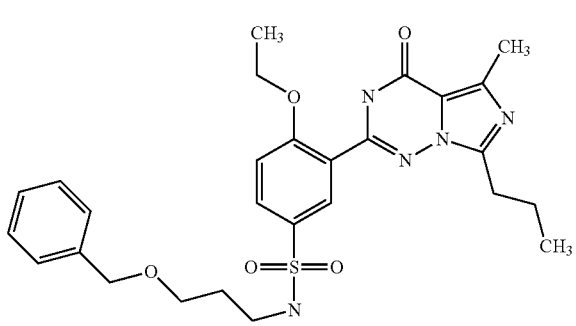 | 539.6586 | 91 | 540 |
| 103 | 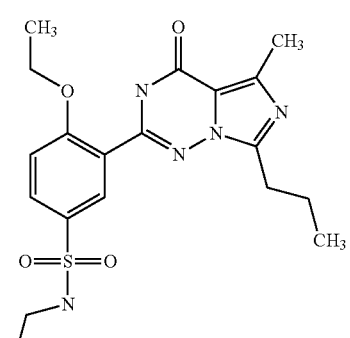 | 520.6121 | 55 | 521 |
| 104 | 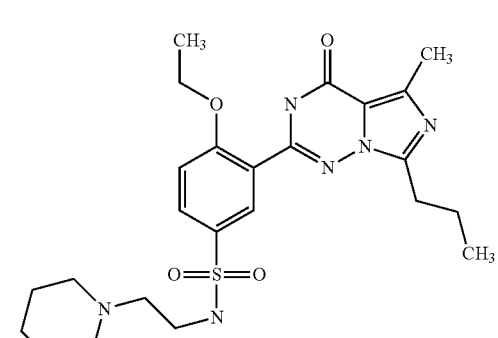 | 502.6404 | 82 | 503 |
| 105 | 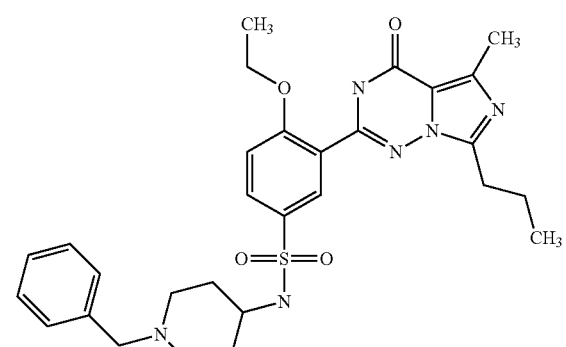 | 564.7121 | 86 | 565 |

TABLE 1-continued

| Ex. No. | Structure | MW [g/mol] | HPLC | MZ + H |
|---|---|---|---|---|
| 106 | 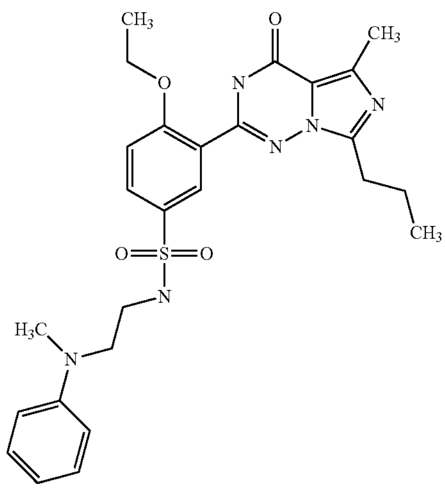 | 524.6467 | 85 | 525 |
| 107 | 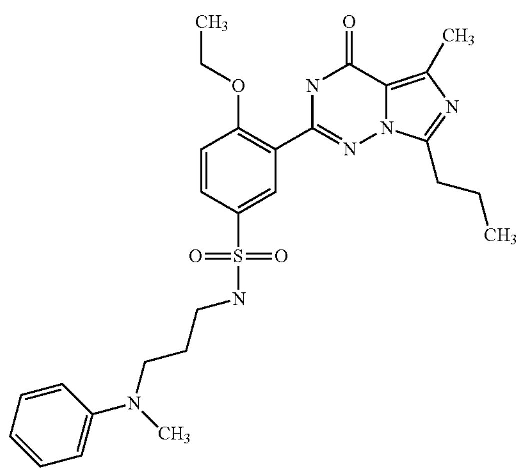 | 538.6738 | 85 | 539 |
| 108 | 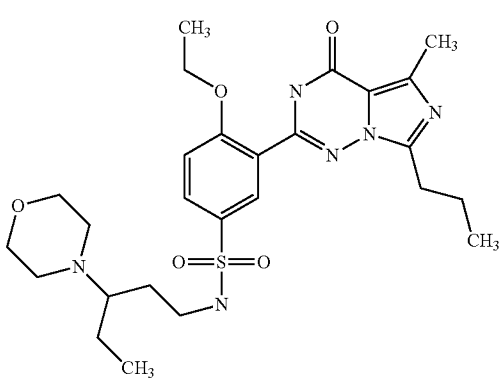 | 546.694 | 84 | 547 |

TABLE 1-continued

| Ex. No. | Structure | MW [g/mol] | HPLC | MZ + H |
|---|---|---|---|---|
| 109 | 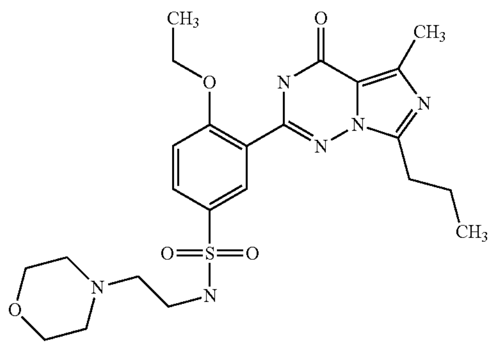 | 504.6127 | 90 | 505 |

TABLE 2

| Ex. No. | Structure | MW [g/mol] | HPLC | MZ + H |
|---|---|---|---|---|
| 110 | 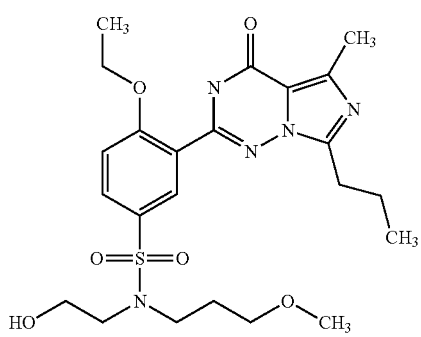 | 507.6134 | 74 | 508 |
| 111 | 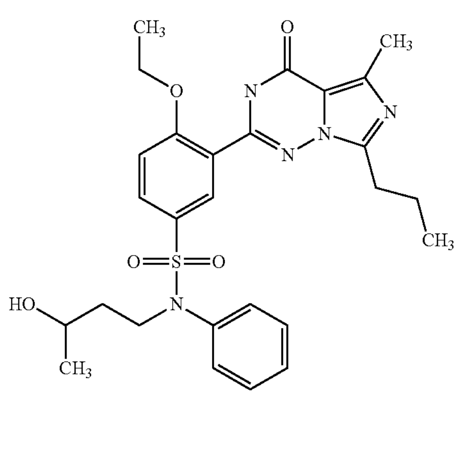 | 539.6586 | 75 | 540 |

TABLE 2-continued

| Ex. No. | Structure | MW [g/mol] | HPLC | MZ + H |
|---|---|---|---|---|
| 112 | 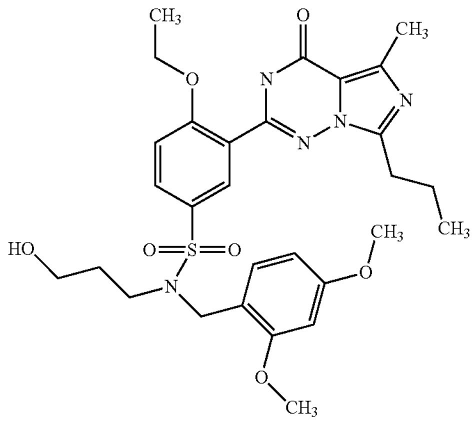 | 599.7115 | 83 | 600 |
| 113 | 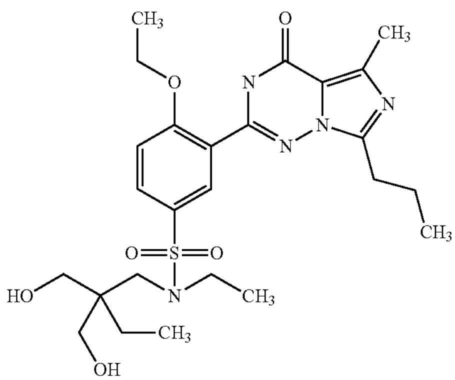 | 535.6675 | 60 | 536 |
| 114 | 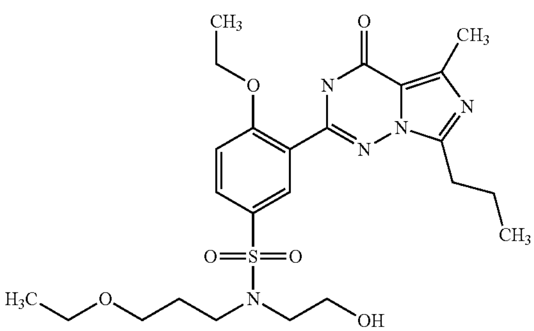 | 521.6405 | 95 | 522 |
| 115 | 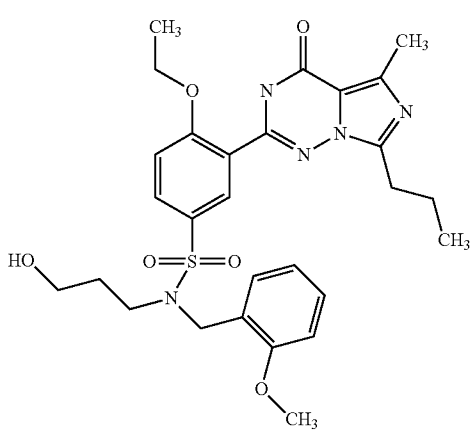 | 569.6851 | 84 | 570 |

TABLE 2-continued

| Ex. No. | Structure | MW [g/mol] | HPLC | MZ + H |
|---|---|---|---|---|
| 116 | 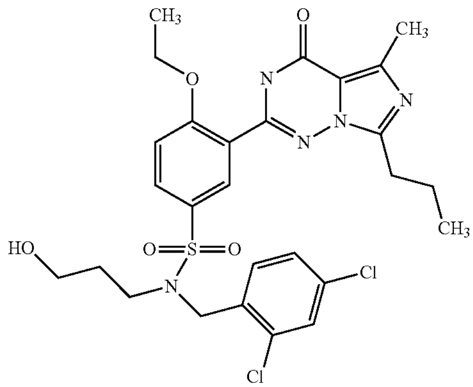 | 608.5486 | 85 | 608 |
| 117 | 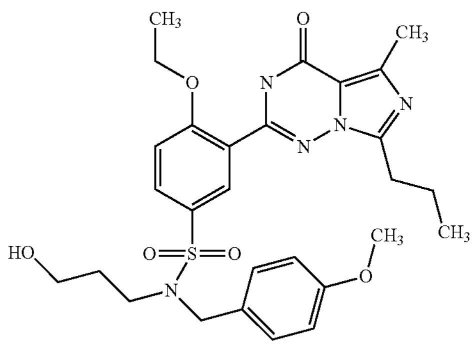 | 569.6851 | 88 | 570 |
| 118 | 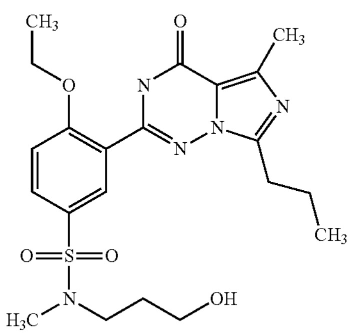 | 463.5598 | 94 | 464 |
| 119 | 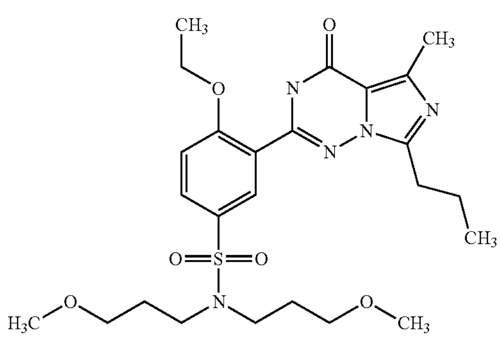 | 535.6675 | 93 | 536 |

TABLE 2-continued

| Ex. No. | Structure | MW [g/mol] | HPLC | MZ + H |
|---|---|---|---|---|
| 120 | 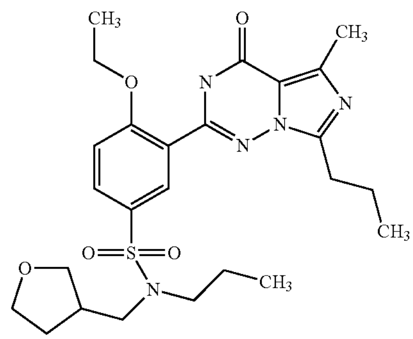 | 517.6522 | 71 | 518 |
| 121 | 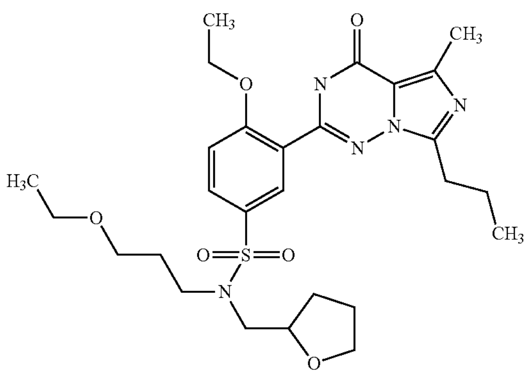 | 561.7058 | 92 | 562 |
| 122 | 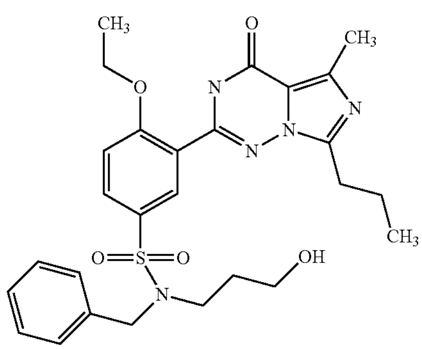 | 539.6586 | 85 | 540 |
| 123 | 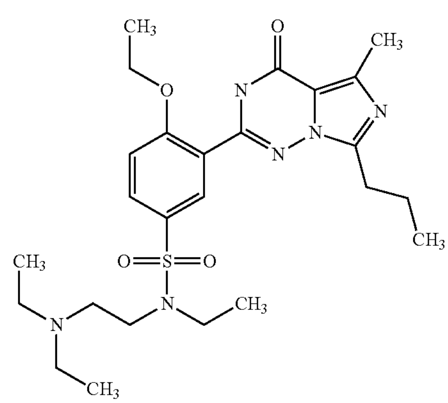 | 518.6834 | 87 | 519 |

TABLE 2-continued

| Ex. No. | Structure | MW [g/mol] | HPLC | MZ + H |
|---|---|---|---|---|
| 124 | 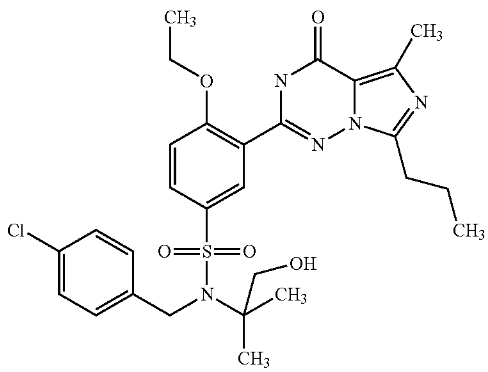 | 588.1307 | 30 | 588 |
| 125 | 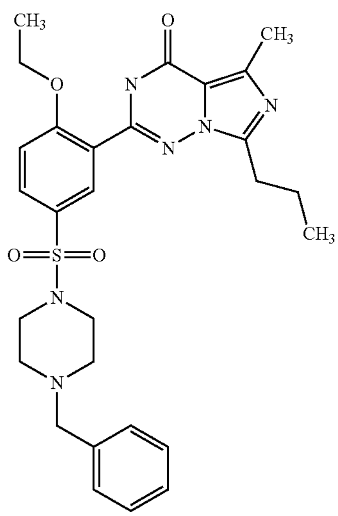 | 550.685 | 83 | 551 |
| 126 | 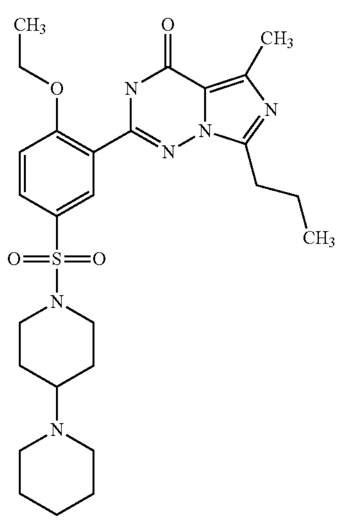 | 542.7057 | 77 | 543 |

TABLE 2-continued

| Ex. No. | Structure | MW [g/mol] | HPLC | MZ + H |
|---|---|---|---|---|
| 127 | 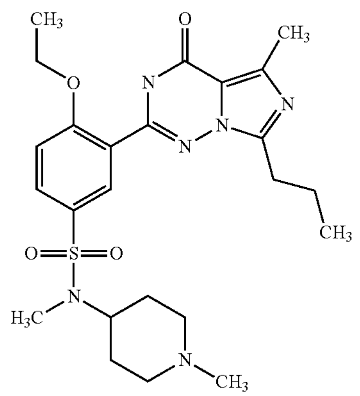 | 502.6404 | 91 | 503 |
| 128 | 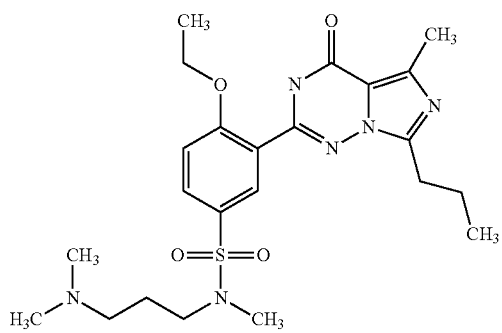 | 490.6292 | 45 | 491 |
| 129 | 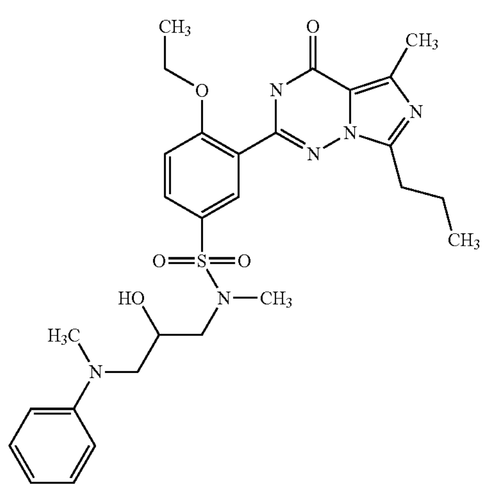 | 568.7003 | 66 | 569 |

TABLE 2-continued

| Ex. No. | Structure | MW [g/mol] | HPLC | MZ + H |
|---|---|---|---|---|
| 130 | 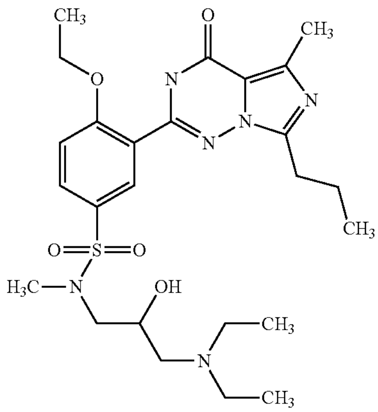 | 534.6828 | 86 | 535 |
| 131 | 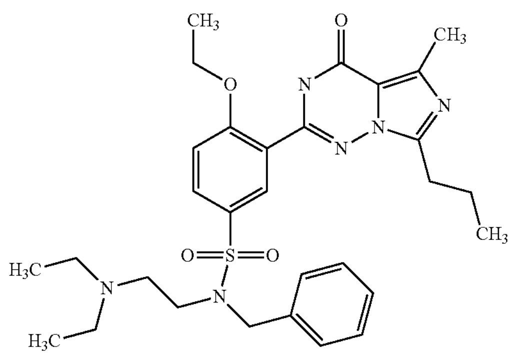 | 580.7551 | 95 | 581 |
| 132 | 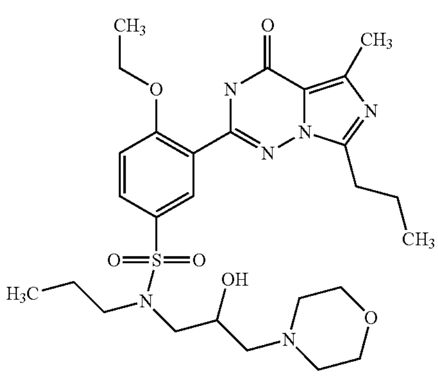 | 576.7205 | 87 | 577 |

TABLE 2-continued

| Ex. No. | Structure | MW [g/mol] | HPLC | MZ + H |
|---|---|---|---|---|
| 133 | 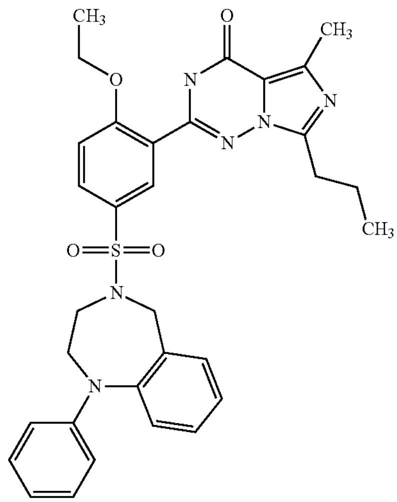 | 598.7296 | 60 | 599 |
| 134 | 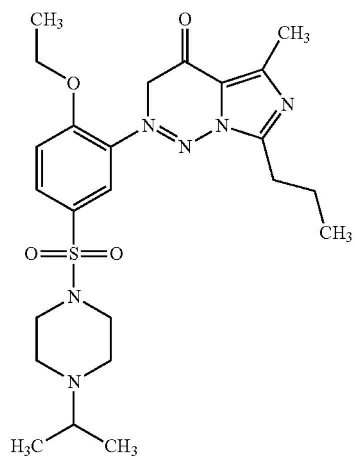 | 516.6675 | 95 | 517 |
| 135 | 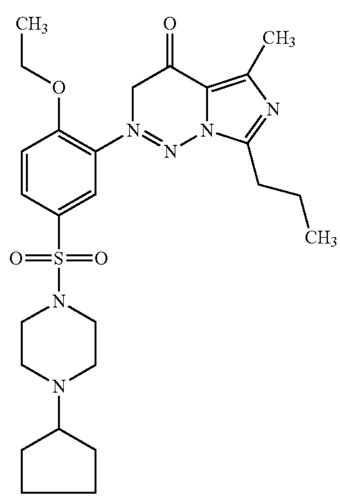 | 528.6786 | 80 | 529 |

TABLE 2-continued

| Ex. No. | Structure | MW [g/mol] | HPLC | MZ + H |
|---|---|---|---|---|
| 136 | 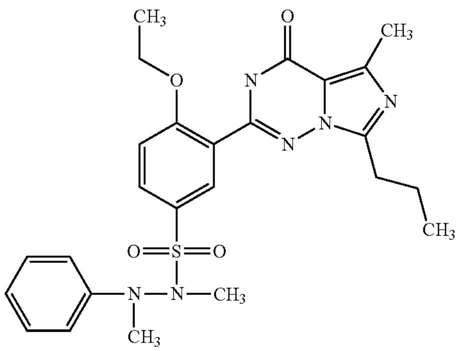 | 538.6738 | 85 | 539 |
| 137 | 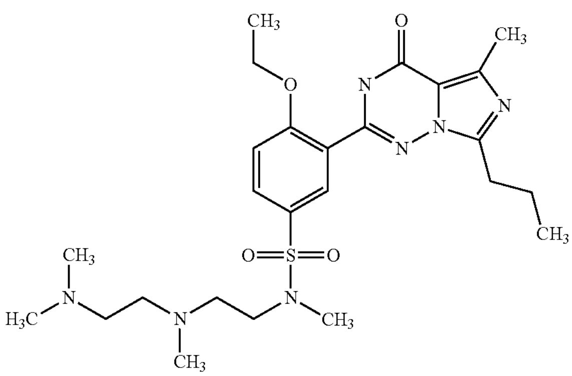 | 533.6981 | 68 | 534 |
| 138 | 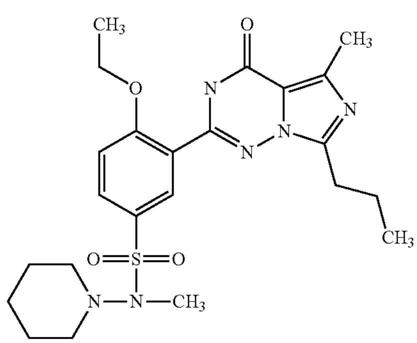 | 516.6675 | 91 | 517 |
| 139 | 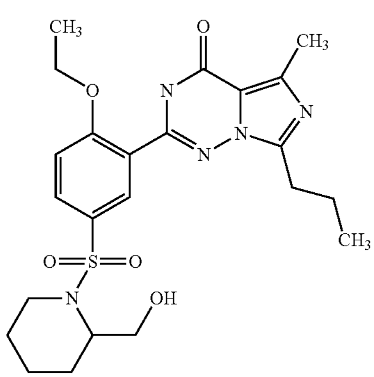 | 489.598 | 85 | 490 |

TABLE 2-continued

| Ex. No. | Structure | MW [g/mol] | HPLC | MZ + H |
|---|---|---|---|---|
| 140 | 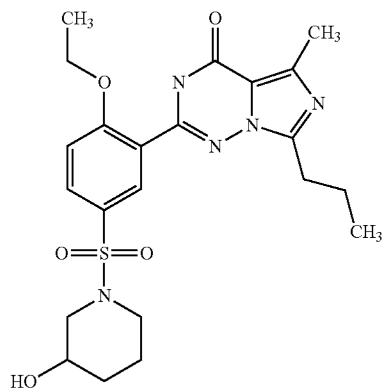 | 475.5709 | 83 | 476 |
| 141 | 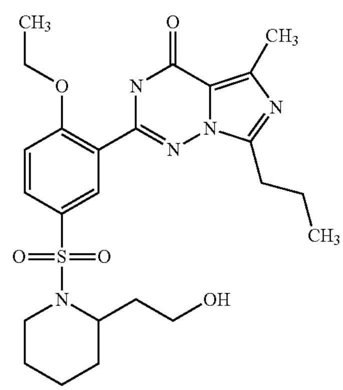 | 503.6251 | 85 | 504 |
| 142 | 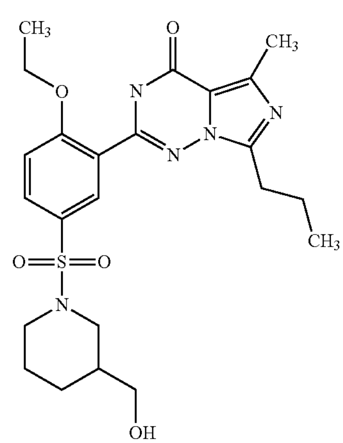 | 489.598 | 91 | 490 |

TABLE 2-continued

| Ex. No. | Structure | MW [g/mol] | HPLC | MZ + H |
|---|---|---|---|---|
| 143 | 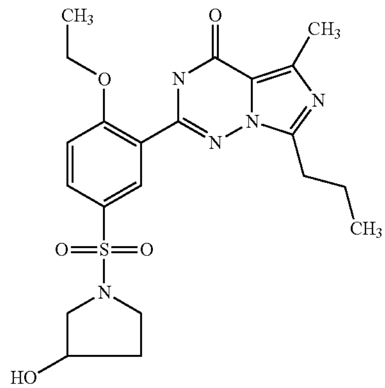 | 461.5438 | 78 | 462 |
| 144 | 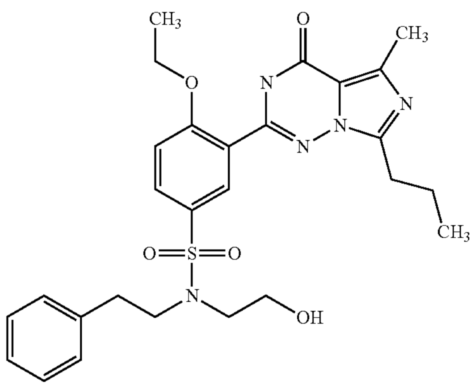 | 539.6586 | 88 | 540 |
| 145 | 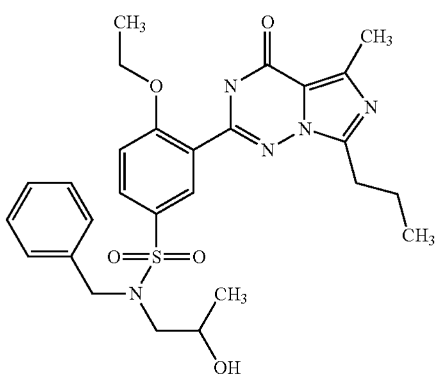 | 539.6586 | 58 | 538 |
| 146 | 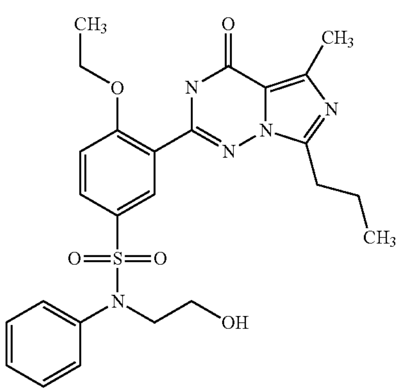 | 511.6044 | 80 | 512 |

TABLE 2-continued

| Ex. No. | Structure | MW [g/mol] | HPLC | MZ + H |
|---|---|---|---|---|
| 147 | 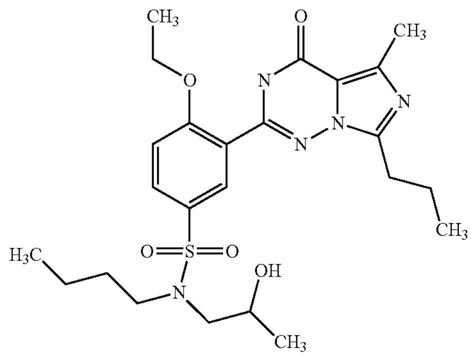 | 505.6411 | 90 | 506 |

TABLE 3

| Ex. No. | Structure | MW [g/mol] | HPLC | MZ + H |
|---|---|---|---|---|
| 148 | 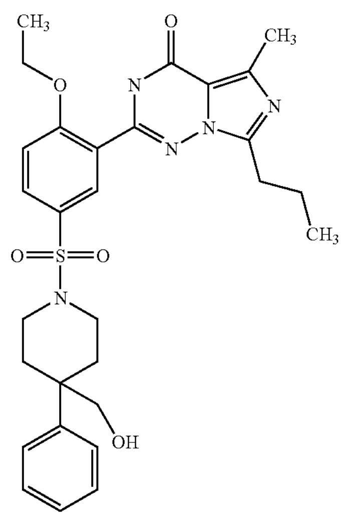 | 565.70 | 38 | 566 |
| 149 | 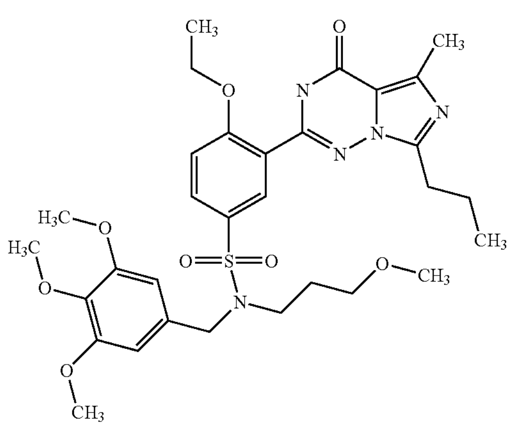 | 643.77 | 85 | 644 |

TABLE 3-continued

| Ex. No. | Structure | MW [g/mol] | HPLC | MZ + H |
|---------|-----------|------------|------|--------|
| 150 | 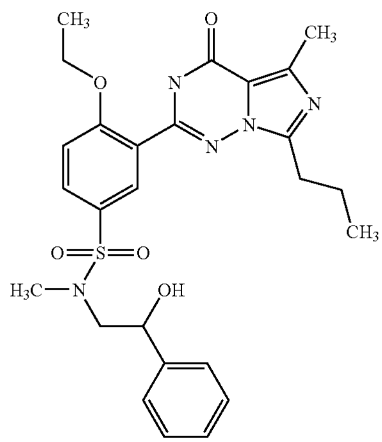 | 525.63 | 80 | 526 |
| 151 | 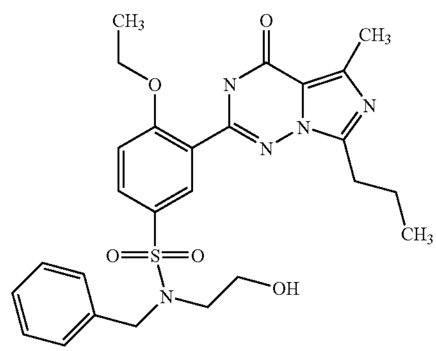 | 525.63 | 78 | 526 |
| 152 | 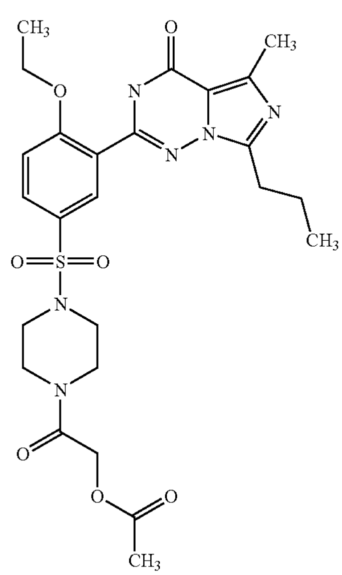 | 560.63 | 51 | 561 |

TABLE 3-continued
| Ex. No. | Structure | MW [g/mol] | HPLC | MZ + H |
|---|---|---|---|---|
| 153 | 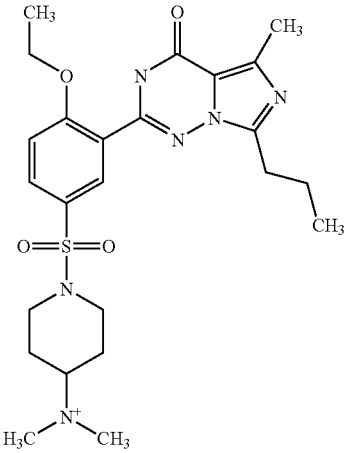 | 503.65 | 78 | 504 |
| 154 | 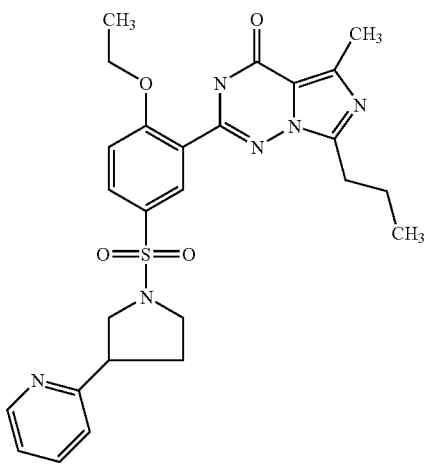 | 522.63 | 82 | 523 |
| 155 | 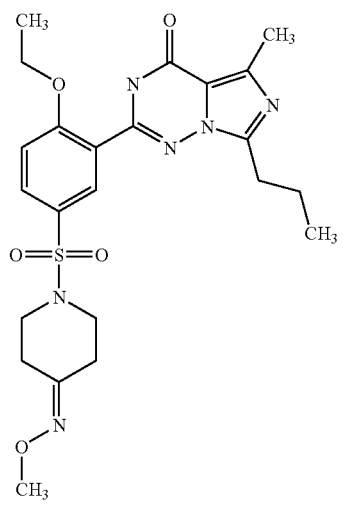 | 502.60 | 84 | 503 |

TABLE 3-continued

| Ex. No. | Structure | MW [g/mol] | HPLC | MZ + H |
|---|---|---|---|---|
| 156 | 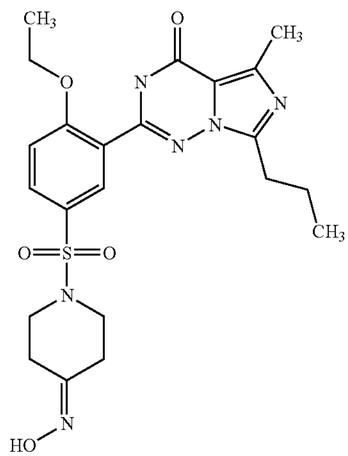 | 488.57 | 83 | 489 |
| 157 | 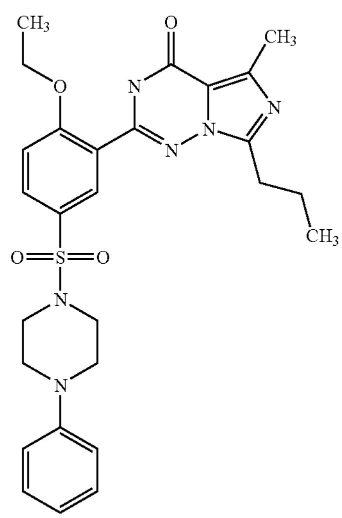 | 536.66 | 82 | 537 |
| 158 | 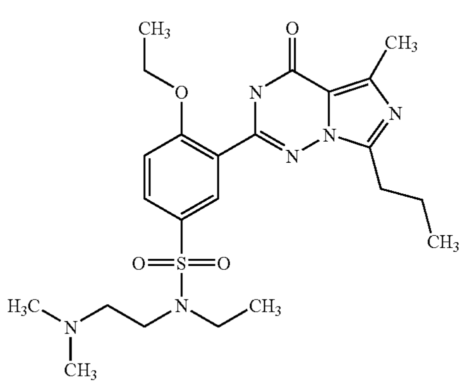 | 490.63 | 90 | 491 |

TABLE 3-continued
| Ex. No. | Structure | MW [g/mol] | HPLC | MZ + H |
|---|---|---|---|---|
| 159 | 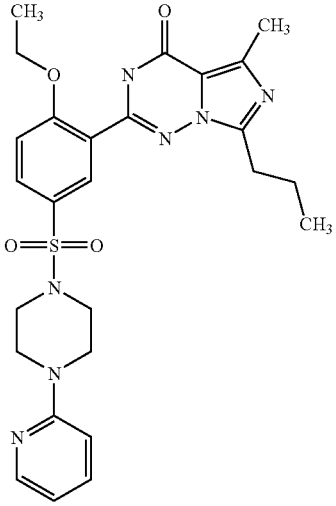 | 537.65 | 83 | 538 |
| 160 | 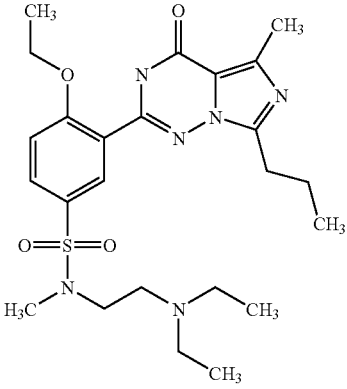 | 504.66 | 91 | 505 |
| 161 | 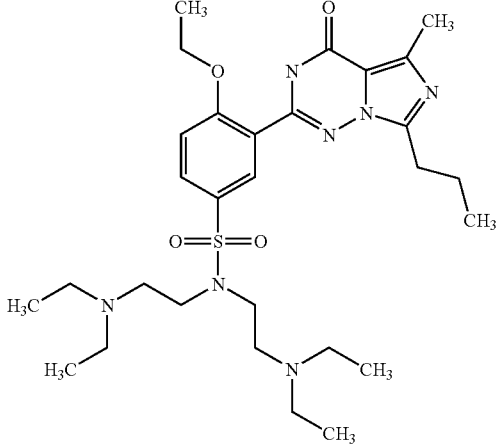 | 589.81 | 65 | 590 |

TABLE 3-continued

| Ex. No. | Structure | MW [g/mol] | HPLC | MZ + H |
|---|---|---|---|---|
| 162 | 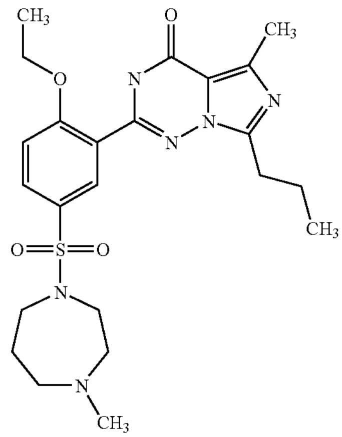 | 488.61 | 88 | 89 |
| 163 | 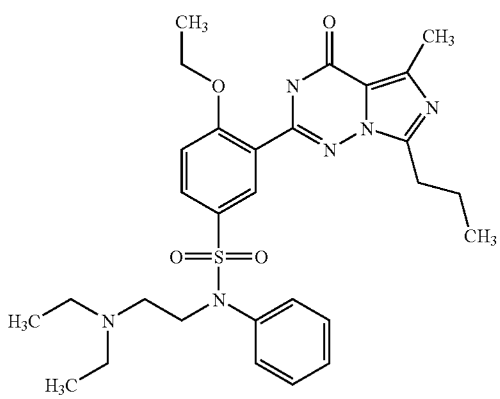 | 566.73 | 32 | 567 |
| 164 | 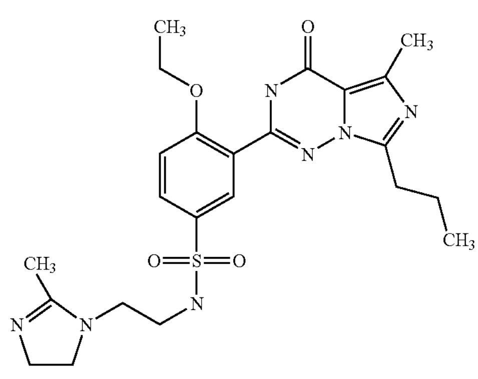 | 501.61 | 75 | 502 |

TABLE 3-continued

| Ex. No. | Structure | MW [g/mol] | HPLC | MZ + H |
|---|---|---|---|---|
| 165 | 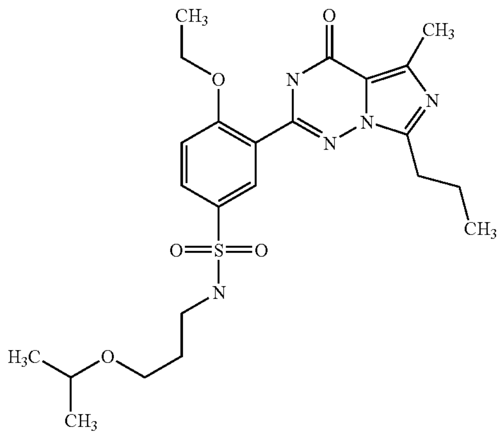 | 491.61 | 91 | 492 |
| 166 | 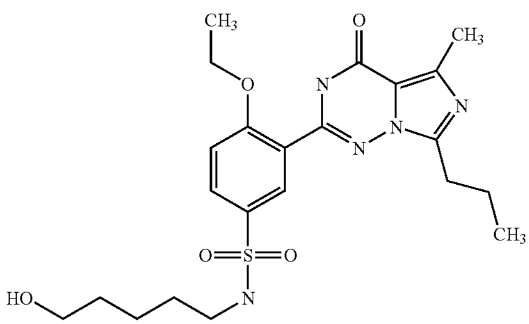 | 477.59 | 73 | 478 |
| 167 | Chiral | 525.63 | 81 | 526 |

TABLE 3-continued
| Ex. No. | Structure | MW [g/mol] | HPLC | MZ + H |
|---|---|---|---|---|
| 168 | 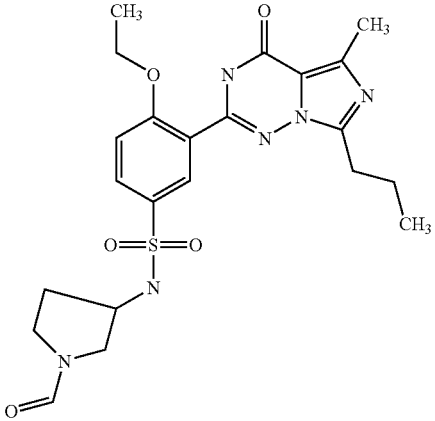 | 488.57 | 70 | 489 |
| 169 | 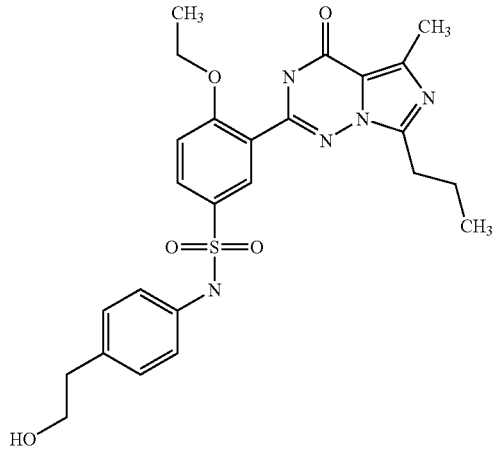 | 511.60 | 76 | 512 |
| 170 | 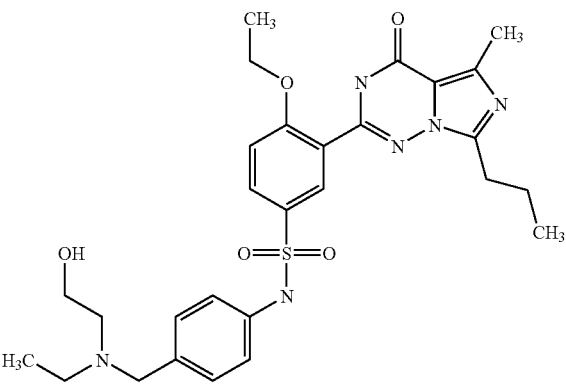 | 568.70 | 50 | 569 |

TABLE 3-continued
| Ex. No. | Structure | MW [g/mol] | HPLC | MZ + H |
|---|---|---|---|---|
| 171 | 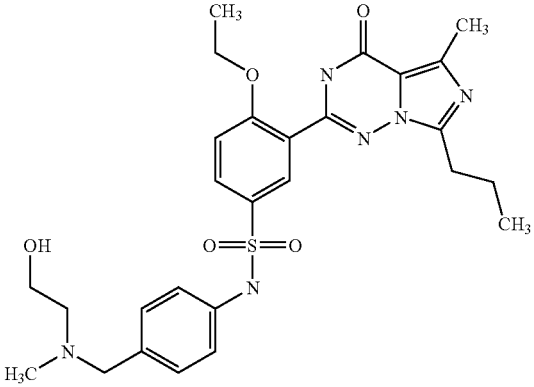 | 554.67 | 63 | 555 |
| 172 | 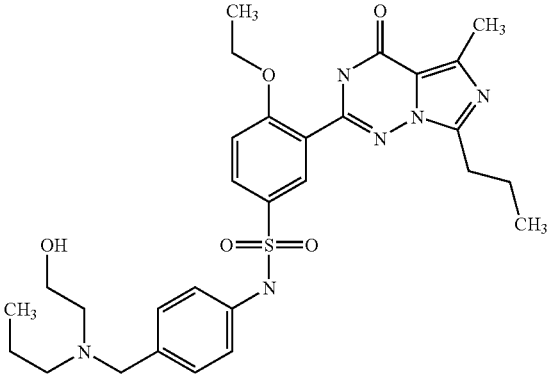 | 582.73 | 50 | 83 |
| 173 | 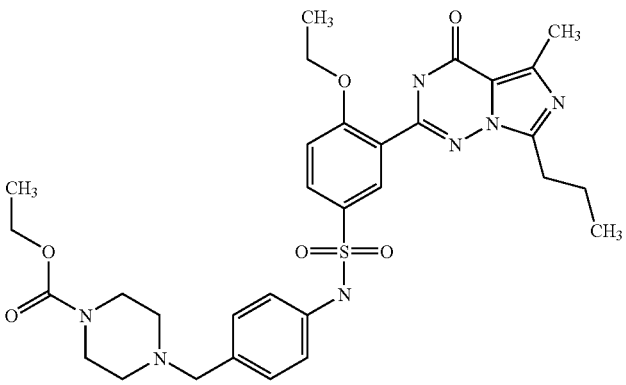 | 637.76 | 30 | 638 |

TABLE 3-continued
| Ex. No. | Structure | MW [g/mol] | HPLC | MZ + H |
|---|---|---|---|---|
| 174 | 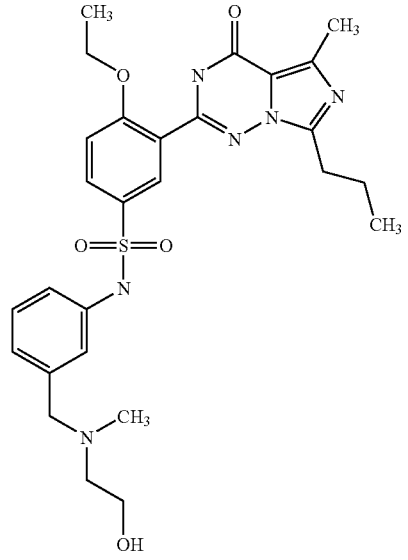 | 554.67 | 70 | 555 |
| 175 | 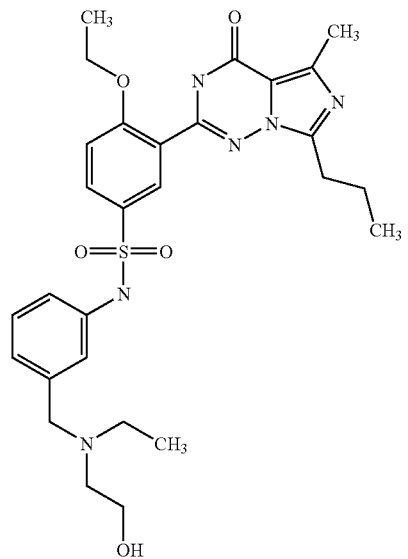 | 568.70 | 44 | 569 |

TABLE 4
| Ex. No. | Structure | MW [g/mol] | HPLC | MZ + H |
|---|---|---|---|---|
| 176 | 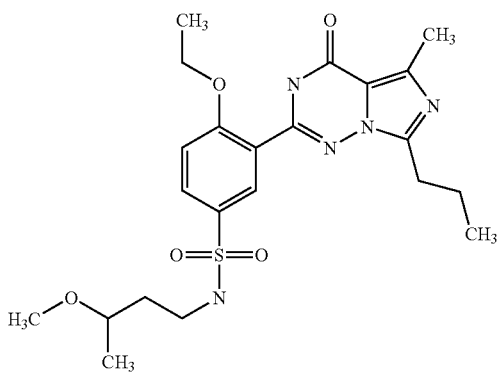 | 477.59 | 82 | 478 |
| 177 | 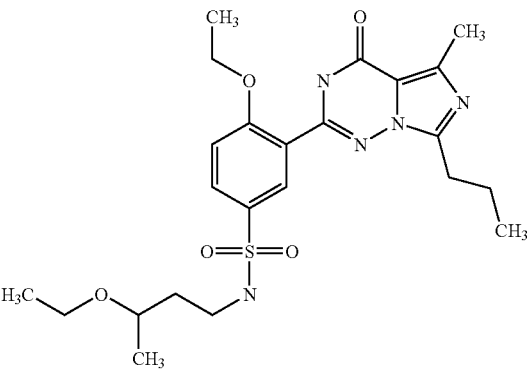 | 491.61 | 89 | 492 |
| 178 | 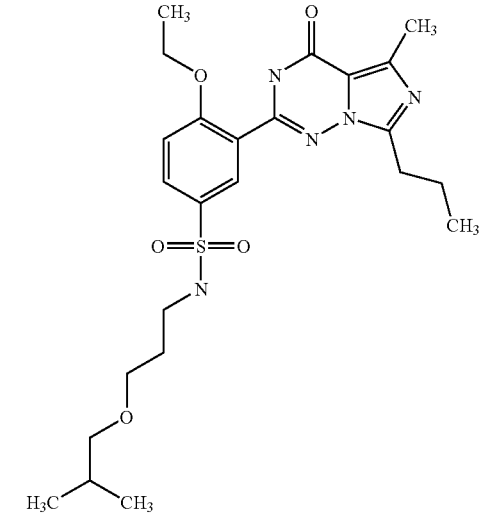 | 505.64 | 88 | 506 |

TABLE 4-continued
| Ex. No. | Structure | MW [g/mol] | HPLC | MZ + H |
|---|---|---|---|---|
| 179 | 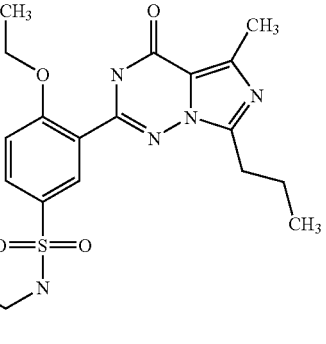 | 513.62 | 47 | 514 |
| 180 | 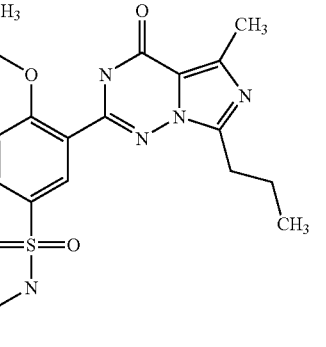 | 504.66 | 83 | 505 |
| 181 | 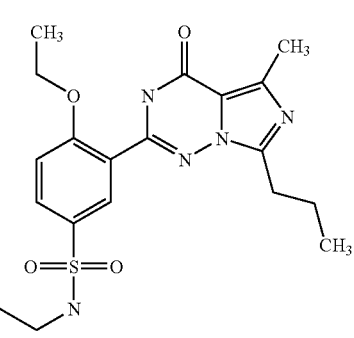 | 552.70 | 83 | 553 |
| 182 | 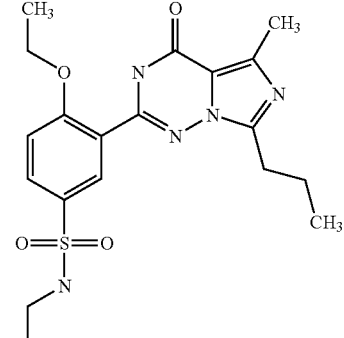 | 492.60 | 72 | 493 |

TABLE 4-continued
| Ex. No. | Structure | MW [g/mol] | HPLC | MZ + H |
|---|---|---|---|---|
| 183 | 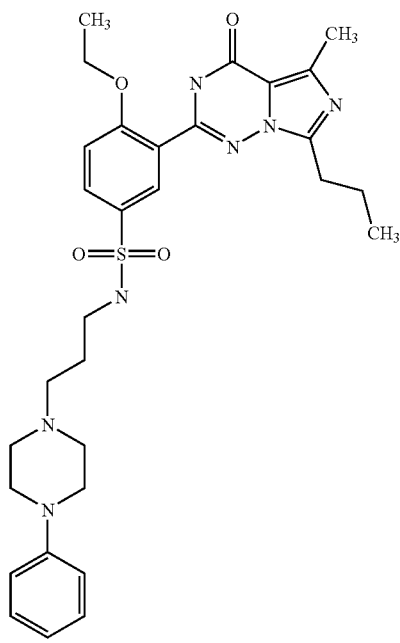 | 593.75 | 52 | 594 |
| 184 | 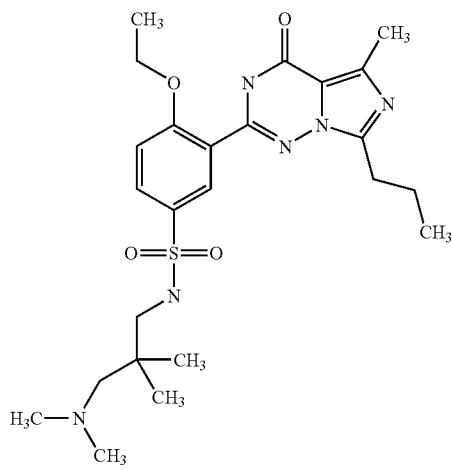 | 504.66 | 82 | 505 |

TABLE 4-continued
| Ex. No. | Structure | MW [g/mol] | HPLC | MZ + H |
|---|---|---|---|---|
| 185 | 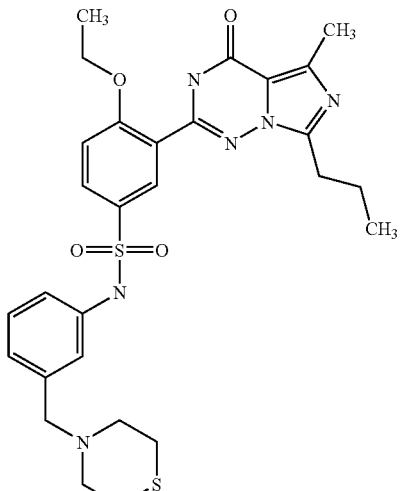 | 582.75 | 59 | 583 |
| 186 | 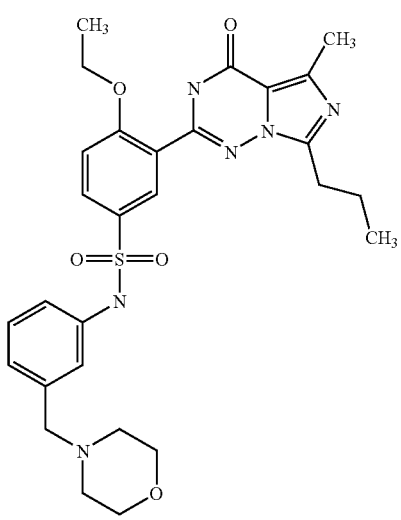 | 566.68 | 60 | 567 |
| 187 | 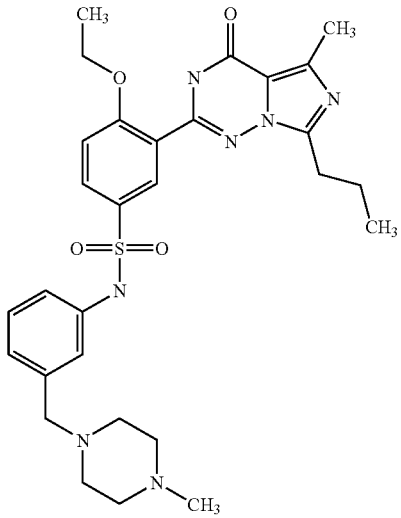 | 579.73 | 30 | 580 |

TABLE 4-continued

| Ex. No. | Structure | MW [g/mol] | HPLC | MZ + H |
|---|---|---|---|---|
| 188 | 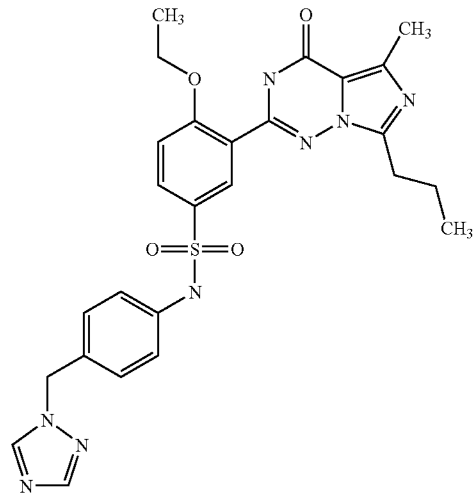 | 548.63 | 73 | 549 |
| 189 | 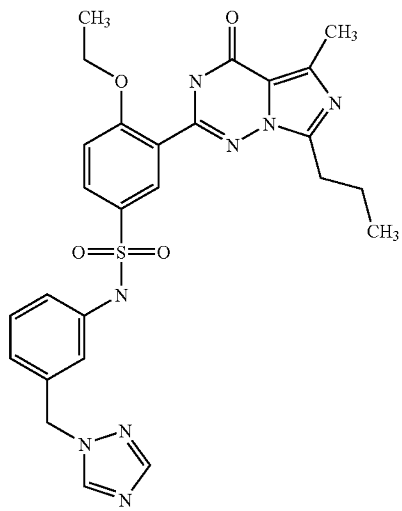 | 548.63 | 72 | 549 |
| 190 | 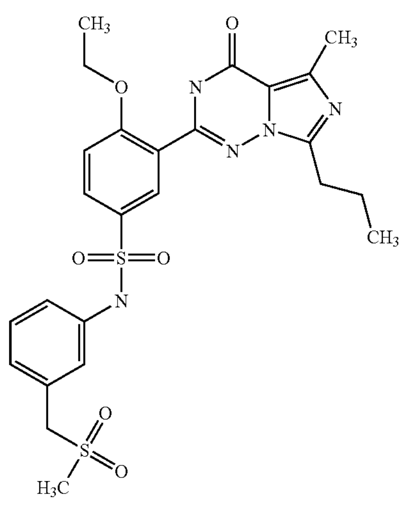 | 559.67 | 54 | 560 |

TABLE 4-continued

| Ex. No. | Structure | MW [g/mol] | HPLC | MZ + H |
|---|---|---|---|---|
| 191 | 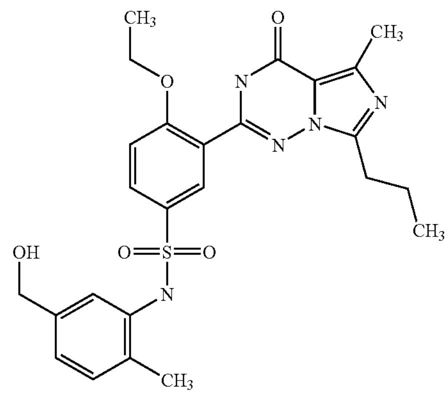 | 511.60 | 70 | 512 |
| 192 | 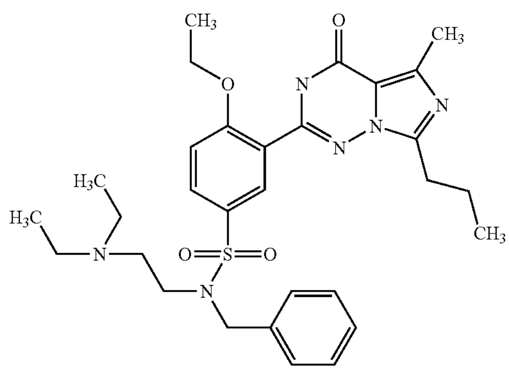 | 580.76 | 68 | 581 |
| 193 | 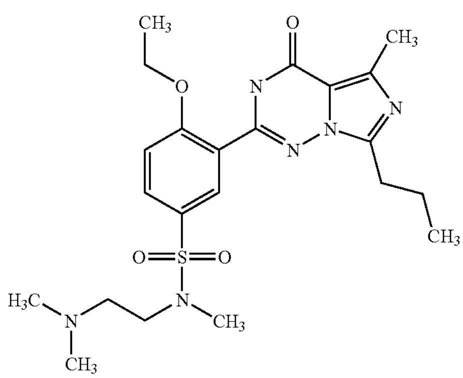 | 476.60 | 89 | 477 |
| 194 | 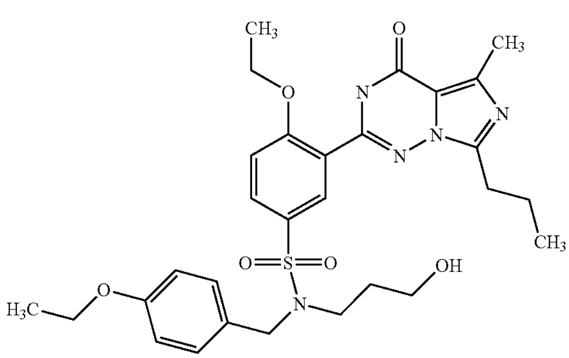 | 583.71 | 80 | 584 |

TABLE 4-continued

| Ex. No. | Structure | MW [g/mol] | HPLC | MZ + H |
|---|---|---|---|---|
| 195 | 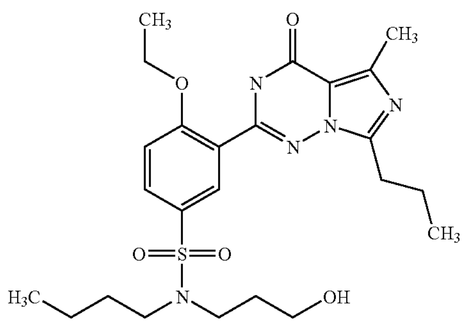 | 505.64 | 84 | 506 |
| 196 | 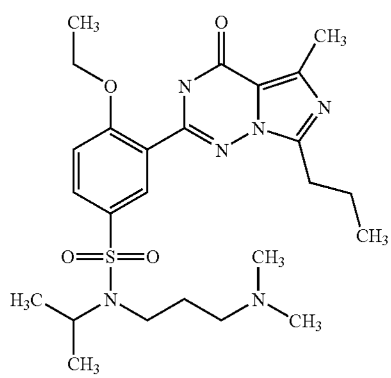 | 518.68 | 40 | 519 |
| 197 | 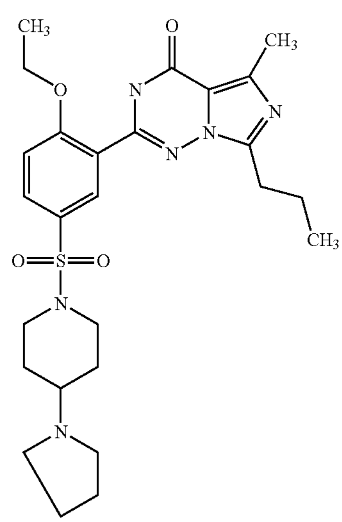 | 528.68 | 82 ? | 529 |

TABLE 4-continued
| Ex. No. | Structure | MW [g/mol] | HPLC | MZ + H |
|---------|-----------|------------|------|--------|
| 198 | 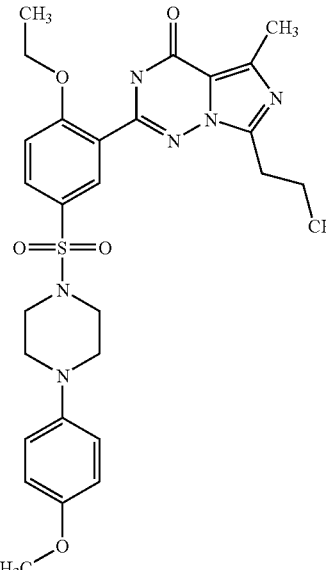 | 566.68 | 63 | 567 |
| 199 | 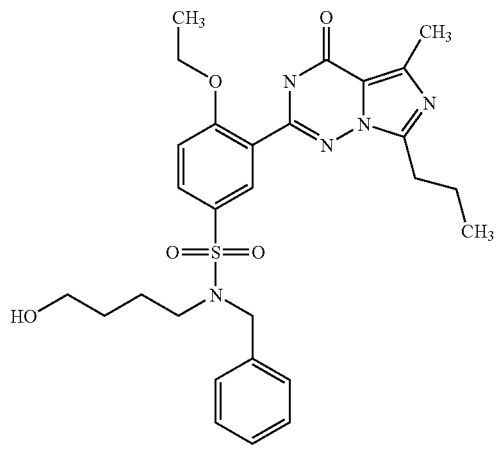 | 553.69 | 87 | 554 |
| 200 | 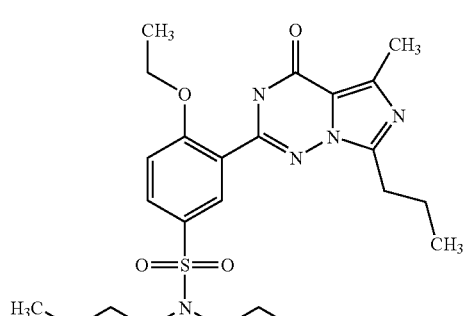 | 491.61 | 84 | 492 |

TABLE 5
| Ex. No. | Structure | MW | HPLC | MZ + H |
|---|---|---|---|---|
| 201 | 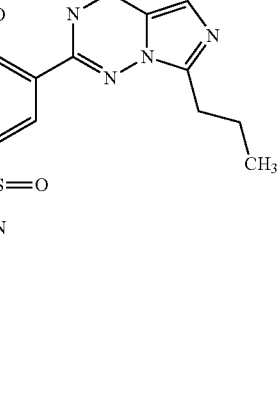 | 516.67 | 87 | 517 |
| 202 | 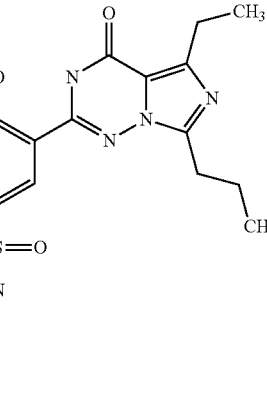 | 502.64 | 84 | 503 |
| 203 | 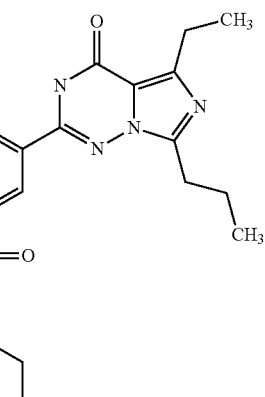 | 516.67 | 87 | 517 |

TABLE 5-continued

| Ex. No. | Structure | MW | HPLC | MZ + H |
|---|---|---|---|---|
| 204 | 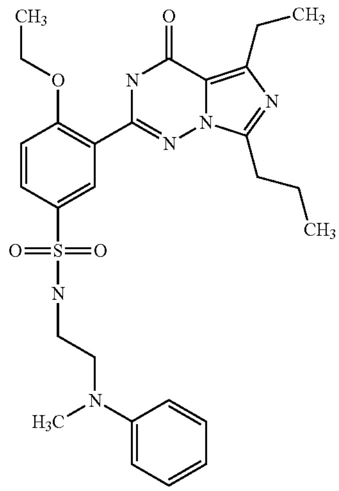 | 538.67 | 91 | 539 |
| 205 | 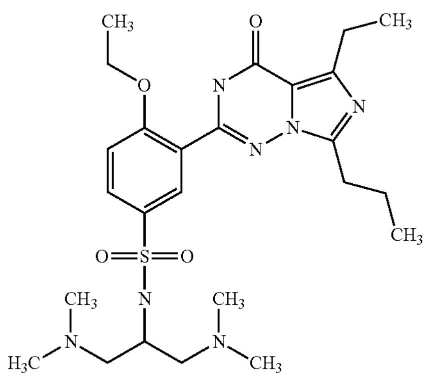 | 533.7 | 85 | 534 |
| 206 | 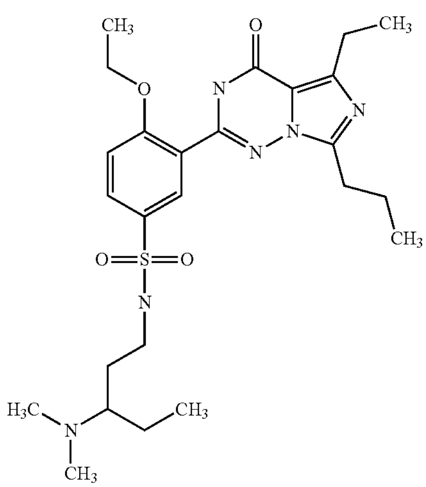 | 518.68 | 77 | 519 |

TABLE 5-continued

| Ex. No. | Structure | MW | HPLC | MZ + H |
|---|---|---|---|---|
| 207 | 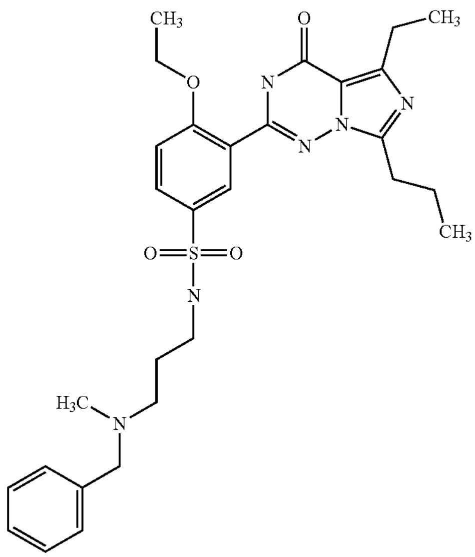 | 566.73 | 92 | 567 |
| 208 | 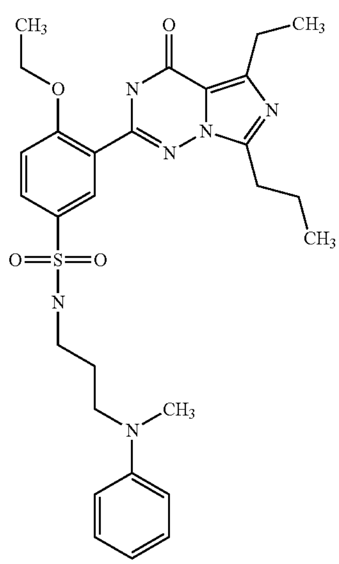 | 552.7 | 87 | 553 |

TABLE 5-continued
| Ex. No. | Structure | MW | HPLC | MZ + H |
|---|---|---|---|---|
| 209 | 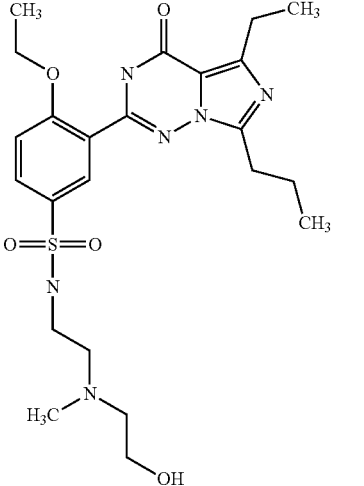 | 506.63 | 52 | 507 |
| 210 | 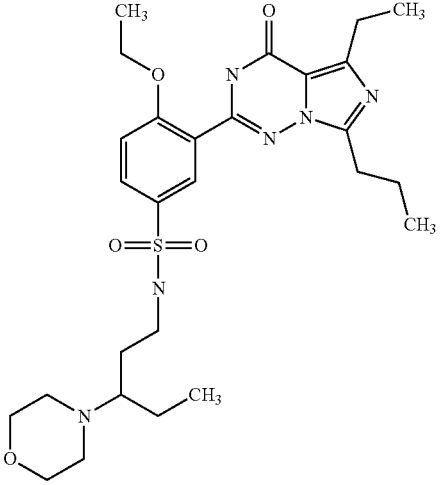 | 560.72 | 62 | 561 |
| 211 | 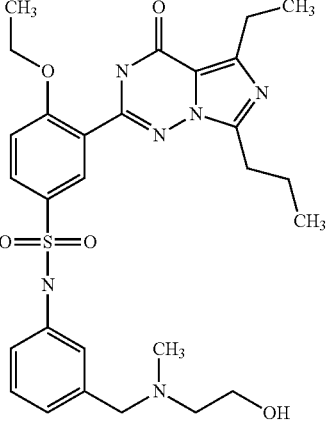 | 568.7 | 88 | 569 |

TABLE 5-continued
| Ex. No. | Structure | MW | HPLC | MZ + H |
|---|---|---|---|---|
| 212 | 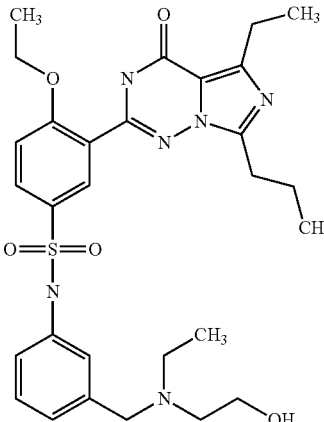 | 582.73 | 89 | 583 |
| 213 | 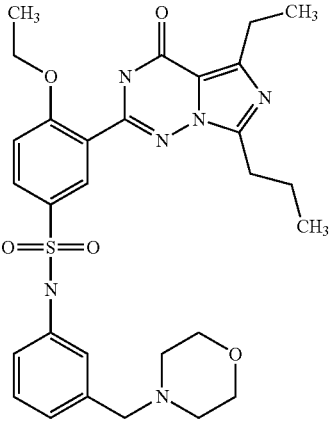 | 580.71 | 83 | 581 |
| 214 | 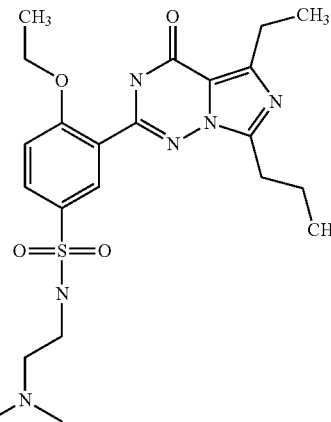 | 518.64 | 89 | 519 |

TABLE 5-continued

| Ex. No. | Structure | MW | HPLC | MZ + H |
|---|---|---|---|---|
| 215 | 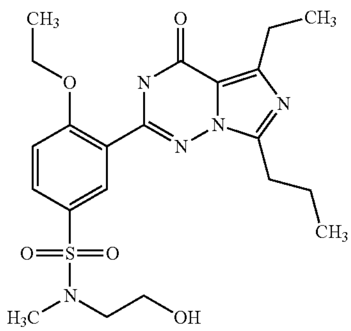 | 463.56 | 90 | 464 |
| 216 | 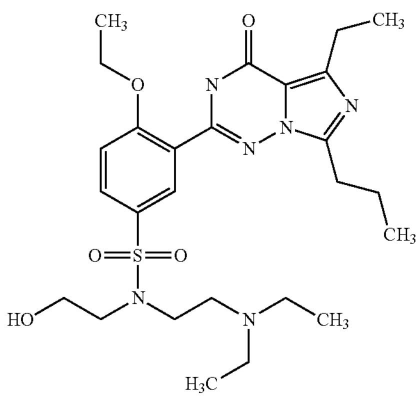 | 548.71 | 78 | 549 |
| 217 | 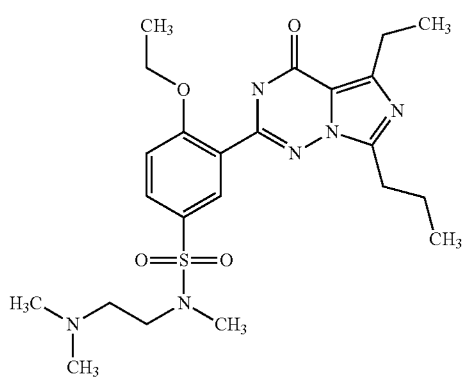 | 490.63 | 87 | 491 |
| 218 | 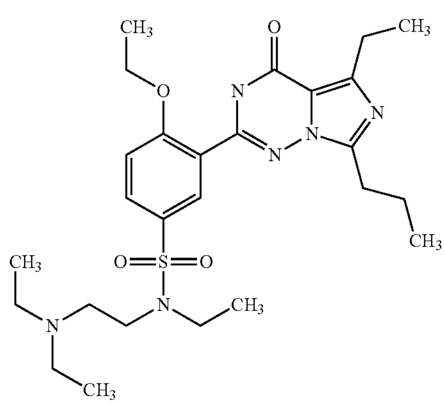 | 532.71 | 93 | 533 |

TABLE 5-continued
| Ex. No. | Structure | MW | HPLC | MZ + H |
|---|---|---|---|---|
| 219 | 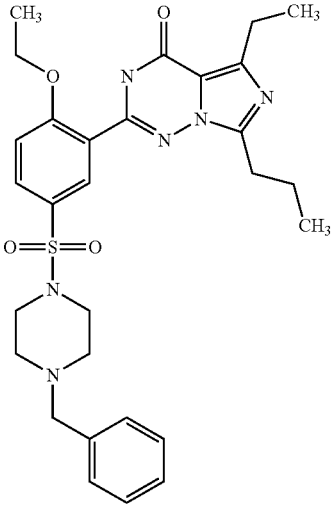 | 564.71 | 91 | 565 |
| 220 | 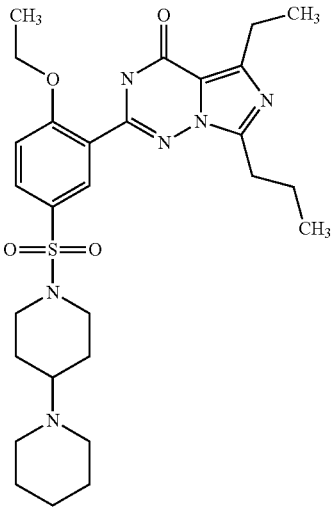 | 556.73 | 92 | 557 |
| 221 | 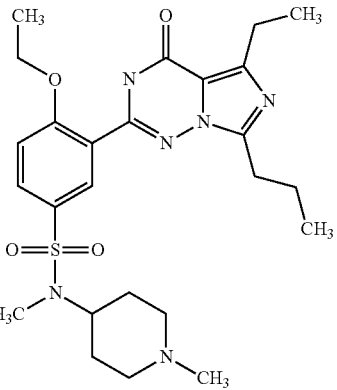 | 516.67 | 92 | 517 |

TABLE 5-continued

| Ex. No. | Structure | MW | HPLC | MZ + H |
|---|---|---|---|---|
| 222 | 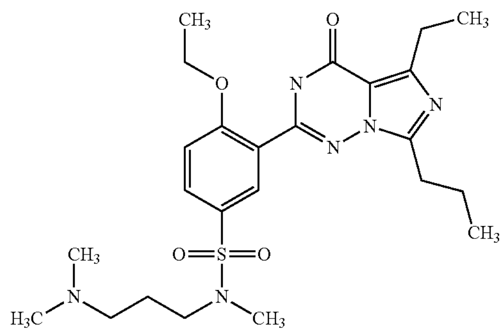 | 504.66 | 83 | 505 |
| 223 | 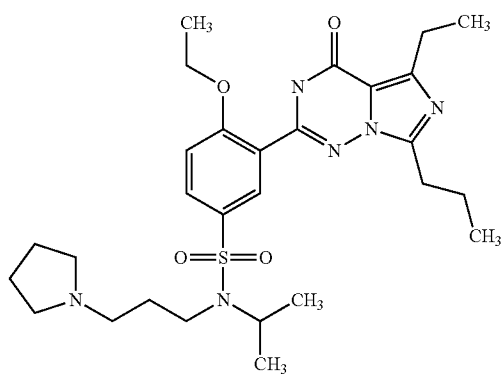 | 558.75 | 90 | 559 |
| 224 | 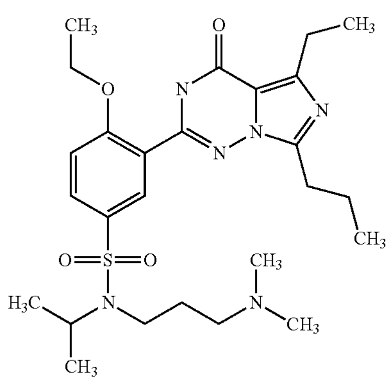 | 532.71 | 86 | 533 |
| 225 | 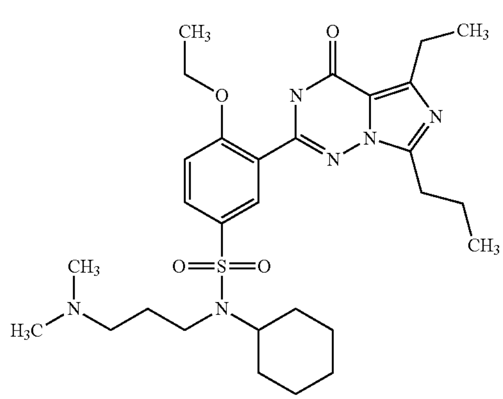 | 572.78 | 68 | 573 |

TABLE 5-continued
| Ex. No. | Structure | MW | HPLC | MZ + H |
|---|---|---|---|---|
| 226 | 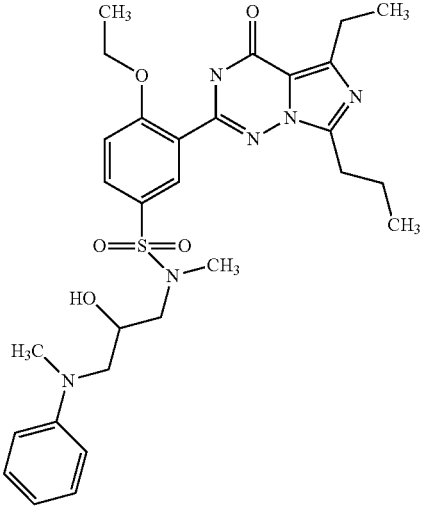 | 582.73 | 87 | 583 |
| 227 | 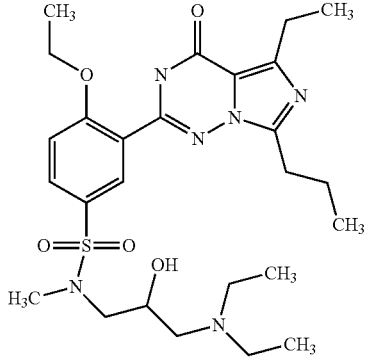 | 548.71 | 85 | 549 |
| 228 | 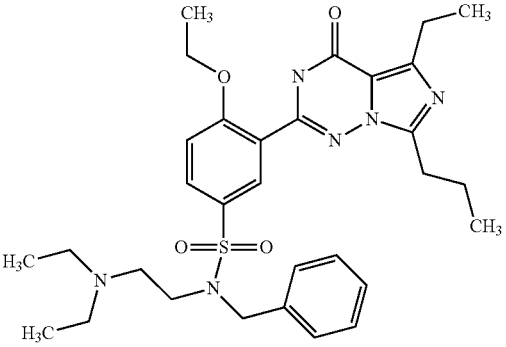 | 594.78 | 97 | 595 |

TABLE 5-continued

| Ex. No. | Structure | MW | HPLC | MZ+H |
|---|---|---|---|---|
| 229 | 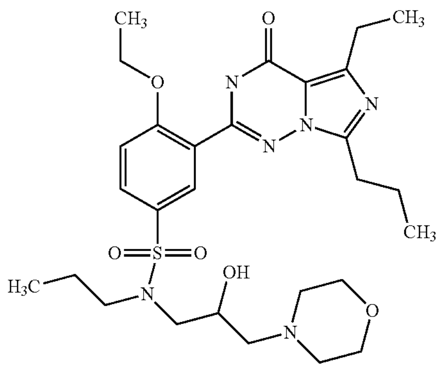 | 590.75 | 90 | 591 |
| 230 | 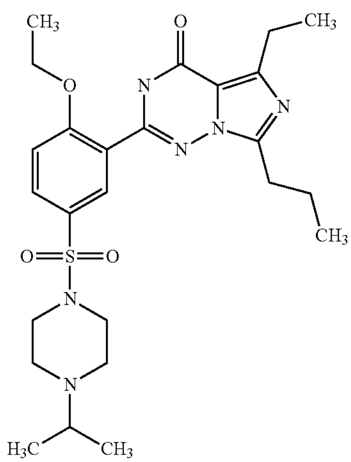 | 530.69 | 95 | 531 |
| 231 | 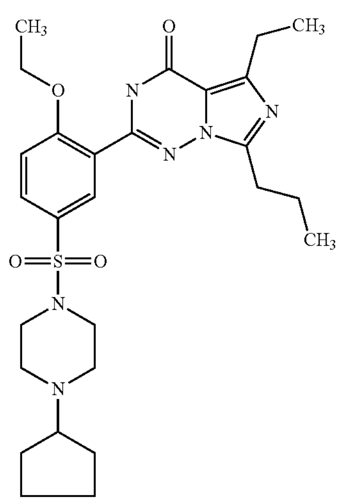 | 542.71 | 88 | 543 |

TABLE 5-continued

| Ex. No. | Structure | MW | HPLC | MZ + H |
|---|---|---|---|---|
| 232 | 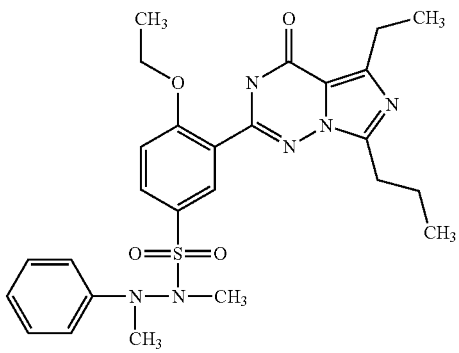 | 552.7 | 91 | 553 |
| 233 | 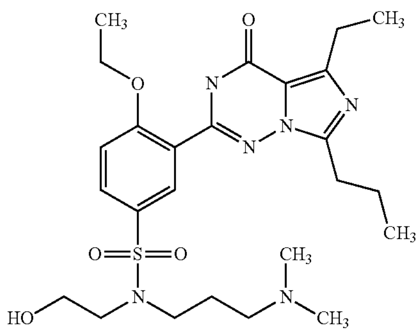 | 534.68 | 65 | 535 |
| 234 | 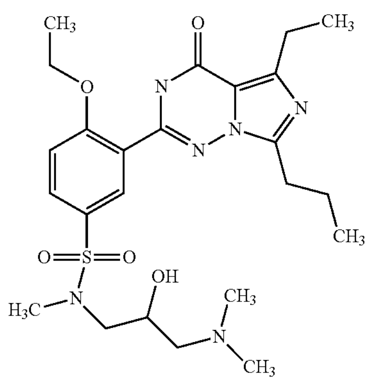 | 520.66 | 83 | 521 |
| 235 | 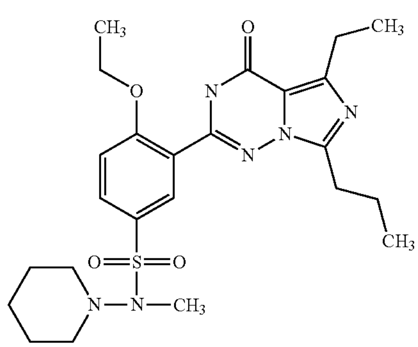 | 530.69 | 89 | 531 |

TABLE 5-continued

| Ex. No. | Structure | MW | HPLC | MZ + H |
|---------|-----------|-----|------|--------|
| 236 | 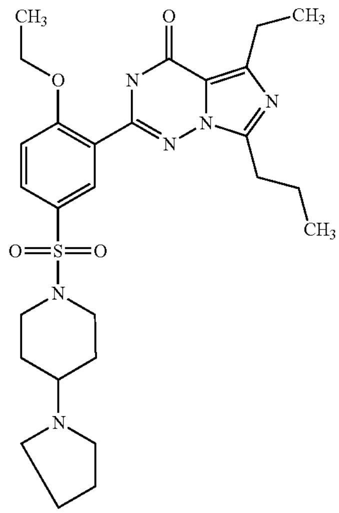 | 542.71 | 70 | 543 |
| 237 | 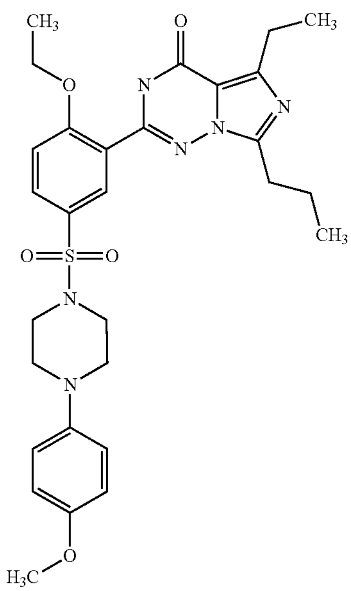 | 580.71 | 81 | 581 |
| 238 | 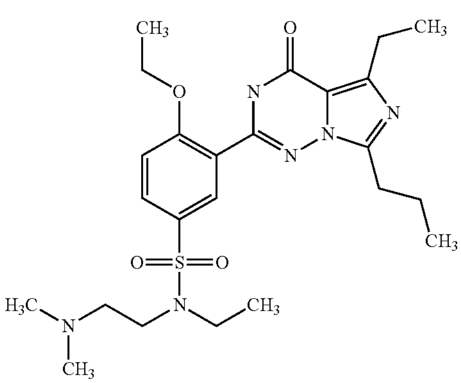 | 504.66 | 81 | 505 |

TABLE 5-continued
| Ex. No. | Structure | MW | HPLC | MZ + H |
|---|---|---|---|---|
| 239 | 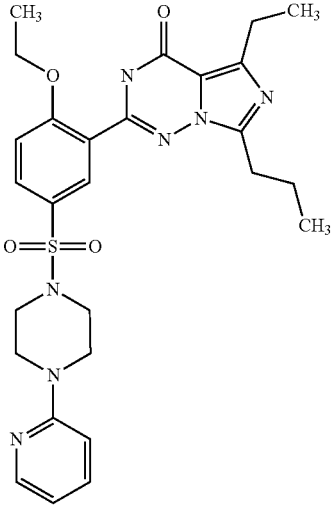 | 551.67 | 86 | 552 |
| 240 | 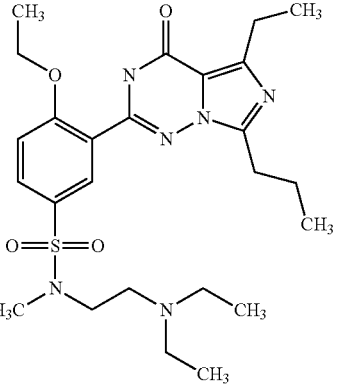 | 518.68 | 85 | 519 |
| 241 | 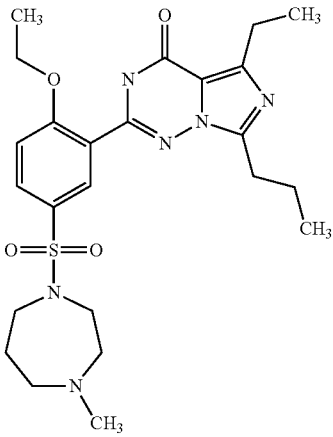 | 502.64 | 85 | 503 |

TABLE 5-continued

| Ex. No. | Structure | MW | HPLC | MZ + H |
|---|---|---|---|---|
| 242 | 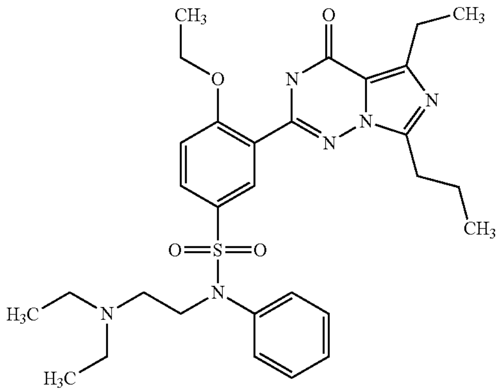 | 580.76 | 79 | 581 |

TABLE 6

| Ex. No. | Structure | MW | HPLC | MZ + H |
|---|---|---|---|---|
| 243 | 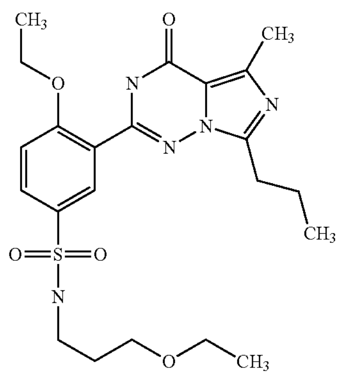 | 477.5869 | 86 | 478 |
| 244 | 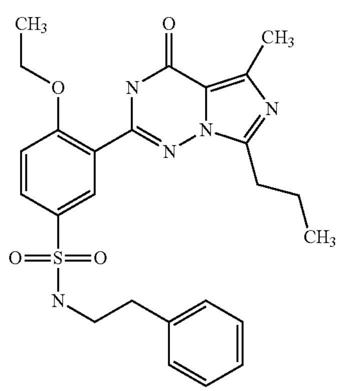 | 495.605 | 62 | 496 |

TABLE 6-continued

| Ex. No. | Structure | MW | HPLC | MZ + H |
|---|---|---|---|---|
| 245 | 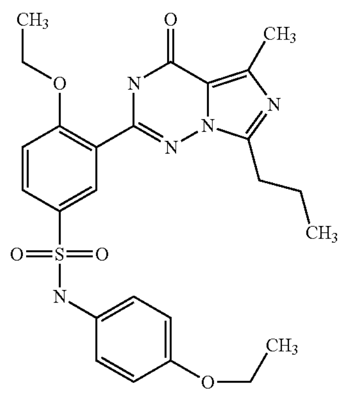 | 511.6044 | 50 | 512 |
| 246 | 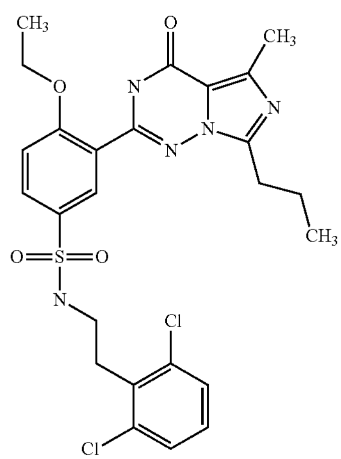 | 564.495 | 40 | 565 |
| 247 | 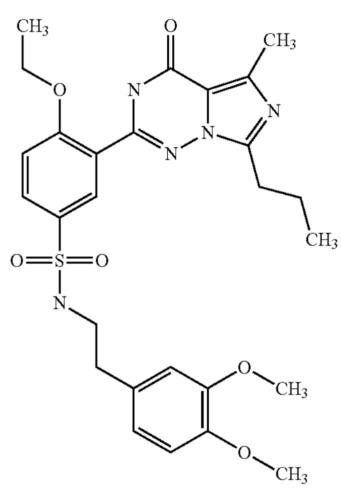 | 555.658 | 61 | 556 |

TABLE 6-continued

| Ex. No. | Structure | MW | HPLC | MZ + H |
|---|---|---|---|---|
| 248 | 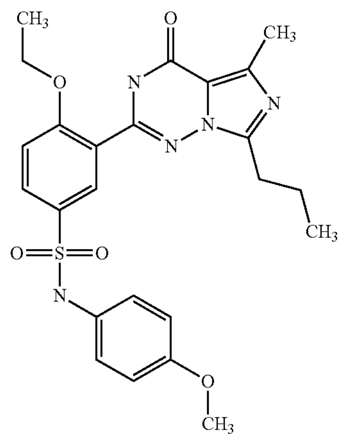 | 497.5773 | 60 | 498 |
| 249 | 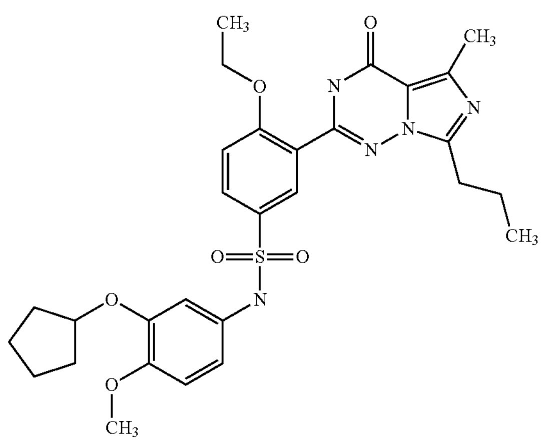 | 581.6963 | 77 | 582 |
| 250 | 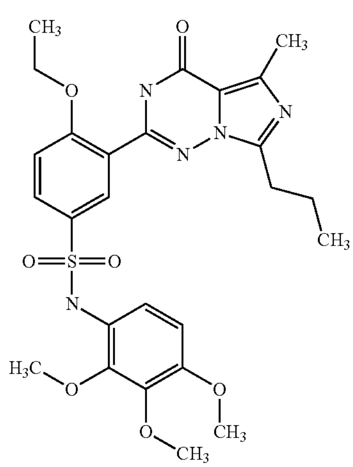 | 557.6303 | 76 | 558 |

TABLE 6-continued
| Ex. No. | Structure | MW | HPLC | MZ + H |
|---|---|---|---|---|
| 251 | 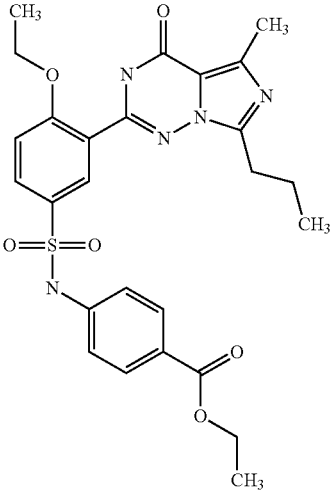 | 539.615 | 74 | 540 |
| 252 | 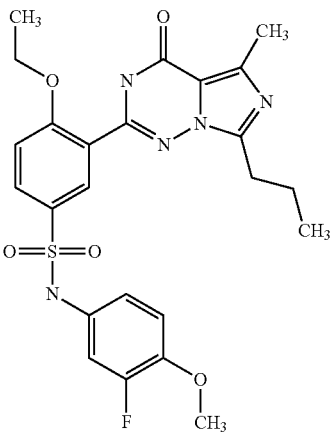 | 515.5677 | 64 | 516 |
| 253 | 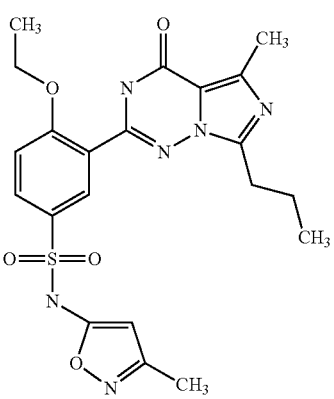 | 472.5266 | 38 | 473 |

TABLE 6-continued

| Ex. No. | Structure | MW | HPLC | MZ + H |
|---|---|---|---|---|
| 254 | 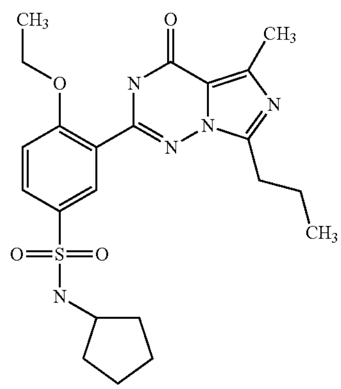 | 459.5715 | 88 | 460 |
| 255 | 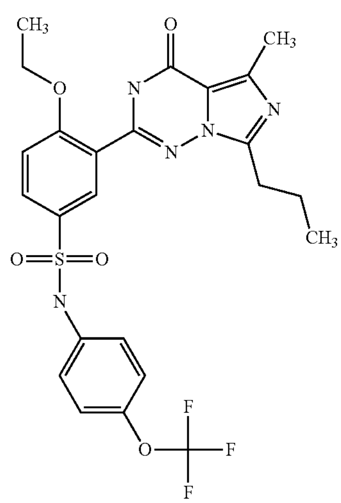 | 551.5486 | 78 | 552 |
| 256 | 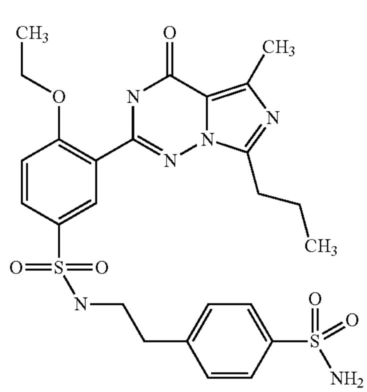 | 574.6824 | 59 | 575 |

TABLE 6-continued
| Ex. No. | Structure | MW | HPLC | MZ + H |
|---|---|---|---|---|
| 257 | 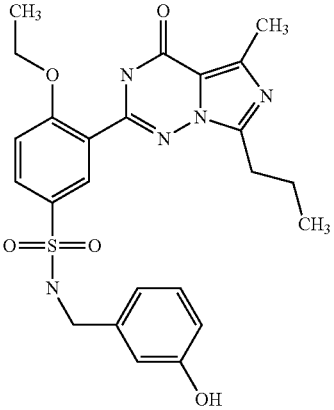 | 497.5773 | 40 | 498 |
| 258 | 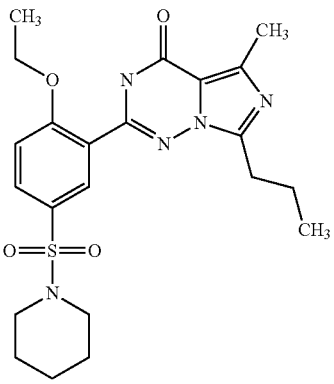 | 459.5715 | 90 | 460 |
| 259 | 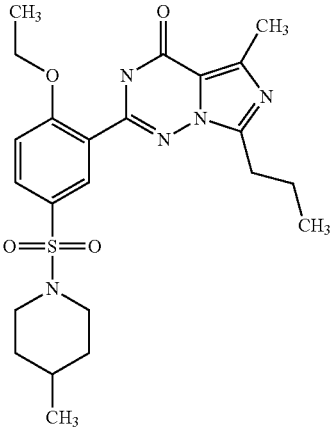 | 473.5986 | 80 | 474 |

TABLE 6-continued
| Ex. No. | Structure | MW | HPLC | MZ + H |
|---|---|---|---|---|
| 260 | 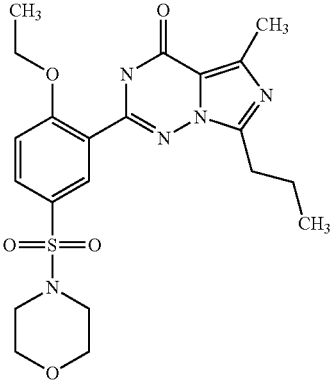 | 461.5439 | 83 | 42 |
| 261 | 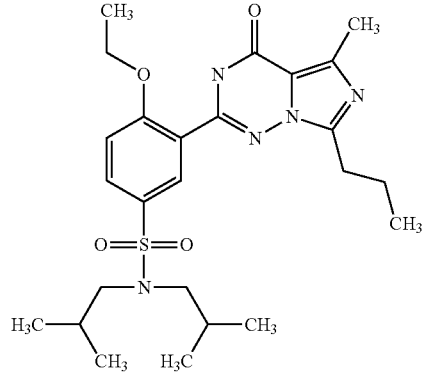 | 503.6687 | 71 | 504 |
| 262 | 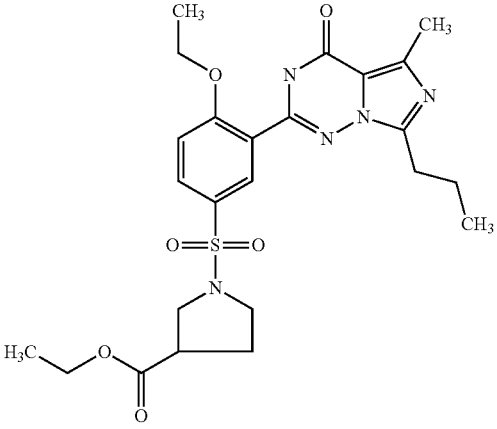 | 517.6086 | 71 | 518 |

TABLE 6-continued

| Ex. No. | Structure | MW | HPLC | MZ + H |
|---|---|---|---|---|
| 263 | 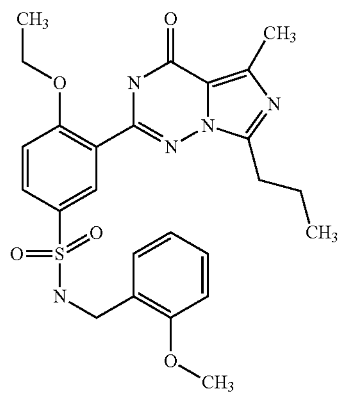 | 511.6044 | 76 | 512 |
| 264 | 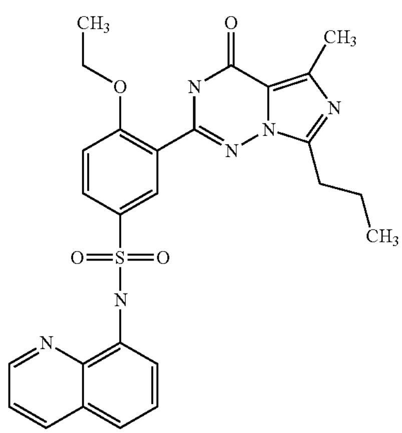 | 518.5989 | 74 | 519 |
| 265 | 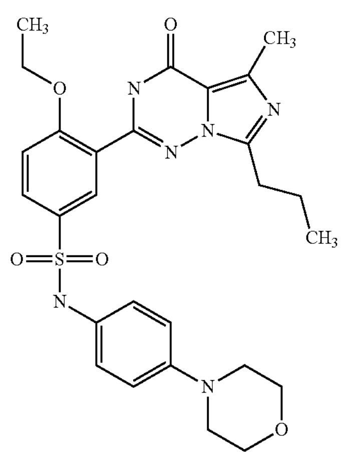 | 552.6573 | 91 | 553 |

TABLE 6-continued
| Ex. No. | Structure | MW | HPLC | MZ + H |
|---|---|---|---|---|
| 266 | 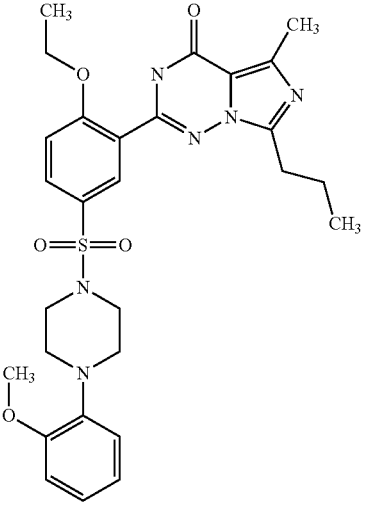 | 566.6844 | 71 | 567 |
| 267 | 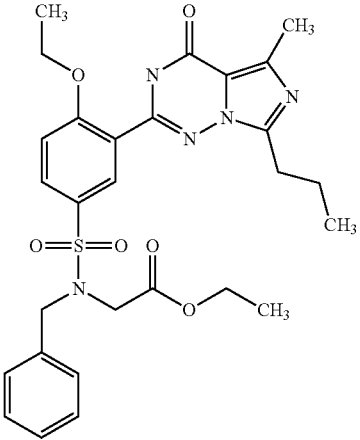 | 567.6692 | 48 | 568 |
| 268 | 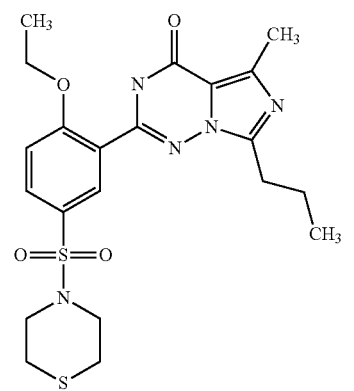 | 477.6084 | 90 | 478 |

TABLE 6-continued

| Ex. No. | Structure | MW | HPLC | MZ + H |
|---|---|---|---|---|
| 269 | 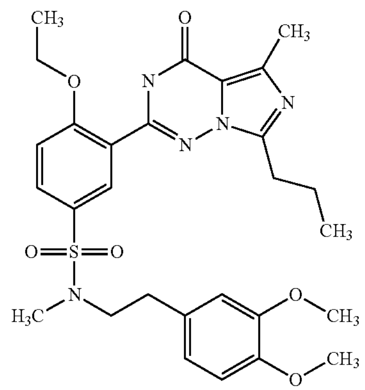 | 569.6851 | 73 | 570 |
| 270 | 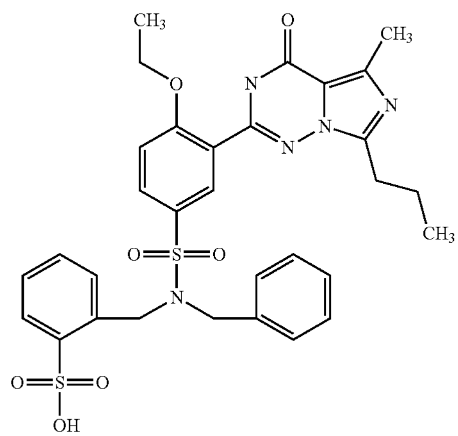 | 651.766 | 65 | 652 |
| 271 | 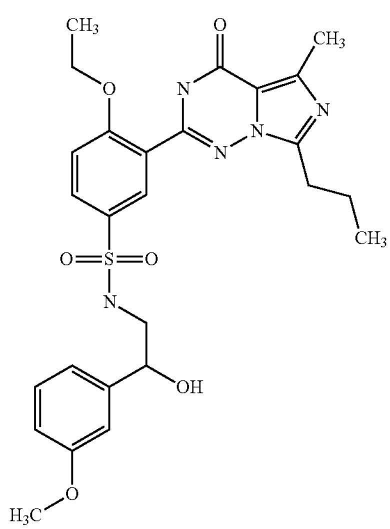 | 541.6309 | 71 | 542 |

TABLE 6-continued
| Ex. No. | Structure | MW | HPLC | MZ + H |
|---|---|---|---|---|
| 272 | 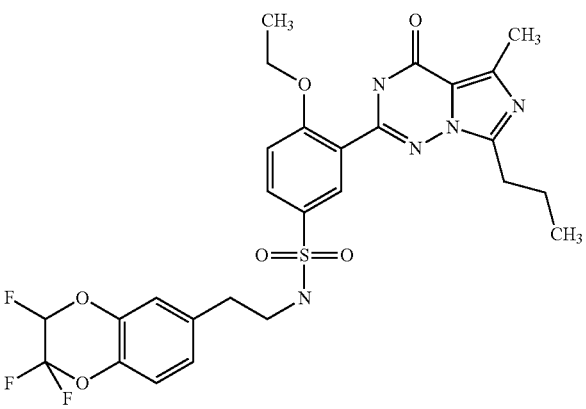 | 607.6133 | 39 | 608 |
| 273 | 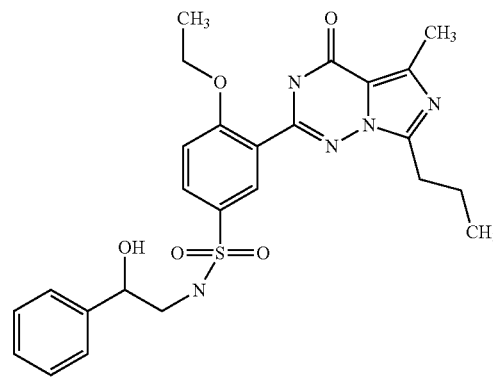 | 511.6044 | 92 | 512 |
| 274 | 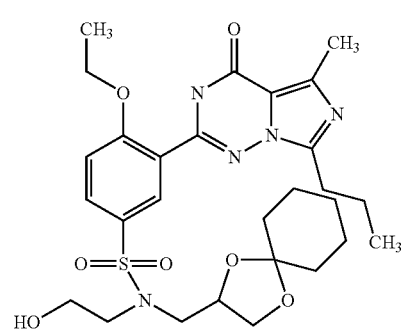 | 589.7164 | >95 | 590 |
| 275 | 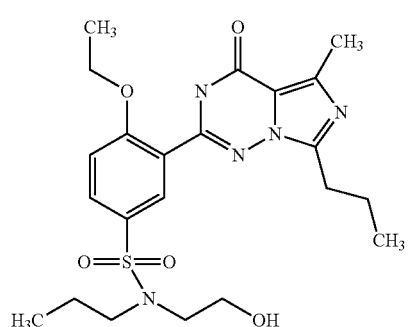 | 477.5869 | >95 | 478 |

TABLE 6-continued

| Ex. No. | Structure | MW | HPLC | MZ + H |
|---|---|---|---|---|
| 276 | 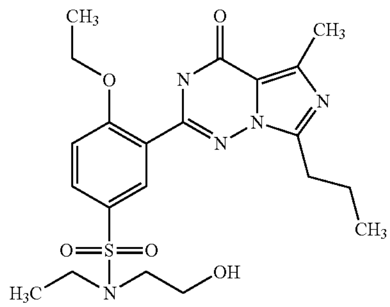 | 463.5598 | 64 | 464 |
| 277 | 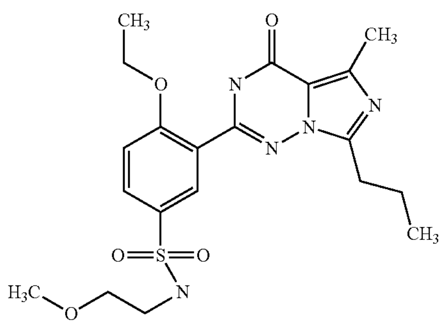 | 449.5327 | >95 | 450 |
| 278 | 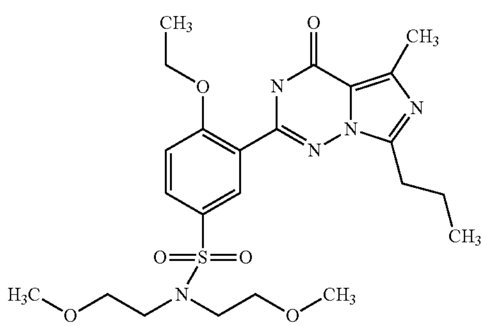 | 507.6134 | >95 | 508 |
| 279 | 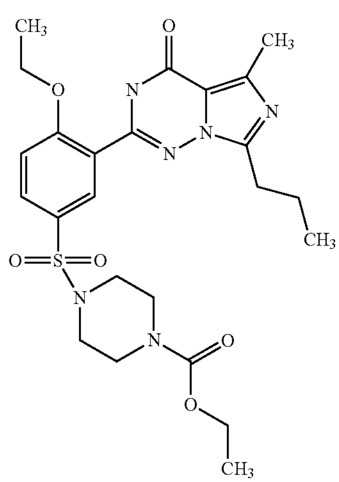 | 532.6232 | >95 | 533 |

TABLE 6-continued
| Ex. No. | Structure | MW | HPLC | MZ + H |
|---|---|---|---|---|
| 280 | 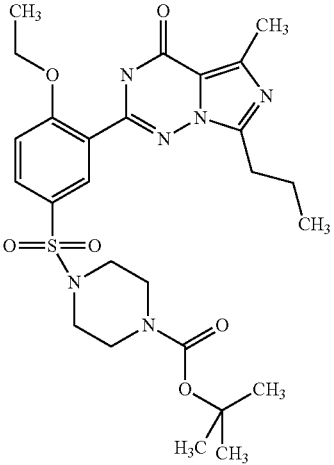 | 560.6775 | 89 | 561 |
| 281 | 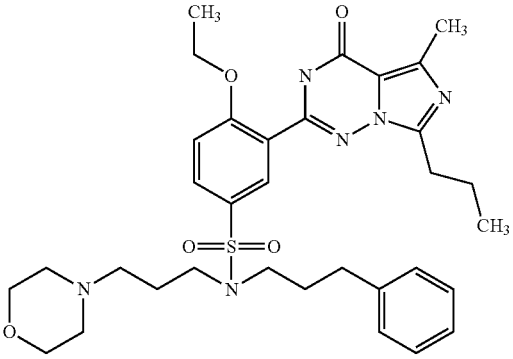 | 636.8199 | 88 | 637 |
| 282 | 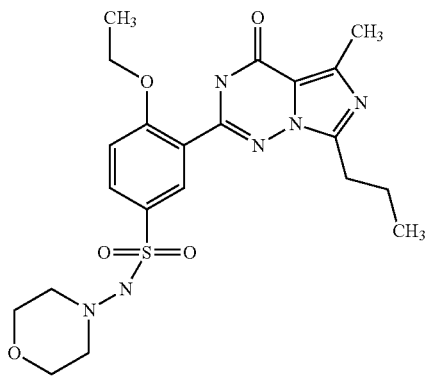 | 476.5585 | 50 | 477 |

TABLE 6-continued

| Ex. No. | Structure | MW | HPLC | MZ + H |
|---|---|---|---|---|
| 283 | 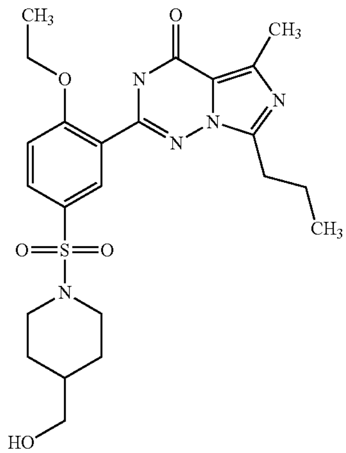 | 489.5981 | 93 | 490 |
| 284 | 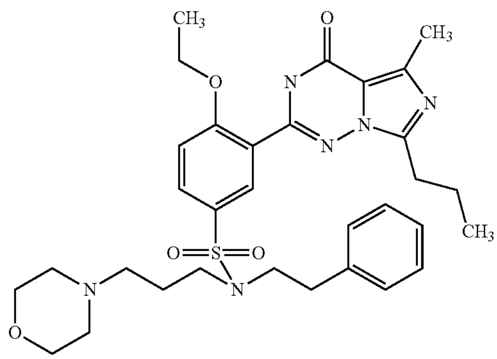 | 622.7928 | 68 | 623 |
| 285 | 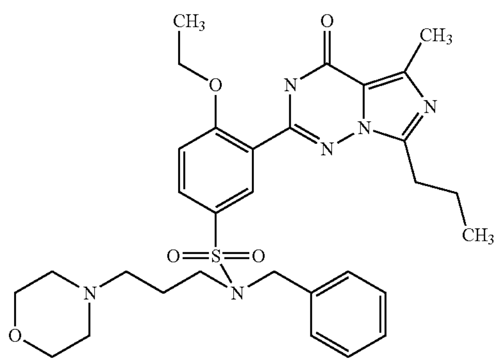 | 608.7657 | >95 | 609 |
| 286 | 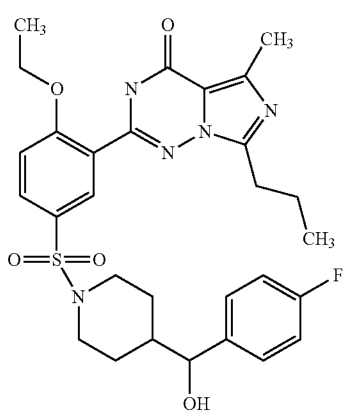 | 583.6873 | 85 | 584 |

TABLE 6-continued
| Ex. No. | Structure | MW | HPLC | MZ + H |
|---|---|---|---|---|
| 287 | 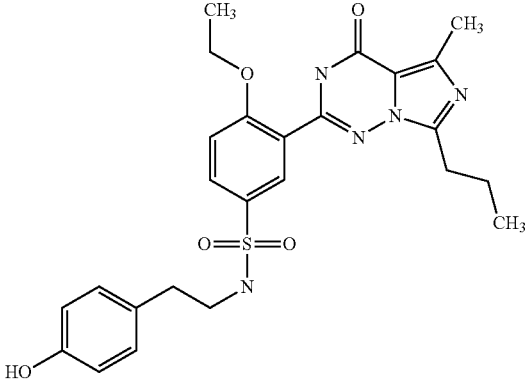 | 511.6044 | >95 | 512 |
| 288 | 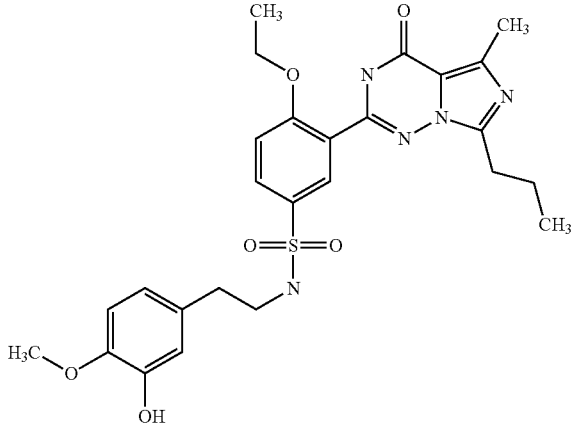 | 541.6309 | >95 | 542 |
| 289 | 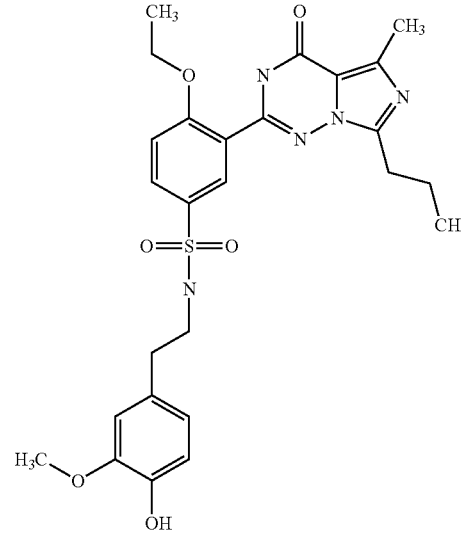 | 541.6309 | >95 | 542 |

TABLE 6-continued
| Ex. No. | Structure | MW | HPLC | MZ+H |
|---|---|---|---|---|
| 290 | 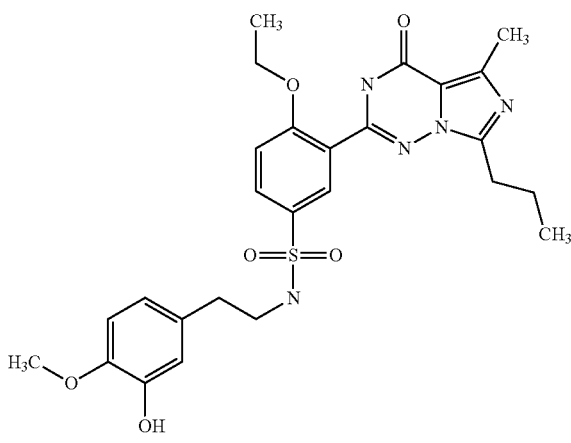 | 571.6574 | 73 | 572 |
| 291 | 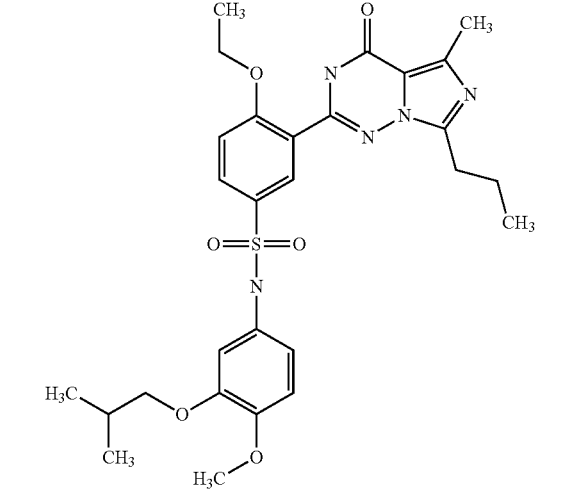 | 569.6851 | 83 | 570 |
| 292 | 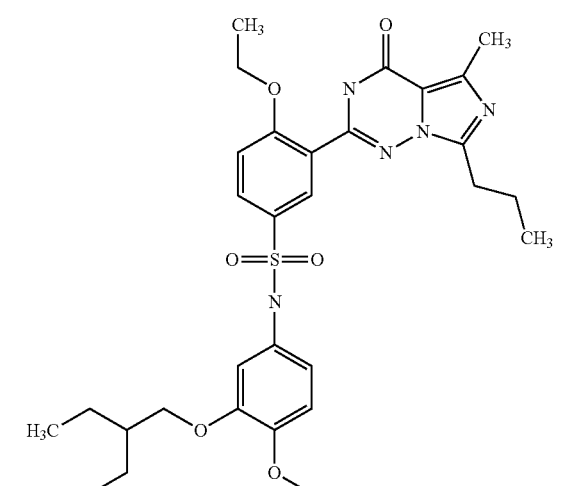 | 597.7393 | 89 | 598 |

TABLE 6-continued

| Ex. No. | Structure | MW | HPLC | MZ + H |
|---|---|---|---|---|
| 293 | 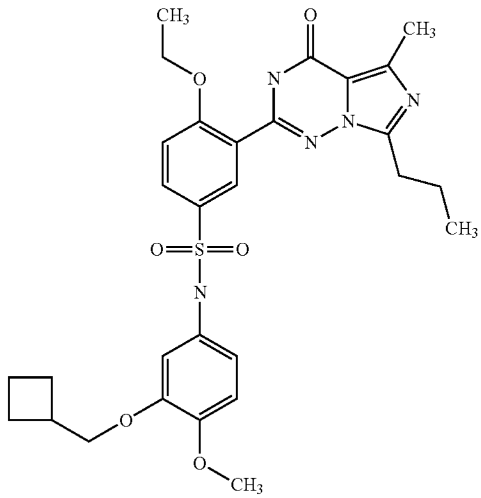 | 581.6963 | 76 | 582 |
| 294 | 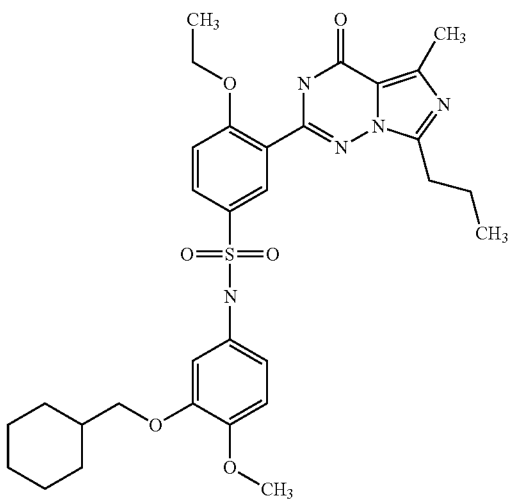 | 609.7504 | 83 | 610 |
| 295 | 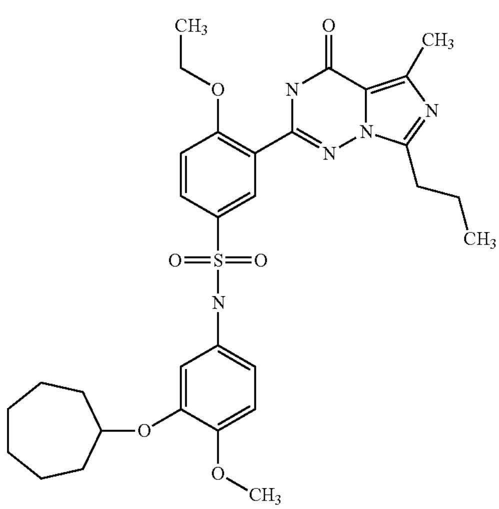 | 609.7504 | 77 | 610 |

TABLE 6-continued
| Ex. No. | Structure | MW | HPLC | MZ + H |
|---|---|---|---|---|
| 296 | 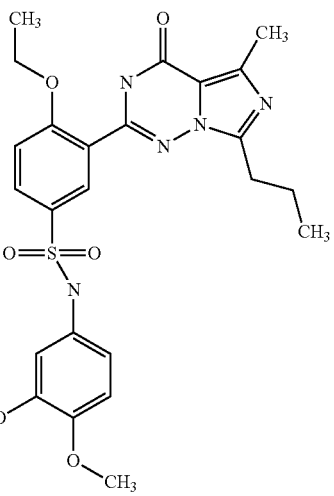 | 583.7122 | 82 | 584 |
| 297 | 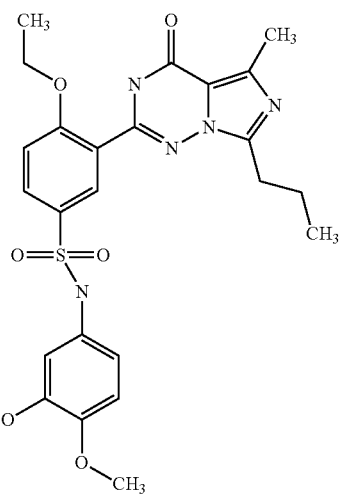 | 611.7227 | 88 | 612 |
| 298 | 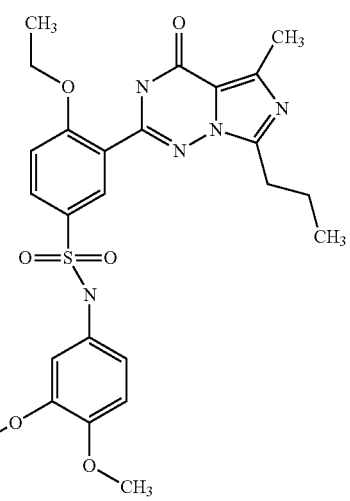 | 571.6574 | 89 | 572 |

TABLE 6-continued

| Ex. No. | Structure | MW | HPLC | MZ + H |
|---|---|---|---|---|
| 299 | 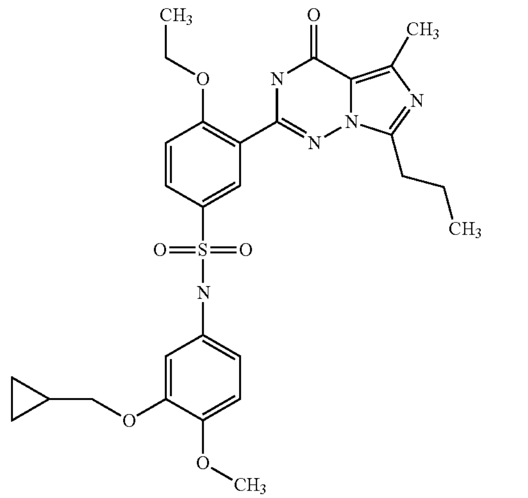 | 567.6692 | 81 | 568 |
| 300 | 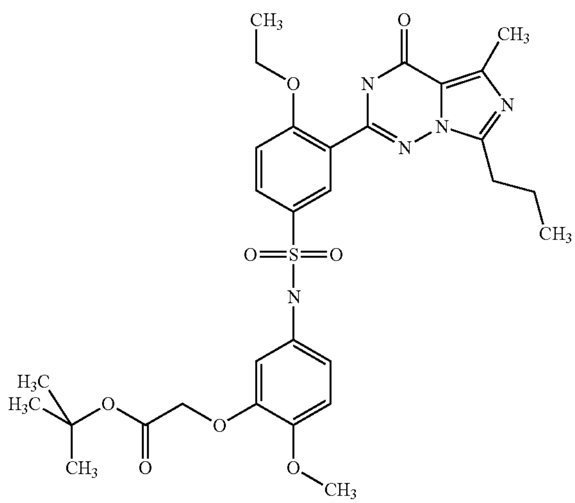 | 627.7221 | 82 | 628 |
| 301 | 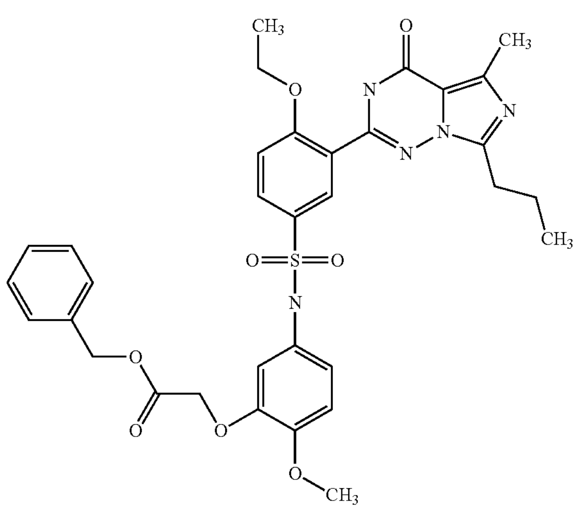 | 661.7396 | 64 | 662 |

TABLE 6-continued

| Ex. No. | Structure | MW | HPLC | MZ + H |
|---------|-----------|-----|------|--------|
| 302 | 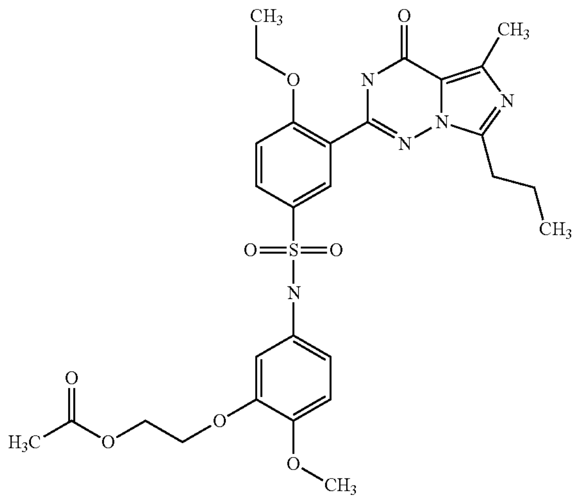 | 599.668 | 77 | 600 |
| 303 | 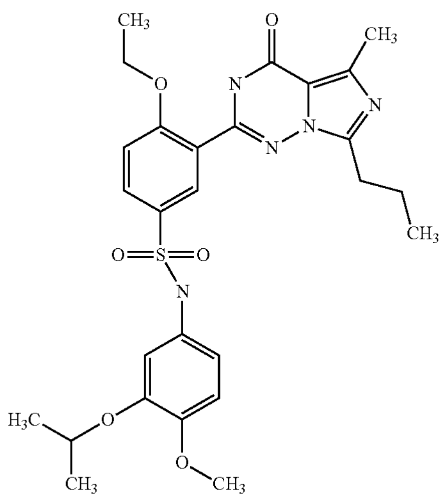 | 555.658 | 83 | 556 |
| 304 | 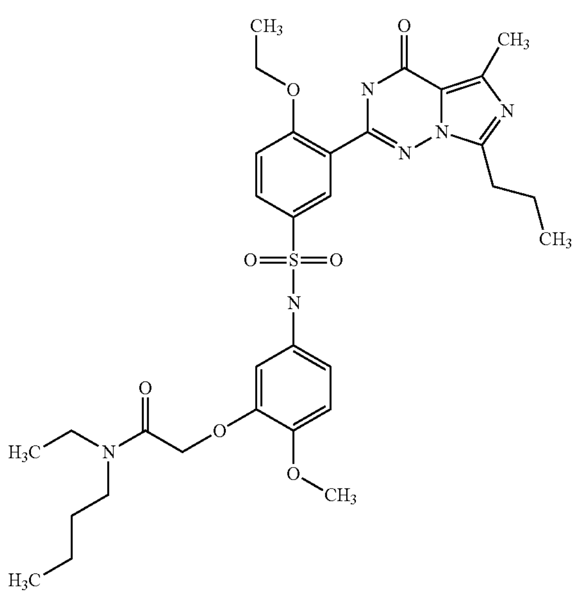 | 654.7916 | 60 | 655 |

TABLE 6-continued
| Ex. No. | Structure | MW | HPLC | MZ + H |
|---|---|---|---|---|
| 305 | 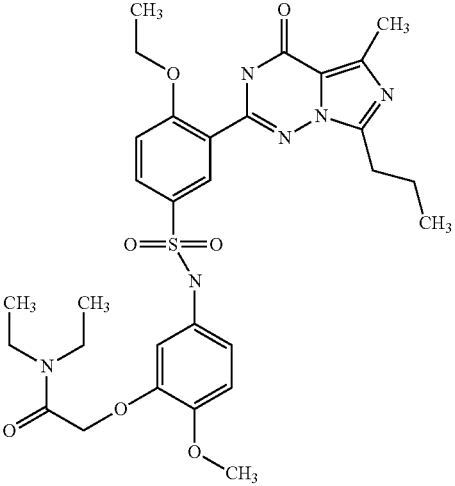 | 626.7374 | 86 | 627 |
| 306 | 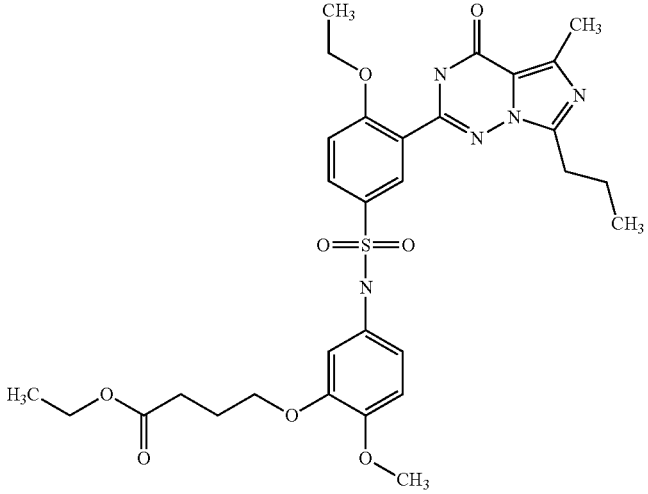 | 627.7221 | 82 | 628 |
| 307 | 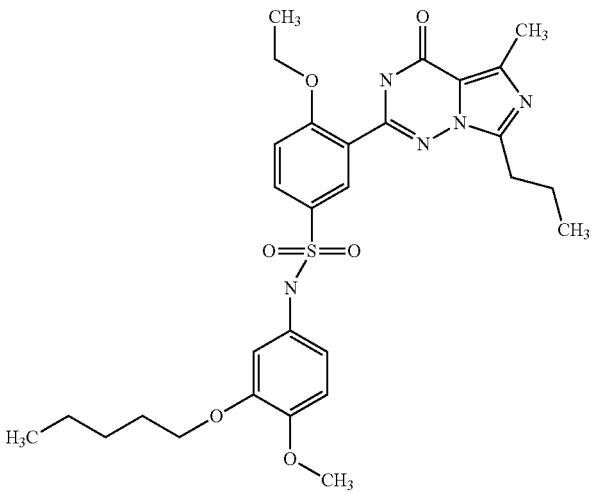 | 583.7122 | 81 | 584 |

TABLE 6-continued
| Ex. No. | Structure | MW | HPLC | MZ + H |
|---|---|---|---|---|
| 308 | 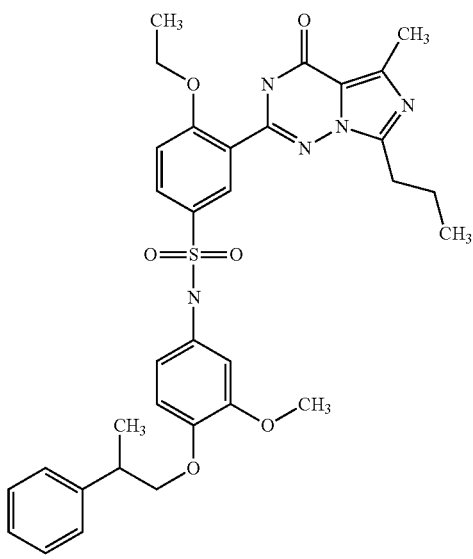 | 631.7568 | 29 | 632 |
| 309 | 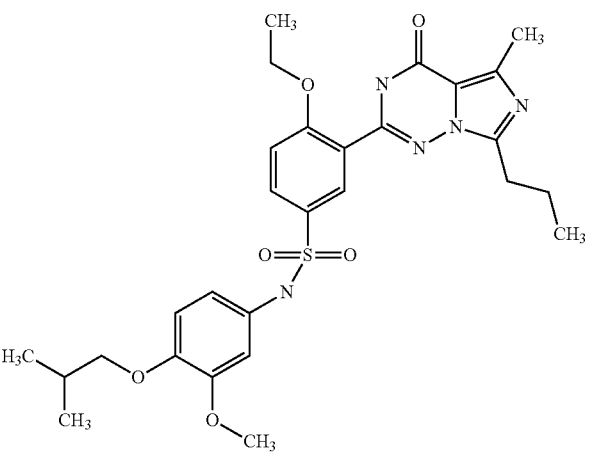 | 569.6851 | 60 | 570 |
| 310 | 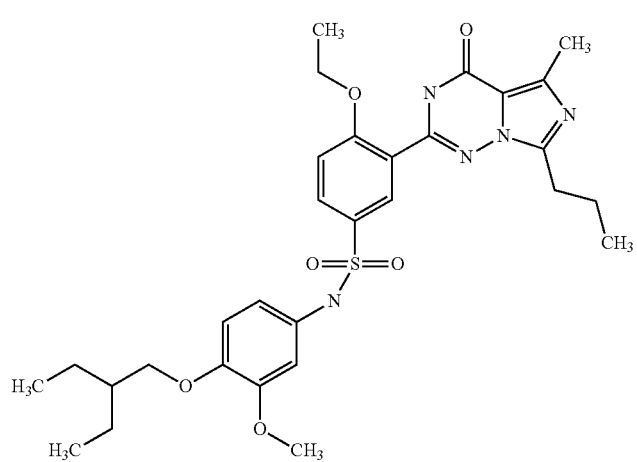 | 597.7393 | 62 | 598 |

TABLE 6-continued
| Ex. No. | Structure | MW | HPLC | MZ + H |
|---|---|---|---|---|
| 311 | 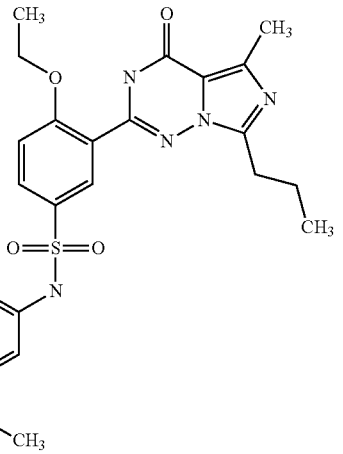 | 581.6963 | 87 | 582 |
| 312 | 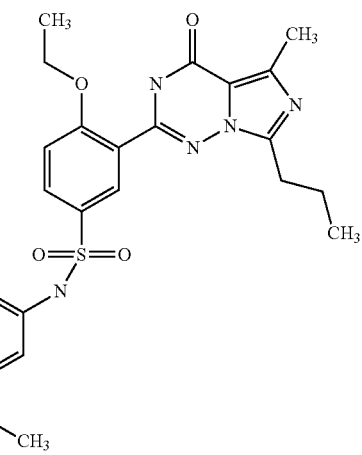 | 609.7504 | 71 | 610 |
| 313 | 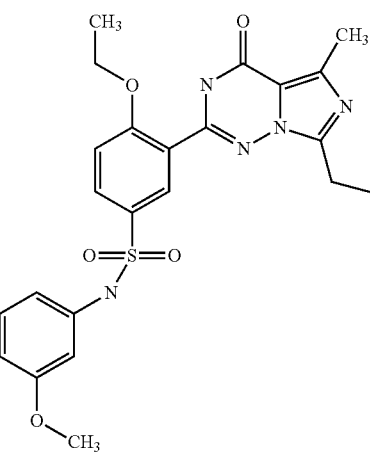 | 633.7291 | 47 | 634 |

TABLE 6-continued

| Ex. No. | Structure | MW | HPLC | MZ + H |
|---|---|---|---|---|
| 314 | 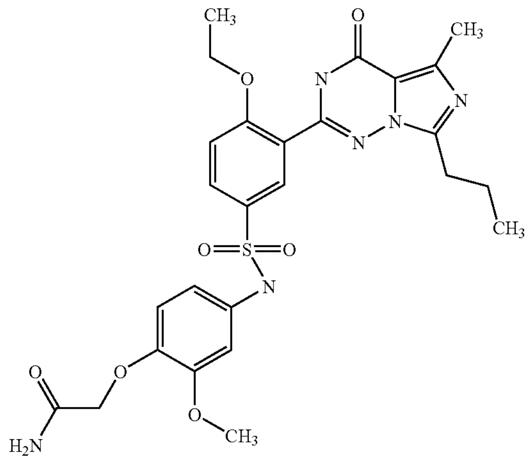 | 570.629 | 59 | 571 |
| 315 | 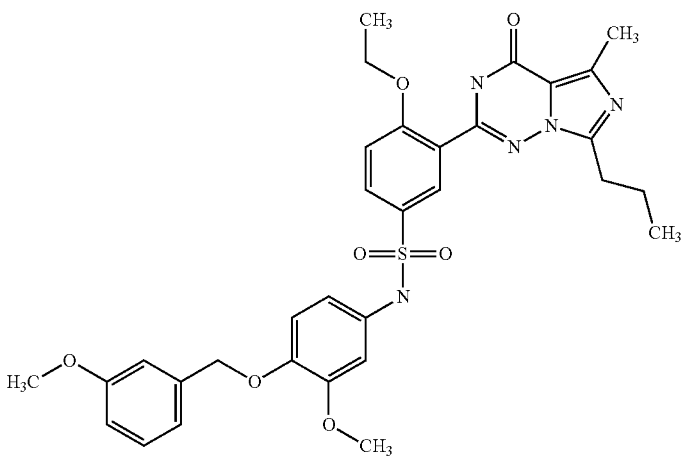 | 633.7291 | 35 | 634 |
| 316 | 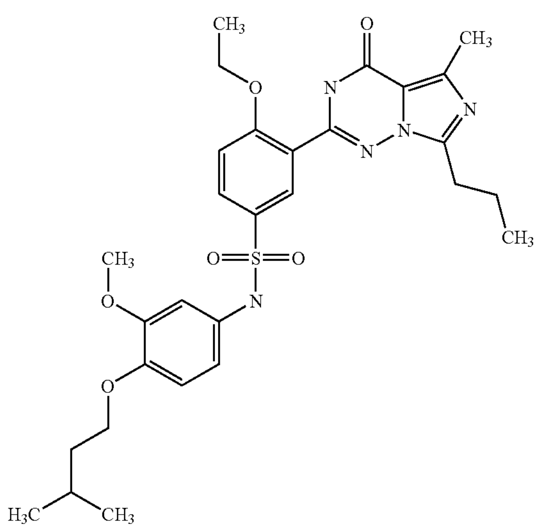 | 583.7122 | 51 | 584 |

TABLE 6-continued
| Ex. No. | Structure | MW | HPLC | MZ + H |
|---------|-----------|-----|------|--------|
| 317 | 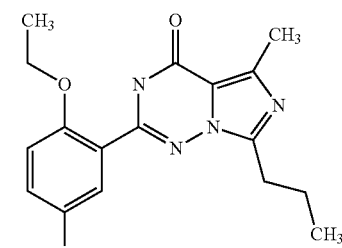 | 611.7227 | 51 | 612 |
| 318 | 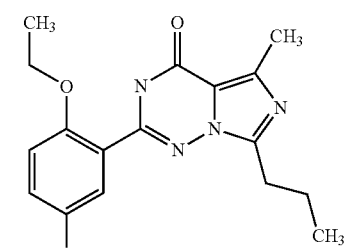 | 571.6574 | 75 | 572 |
| 319 | 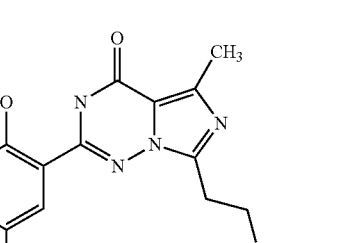 | 603.7026 | 64 | 604 |

TABLE 6-continued
| Ex. No. | Structure | MW | HPLC | MZ + H |
|---|---|---|---|---|
| 320 | 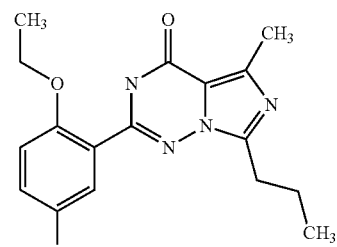 | 567.6692 | 74 | 568 |
| 321 | 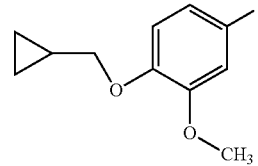 | 597.652 | 88 | 598 |
| 322 | 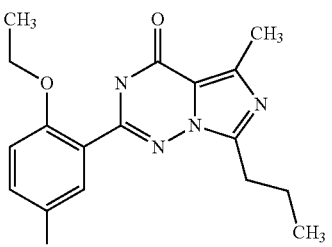 | 627.7221 | 80 | 628 |

TABLE 6-continued
| Ex. No. | Structure | MW | HPLC | MZ + H |
|---|---|---|---|---|
| 323 | 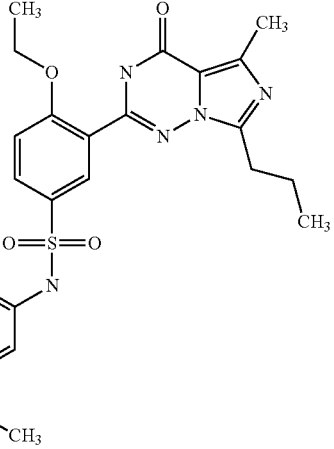 | 647.7562 | 47 | 648 |
| 324 | 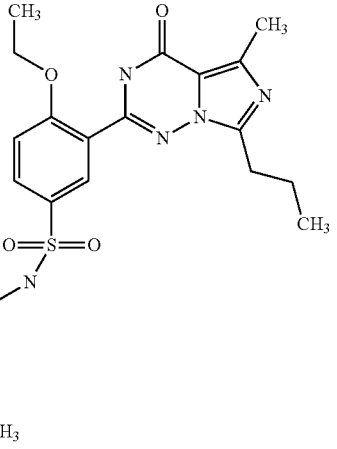 | 555.658 | 43 | 556 |
| 325 | 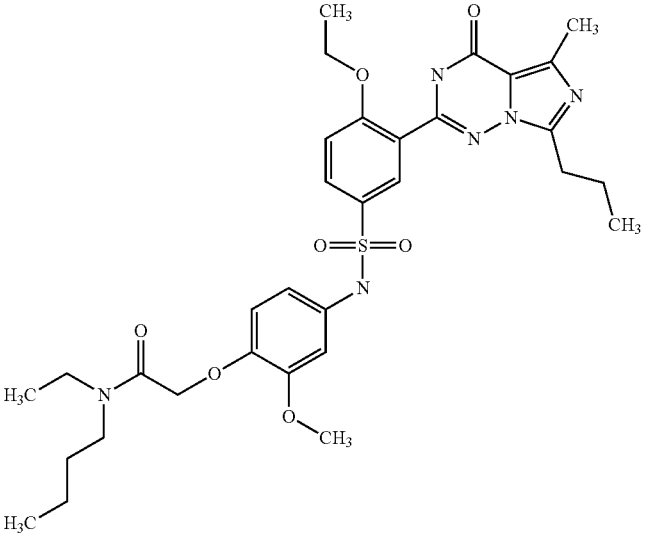 | 654.7916 | 54 | 655 |

TABLE 6-continued
| Ex. No. | Structure | MW | HPLC | MZ + H |
|---|---|---|---|---|
| 326 | 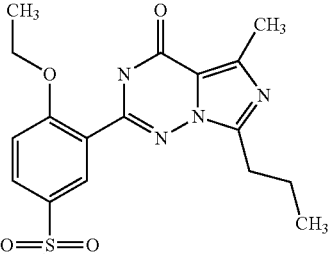 | 624.7214 | 71 | 625 |
| 327 | 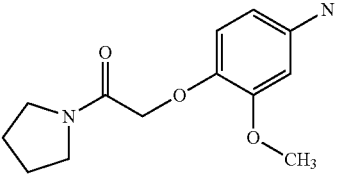 | 689.8375 | 42 | 690 |
| 328 | 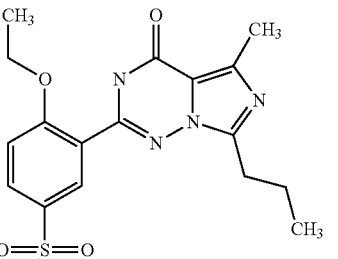 | 583.7122 | 40 | 584 |

TABLE 6-continued
| Ex. No. | Structure | MW | HPLC | MZ + H |
|---|---|---|---|---|
| 329 | 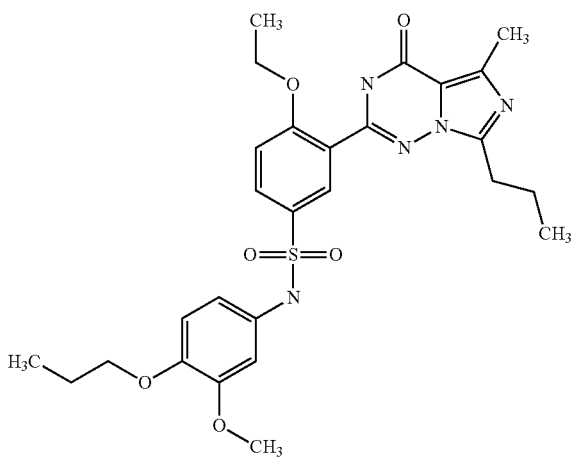 | 555.658 | 49 | 556 |
| 330 | 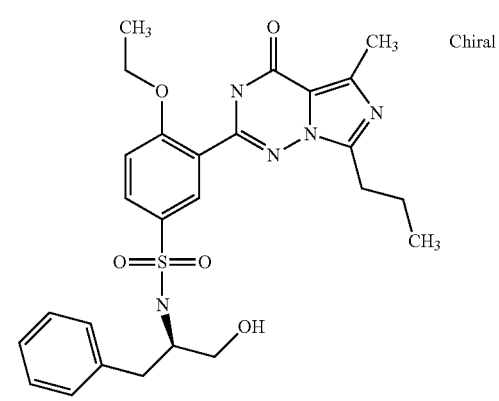 Chiral | 525.6315 | 83 | 526 |
| 331 | 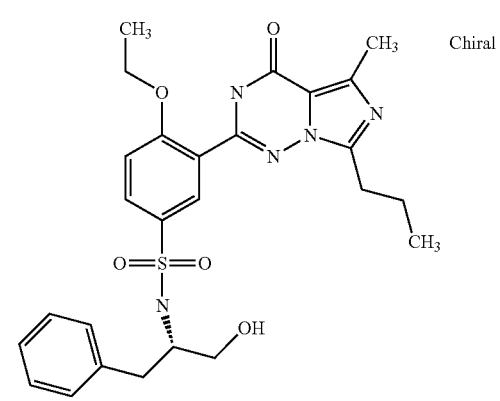 Chiral | 525.6315 | 71 | 526 |

TABLE 6-continued
| Ex. No. | Structure | MW | HPLC | MZ + H |
|---|---|---|---|---|
| 332 | 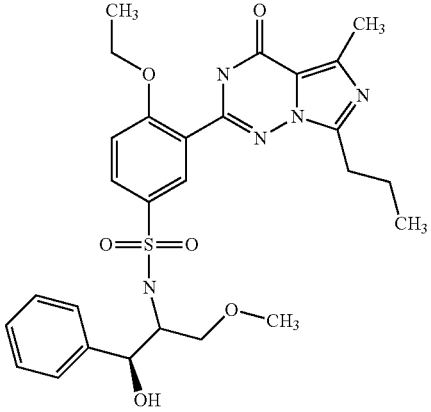 | 555.658 | 91 | 556 |
| 333 | 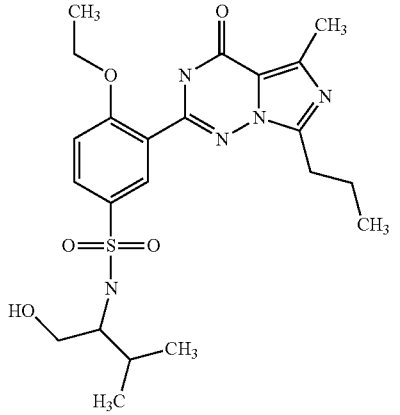 | 477.5869 | 76 | 478 |
| 334 | 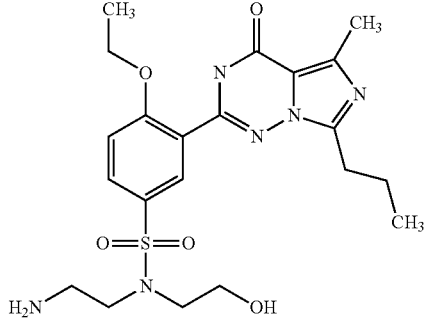 | 478.5745 | 62 | 479 |

| Ex. No. | Structure | MW | HPLC | MZ + H |
|---|---|---|---|---|
| 335 | 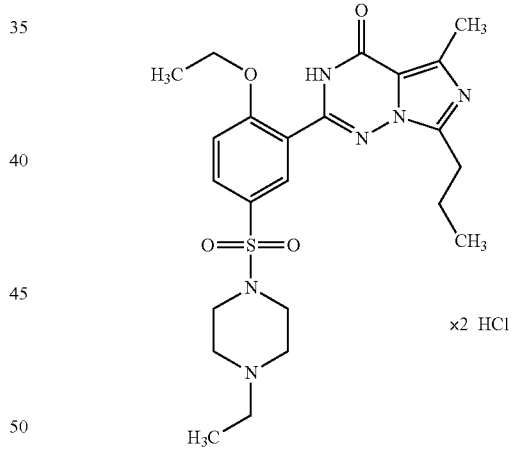 | 490.6292 | 42 | 491 |

Example 336

2-[2-Ethoxy-5-(4-ethyl-piperazine-1-sulphonyl)-phenyl]-5-methyl-7-propyl-3H-imidazol[5,1-f][1,2,4]triazine-4-one hydrochloride trihydrate

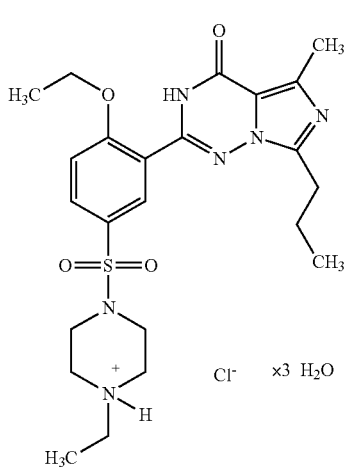

If the free base from Example 19 is crystallized from a mixture of an organic solvent and dilute aqueous hydrochloric acid, a hydrochloride trihydrate is obtained.

m.p.: 218° C.

Water content: 9.4% (K. Fischer)

Chloride content: 6.1%

Example 337

2-[2-Ethoxy-5-(4-ethyl-piperazine-1-sulphonyl)-phenyl]-5-methyl-7-propyl-3H-imidazo[5,1-f][1,2,4]triazine-4-one dihydrochloride 0.35 g (0.712 mmol) of 2-[2-ethoxy-5-(4-ethyl-piperazine-1-sulphonyl)-phenyl]-5-methyl-7-propyl-3H-imidazo[5,1-f][1,2,4]triazine-4-one are suspended in 8 ml of ether and dichloromethane is added until a homogeneous solution is formed. 24 ml of a 1M solution of HCl in ether are added and the mixture is stirred at room temperature for 20 minutes and filtered off with suction. This gives 372 mg (99%) of 2-[2-ethoxy-5-(4-ethyl-piperazine-1-sulphonyl)-phenyl]-5-methyl-7-propyl-3H-imidazo[5,1-f][1,2,4]triazine-4-one dihydrochloride.

200 MHz $^1$H-NMR (DMSO-$d_6$): 0.96, t, 3H, 1.22, t, 3H, 1.36, t, 3H, 1.82, sex., 2H, 2.61, s, 3H, 2.88, m, 2H, 3.08, m, 6H, 3.50, m, 2H, 3.70, m, 2H, 4.25, quart., 2H, 7.48, d, 1H; 7.95, m, 2H, 11.42, s, 1H, 12.45, s, 1H.

What is claimed is:

1. A compound of the formula:

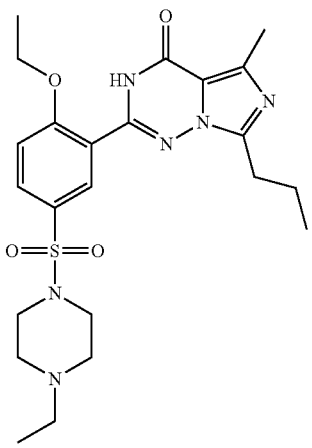

or a salt, a hydrate, or a hydrate of a salt thereof.

2. The compound according to claim 1 having the chemical name 2-[2-ethoxy-5-(4-ethyl-piperazine-1-sulphonyl)-phenyl]-5-methyl-7-propyl-3H-imidazo[5,1-f][1,2,4]triazin-4-one hydrochloride.

3. The compound according to claim 1 having the chemical name 2-[2-ethoxy-5-(4-ethyl-piperazine-1-sulphonyl)-phenyl]-5-methyl-7-propyl-3H-imidazo[5,1-f][1,2,4]triazin-4-one hydrochloride trihydrate.

4. A pharmaceutical composition comprising a compound according to claim 1 and a pharmacologically acceptable formulating agent.

5. A method of treating erectile dysfunction comprising administering to a mammal an effective amount of a compound according to claim 1.

6. The method of treating erectile dysfunction according to claim 5 wherein the mammal is a human.

* * * * *